US011220671B2

(12) United States Patent
Block et al.

(10) Patent No.: US 11,220,671 B2
(45) Date of Patent: Jan. 11, 2022

(54) METHODS FOR THE MATURATION OF CARDIOMYOCYTES ON AMNIOTIC FLUID CELL-DERIVED ECM, CELLULAR CONSTRUCTS, AND USES FOR CARDIOTOXICITY AND PROARRHYTHMIC SCREENING OF DRUG COMPOUNDS

(71) Applicant: STEMBIOSYS, INC., San Antonio, TX (US)

(72) Inventors: Travis Block, San Antonio, TX (US); Edward S. Griffey, San Antonio, TX (US); Todd Herron, New Hudson, MI (US)

(73) Assignee: STEMBIOSYS, INC., San Antonio, TX (US)

( * ) Notice: Subject to any disclaimer, the term of this patent is extended or adjusted under 35 U.S.C. 154(b) by 0 days.

(21) Appl. No.: 16/797,945

(22) Filed: Feb. 21, 2020

(65) Prior Publication Data

US 2020/0270577 A1    Aug. 27, 2020

Related U.S. Application Data

(60) Provisional application No. 62/808,690, filed on Feb. 21, 2019.

(51) Int. Cl.
*C12N 5/077* (2010.01)
*G01N 33/50* (2006.01)

(52) U.S. Cl.
CPC ....... *C12N 5/0657* (2013.01); *G01N 33/5061* (2013.01); *C12N 2503/02* (2013.01); *C12N 2506/45* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | |
|---|---|---|
| 5,563,067 A | 10/1996 | Sugihara et al. |
| 6,352,853 B1 | 3/2002 | King et al. |
| 6,890,762 B1 | 5/2005 | Sugihara et al. |
| 6,969,449 B2 | 11/2005 | Maher et al. |
| 7,311,904 B2 | 12/2007 | Hariri |
| 7,459,303 B2 | 12/2008 | Wang et al. |
| 7,470,533 B2 | 12/2008 | Xu et al. |
| 7,501,301 B2 | 3/2009 | Kovacs et al. |
| 8,084,023 B2 | 12/2011 | Chen et al. |
| 8,921,041 B2 | 12/2014 | Wang et al. |
| 9,290,756 B2 | 3/2016 | Ross et al. |
| 9,612,234 B2 | 4/2017 | Li et al. |
| 9,617,511 B2 | 4/2017 | Chen |
| 9,709,548 B2 | 7/2017 | Wang et al. |
| 9,994,812 B2 | 6/2018 | Kim et al. |
| 10,067,117 B2 | 9/2018 | Tyler et al. |
| 10,067,121 B2 | 9/2018 | Abassi et al. |
| 2006/0153894 A1 | 7/2006 | Ghabrial et al. |
| 2008/0281434 A1 | 11/2008 | Schmidt et al. |
| 2011/0039294 A1 | 2/2011 | Wang et al. |
| 2011/0293667 A1 | 12/2011 | Baksh et al. |
| 2012/0142102 A1 | 6/2012 | Chen et al. |
| 2012/0225424 A1 | 9/2012 | Abassi et al. |
| 2015/0246072 A1 | 9/2015 | Bhatia et al. |
| 2015/0329825 A1* | 11/2015 | Herron ............... A61L 27/3804 435/29 |
| 2016/0157982 A1 | 6/2016 | Matheny et al. |
| 2016/0215264 A1 | 7/2016 | Zimmermann et al. |
| 2017/0182216 A1 | 6/2017 | Thomas et al. |
| 2017/0198256 A1 | 7/2017 | Lipke et al. |
| 2017/0281686 A1 | 10/2017 | Zamilpa et al. |
| 2017/0335286 A1 | 11/2017 | Zamilpa et al. |
| 2018/0044640 A1 | 2/2018 | Lu et al. |
| 2018/0320140 A1 | 11/2018 | Block et al. |
| 2019/0017028 A1 | 1/2019 | Herron et al. |
| 2019/0185816 A1 | 6/2019 | Herron et al. |
| 2020/0109367 A1 | 4/2020 | Block et al. |

FOREIGN PATENT DOCUMENTS

| | | |
|---|---|---|
| WO | WO 2009/035612 | 3/2009 |
| WO | WO 2009/052132 | 4/2009 |
| WO | WO 2013/151755 | 10/2013 |

(Continued)

OTHER PUBLICATIONS

Liang (Circulation, 127(16): 1-29, 2013). (Year: 2013).*
Deutsch et al. (Journal of Materials Chemistry, 2010) (Year: 2010).*
Feaster (Circ Res, 117(12): 995-1000, 2015). (Year: 2015).*
Huebsch (Scientific Reports, 6: 24726: 1-12, 2016 (Year: 2016).*
Alitalo (Cell, 19: 1053-1062, 1980 (Year: 1980).*
Alitalo et al., "Extracellular Matrix Components Synthesized by Human Amniotic Epithelial Cells in Culture," *Cell*, 1980, 19:1053-1062.
Arshi, et al. "Rigid microenvironments promote cardiac differentiation of mouse and human embryonic stem cells," *Science and Technology of Advanced Materials*, 2013, 025003.
Baharvand, et al. "The effect of extracellular matrix on embryonic stem cell-derived cardiomyocytes," *Journal of Molecular and Cellular Cardiology*, 2005, 38:495-503.

(Continued)

*Primary Examiner* — Anoop K Singh
*Assistant Examiner* — Magdalene K Sgagias
(74) *Attorney, Agent, or Firm* — Norton Rose Fulbright US LLP

(57) ABSTRACT

Disclosed herein are methods of using a cell-derived extracellular matrix derived in-vitro from cells isolated from amniotic fluid (AFC-ECM) for the maturation of immature cardiomyocytes derived from human induced pluripotent stem cells (immature hiPSC-CMs) in culture forming mature cardiomyocytes. Also disclosed herein is a cell construct comprising a monolayer of these mature cardiomyocytes on an AFC-ECM useful for cardiotoxicity and/or proarrhythmic screening assays of drug compounds. Also disclosed herein are methods for determining the cardiotoxicity and/or proarrhythmic effect of a drug compound in vitro using such cell constructs.

9 Claims, 39 Drawing Sheets

(56) References Cited

FOREIGN PATENT DOCUMENTS

| WO | WO 2016/161192 | 10/2016 |
| WO | WO 2017/136786 | 8/2017 |
| WO | WO 2018/029535 | 2/2018 |
| WO | WO 2018/035574 | 3/2018 |
| WO | WO 2020/072791 | 4/2020 |

OTHER PUBLICATIONS

Balistreri, et al. "Effect of Glucose on 3D Cardiac Microtissues Derived from Human Induced Pluripotent Stem Cells," *Pediatr. Cardiol.*, 2017, 38:1575-1582.

Bedut, et al. "High-throughput drug profiling with voltage- and calcium-sensitive fluorescent probes in human iPSC-derived cardiomyocytes," *Am. J. Physiol. Heart Circ. Physiol.*, 2016, 311:H44-H53.

Bizy, et al. "Myosin light chain 2-based selection of human iPSC-derived early ventricular cardiac myocytes," *Stem Cell Research*, 2013, 11:1335-1347.

Blinova, et al. "Comprehensive Translational Assessment of Human-Induced Pluripotent Stem Cell Derived Cardiomyocytes for Evaluating Drug-Induced Arrhythmias," *Toxicological Sciences*, 2017, 155(1):234-247.

Blinova, et al. "International Multisite Study of Human-Induced Pluripotent Stem Cell-Derived Cardiomyocytes for Drug Proarrhythmic Potential Assessment," *Cell Reports*, 2018, 24:3582-3592.

Burridge, et al. "Human induced pluripotent stem cell-derived cardiomyocytes recapitulate the predilection of breast cancer patients to doxorubicin-induced cardiotoxicity," *Nature Medicine*, 2016, 22(5):547-560.

Chen et al., "Extracellular Matrix Made by Bone Marrow Cells Facilitates Expansion of Marrow-Derived mesenchymal Progenitor Cells and Prevents their Differentiation into Osteoblasts," *Journal of Bone and Mineral Research*, 2007, 22:1943-1956.

Da Rocha, et al. "Deficient cMyBP-C protein expression during cardiomyocyte differentiation underlies human hypertrophic cardiomyopathy cellular phenotypes in disease specific human ES cell derived cardiomyocytes," *J. Mol. Cell Cardiol*, 2016, 99:197-206.

Da Rocha, et al. "hiPSC-CM Monolayer Maturation State Determines Drug Responsiveness in High Throughput Pro-Arrhythmia Screen," *Scientific Reports*, 2017, 7:13834.

Deutsch et al., "Stem cell-synthesized extracellular matrix for bone repair," *Journal of Materials Chemistry*, 2010, 20:8942-8951.

Doss, et al. "Maximum Diastolic Potential of Human Induced Pluripotent Stem Cell-Derived Cardiomyocytes Depends Critically on IKr," *PLOS One*, 2012, 7(7):e40288.

Eloff, et al. "High resolution optical mapping reveals conduction slowing in connexin43 deficient mice," *Cardiovascular Research*, 2001, 51:681-690.

Feaster, et al. "Matrigel Mattress: A Method for the Generation of Single Contracting Human-Induced Pluripotent Stem Cell-Derived Cardiomyocytes," *Circulation Research*, 2015, 995-1000.

Fermini, et al. "A New Perspective in the Field of Cardiac Safety Testing through the Comprehensive In Vitro Proarrhythmia Assay Paradigm," *Journal of Biomolecular Screening*, 2016, 21(1):1-11.

Forte, et al. "Substrate Stiffness Modulates Gene Expression and Phenotype in Neonatal Cardiomyocytes In Vitro," *Tissue Engineering: Part A*, 2012, 18(17-18):1837-1848.

Gintant, "An evaluation of hERG current assay performance: Translating preclinical safety studies to clinical QT prolongation," *Pharmacology & Therapeautics*, 2011, 129:109-119.

Gintant, et al. "Evolution of strategies to improve preclinical cardiac safety testing," *Nature Reviews*, 2016, 15:457-471.

Gintant, et al. "The Evolving Roles of Human iPSC-Derived Cardiomyocytes in Drug Safety and Discovery," *Cell Stem Cell*, 2017, 21:13-17.

Han, et al. "Cell alignment induced by anisotropic electrospun fibrous scaffolds alone has limited effect on cardiomyocyte maturation," *Stem Cell Research*, 2016, 16:740-750.

Herron, "Calcium and voltage mapping in hiPSC-CM monolayers," *Cell Calcium*, 2016, 59:84-90.

Herron, et al. "Cardiomyocyte purification from pluripotent stem cells," *MACS Miltenyi Biotec*, 2017, 1-4.

Herron, et al. "Extracellular Matrix-Mediated Maturation of Human Pluripotent Stem Cell-Derived Cardiac Monolayer Structure and Electrophysiological Function," *Circulation: Arrhythmia and Electrophysiology*, 2016, 9:e003638.

Hondeghem, et al. "Instability and Triangulation of the Action Potential Predict Serious Proarrhythmia, but Action Potential Duration Prolongation is Antiarrhythmic," *Circulation*, 2001,103:2004-2013.

Hoynowski, et al. "Characterization and Differentiation of Equine Umbilical Cord-Derived Matrix cells," *Biochemical and Biophysical Research Communications*, 362:347-353, 2007.

Huebsch, et al. "Miniaturized iPS-Cell-Derived Cardiac Muscles for Physiologically Relevant Drug Response Analyses," *Scientific Reports*, 2016, 6(24726):1-12.

Jiang, et al. "Human Cardiomyocytes Prior to Birth by Integration-Free Reprogramming of Amniotic Fluid Cells" Stem Cells Translation Medicine, 2016;5:1595-1606.

Ilic, et al. "Stem Cells in Regenerative Medicine: Introduction," *British Medical Bulletin*, 2011, 98:117-126.

Kirchhoff, et al. "Reduced cardiac conduction velocity and predisposition to arrhythmias in connexin40-deficient mice," *Current Biology*, 1998, 8(5):299-302.

Kusuma, et al. "Decellularized Extracellular Matrices Produced from Immortal Cell Lines Derived from Different Parts of the Placenta Support Primary Mesenchymal Stem Cell Expansion," *PLOS ONE*, 2017, 1-18.

Lai et al., "Reconstitution of marrow-derived extracellular matrix ex vivo: a robust culture system for expanding large-scale highly functional human mesenchymal stem cells," *Stem Cells and Development*, 2010, 19:1095-1107.

Lee, et al. "Simultaneous Voltage and Calcium Mapping of Genetically Purified Human Induced Pluripotent Stem Cell-Derived Cardiac Myocyte Monolayers," *Circulation Research*, 2012, 110:1556-1563.

Marinkovic, et al., "One size does not fit all: developing a cell-specific niche for in vitro study of cell behavior" *Matrix Biol.*, 2016, 54-55:426-441.

Mehrabadi, et al. "Domperidone for insufficient lactation in England 2002-2015: A drug utilization study with interrupted time series analysis," *Pharmacoepidemial Drug Saf.*, 2018, 27:1316-1324.

Millard, et al. "Cross-Site Reliability of Human Induced Pluripotent stem cell-derived Cardiomyocyte Based Safety Assays Using Microelectrode Arrays: Results from a Blinded CiPA Pilot Study," *Toxicological Sciences*, 2018, 164(2):550-562.

Mummery, et al. "Differentiation of Human Embryonic Stem Cells and Induced Pluripotent Stem Cells to Cardiomyocytes: A Methods Overview," *Circulation Research*, 2012, 111:344-358.

Murphy & Atala, "Amniotic Fluid Stem Cells," *Perinatal Stem Cells. Second Edition*, 2013, Wiley-Blackwell, p. 1-15.

Pandit, et al. "Rotors and the Dynamics of Cardiac Fibrillation," *Circulation Research*, 2013, 112:849-862.

Thavandiran, et al. "Design and formulation of functional pluripotent stem cell-derived cardiac microtissues," PNAS, 2013, E4698-E4707.

Gosden, C M, "Amniotic Fluid Cell Types and Culture" *British Medical Bulletin* 1983, 39(4), 348-354.

International Search Report and Written Opinion issued in Corresponding PCT Application No. PCT/US2020/019311, dated Apr. 5, 2020.

Parveen et al., "Amniotic membrane as novel scaffold for human iPSC-derived cardiomyogenesis" *In Vitro Cellular & Developmental Biology—Animal* 2019, 55, 272-284.

* cited by examiner

Mature cardiomyocytes on AFC-ECM – 3.13 mm²

Mature cardiomyocytes on AFC-ECM – 2.15 mm$^2$

Mature cardiomyocytes on AFC-ECM – 1.46 mm$^2$

Mature cardiomyocytes on AFC-ECM – 0.54 mm$^2$

Mature cardiomyocytes on AFC-ECM – 0.54 mm$^2$

Mature cardiomyocytes on AFC-ECM – 0.54 mm$^2$

Mature cardiomyocytes on AFC-ECM – 0.54 mm$^2$

Mature cardiomyocytes on AFC-ECM – 0.13 mm$^2$

Mature cardiomyocytes on AFC-ECM – 0.04 mm$^2$

Cardiomyocytes on standard Matrigel™ ECM – 3.13 mm$^2$

Cardiomyocytes on standard Matrigel™ ECM – 2.15 mm$^2$

Cardiomyocytes on standard Matrigel™ ECM – 1.46 mm$^2$

Cardiomyocytes on standard Matrigel™ ECM – 0.54 mm²

Cardiomyocytes on standard Matrigel™ ECM – 0.13 mm$^2$

Cardiomyocytes on BM-ECM – 2.15 mm$^2$

Cardiomyocytes on BM-ECM – 1.46 mm$^2$

Matrigel™ ECM    AFC-ECM

Matrigel™ ECM					AFC-ECM

Matrigel™ ECM                AFC-ECM

Matrigel™ ECM          AFC-ECM

Matrigel™ ECM               AFC-ECM

Matrigel™ ECM  AFC-ECM

Matrigel™ ECM        AFC-ECM

METHODS FOR THE MATURATION OF CARDIOMYOCYTES ON AMNIOTIC FLUID CELL-DERIVED ECM, CELLULAR CONSTRUCTS, AND USES FOR CARDIOTOXICITY AND PROARRHYTHMIC SCREENING OF DRUG COMPOUNDS

CROSS REFERENCE TO RELATED APPLICATIONS

This application claims the benefit of U.S. Provisional Patent Application No. 62/808,690, filed Feb. 21, 2019, which is incorporated by reference herein in its entirety

FIELD

The disclosure generally relates to the use of cellular constructs of cardiomyocytes derived from human stem cells on cell-derived extracellular matrices, methods of making the constructs, and methods for cardiotoxicity and proarrhythmic screening assays of drug compounds using the constructs.

BACKGROUND

Cardiotoxicity, or the perceived potential for cardiotoxicity, is a leading cause of toxicity related drug attrition during the investigation and selection of new drugs. Cardiac safety testing of new chemical entities that become lead drug candidates is a critical aspect of the drug discovery and development pipeline. A large number of cardiac side effects of cardiac and non-cardiac drugs are caused by drug interaction with one or more cardiac ion channels. Cardiac ion channels regulate cellular excitability, contractility and overall cardiac performance, and alteration of cardiac ion channel function can lead to sudden cardiac death. This contributed to the release of drug candidate testing guidelines from The International Conference on Harmonization (ICH).

The current preclinical drug candidate testing guidelines from the IHC (ICH S7A and S7B-Pharmacology Studies) rely on genetically modified heterologous cells and in vivo animal models. It has become increasingly recognized that these studies, such as hERG assay and QT prolongation studies, do not accurately predict cardiotoxicity and proarrhythmia risk for humans. Since 2005, cardiac safety of a drug compound has been determined almost exclusively by its effect or potential effect on the QT interval of the electrocardiogram (ECG) or the action potential duration (APD), and the potential to lead to a life-threatening arrhythmia called Torsades de Pointes (TdP). However, QT prolongation is not the ideal indicator for TdP as drugs that prolong the QT interval do not always cause TdP. It is now recognized that the QT prolongation parameter is only a surrogate marker for proarrhythmia. Data from pre-clinical and clinical trials have shown that there is no fixed relationship between the magnitude of QT prolongation and the risk for development of fatal arrhythmias such as TdP.

Therefore, the US Food and Drug Administration (FDA) and other stakeholders in drug discovery have called for an evolution in pre-clinical cardiotoxicity testing. The proposed new paradigm is called the Comprehensive In-Vitro Proarrhythmia Assay (CiPA). An integral part of the CiPA Initiative (cipaproject.org/) includes incorporation of data collected from human stem cell derived cardiomyocytes for cardiotoxicity and proarrhythmia assays. The overall goal of these new proposed guidelines is to provide a more accurate and comprehensive mechanistic based assessment of proarrhythmic potential that would more accurately assess the risk of new drugs. In review of the proposed CiPA Initiative's guidelines, the FDA has defined two advances that must be made before human cardiomyocytes can be incorporated in the new initiative. First, the growth and maturation state of human stem cell derived cardiomyocytes needs to be advanced to more closely resemble the structure and function of adult human cardiomyocytes. Second, a reliable high throughput screening platform using these cells must be developed.

There are generally three types of systems currently utilized to evaluate the electrophysiology of cardiomyocytes in vitro: 1) Patch clamping systems; 2) micro-electrode array (MEA) systems; and 3) voltage sensitive dye (VSD) visualization methods. Manual patch clamping systems are most commonly used in very early research studies to evaluate the electrophysiology of individual cells. These devices, while providing accurate and sensitive ionic current measurements, cannot be used for in vitro cell systems that more closely mimic cell-cell interaction in cardiac tissue. MEA systems include electrodes that are incorporated into cell culture wells allowing for the measurement of current across the well. While allowing for high throughput analysis and ability to measure impedance in in vitro cell systems, these systems have low spatial resolution, do not provide data on action potential shape, and hinder direct visualization of the cells and the ability to assess 3-D culture systems that more closely mimic cardiac tissue architecture. VSD systems are gaining interest as they address many of the shortcomings of the current technologies described above with features that include: 1) allowing for high throughput analysis; 2) providing high spatial resolution; 3) allowing visualization of impulse propagation across a culture dish; and 4) allowing for modification of the culture conditions including addition of extracellular matrix leading to a more natural testing environment.

The use of cardiomyocytes derived from human stem cells, such as induced pluripotent stem cells, have had limited success to date in cardiotoxicity and proarrhythmic assay screening. Cardiomyocytes derived from induced human pluripotent stem cells (hiPSC-CMs) are commercially available and can be purchased from several companies in cryopreserved vials that can be thawed and plated as monolayers. These hiPSC-CMs can be made in large scale in vitro. Also, hiPSC-CMs can be obtained from patient specific hiPSCs for a specific individual. However, there are hurdles that still need to be overcome to make the hiPSC-CMs a meaningful part of the new CiPA Initiative paradigm. 1) The maturation of hiPSC-CM structure and function must be advanced. Notably, the Kir2.1 potassium channel is absent in currently available hiPSC-CMs and sodium channel expression is low. Currently available hiPSC-CMs are very immature functionally and structurally. The vast majority of currently used hiPSC-CM-based proarrhythmia screening assays rely on immature, fetal-like cells that do not resemble the structure of function of the adult cardiomyocyte. 2) Electrical pacing of hiPSC-CM monolayers in a high throughput electrophysiological screening platform is needed. The vast majority of current hiPSC-CM-based proarrhythmia screens rely solely on field potential duration (MEA technology) or action potential duration prolongation (VSD technology) as surrogate marker for TdP induction. This is a limitation because not all drugs that prolong the action potential (QT interval) will cause fatal TdP arrhythmias. Although certain maturation states of immature hiPSC-CMs have been achieved using Matrigel™ ECM and bone-marrow cell-derived ECM in culture, use of these hiPSC-CMs in proarrhythmia screening assays did not produce consistent results in the observation of arrhythmia activation patters consistent with what is known to occur in cases of TdP in humans, especially between low risk and high risk drugs.

Thus, advanced materials and new methods are needed for the precise assessment and screening of the cardiac safety liability of drug compounds for accurate, reliable and efficient development of new drug candidates.

SUMMARY

The present disclosure provides a solution to at least some of the aforementioned limitations and deficiencies in the art relating to the assessment and screening of the cardiac safety liability of drug candidates. The solution is premised on the discovery of an extracellular matrix derived from cells isolated from amniotic fluid (AFC-ECM), which can be used for the maturation of human stem cell derived cardiomyocytes. These mature cardiomyocytes can then be used in a cellular construct with the AFC-ECM for cardiotoxicity and proarrhythmic testing of drugs.

In one aspect, disclosed is a method for the maturation of immature cardiomyocytes derived from human induced pluripotent stem cells, the method comprising: (a) providing immature cardiomyocytes derived from human induced pluripotent stem cells (immature hiPSC-CMs); (b) providing an extracellular matrix derived in vitro from cells isolated from amniotic fluid (AFC-ECM); (c) contacting the immature hiPSC-CMs with the AFC-ECM; and (d) culturing the immature hiPSC-CMs with the AFC-ECM in a culture media to induce maturation of the immature hiPSC-CMs, thereby forming mature cardiomyocytes; wherein the mature cardiomyocytes are characterized by rod shaped cells with distinct sarcomere structure resembling adult human cardiac tissue. In some embodiments the mature cardiomyocytes have a similar or the same morphology as illustrated in any one of FIGS. 6 to 14. In some embodiments, the immature hiPSC-CMs are plated on the AFC-ECM. In some embodiments, the mature cardiomyocytes form as a monolayer on the AFC-ECM, thereby forming a cellular construct comprising a monolayer of mature cardiomyocytes on the AFC-ECM, wherein the mature cardiomyocytes are aligned on the AFC-ECM. In some embodiments, the immature hiPSC-CMs do not express inward-rectifier potassium channel Kir2.1. In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus. In some embodiments, the mature cardiomyocytes can be further characterized by having greater amounts of mitochondria than immature hiPSC-CMs, by having organized, compact myofilaments, and/or by having two nuclei (bi-nucleated).

In another aspect, disclosed is a cellular construct comprising a monolayer of mature cardiomyocytes on an extracellular matrix derived from cells isolated in vitro from amniotic fluid (AFC-ECM), wherein the mature cardiomyocytes are AFC-ECM cultured cardiomyocytes derived from human induced pluripotent stem cells (hiPSC-CMs), and wherein the mature cardiomyocytes are characterized by rod shaped cells with distinct sarcomere structure resembling adult human cardiac tissue. In some embodiments the mature cardiomyocytes have a similar or the same morphology as illustrated in any one of FIGS. 6 to 14. In some aspects, the mature cardiomyocytes include the inward-rectifier Kir2.1 potassium channel and/or express inward-rectifier potassium channel Kir2.1. In certain aspects, the mature cardiomyocytes can be matured from immature cardiomyocytes derived from human induced pluripotent stem cells (immature hiPSC-CMs) in culture on the AFC-ECM, wherein the mature cardiomyocytes are characterized by rod shaped cells with distinct sarcomere structure (striped appearance) resembling adult human cardiac tissue. In some embodiments, the monolayer of mature cardiomyocytes is aligned on the AFC-ECM. In some embodiments, fiber tracks are present on the construct. In some embodiments, the AFC-ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the AFC-ECM further comprises fibronectin and/or an isoform thereof. In some embodiments, the AFC-ECM does not contain decorin, perlecan, and/or collagen (III). In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus. In some embodiments, the mature cardiomyocytes can be further characterized by having greater amounts of mitochondria than immature hiPSC-CMs, by having organized, compact myofilaments, and/or by having two nuclei (bi-nucleated).

In another aspect, disclosed is a method for making a cellular construct of mature cardiomyocytes on an extracellular matrix derived in vitro from cells isolated from amniotic fluid (AFC-ECM), the method comprising: (a) providing immature cardiomyocytes derived from human induced pluripotent stem cells (immature hiPSC-CMs); (b) providing an extracellular matrix derived in vitro from cells isolated from amniotic fluid (AFC-ECM); (c) plating the immature hiPSC-CMs on the AFC-ECM; and (d) culturing the plated immature hiPSC-CMs on the AFC-ECM in a culture media to induce maturation of the immature hiPSC-CMs into mature cardiomyocytes and to form a monolayer of the mature cardiomyocytes on the AFC-ECM, thereby forming the cellular construct, wherein the mature cardiomyocytes are characterized by rod shaped cells with distinct sarcomere structure resembling adult human cardiac tissue. In some embodiments the mature cardiomyocytes have a similar or the same morphology as illustrated in any one of FIGS. 6 to 14. In some embodiments, the monolayer of mature cardiomyocytes is aligned on the AFC-ECM. In some embodiments, fiber tracks are present on the cellular construct. In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus. In some embodiments, the mature cardiomyocytes can be further characterized by having greater amounts of mitochondria than immature hiPSC-CMs, by having organized, compact myofilaments, and/or by having two nuclei (bi-nucleated).

In another aspect, disclosed is a method for determining the cardiotoxicity and/or proarrhythmic effect of a drug compound in vitro, the method comprising contacting the drug compound with the mature cardiomyocytes of any one of the cellular constructs disclosed throughout the specification, and observing for a change in the electrophysiology of the mature cardiomyocytes to confirm whether the drug compound has a cardiotoxic and/or proarrhythmic effect on the mature cardiomyocytes. A change in the electrophysiology of the mature cardiomyocytes confirms that the drug compound has a cardiotoxic and/or proarrhythmic effect on the mature cardiomyocytes. The changes in the electrophysiology of the mature cardiomyocytes can include, but are not limited to, APD prolongation, APD prolongation plus rotors, and/or various types of arrhythmias, such as tachyarrhythmia (TA), quiescence (Q), delayed after depolarization (DAD), and/or early after depolarization (EAD). Observations can also include the cell viability, cell density, and/or morphology of the cells. In some embodiments, the change in the electrophysiology of the mature cardiomyocytes is prolongation of action potential duration (APD). In some embodiments, the change in the electrophysiology of the mature cardiomyocytes is early after depolarization (EAD). In some embodiments, the change in the electrophysiology of the mature cardiomyocytes is delayed after depolarization (DAD). In some embodiments, the change in the electrophysiology of the mature cardiomyocytes is action potential duration prolongation (APD prolongation) plus rotors. In some embodiments, the change in the electrophysiology of the mature cardiomyocytes is an arrhythmia. In some aspects, the cellular construct can be prepared by a process comprising: (a) providing immature cardiomyocytes derived from human induced pluripotent stem cells (immature hiPSC-CMs); (b) providing an extracellular matrix derived in vitro from cells isolated from amniotic fluid (AFC-ECM); (c) plating the immature hiPSC-CMs on the AFC-ECM; and (d) culturing the plated immature hiPSC-CMs on the AFC-ECM in a culture media to induce maturation of the immature hiPSC-CMs into mature cardiomyocytes and to form a monolayer of the mature cardiomyocytes on the AFC-ECM, thereby forming a cellular construct, wherein the mature cardiomyocytes are characterized by rod shaped cells with distinct sarcomere structure resembling adult human cardiac tissue. In some embodiments the mature cardiomyocytes have a similar or the same morphology as illustrated in any one of FIGS. 6 to 14. In one embodiment, the immature hiPSC-CMs do not express inward-rectifier potassium channel Kir2.1. In another embodiment, the monolayer of mature cardiomyocytes is aligned on the AFC-ECM. In another embodiment, fiber tracks are present on the cellular construct. In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus. In some embodiments, the mature cardiomyocytes can be further characterized by having greater amounts of mitochondria than immature hiPSC-CMs, by having organized, compact myofilaments, and/or by having two nuclei (binucleated).

Also, disclosed in the context of the present invention are the following embodiments 1 to 20:

Embodiment 1 is a method for the maturation of immature cardiomyocytes derived from human induced pluripotent stem cells, the method comprising:
(a) providing immature cardiomyocytes derived from human induced pluripotent stem cells (immature hiPSC-CMs);
(b) providing an extracellular matrix derived in vitro from cells isolated from amniotic fluid (AFC-ECM);
(c) contacting the immature hiPSC-CMs with the AFC-ECM; and
(d) culturing the immature hiPSC-CMs with the AFC-ECM in a culture media to induce maturation of the immature hiPSC-CMs, thereby forming mature cardiomyocytes; wherein the mature cardiomyocytes are characterized by rod shaped cells with distinct sarcomere structure resembling adult human cardiac tissue.

Embodiment 2 is the method of embodiment 1, wherein the immature hiPSC-CMs are plated on the AFC-ECM.

Embodiment 3 is the method of any one of embodiments 1 or 2, wherein the mature cardiomyocytes form as a monolayer on the AFC-ECM, thereby forming a cellular construct comprising a monolayer of mature cardiomyocytes on the AFC-ECM, wherein the mature cardiomyocytes are aligned on the AFC-ECM.

Embodiment 4 is the method of any one of embodiments 1 to 3, wherein the immature hiPSC-CMs do not express inward-rectifier potassium channel Kir2.1.

Embodiment 5 is a cellular construct comprising a monolayer of mature cardiomyocytes on an extracellular matrix derived from cells isolated in vitro from amniotic fluid (AFC-ECM), wherein the mature cardiomyocytes are AFC-ECM cultured cardiomyocytes derived from human induced pluripotent stem cells (hiPSC-CMs), and wherein the mature cardiomyocytes are characterized by rod shaped cells with distinct sarcomere structure resembling adult human cardiac tissue.

Embodiments 6 is the cellular construct of embodiment 5, wherein the monolayer of mature cardiomyocytes is aligned on the AFC-ECM.

Embodiment 7 is the cellular construct of any one of embodiments 5 or 6, wherein fiber tracks are present on the construct.

Embodiment 8 is the cellular construct of any one of embodiments 5 to 7, wherein the AFC-ECM comprises laminin, collagen alpha-1 (XVIII), basement membrane-specific heparan sulfate proteoglycan core protein, agrin, vimentin, and collagen alpha-2 (IV), and/or isoforms thereof.

Embodiment 9 is the cellular construct of embodiment 8, wherein the isoform of collagen alpha-1 (XVIII) is isoform 2, and/or wherein the isoform of agrin is isoform 6.

Embodiment 10 is the cellular construct of any one of embodiments 8 or 9, wherein the AFC-ECM further comprises fibronectin and/or an isoform thereof.

Embodiment 11 is the cellular construct of any one of embodiments 5 to 10, wherein the AFC-ECM does not contain decorin, perlecan, and/or collagen (III).

Embodiment 12 is a method for making a cellular construct of mature cardiomyocytes on an extracellular matrix derived in vitro from cells isolated from amniotic fluid (AFC-ECM), the method comprising:
(a) providing immature cardiomyocytes derived from human induced pluripotent stem cells (immature hiPSC-CMs),
(b) providing an extracellular matrix derived in vitro from cells isolated from amniotic fluid (AFC-ECM);
(c) plating the immature hiPSC-CMs on the AFC-ECM;
(d) culturing the plated immature hiPSC-CMs on the AFC-ECM in a culture media to induce maturation of the immature hiPSC-CMs into mature cardiomyocytes and to form a monolayer of the mature cardiomyocytes on the AFC-ECM, thereby forming the cellular construct; wherein the mature cardiomyocytes are characterized by rod shaped cells with distinct sarcomere structure resembling adult human cardiac tissue.

Embodiment 13 is the method of embodiment 12, wherein the monolayer of mature cardiomyocytes is aligned on the AFC-ECM.

Embodiment 14 is the method of any one of embodiments 12 or 13, wherein fiber tracks are present on the cellular construct.

Embodiment 15 is a method for determining the cardiotoxicity and/or proarrhythmic effect of a drug compound in vitro, the method comprising contacting the drug compound with the mature cardiomyocytes of any one of the cellular constructs of embodiments 5 to 11, and observing for a change in the electrophysiology of the mature cardiomyocytes to confirm whether the drug compound has a cardiotoxic and/or proarrhythmic effect on the mature cardiomyocytes.

Embodiment 16 is the method of embodiment 15, wherein the change in the electrophysiology of the mature cardiomyocytes is prolongation of action potential duration (APD), and wherein prolongation of APD confirms that the drug compound has a cardiotoxic and/or proarrhythmic effect on the mature cardiomyocytes.

Embodiment 17 is the method of embodiment 15, wherein the change in the electrophysiology of the mature cardiomyocytes is early after depolarization, and wherein early after depolarization (EAD) confirms that the drug compound has a cardiotoxic and/or proarrhythmic effect on the mature cardiomyocytes.

Embodiment 18 is the method of embodiment 15, wherein the change in the electrophysiology of the mature cardiomyocytes is delayed after depolarization, and wherein delayed after depolarization (DAD) confirms that the drug compound has a cardiotoxic and/or proarrhythmic effect on the mature cardiomyocytes.

Embodiment 19 is the method of embodiment 15, wherein the change in the electrophysiology of the mature cardiomyocytes is action potential duration (APD) plus rotors, and wherein prolongation of APD plus rotors confirms that the drug compound has a cardiotoxic and/or proarrhythmic effect on the mature cardiomyocytes.

Embodiment 20 is the method of embodiment 15, wherein the change in the electrophysiology of the mature cardiomyocytes is an arrhythmia, and wherein the arrhythmia confirms that the drug compound has a cardiotoxic and/or proarrhythmic effect on the mature cardiomyocytes.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

As used herein, the terms "% w/w" or "wt. %" refers to a weight percentage of a component based on the total weight of material (e.g. a composition) that includes the component. In a non-limiting example, 10 grams of a component in 100 grams of a composition is 10% w/w of the component in the total weight of composition. As used herein, the terms "% v/v" or "vol. %" refers to a volume percentage of a component based on the total volume of material (e.g. a composition) that includes the component. In a non-limiting example, 10 mL of a component in 100 mL of a composition is 10% v/v of the component in the total volume of composition. As used herein, the term "% w/v" refers to a weight percentage of a component based on the total volume of material (e.g. a composition) that includes the component. In a non-limiting example, 10 grams of a component in 100 mL of a composition is 10% w/v of the component in the total volume of composition. As used herein, the term "% v/w" refers to a volume percentage of a component based on the total weight of material (e.g. a composition) that includes the component. In a non-limiting example, 10 mL of a component in 100 grams of a composition is 10% v/w of the component in the total weight of the composition.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the terms "comprising," "having," "including," or "containing" (or any variations of these words) may mean "one," but it is also consistent with the meaning of "one or more," "at least one," and "one or more than one."

The compositions and methods for their use can "comprise," "consist essentially of," or "consist of" any of the ingredients or steps disclosed throughout the specification. With respect to the transitional phrase "consisting essentially of," in one non-limiting aspect, a basic and novel characteristic of the cellular constructs disclosed herein is their use in cardiotoxicity and/or proarrhythmic screening testing of drug compounds due to their ability to mature cardiomyocytes derived from stem cells to a maturation state resembling that of mature native adult cardiomyocytes and native heart tissue.

It is contemplated that any embodiment discussed in this specification can be implemented with respect to any method or composition of the invention, and vice versa. Furthermore, compositions of the invention can be used to achieve methods of the invention.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION

Figure 14:
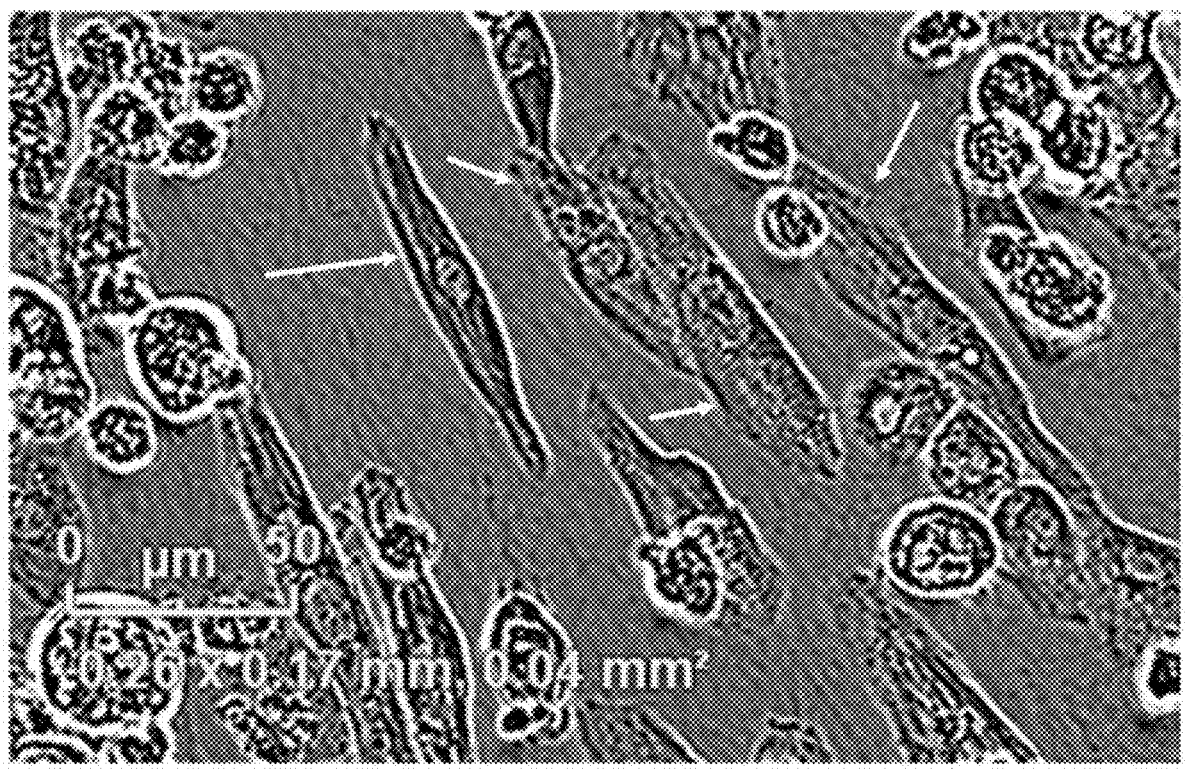
FIG. 14: A photomicrograph of mature cardiomyocytes on AFC-ECM in a single well—0.04 mm$^2$.
Figure 15:
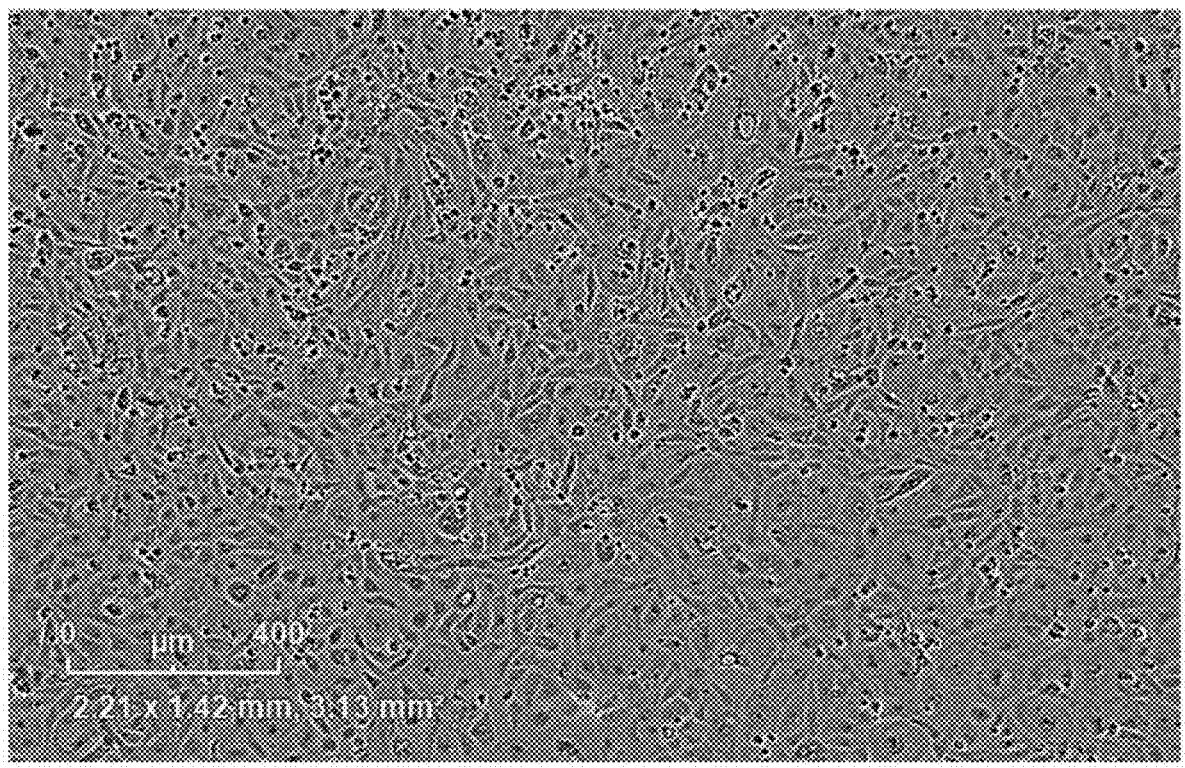
FIG. 15: A photomicrograph of cardiomyocytes on standard Matrigel™ ECM in a single well—3.13 mm$^2$.
Figure 16:
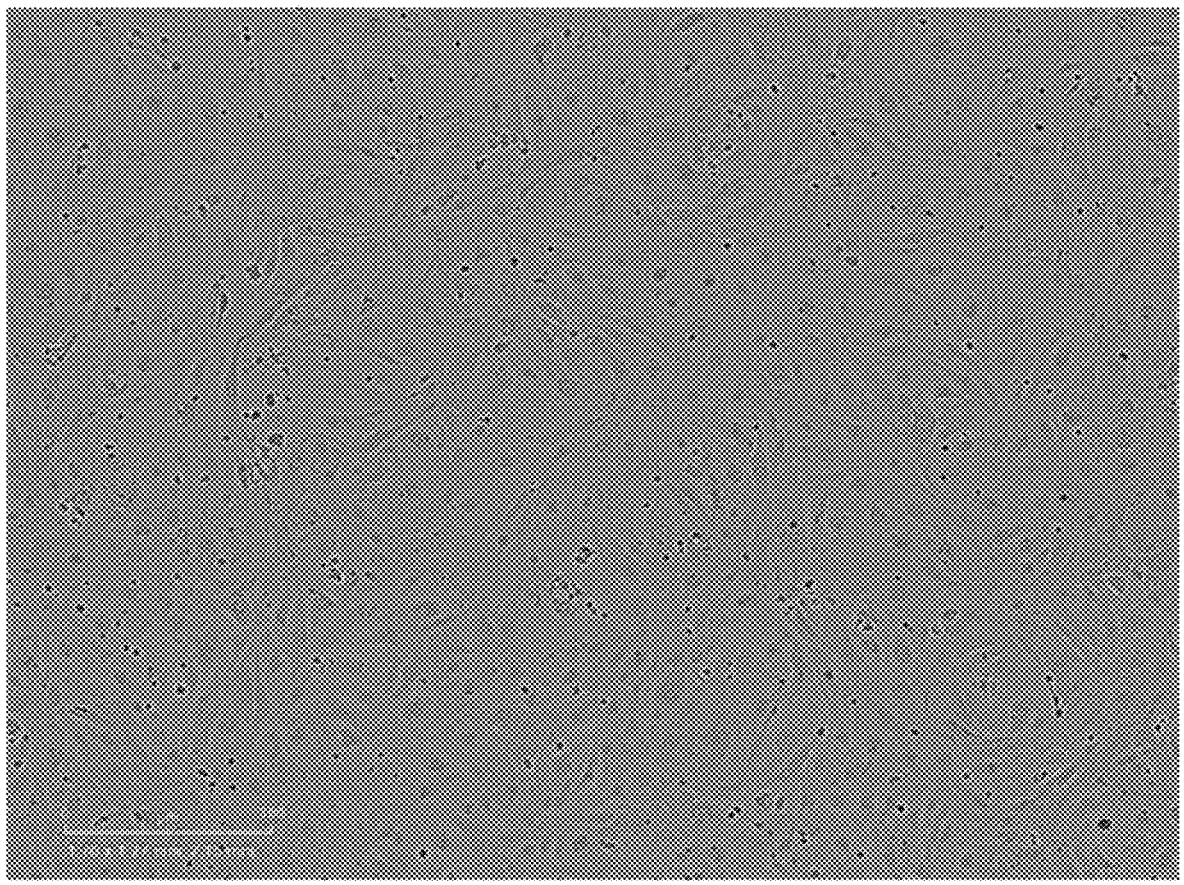
FIG. 16: A photomicrograph of cardiomyocytes on standard Matrigel™ ECM in a single well—2.15 mm$^2$.
Figure 17:
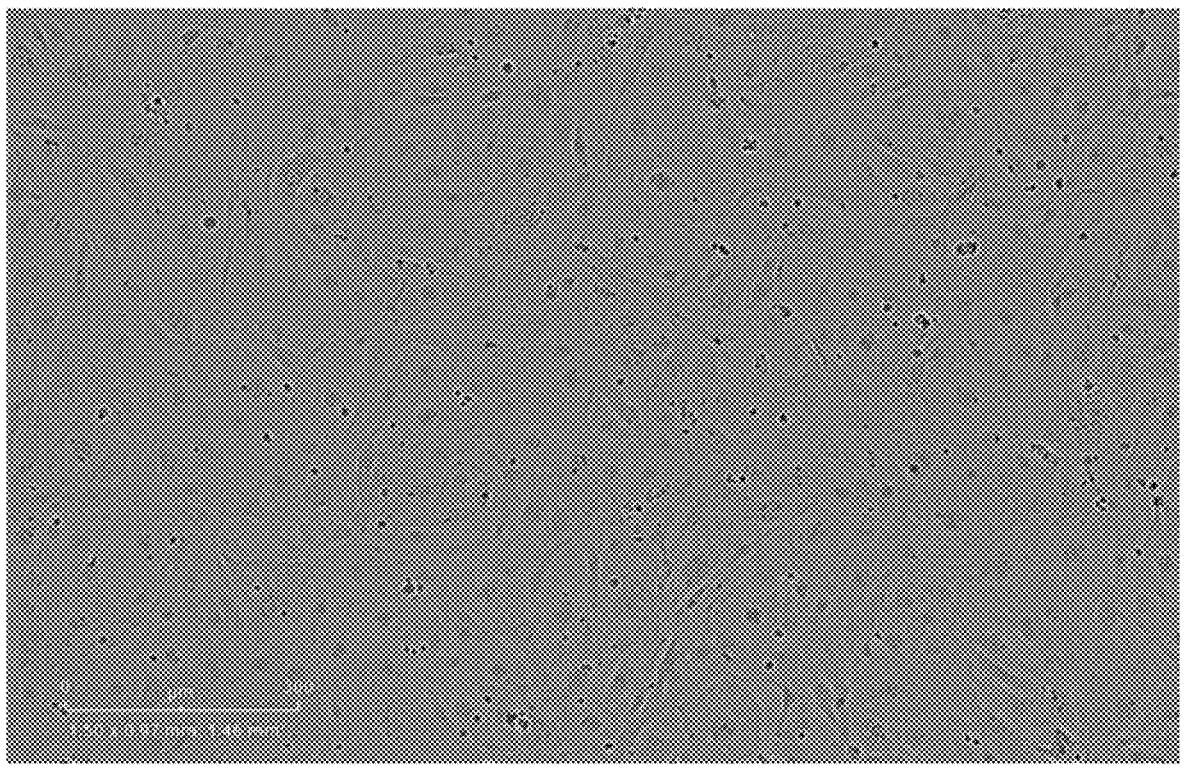
FIG. 17: A photomicrograph of cardiomyocytes on standard Matrigel™ ECM in a single well—1.46 mm$^2$.
Figure 18:
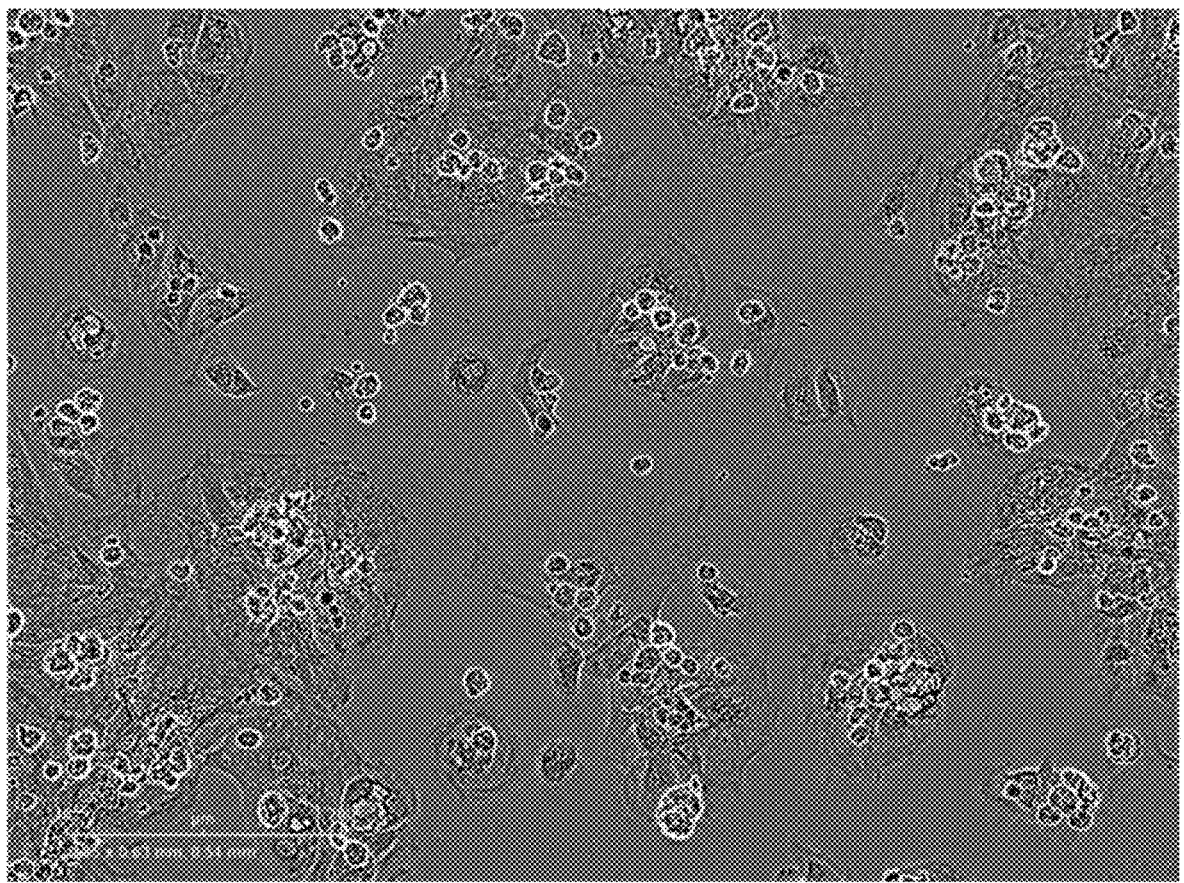
FIG. 18: A photomicrograph of cardiomyocytes on standard Matrigel™ ECM in a single well—0.54 mm$^2$.
Figure 19:
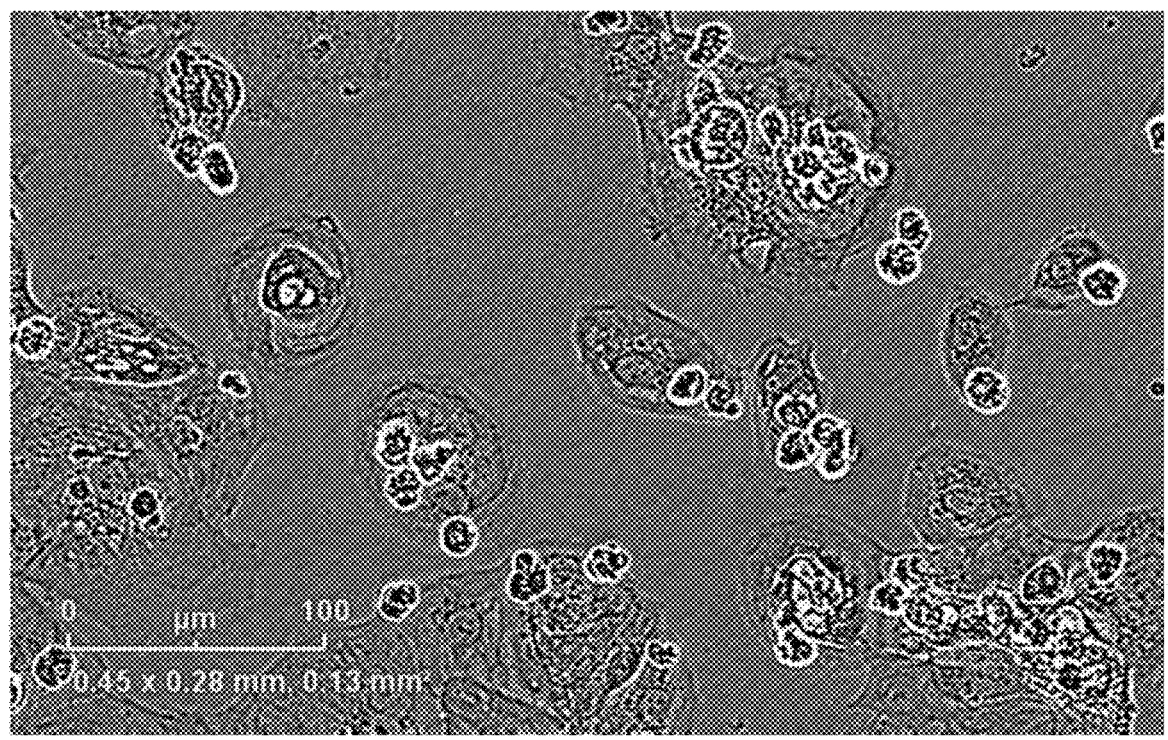
FIG. 19: A photomicrograph of cardiomyocytes on standard Matrigel™ ECM in a single well—0.13 mm$^2$.
Figure 20:
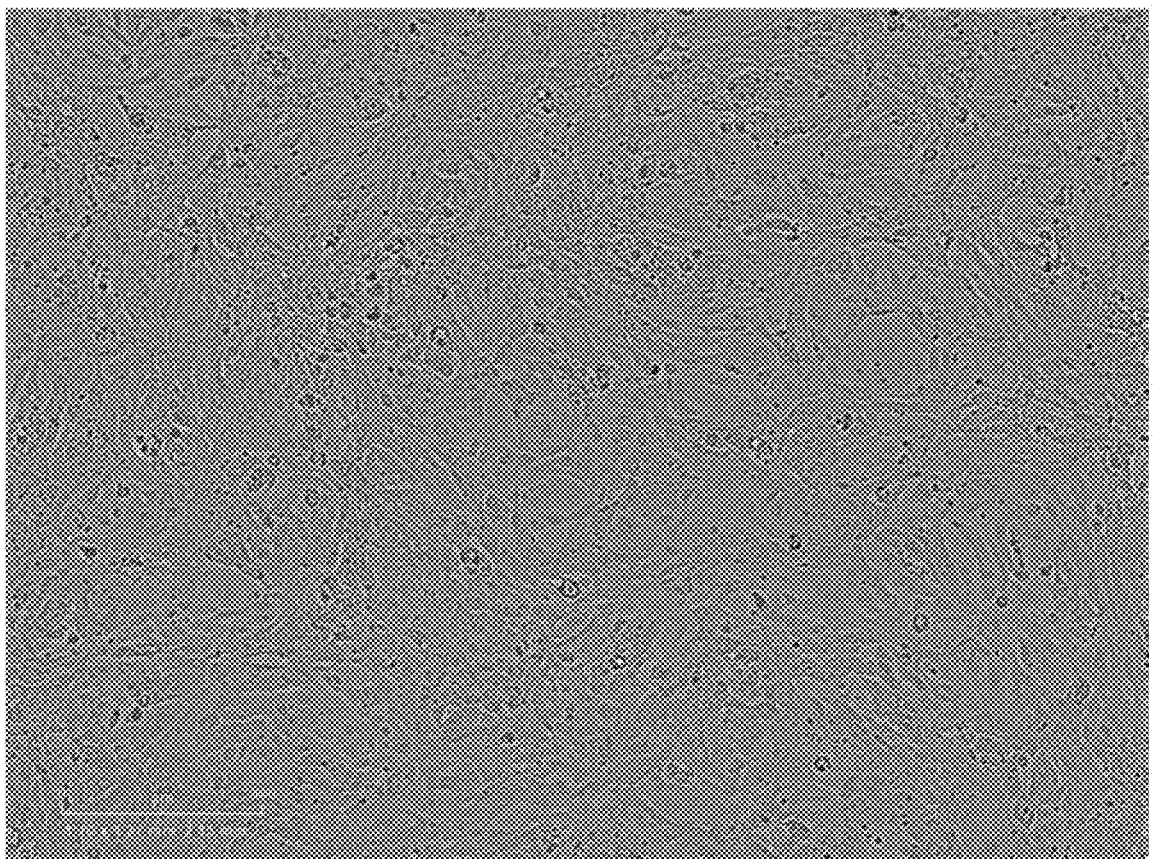
FIG. 20: A photomicrograph of mature cardiomyocytes on a BM-ECM in a single well—2.15 mm$^2$.
Figure 21:
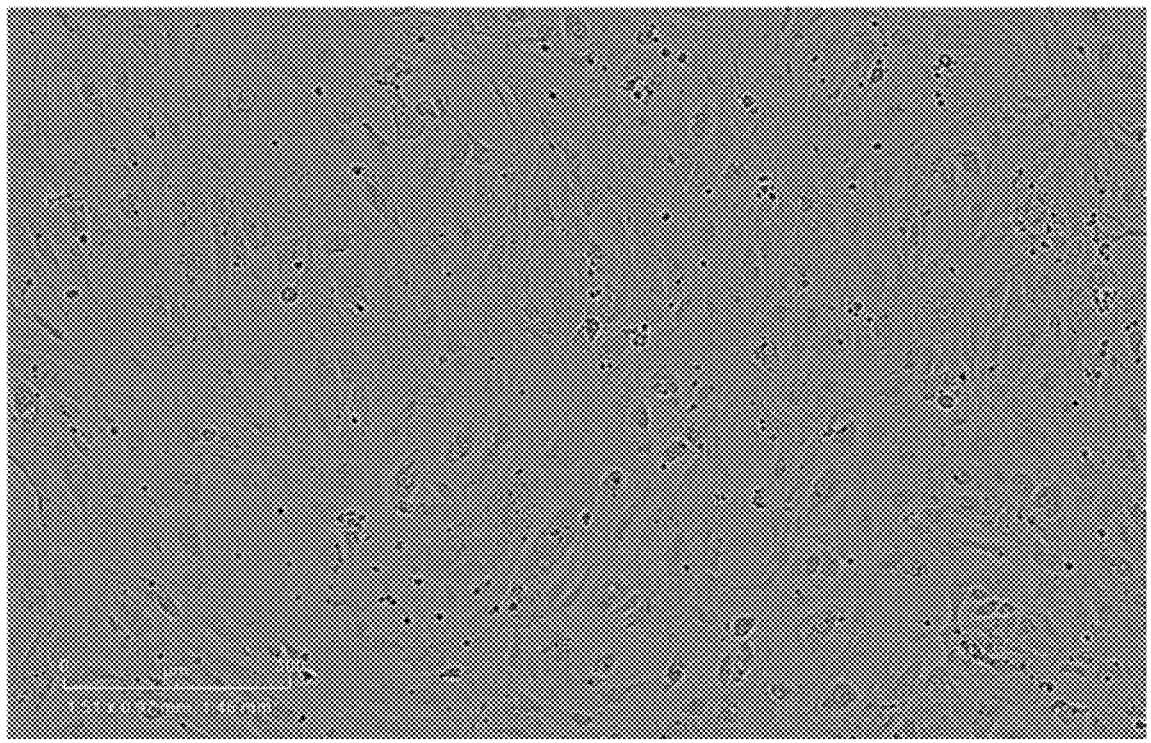
FIG. 21: A photomicrograph of mature cardiomyocytes on a BM-ECM in a single well—1.46 mm$^2$.

Human stem cell derived cardiomyocytes, such as those derived from human induced pluripotent stem cells (hiPSC-CMs), that have been matured in culture on an extracellular matrix derived in vitro from cells isolated from amniotic fluid (AFC-ECM) have demonstrated better, more consistent cardiotoxicity and proarrhythmia assay results than immature hiPSC-CMs or hiPSC-CMs matured on other ECMs, such as Matrigel™ ECM and bone marrow cell-derived ECM. The hiPSC-CMs matured on an AFC-ECM surprisingly have demonstrated a higher state of maturation than hiPSC-CMs matured on other ECMs, such as Matrigel™ ECM and even on other natural cell derived ECMs such as bone marrow cell-derived ECM, as shown by their cellular morphology and sarcomere structure that are found in cardiomyocytes of normal adult human cardiac tissue. Furthermore, a more robust expression of cTnI (cardiac troponin I) protein, as demonstrated by western blotting techniques, has been seen for hiPSC-CMs cultured on AFC-ECM than for hiPSC-CMs cultured on Matrigel™ ECM. Also, hiPSC-CMs cultured on AFC-ECM have more mitochondria and mitochondria with more polarized inner membrane potential than hiPSC-CMs cultured on Matrigel™ ECM. Thus, the AFC-EMC can stimulate mitochondrial biogenesis, maturation, and function in the hiPSC-CMs. Normal adult or mature human cardiac human tissue is characterized by rod shaped cells with sarcomere structure (striped appearance). The morphology and sarcomere structures of the cardiomyocytes can be identified visually by microscopy (transmitted light or by immunofluorescent staining). As a non-limiting example, the morphology and sarcomere structure of the cardiomyocytes matured on AFC-ECM can be distinctly seen by the presence of rod shaped cells with a striped appearance identified by arrows in the photomicrograph of FIG. 14. Additionally, the use of a silicone substrate such as PDMS were not needed to achieve these results. Surprisingly, a cellular construct comprising an AFC-ECM and a monolayer of mature cardiomyocytes that have been matured from immature hiPSC-CMs in culture on the AFC-ECM has shown to be useful, for example, by allowing consistent visualization of drug induced arrhythmias such as Torsades de Pointes (TdP) in high throughput in vitro screening assays. This "TdP in a dish" technology is a major advance over the reliance on field potential duration (MEA technology) or action potential duration prolongation as surrogate markers for drug induced TdP. Thus, the cellular construct and methods disclosed herein go beyond the current CiPA Initiative's guidelines by developing a more comprehensive and predictive in vitro arrhythmia assay that allows for visualization of arrhythmic events in an in vitro model, rather than simple polarization and depolarization events that are indirect indicators of proarrhythmia. The cellular system and methods outlined in this disclosure allow for arrhythmic events to be propagated and visualized in an in vitro human cardiac monolayer model system. In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus. In some embodiments, the mature cardiomyocytes can be characterized by having rod shaped cells with distinct sarcomere structure (striped appearance). In some embodiments, the mature cardiomyocytes can be further characterized by having greater amounts of mitochondria than immature hiPSC-CMs, by having organized, compact myofilaments, and/or by having two nuclei (bi-nucleated).

Disclosed herein are methods of using a cell-derived extracellular matrix derived in-vitro from cells isolated from amniotic fluid (AFC-ECM) for the maturation of immature cardiomyocytes derived from human induced pluripotent stem cells (immature hiPSC-CMs) in culture forming mature cardiomyocytes (mature hiPSC-CMs). Also disclosed herein is a cell construct comprising a monolayer of these mature cardiomyocytes on an AFC-ECM useful for cardiotoxicity and/or proarrhythmic screening assays of drug compounds. Also disclosed herein are methods for determining the cardiotoxicity and/or proarrhythmic effect of a drug compound in vitro using such cell constructs.

A. Amniotic Fluid Cell-Derived Extracellular Matrix (AFC-ECM)

Perinatal cells can be divided into three groups: cells from amniotic fluid; cells from the placenta; and cells from the umbilical cord. Amniotic fluid has several sources of cells including cells derived from the developing fetus sloughed from the fetal amnion membrane, skin, and alimentary, respiratory, and urogenital tracts. Placenta also has several sources of cells including the membrane sheets (amnion and chorion), the villi, and the blood. Umbilical cord cells generally come from two sources, cord blood and Wharton's jelly. The cells from these three perinatal sources can include stem cells. The cells used to produce the amniotic fluid cell-derived ECM of the invention are obtained from the amniotic fluid of a mammal including but not limited to a human (*Homo sapiens*), murine, rabbit, cat, dog, pig, equine, or primate. In preferred embodiments, the cells are from the amniotic fluid of a human. The amniotic fluid can be sourced from humans at full-term births (greater than about 37 weeks gestational age) or pre-term births (less than about 37 weeks gestational age). Pre-term births include late pre-term births (about 33 to about 37 weeks gestational age) moderate pre-term births (about 29 to about 33 weeks gestational age), and extreme pre-term births (about 23 to about 29 weeks gestational age). The amniotic fluid can be sourced from humans prior to birth at any gestational age where amniotic fluid is present, and can be combined with sources of amniotic fluid from births. Generally, prior to birth, amniotic fluid is collected by an amniocentesis procedure. In some embodiments the amniotic fluid is sourced from humans at full-term births, at pre-term births, at late pre-term births, at moderate pre-term births, at extreme pre-term births, or prior to birth, or combinations thereof. In some embodiments, the amniotic fluid is sourced prior to birth and is collected from about 10 weeks gestational age up to birth, or from about 10 weeks to about 23 weeks gestational age, or from about 10 weeks to about 16 weeks gestational age, or from about 12 weeks gestational age up to birth, or from about 12 weeks to about 23 weeks gestational age, or from about 12 weeks to about 16 weeks gestational age. In some embodiments, the amniotic fluid sourced prior to birth is collected by an amniocentesis procedure. The cells can be obtained and isolated from amniotic fluid by techniques known in the art, such as those disclosed in Murphy et. al., Amniotic Fluid Stem Cells, *Perinatal Stem Cells*, Second Ed. 2013.

Amniotic fluid is comprised of cells having the ability to differentiate into cell types derived from all 3 embryonic germ layers (ectoderm, endoderm, mesoderm) spontaneously or as a result of treatment with specific growth factors or combinations of growth factors known to one of skill in the art. That is, a single cell has the capacity to be induced to express genes which are specific to any of the three germ layers. Amniotic fluid also contains a mixture of different cell types including cells derived from the developing fetus sloughed from the fetal amnion membrane, skin, and alimentary, respiratory, and urogenital tracts. Because of the origin of the amniotic fluid and placental membranes, these cells can maintain highly multipotent differentiation potential and comprise a cell population that contains cells of all three germ layers. The amniotic fluid cells can comprise stem cells. In some embodiments, the amniotic fluid cells are isolated stem cells. In some embodiments, the amniotic fluid cells comprise stem cells having the ability to differentiate into cell types derived from all 3 embryonic germ layers (ectoderm, endoderm, mesoderm) and/or multipotent stem cells, and/or pluripotent stem cells.

The amniotic fluid cell-derived ECM disclosed herein can comprise various proteins. The proteins of the ECM can be identified by techniques known in the art and include mass spectroscopy and immunohistochemical staining. The ECM can include, but is not limited to the components listed in Table 2 (see Example 1 below) and any variants, derivatives, or isoforms thereof. The amniotic fluid-cell derived ECM can include any combination of any of the components and any variants, derivatives, or isoforms thereof from Table 2. In some embodiments, a combination can comprise, consist essentially of, or consist of: laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2. In some embodiments, the isoform of agrin is isoform 6. In some embodiments, the cell-derived ECM further comprises, consist essentially of, or consists of fibronectin and/or an isoform thereof. In some embodiments, the amniotic fluid cell-derived ECM does not contain any one of or all of decorin, perlecan, and collagen (III). Some noteworthy differences in proteins between the amniotic fluid cell-derived ECM of the present inventions and a bone marrow cell-derived matrix are described in Table 1.

TABLE 1

Differences Between the Amniotic Fluid Cell-Derived ECM (AFC-Matrix) and a Bone Marrow Cell-Derived Matrix (BM-Matrix)

| Protein/ Gene Code | Difference between AFC-Matrix & BM-Matrix | Physiologic Relevance |
| --- | --- | --- |
| Laminin | 5 sub-units are abundant in AFC Matrix; Low expression in BM-Matrix | Laminin is known to support adhesion and expansion of pluripotent cells. |
| Collagen XVIII | Abundant in AFC Matrix; Absent in BM-Matrix | Important for ocular development |
| Agrin | Present in AFC Matrix; Absent in BM-Matrix | produced by motoneurons to induce aggregation of acetylcholine receptors |
| Biglycan | Abundant in BM-Matrix; Low expression in AFC Matrix | Regulates bone and muscle development |
| Collagen I | Overexpressed in BM-Matrix relative to AFC Matrix | Key to fibrillar proteins; highly abundant in bone |
| Periostin | Present in BM-Matrix; Absent in AFC Matrix | Regulates mineralization; Marker of noncardiomyocyte lineage cells in heart |

The amniotic fluid cell-derived ECM can be produced by the following process:
  (a) isolating cells from amniotic fluid,
  (b) seeding the isolated cells onto a cell culture container or onto a cell culture container coated with a substrate,
  (c) adding a culture media to the cell culture container, and
  (d) culturing the cells, thereby producing a cell-derived ECM, and
  (e) optionally decellularizing the cell-derived ECM.

Any cell seeding density may be used which allows cells to form a confluent monolayer immediately or after a period of time in culture. In some embodiments, the seeding density is about 10 cells/cm$^2$-about 100,000 cells/cm$^2$, or about 100 cells/cm$^2$-about 75,000 cells/cm$^2$, or about 500 cells/cm$^2$-about 50,000 cells/cm$^2$, or about 500 cells/cm$^2$-about 10,000 cells/cm$^2$, or about 500 cells/cm$^2$-about 5,000 cells/cm$^2$, or about 500 cells/cm$^2$-about 2,500 cells/cm$^2$, or about 1,000 cells/cm$^2$-about 25,000 cells/cm$^2$, or about 2,000 cells/cm$^2$-about 10,000 cells/cm$^2$, or about 3,000 cells/cm$^2$-about 5000 cells/cm$^2$.

Any type of container suitable for cultivation of cells can be used for the present invention. Examples include, but are not limited to cell culture flasks, T-flasks, stirred flasks, spinner flasks, fermenters, and bioreactors. Rocking bottles, shaking flasks, tubes, and other containers are also suitable containers when placed on a rocking platform or shaker. The cell culture container can be coated with a substrate to allow for better cell adhesion. A non-limiting example of a suitable substrate for coating the cell container is fibronectin.

Various commercially available cell culture media, e.g., alpha Minimum Essential Media (α-MEM) culture media (Thermo Fisher Scientific, Grand Island, N.Y.), are suitable for culturing amniotic fluid cells. The commercially available culture media can be modified by adding various supplemental substances to the media, e.g. sodium bicarbonate, L-glutamine, penicillin, streptomycin, Amphotericin B and/or serum. The serum can be fetal bovine serum. The media can also be serum free. Additionally, substances such as L-ascorbic acid can be added to the media or modified media to induce cell production of an ECM.

The initial culture media can be changed and/or replaced with another media at various times during the culturing process. For example, the initial media can be a "Complete Media" and then be replaced by an "Inducing Media" during the culturing process. A non-limiting example of a "Complete Media" contains (α-MEM) plus 2 mM L-Glutamine plus antibiotic-antimycotic plus 15% Fetal Bovine Serum. A non-limiting example of an "Inducing Media" contains the "Complete Media" plus 50 mM L-Ascorbic Acid.

The culturing of the amniotic fluid cells can take place in an incubator at 37° C., 5% $CO_2$, and 90% humidity. Culturing can take place under various environmental conditions including, but not limited to normoxic, i.e., 20-21% oxygen in the atmosphere, or hypoxic conditions.

Decellularizing the amniotic fluid cell-derived ECM of the amniotic fluid cells can include removing the viable amniotic fluid cells or rendering the amniotic fluid cells non-viable. The amniotic fluid cells can be decellularized from the ECM by using methods known in the art and can include, but are not limited to lysing the amniotic fluid cells and then removing the lysed amniotic fluid cells by washing. Various substances can be used to remove the amniotic fluid cells from the ECM. Non-limiting examples include an "Extraction Buffer" containing TRITON X-100 and ammonium hydroxide in PBS buffer. After the ECM has been decellularized of amniotic fluid cells, the resulting ECM is thereby essentially cell-free or free of viable amniotic fluid cells. If feeder cells are used, then the decellularizing methods also apply to any viable feeder cells present on the ECM, thereby resulting in the ECM being essentially free or free of viable feeder cells. The decellularizing methods also apply to any viable cells present on the ECM, thereby resulting in the ECM being essentially free or free of any viable cells. Thus, a decellularized ECM means that the ECM is acellular, meaning that the ECM is free of any viable cells.

In some embodiments, the amniotic fluid cell-derived ECM (AFC-ECM) is a three-dimensional (3D) ECM.

The methods described supra also apply to producing cell-derived ECMs from other perinatal cells such as cells from the umbilical cord including the cord blood and Wharton's jelly; and cells from placenta tissue including the membrane sheets (amnion and chorion), the villi and the blood.

In one embodiment, a perinatal cell-derived ECM is produced by the following process:
  (a) isolating cells from an umbilical cord,
  (b) seeding the isolated cells onto a cell culture container or onto a cell culture container coated with a substrate,
  (c) adding a culture media to the cell culture container, and
  (d) culturing the cells, thereby producing a cell-derived ECM, and
  (e) optionally decellularizing the cell-derived ECM.

In some embodiments, the cells isolated from the umbilical cord are from the cord blood and/or the Wharton's jelly.

In another embodiment, a perinatal cell-derived ECM is produced by the following process:
(a) isolating cells from placenta tissue,
(b) seeding the isolated cells onto a cell culture container or onto a cell culture container coated with a substrate,
(c) adding a culture media to the cell culture container, and
(d) culturing the cells, thereby producing a cell-derived ECM, and
(e) optionally decellularizing the cell-derived ECM.

In some embodiments, the cells isolated from the placenta tissue are from the membrane sheets (amnion and/or chorion), the villi, and/or the blood.

In one aspect, disclosed is a cell-derived extracellular matrix (ECM) derived in vitro from cells isolated from an umbilical cord. In some embodiments, the cells isolated from the umbilical cord are from the cord blood and/or the Wharton's jelly.

In another aspect, disclosed is a cell-derived extracellular matrix (ECM) derived in vitro from cells isolated from placenta tissue. In some embodiments, the cells isolated from the placenta tissue are from the membrane sheets (amnion and/or chorion), the villi, and/or the blood.

B. Cellular Constructs and Methods for the Maturation of Immature hiPSC-CMs

Disclosed herein is a method for the maturation of immature cardiomyocytes derived from human induced pluripotent stem cells, the method comprising: (a) providing immature cardiomyocytes derived from human induced pluripotent stem cells (immature hiPSC-CMs); (b) providing an extracellular matrix derived in vitro from cells isolated from amniotic fluid (AFC-ECM); (c) contacting the immature hiPSC-CMs with the AFC-ECM; and (d) culturing the immature hiPSC-CMs with the AFC-ECM in a culture media to induce maturation of the immature hiPSC-CMs, thereby forming mature cardiomyocytes (mature hiPSC-CMs); wherein the mature cardiomyocytes are characterized by rod shaped cells with distinct sarcomere structure resembling adult human cardiac tissue. Normal adult human cardiac human tissue is characterized by rod shaped cells with sarcomere structure (striped appearance). The morphology and sarcomere structures of the cardiomyocytes can be identified visually by microscopy. As a non-limiting example, the morphology and sarcomere structure of the cardiomyocytes matured on AFC-ECM can be distinctly seen by the presence of rod shaped cells with a striped appearance identified by arrows in the photomicrograph of FIG. 14.

Also disclosed herein is a cellular construct comprising a monolayer of mature cardiomyocytes on an extracellular matrix derived from cells isolated in vitro from amniotic fluid (AFC-ECM), wherein the mature cardiomyocytes are AFC-ECM cultured cardiomyocytes derived from human induced pluripotent stem cells (hiPSC-CMs), and wherein the mature cardiomyocytes are characterized by rod shaped cells with distinct sarcomere structure resembling adult human cardiac tissue. In certain aspects, the mature cardiomyocytes can be matured from immature cardiomyocytes derived from human induced pluripotent stem cells (immature hiPSC-CMs) in culture on the AFC-ECM, wherein the mature cardiomyocytes are characterized by rod shaped cells with distinct sarcomere structure resembling adult human cardiac tissue. In some aspects, the mature cardiomyocytes include the inward-rectifier Kir2.1 potassium channel and/or express inward-rectifier potassium channel Kir2.1. In some embodiments, the monolayer of mature cardiomyocytes is aligned on the AFC-ECM. In some embodiments, fiber tracks are present on the construct. In some embodiments, the AFC-ECM comprises laminin, collagen alpha-1 (XVIII), basement membrane-specific heparan sulfate proteoglycan core protein, agrin, vimentin, and collagen alpha-2 (IV), and/or isoforms thereof. In some embodiments, the isoform of collagen alpha-1 (XVIII) is isoform 2, and/or wherein the isoform of agrin is isoform 6. In some embodiments, the AFC-ECM further comprises fibronectin and/or an isoform thereof. In some embodiments, the AFC-ECM does not contain decorin, perlecan, and/or collagen (III). In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus. In some embodiments, the mature cardiomyocytes can be further characterized by having greater amounts of mitochondria than immature hiPSC-CMs, by having organized, compact myofilaments, and/or by having two nuclei (bi-nucleated).

Also disclosed herein is a method for the preparation of a cellular construct comprising mature cardiomyocytes on an extracellular matrix derived in vitro from cells isolated from amniotic fluid (AFC-ECM), the method comprising (a) providing immature cardiomyocytes derived from human induced pluripotent stem cells (immature hiPSC-CMs), (b) providing an extracellular matrix derived in vitro from cells isolated from amniotic fluid (AFC-ECM); (c) plating the immature hiPSC-CMs on the AFC-ECM; and (d) culturing the plated immature hiPSC-CMs on the AFC-ECM in a culture media to induce maturation of the immature hiPSC-CMs into mature cardiomyocytes and to form a monolayer of the mature cardiomyocytes on the AFC-ECM, thereby forming the cellular construct, wherein the mature cardiomyocytes are characterized by rod shaped cells with distinct sarcomere structure resembling adult human cardiac tissue. In some embodiments, the monolayer of mature cardiomyocytes is aligned on the AFC-ECM. In some embodiments, fiber tracks are present on the construct.

Immature hiPSC-CMs can be obtained from commercial sources such as Cellular Dynamics International-FUJI under the trade name iCell®, and Takara Bio under the trade name Cellartis®. iCell® Cardiomyocytes, iCell® Cardiomyocytes$^2$, and Cellartis® Cardiomyocytes are cryopreserved viable cardiomyocytes derived from human induced pluripotent stem cells (hiPSCs) available in vials. Immature hiPSC-CMs can also be generated from patient specific hiPSCs in a laboratory setting for a specific individual. In this case, differentiation of the hiPSCs can be accomplished using the small molecule protocol to obtain beating cardiomyocytes by day 8-10 using GSK3 inhibitor, RPMI/B27 minus insulin, Wnt Inhibitor and RPMI/B27 plus insulin at various days during the 7-day differentiation period. Suitable non-limiting examples of methods to generate immature hiPSC-CMs are disclosed in US publication 2015/0329825 herein incorporated by reference. In some embodiments, the immature hiPSC-CMs do not express inward-rectifier potassium channel Kir2.1. In some embodiments, the immature hiPSC-CMs do not include rod shaped cells with distinct sarcomere structure. In some embodiments, the immature hiPSC-CMs can be characterized by having less mitochondria than mature cardiomyocytes, by having disorganized myofilaments, by having a circular shape, and/or by having a single nucleus.

The AFC-ECM can be obtained using the production methods disclosed herein in this disclosure and can have the characteristics as described in this disclosure. In some embodiments, the AFC-ECM is decellularized prior to contact with the immature hiPSC-CMs.

The immature hiPSC-CMs can be in suspension when in contact with the AFC-ECM or the cells can be plated directly on the AFC-ECM which is in or on suitable cell culture containers or in multi-well plates. Non-limiting examples of suitable multi-well plates include 6-, 12-, 24-, 48, 96- and 384-well plates. In some embodiments, the contact surfaces of the cell culture containers or multi-well plates are coated with polydimethylsiloxane (PDMS) prior to the formation of the AFC-ECM. In some embodiments, the contact surfaces of the cell culture containers or multi-well plates are not coated with PDMS prior to the formation of the AFC-ECM. Any cell seeding density of immature hiPSC-CMs can be used. In some embodiments, a cell seeding density of immature hiPSC-CMs which allows the cells to form a confluent monolayer immediately or after a period of time in culture is used. Cell density can be modified as desired to improve monolayer formation. In multi-well plates, the immature hiPSC-CM cells are placed in the center of each well. Non-limiting examples of cell seeding densities of immature hiPSC-CMs in various multi-well plates are as follows: in 6-well plates, about 200,000 cells can be plated per well; in 12-well plates, about 150,000 cells can be plated per well; in 24-well plates about 175,000 cells can be plated per well; in 48-well plates about 100,000 cells can be plated per well; in 96-well plates about 50,000 cells can be plated per well; in 384-well plates, about 15,000 cells can be plated per well. In some embodiments, the cell seeding density of immature hiPSC-CMs is about 50,000 cells per well in a 96-well plate. In some embodiments, the cell seeding density is about 200,000 cells per well in a 6-well plate. To induce maturation of the immature hiPSC-CMs, a suitable culture media such as RPMI media or Media 199 media is added to the immature hiPSC-CMs in contact with the AFC-ECM, and the cells are cultured with the AFC-ECM using standard cell culture techniques for a period of time, generally 7 days, until the cells have matured into mature cardiomyocytes having similar morphology as native adult cardiomyocytes. During the first 3 to 4 days, the immature hiPCS-CMs are adhering, forming a continuous monolayer, and beginning the maturation process. Surprisingly, the period of time for maturation of the cardiomyocytes can take 7 days or less, whereas generally a much longer period of time is typical with other substrates, e.g., up to 100 days. The morphology of these mature cardiomyocytes can be characterized by rod shaped cells with distinct sarcomere structure (striped appearance), the fundamental contractile unit of muscle, that can be visualized using conventional light microscopy techniques. In some embodiments, the mature cardiomyocytes can be further characterized by having greater amounts of mitochondria than immature hiPSC-CMs, by having organized, compact myofilaments, and/or by having two nuclei (bi-nucleated). Also, the AFC-ECM can naturally produce fiber tracks that the mature cardiomyocytes follow. This produces a degree of anisotropy to the monolayer that more closely mimics the native heart. Thus, the cardiomyocytes can be naturally aligned on the AFC-ECM following the alignment of the AFC-ECM that has been laid down in a natural anisotropic configuration by the amniotic fluid cells during formation of the AFC-ECM. In various embodiments, the period of time for the immature hiPSC-CMs to mature in culture can be 4, 5, 6, 7, 8, 9, 10, 11, 12, 13, 14, 15, 20, 25, 30, 40, 50, 60, 70, 80, 90, 100, 110, or 120 days. Preferably, the period of time for the maturation of the cardiomyocytes is 14 days, or more preferably, 10 days, or even more preferably 7 days. In some embodiments the period of time for the immature hiPSC-CMs to mature in culture is 7 days. In some embodiments, the immature hiPSC-CMs are plated on the AFC-ECM. In some embodiments, the mature cardiomyocytes form as a confluent monolayer on the AFC-ECM during culture, thereby forming a cellular construct comprising a monolayer of mature cardiomyocytes on the AFC-ECM. In some embodiments, the mature cardiomyocytes are aligned on the AFC-ECM. In some embodiments, the immature hiPSC-CMs are plated on the AFC-ECM in multi-well plates. In some embodiments, the multi-well plates have inserts of polydimethylsiloxane (PDMS). In some embodiment, the multi-well plates do not have inserts of PDMS.

C. Methods for Determining the Cardiotoxicity and/or Proarrhythmic Effect of a Drug Compound Disclosed herein is a method for determining the cardiotoxicity and/or proarrhythmic effect of a drug compound in vitro, the method comprising contacting the drug compound with the mature cardiomyocytes of any one of the cellular constructs disclosed throughout the specification, and observing for one or more changes in the electrophysiology of the mature cardiomyocytes to confirm whether the drug compound has a cardiotoxic and/or proarrhythmic effect on the mature cardiomyocytes. One or more changes in the electrophysiology of the mature cardiomyocytes indicates and confirms that the drug compound has a cardiotoxic and/or proarrhythmic effect on the mature cardiomyocytes. The one or more changes of the electrophysiology of the mature cardiomyocytes can include, but are not limited to, APD prolongation, APD prolongation plus rotors, and/or various types of arrhythmias, such as tachyarrhythmia (TA), quiescence (Q), delayed after depolarization (DAD), and/or early after depolarization (EAD). In some embodiments, the change in the electrophysiology of the mature cardiomyocytes is prolongation of action potential duration (APD). In some embodiments, the change in the electrophysiology of the mature cardiomyocytes is early after depolarization (EAD). In some embodiments, the change in the electrophysiology of the mature cardiomyocytes is delayed after depolarization (DAD). In some embodiments, the change in the electrophysiology of the mature cardiomyocytes is action potential duration (APD) plus rotors. In some embodiments, the change in the electrophysiology of the mature cardiomyocytes is an arrhythmia. In some embodiments, the change in the electrophysiology of the mature cardiomyocytes is tachyarrhythmia (TA). In some embodiments, the change in the electrophysiology of the mature cardiomyocytes is quiescence (Q). Observations can also include the cell viability, cell density, and/or morphology of the cells. In some aspects, the cellular construct can be prepared by a process comprising: (a) providing immature cardiomyocytes derived from human induced pluripotent stem cells (immature hiPSC-CMs); (b) providing an extracellular matrix derived in vitro from cells isolated from amniotic fluid (AFC-ECM); (c) plating the immature hiPSC-CMs on the AFC-ECM; and (d) culturing the plated immature hiPSC-CMs on the AFC-ECM in a culture media to induce maturation of the immature hiPSC-CMs into mature cardiomyocytes and to form a monolayer of the mature cardiomyocytes on the AFC-ECM, thereby forming a cellular construct, wherein the mature cardiomyocytes are characterized by rod shaped cells with distinct sarcomere structure resembling adult human cardiac tissue. In other aspects, the method can comprise contacting the drug compound with any one of the cellular constructs disclosed throughout the specification and observing for cardiotoxic and/or proarrhythmic events. In one particular instance, the method comprises: (a) providing immature cardiomyocytes derived from human induced pluripotent stem cells (immature hiPSC-CMs); (b) providing an extracellular matrix derived in vitro from cells isolated from amniotic fluid (AFC-ECM); (c) plating the immature hiPSC-CMs on the AFC-ECM; (d) culturing the plated immature hiPSC-CMs on the AFC-ECM in a culture media to induce maturation of the immature hiPSC-CMs into mature cardiomyocytes and to form a monolayer of the mature cardiomyocytes on the AFC-ECM, thereby forming a cellular construct; (e) contacting the drug compound with the monolayer of the mature cardiomyocytes of the construct; and (f) observing for a change in the electrophysiology of the mature cardiomyocytes to confirm whether the drug compound has a cardiotoxic and/or proarrhythmic effect on the mature cardiomyocytes; wherein the mature cardiomyocytes are characterized by rod shaped cells with distinct sarcomere structure resembling adult human cardiac tissue. In some embodiments, the immature hiPSC-CMs are plated on the AFC-ECM in a multi-well plate. In some embodiments, the multi-well plates have inserts of polydimethylsiloxane (PDMS). In some embodiment, the multi-well plates do not have inserts of PDMS. In some embodiments, the immature hiPSC-CMs do not express inward-rectifier potassium channel Kir2.1. In some embodiments, the monolayer of mature cardiomyocytes is aligned on the AFC-ECM. In some embodiments, fiber tracks are present on the cellular construct.

The cardiotoxicity and/or proarrhythmia testing can be conducted using any type of equipment suitable for measuring such activity. In some embodiments, the cellular constructs of monolayers of mature cardiomyocytes on AFC-ECM are prepared as described supra. After the maturation process (generally 7 days or less), the electrophysiology of each well is observed using a plate reader. A suitable voltage sensitive or calcium sensitive fluorescent dye is loaded into each well. Non-limiting voltage sensitive dyes include FluoVolt™ dye commercially available from ThermoFisher. In some embodiments, the plate reader can rely on a suitable high spatiotemporal CCD camera combined with suitable lighting, such as light emitting diodes (LEDs), of the appropriate wavelength to excite each dye. Such high spatiotemporal CCD cameras are commercially available from SciMeasure. In some embodiments, the camera image acquisition rate is greater than or equal to 150 frames per second. In some embodiments, the camera and lens combination are designed such that it allows visualization of all the wells of the multi-well plate simultaneously with sufficient resolution to observe action potential and calcium wave propagation. Each plate is centered under the camera system, lighting is switched on and camera acquisition is initiated and electrophysiological activity is recorded. Experiments are performed at about 37° C. After baseline readings are made, the drug to be tested is added to the wells and the effects are recorded. Spontaneous activity is recorded for a sufficient period of time to obtain images, e.g. at least 10 seconds. The images can be stored on a computer. Images are analyzed and action potential duration, conduction velocity, beat rate and activation patterns can be quantified using image analysis software. Visualization of electrical wave patterns is important to determine a drug compound's effect to cause potentially fatal arrhythmias, e.g., Torsades de Pointes (TdP). Thus, in addition to providing information on a compound's effect on spontaneous action potential duration, the methods disclosed herein can also provide information on impulse conduction velocity and activation pattern depending on the type of equipment used.

D. Methods to Expand/Proliferate Mammalian Stem Cells

Also disclosed herein are methods of using a cell-derived extracellular matrix derived in vitro from cells isolated from amniotic fluid (AFC-ECM) for the isolation, maintenance, and expansion/proliferation of mammalian cells. In vitro cell culture is perhaps the most ubiquitous, important, and poorly understood aspect of all cell biology as well as the developing fields of regenerative medicine and tissue engineering. Firstly, it allows for the observation of cell behavior so that various aspects of cell function may be studied in detail. Secondly, it allows for increase in numbers of specific cell groups. For basic research, as well as many clinical applications, it is necessary to achieve large quantities of relatively rare cells from small biological samples. In-vitro cell culture permits small numbers of cells to be expanded outside the body to achieve more relevant numbers. Lastly, it permits the storage of cells for later use. By expanding cell numbers in-vitro, and freezing viable cells for later use, relatively small biological samples can yield cells for multiple experiments over the span of days, months, or even years.

Despite the omnipresence of cell culture, the effects that in vitro culture has on the native characteristics of the cells is still relatively poorly understood. Many of the current practices have arisen not from deliberate thought, planning, and experimentation, but instead from chance observations. Mammalian cell culture began in the early 1900s when, in 1911, Alexis Carrel and Montrose Burrows first published an academic paper on the cultivation of mammalian tissues in vitro. They were studying the physiology and anatomy of tissues by cutting sections of mammalian tissues and placing them on microscope slides. They then noticed that some cells migrated out of the tissue onto the slide. They went on to describe techniques for culturing cells in perpetuity. It now appears that some of their observations may not have been valid, but their work paved the way for modern cell culture.

After the discovery of hematopoietic stem cells (HSCs), groups all over the world were studying (HSCs). During their culture (in suspension), it was observed that a subpopulation of bone marrow cells stuck to the bottom of the plastic flasks and began to proliferate. These cells were later recognized to be distinct from HSCs, and were eventually dubbed mesenchymal stem cells (MSCs). Because of this chance observation that lead to the discovery of MSCs, plastic adherence is still widely used as a defining attribute of MSCs and many other mammalian cell types.

The practice of culturing cells on plastic substrates can be problematic because there is substantial evidence, that is now widely accepted in the literature, demonstrating the critical role of the microenvironment in regulating cell function. The microenvironment has been shown to help direct the differentiation of stem and progenitor cells, and regulate the behavior of mature cell types.

When cells are removed from their native environment to be expanded in-vitro they can lose important cues from their surrounding extracellular matrix or microenvironment which relay important information to the cells regarding the composition and state of their surroundings. Changes to a cell's microenvironment can have a profound effect on the behavior of those cells. The current standard for isolation and expansion of most adherent cells in vitro is to place the cells in culture vessels composed of polystyrene (plastic). The polystyrene may have been treated in some manner to facilitate cell attachment and growth but the surface is, in most cases, completely foreign to the cell. In other cases, the surface may be coated with individual matrix proteins (e.g.

fibronectin or collagen) or some combination of proteins. These simple substrates disregard the complexity of the native microenvironment as well as the critical role of the microenvironment in normal cell function. The cell will immediately begin to respond to this foreign environment in a manner that is much different than when the cell is in its native environment.

Five major approaches are currently employed to address this issue of culturing cells on plastic substrates:

1. Ignore the problem.—Instead of trying to achieve a desired function that matches what would be expected in vivo, a multitude of cell types can be tested in various media in order to find cells that will exhibit a specific desired function without the appropriate matrix substrate. This approach is unsophisticated and often fails to produce desired results because of the complex interplay of variables and the breadth of interactions between cells and the extracellular matrix.

2. Identify key components.—Many academic laboratories and several companies have taken the approach of considering the tissue from which cells are isolated and looking for unique elements of that tissue that may be important for cell function. Cells are then cultured on simple substrates consisting of only one or a few matrix components. This approach often fails because matrices are naturally very complex environments including over one-hundred different proteins in some cases. Cells respond just as strongly to signals they need and fail to receive, as to signals they do not need and do receive.

3. Shotgun approach—The use of protein gels like MATRIGEL™ employs a sort of shotgun approach. A gel is created that contains many different matrix proteins with the hopes that it will contain the necessary binding motifs for many different cell types. This approach may fail by providing cues that push cells in a particular direction or by failing to provide all the cues that cells are expecting.

4. Tissue-derived matrices—This is a biomimetic approach that typically involves isolating a tissue of interest from a genetically similar animal, physically disrupting or chemically digesting the tissue to obtain a solution or uniform suspension, and then coating culture vessels with the deconstructed tissue. For example, someone who wishes to culture satellite cells, might collect muscle, homogenize the tissue, and then coat a culture vessel with homogenized muscle prior to seeding the cells. This method often fails for a few reasons. Firstly, even within a specific tissue type, the stem cell/progenitor cell niche, may be distinct from the rest of the tissue. Simply homogenizing muscle does not guarantee that an appropriate niche is being created. Secondly, the niche consists of structural and physical cues, in addition to biochemical cues. Even if many/most of the biochemical cues are present in a tissue homogenate, the structure has been destroyed, and cells may sense very different mechanical cues. Lastly, manufacturability of tissue derived matrices is dependent on availability of tissues. This affects the total amount of cell culture possible and contributes to lot-to-lot variability.

5. Cell-derived matrices—Cells in culture can be induced to secrete a matrix in their culture vessel. This matrix is the best approximation available of the in vivo niche, and can be manufactured in vitro. Cells can be induced in vitro to elaborate a matrix and then the cells can subsequently be eliminated from the matrix, for example by using non-ionizing detergent to retain structure and chemistry of the matrix. This approach has several key advantages. (1) The matrix structure can be recreated and left undisturbed. (2) The matrix can be customized based on tissue/cell type of interest. (3) The matrix can be specific to stem and progenitor cell niche. (4) The matrix can be manufactured in large quantities.

With respect to cell-derived matrices, not all cell types can be efficiently isolated and expanded on any given cell-derived matrix. In fact, pluripotent stem cells (PSCs) appear to have much different requirements for a supportive growth substrate than do other types of cells. It is known that the specific cell type used to produce a matrix will have an effect on the composition of the matrix, and therefore, the reaction of various cell types to that matrix (see Marinkovic, M. et al., One size does not fit all: developing a cell-specific niche for in vitro study of cell behavior. *Matrix Biol.* 54-55, 426-441 (2016)). Prior work disclosed in U.S. Pat. No. 8,084,023 has described the production and composition of an extracellular matrix produced by bone marrow stromal or mesenchymal stem cells (see also Chen, X. et al., Extracellular Matrix Made by Bone Marrow Cells Facilitates Expansion of Marrow-Derived Mesenchymal Progenitor Cells and Prevents Their Differentiation into Osteoblasts. *Journal of Bone and Mineral Research* 22, 1943-1956 (2007) and Lai, Y. et al., Reconstitution of marrow-derived extracellular matrix ex vivo: a robust culture system for expanding large-scale highly functional human mesenchymal stem cells. *Stem cells and development* 19, 1095-107 (2010)). This bone marrow cell derived matrix has been shown to support the expansion of other MSCs but has not been effective for the attachment and growth of other types of stem cells, specifically, induced pluripotent stem cells (iPSCs). iPSCs have exhibited an expanded potential to form cells and tissues from a much broader category than MSCs. This represents a particularly interesting challenge, because the difficulty of growing a confluent monolayer of iPSCs in standard culture conditions makes it impractical to produce a cell-derived matrix from iPSCs. A major limitation of previous cell-derived matrices, is that in order to make a tissue-specific matrix (e.g., bone marrow matrix from bone marrow MSCs, adipose matrix from adipose MSCs, or endothelial matrix from hUVECs), it is necessary that the target population of cells already be capable of adhering to the starting substrate. A difficulty with iPSCs, embryonic stem cells (ES), and many other cell types is that they do not readily adhere to simple substrates.

The present disclosure provides a solution to at least some of the aforementioned limitations and deficiencies in the art relating to cell-derived extracellular matrices (ECMs) to support the isolation, expansion and proliferation of pluripotent stem cells (PSCs), including but not limited to induced pluripotent stem cells (iPSCs) and embryonic stem cells (ES). The solution is premised on the use of an amniotic fluid cell-derived extracellular matrix. The use of uncommitted, readily adherent, and highly proliferative perinatal cells found in amniotic fluid allows for the creation of an extracellular matrix (ECM) that surprisingly, supports adhesion, isolation, expansion, and proliferation of these PSCs. This technical achievement was not possible with the cell-derived ECMs of the prior art.

The function of mammalian cells is determined, largely, by the environment, e.g., an extracellular matrix, in which they reside. They react to signals that are present in their environment (positive signals) and also to signals that are required but are not present (negative signals). It is likely that uncommitted stem cells can produce a matrix that contains niche motifs necessary to maintain stem cell viability and stemness, but lack many lineage specific signals that more mature cells may secrete which would push a stem cell toward a particular fate. Without being bound by theory, it is suggested that a less mature cell, e.g., a perinatal cell or perinatal stem cell, may produce an ECM that is different from ECMs disclosed previously in the art, such as bone marrow stromal cell-derived ECMs, and may allow for better isolation and expansion/proliferation of stem cells with higher potential than mesenchymal stem cells (MSCs), such as pluripotent stem cells (PSCs). Mass spectrometry demonstrated, that compared to previously known cell-derived ECMs, the amniotic fluid cell-derived ECM of the invention contains matrix proteins found in all 3 germ layers and lacked specific proteins strongly associated with osteogenic lineages. Moreover, the ECM of the disclosure contain specific motifs, such as laminin, that are known to facilitate pluripotent cell adhesion and expansion.

Pluripotent stem cells (PSCs) can self-renew and differentiate into any of the three germ layers: ectoderm, endoderm, and mesoderm, from which all tissues and organs develop. Embryonic stem cells (ES) are currently the only known natural pluripotent stem cells. Induced pluripotent stem (iPSCs) cells also are PSCs. iPSCs are derived from cells generally taken from adult tissue or adult cells, and reprogrammed to the level of embryonic stem cells. Methods for producing iPSCs are known in the art.

Methods to expand/proliferate pluripotent stem cells (PSCs) include obtaining PSCs and culturing them in the presence of the amniotic fluid cell-derived ECM of the invention. The PSCs can be iPSCs or ES. Any seeding density may be used which allows cells to form a confluent monolayer immediately or after a period of time in culture. In some embodiments, the seeding density is about 10 cells/cm$^2$-about 100,000 cells/cm$^2$, or about 100 cells/cm$^2$-about 75,000 cells/cm$^2$, or about 500 cells/cm$^2$-about 50,000 cells/cm$^2$, or about 500 cells/cm$^2$-about 10,000 cells/cm$^2$, or about 500 cells/cm$^2$-about 5,000 cells/cm$^2$, or about 500 cells/cm$^2$-about 2,500 cells/cm$^2$, or about 1,000 cells/cm$^2$-about 25,000 cells/cm$^2$, or about 2,000 cells/cm$^2$-about 10,000 cells/cm$^2$, or about 3,000 cells/cm$^2$-about 5000 cells/cm$^2$.

In some embodiments the PSCs are maintained in an undifferentiated state and maintain their stemness. Cell culture techniques suitable for proliferation of PSCs in culture are known in the art. Suitable commercially available culture media for stem cell proliferation includes, but is not limited to StemMACS™ iPS-Brew XF, available from Miltenyl Biotec. In some embodiments, no Rock inhibitor is used. Once cells begin to approach confluence (e.g., as determined by brightfield microscopy), cells can be passaged manually, by cutting large colonies into smaller colonies and then re-plate those by physically lifting them off the dish and placing them on a fresh plate of amniotic fluid cell-derived ECM. This procedure can be repeated indefinitely. In some embodiments disclosed is a method of proliferating pluripotent stem cells (PSCs) in culture, the method comprising culturing the PSCs in the presence of a cell-derived extracellular matrix (ECM) in a culture media thereby proliferating the PSCs, wherein the cell-derived ECM is derived in-vitro from cells isolated from amniotic fluid.

The methods of expanding/proliferating PSCs described supra also apply to the use of expanding/proliferating PSCs in culture in the presence of other perinatal cell-derived ECMs. In some embodiments, disclosed is a method of proliferating pluripotent stem cells (PSCs) in culture, the method comprising culturing the PSCs in the presence of a cell-derived extracellular matrix (ECM) in a culture media thereby proliferating the PSCs, wherein the cell-derived ECM is derived in-vitro from cells isolated from an umbilical cord or placenta tissue. In some embodiments, the cells isolated from the umbilical cord are from the cord blood and/or the Wharton's jelly. In other embodiments, the cells isolated from the placenta tissue are from the membrane sheets (amnion and/or chorion), the villi, and/or the blood.

EXAMPLES

The following examples are included to demonstrate certain non-limiting aspects of the invention. It should be appreciated by those of skill in the art that the techniques disclosed in the examples that follow represent techniques discovered by the applicants to function well in the practice of the invention. However, those of skill in the art should, in light of the present disclosure, appreciate that many changes can be made in the specific embodiments that are disclosed and still obtain a like or similar result without departing from the spirit and scope of the invention.

Example 1—Production of an Amniotic Fluid Cell-Derived ECM (AFC-ECM)

Four amniotic fluid cell-derived ECMs (Matrix A, Matrix B, Matrix C, and Matrix D) were made using the following procedure: cells aseptically isolated from amniotic fluid collected from full term birth (>37 weeks gestational age) from 4 donors were seeded onto fibronectin coated tissue-culture treated flasks and cultured in Complete Media at 37° C., 5% $CO_2$ and 90% RH in an incubator. The Complete Media was alpha Minimum Essential Media (aMEM) plus 2 mM L-Glutamine plus antibiotic-antimycotic plus 15% Fetal Bovine Serum.

At day 3-4, one-half of the complete medium was aspirated from the flasks and replaced with one-half of new Complete Media. The flasks were placed back into the incubator at the same conditions as stated above.

At day 7-8, the Complete Media was aspirated from the culture flasks and was replenished with Inducing Media. The flasks were placed back into the incubator at the same conditions as stated above. The Inducing Media was Complete Media plus 50 mM L-Ascorbic Acid.

At day 10-11, the Inducing Media aspirated from the culture flasks and the ECM which had formed inside the flasks was washed one time with phosphate buffered saline (PBS). Then the PBS was aspirated from the flasks. An Extraction Buffer was added to the flasks and incubated for 7-10 minutes at RT to decellularize each ECM, then the Extraction Buffer was aspirated from the flasks. The Extraction Buffer was PBS containing 0.5% (v/v) TRITON-X100 and 20 mM ammonium hydroxide ($NH_4OH$).

Each of the decellularized ECMs in the flasks was washed three times with PBS followed by one wash with sterile water and then the sterile water was aspirated from the flasks. The four decellularized ECMs in the flasks were allowed to dry at RT and then stored at 4° C.

Figure 1:
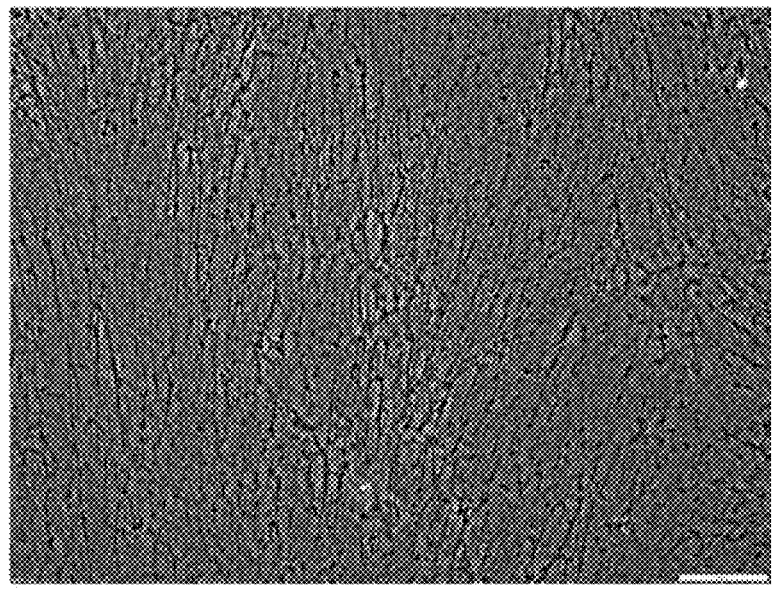
FIG. 1: A photomicrograph of a Brightfield Image of the amniotic fluid cell-derived ECM at 100× power using a 10× objective lens.
Figure 2:
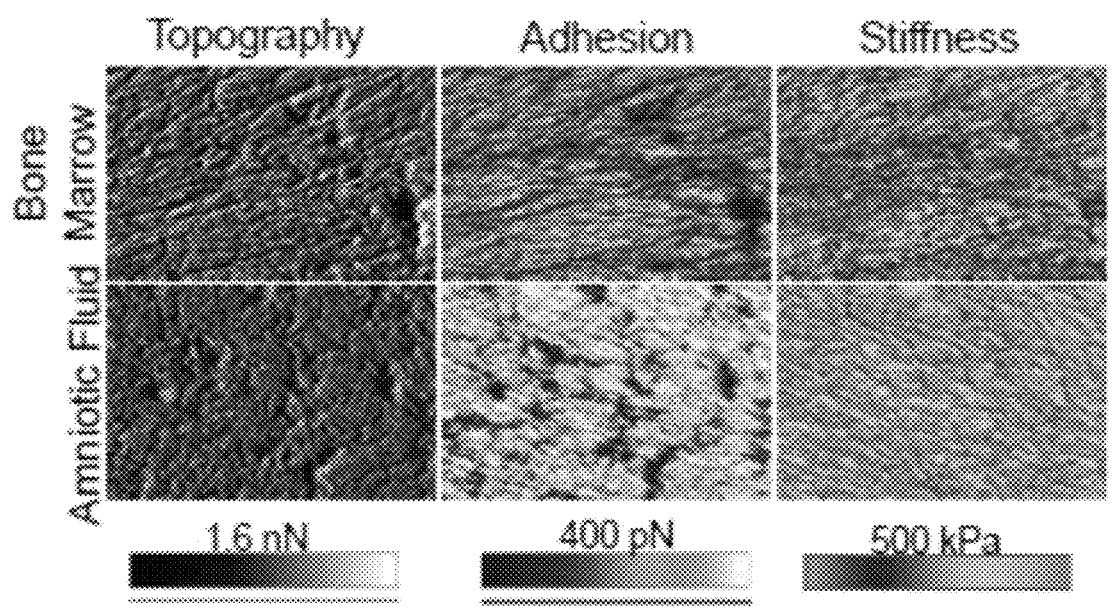
FIG. 2: An atomic force photomicrograph of 3 representative 40×40 um sections of the amniotic fluid cell-derived ECM and a bone marrow cell-derived ECM showing topography, adhesion, and stiffness.
Figure 3:
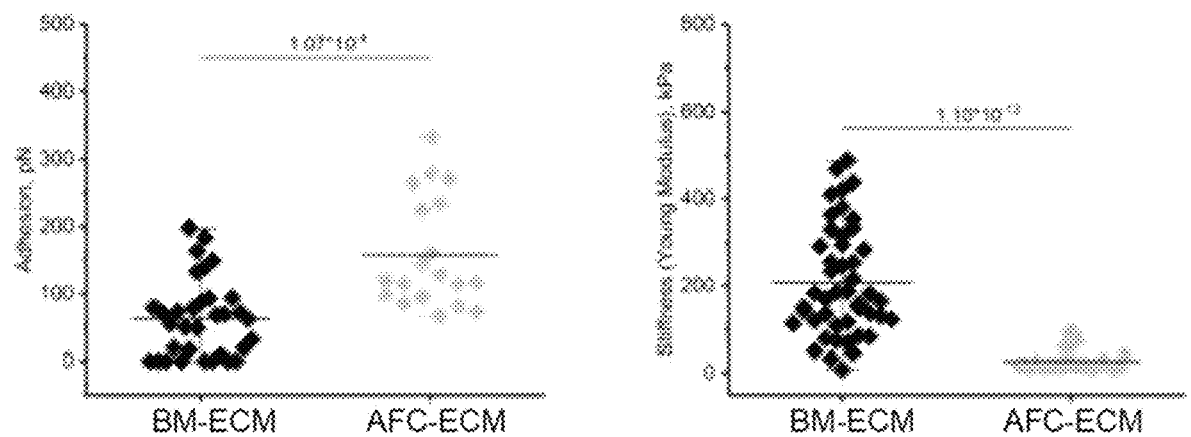
FIG. 3: Scatter plots showing quantification of adhesion and stiffness (elastic modulus) of bone marrow- and amniotic fluid-cell-derived ECMs. Each point represents an independent point of measurement.

A photomicrograph of a Brightfield Image of an amniotic fluid cell-derived ECM (Matrix B) is shown in FIG. 1 at 100× power using a 10× objective lens. An atomic force photomicrograph of 3 representative 40×40 um sections of the amniotic fluid cell-derived ECM (Matrix B) and a bone marrow cell-derived ECM showing topography, adhesion, and stiffness is shown in FIG. 2. The bone marrow- and amniotic fluid-cell-derived ECMs are structurally and physically distinct. Quantification of adhesion and stiffness (elastic modulus) of bone marrow- and amniotic fluid-cell-derived ECMs show bone marrow ECM is 10-fold stiffer, and 3-fold less adhesive, relative to amniotic fluid ECM as shown in the scatter plots in FIG. 3a (Adhesion) and FIG. 3b (Stiffness) where BM=bone marrow cell-derive ECM, AD=amniotic fluid cell-derived ECM (Matrix B). Each point represents an independent point of measurement.

Example 2—Composition of Amniotic Fluid Cell-Derived ECM

The composition of the each of the amniotic fluid cell-derived ECMs produced in Example 1 was determined by mass spectrometry. The components with their spectral count and molecular weight are listed in Table 2.

TABLE 2

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform 7 of Fibronectin OS = Homo sapiens OX = 9606 GN = FN1 | 269 kDa | 817 | 13965 | 1143 | 794 |
| Isoform 3 of Fibronectin OS = Homo sapiens OX = 9606 GN = FN1 | 259 kDa | 807 | 13836 | 1150 | 790 |
| Fibronectin OS = Homo sapiens OX = 9606 GN = FN1 PE = 1 SV = 4 | 263 kDa | 802 | 13851 | 1138 | 781 |
| Isoform 14 of Fibronectin OS = Homo sapiens OX = 9606 GN = FN1 | 249 kDa | 770 | 12625 | 1103 | 763 |
| Isoform 10 of Fibronectin OS = Homo sapiens OX = 9606 GN = FN1 | 240 kDa | 758 | 12506 | 1082 | 746 |
| Myosin-9 OS = Homo sapiens OX = 9606 GN = MYH9 PE = 1 SV = 4 | 227 kDa | 564 | 3923 | 295 | 340 |
| SWISS-PROT: P60712 (Bos taurus) Actin, cytoplasmic1 | 42 kDa | 293 | 2496 | 450 | 395 |
| Vimentin OS = Homo sapiens OX = 9606 GN = VIM PE = 1 SV = 4 | 54 kDa | 263 | 1179 | 178 | 338 |
| Neuroblast differentiation-associated protein AHNAK OS = Homo sapiens OX = 9606 GN = AHNAK PE = 1 SV = 2 | 629 kDa | 250 | 803 | 17 | 184 |
| Histone H2B type 1-D OS = Homo sapiens OX = 9606 GN = HIST1H2BD PE = 1 SV = 2 | 14 kDa | 212 | 1121 | 176 | 187 |
| Isoform 2 of Filamin-A OS = Homo sapiens OX = 9606 GN = FLNA | 280 kDa | 212 | 342 | 12 | 143 |
| Basement membrane-specific heparan sulfate proteoglycan core protein OS = Homo sapiens OX = 9606 GN = HSPG2 PE = 1 SV = 4 | 469 kDa | 202 | 0 | 402 | 338 |
| Isoform 4 of Plectin OS = Homo sapiens OX = 9606 GN = PLEC | 516 kDa | 185 | 337 | 10 | 83 |
| SWISS-PROT: P02769 (Bos taurus) Bovine serum albumin precursor | 69 kDa | 122 | 112 | 53 | 72 |
| Tubulin beta chain OS = Homo sapiens OX = 9606 GN = TUBB PE = 1 SV = 2 | 50 kDa | 117 | 0 | 36 | 92 |
| Spectrin alpha chain, non-erythrocytic 1 OS = Homo sapiens OX = 9606 GN = SPTAN1 PE = 1 SV = 3 | 285 kDa | 107 | 342 | 10 | 78 |
| Tubulin beta-4B chain OS = Homo sapiens OX = 9606 GN = TUBB4B PE = 1 SV = 1 | 50 kDa | 107 | 0 | 34 | 84 |
| Isoform 3 of Spectrin alpha chain, non-erythrocytic 1 OS = Homo sapiens GN = SPTAN1 | 282 kDa | 106 | 345 | 0 | 77 |
| Histone H4 OS = Homo sapiens OX = 9606 GN = HIST1H4A PE = 1 SV = 2 | 11 kDa | 100 | 1257 | 91 | 96 |
| Tubulin beta-4A chain OS = Homo sapiens OX = 9606 GN = TUBB4A PE = 1 SV = 2 | 50 kDa | 99 | 0 | 31 | 76 |
| Protein-glutamine gamma-glutamyltransferase 2 OS = Homo sapiens OX = 9606 GN = TGM2 PE = 1 SV = 2 | 77 kDa | 94 | 188 | 73 | 25 |
| SWISS-PROT: P00761\|TRYP_PIG Trypsin - Sus scrofa (Pig). | 24 kDa | 94 | 362 | 121 | 96 |
| Tubulin alpha-1B chain OS = Homo sapiens OX = 9606 GN = TUBA1B PE = 1 SV = 1 | 50 kDa | 93 | 295 | 37 | 86 |
| Isoform 2 of Clathrin heavy chain 1 OS = Homo sapiens OX = 9606 GN = CLTC | 188 kDa | 92 | 97 | 1 | 15 |
| Tubulin beta-2A chain OS = Homo sapiens OX = 9606 GN = TUBB2A PE = 1 SV = 1 | 50 kDa | 92 | 0 | 32 | 73 |
| Elongation factor 1-alpha 1 OS = Homo sapiens OX = 9606 GN = EEF1A1 PE = 1 SV = 1 | 50 kDa | 89 | 132 | 14 | 70 |
| Isoform 2 of Tubulin alpha-1A chain OS = Homo sapiens OX = 9606 GN = TUBA1A | 46 kDa | 88 | 305 | 34 | 82 |
| Talin-1 OS = Homo sapiens OX = 9606 GN = TLN1 PE = 1 SV = 3 | 270 kDa | 88 | 109 | 4 | 41 |
| Myosin-10 OS = Homo sapiens GN = MYH10 PE = 1 SV = 3 | 229 kDa | 84 | 417 | 56 | 46 |
| Spectrin beta chain, non-erythrocytic 1 OS = Homo sapiens OX = 9606 GN = SPTBN1 PE = 1 SV = 2 | 275 kDa | 84 | 260 | 7 | 61 |
| Pyruvate kinase PKM OS = Homo sapiens OX = 9606 GN = PKM PE = 1 SV = 4 | 58 kDa | 83 | 73 | 21 | 46 |
| Tubulin alpha-1C chain OS = Homo sapiens OX = 9606 GN = TUBA1C PE = 1 SV = 1 | 50 kDa | 83 | 0 | 0 | 78 |

TABLE 2-continued

Amniotic Fluid Cell-Derived ECM (AFC-ECM) Components

| Protein | MW | Total Spectra Count ||||
|---|---|---|---|---|---|
| | | Matrix A | Matrix B | Matrix C | Matrix D |
| Major vault protein OS = Homo sapiens OX = 9606 GN = MVP PE = 1 SV = 4 | 99 kDa | 82 | 360 | 68 | 108 |
| Actin, aortic smooth muscle OS = Homo sapiens OX = 9606 GN = ACTA2 PE = 1 SV = 1 | 42 kDa | 78 | 0 | 126 | 77 |
| Actin, gamma-enteric smooth muscle OS = Homo sapiens OX = 9606 GN = ACTG2 PE = 1 SV = 1 | 42 kDa | 76 | 313 | 122 | 73 |
| Alpha-actinin-4 OS = Homo sapiens OX = 9606 GN = ACTN4 PE = 1 SV = 2 | 105 kDa | 75 | 199 | 11 | 76 |
| Isoform 8 of Filamin-B OS = Homo sapiens OX = 9606 GN = FLNB | 282 kDa | 75 | 123 | 2 | 94 |
| Tubulin alpha-4A chain OS = Homo sapiens OX = 9606 GN = TUBA4A PE = 1 SV = 1 | 50 kDa | 73 | 262 | 0 | 65 |
| Glyceraldehyde-3-phosphate dehydrogenase OS = Homo sapiens OX = 9606 GN = GAPDH PE = 1 SV = 3 | 36 kDa | 71 | 145 | 24 | 66 |
| Cytoplasmic dynein 1 heavy chain 1 OS = Homo sapiens OX = 9606 GN = DYNC1H1 PE = 1 SV = 5 | 532 kDa | 65 | 49 | 0 | 5 |
| Histone H2A.J OS = Homo sapiens OX = 9606 GN = H2AFJ PE = 1 SV = 1 | 14 kDa | 65 | 216 | 62 | 79 |
| Serpin H1 OS = Homo sapiens OX = 9606 GN = SERPINH1 PE = 1 SV = 2 | 46 kDa | 64 | 731 | 128 | 97 |
| Histone H2A type 2-C OS = Homo sapiens OX = 9606 GN = HIST2H2AC PE = 1 SV = 4 | 14 kDa | 63 | 0 | 61 | 82 |
| Alpha-actinin-1 OS = Homo sapiens GN = ACTN1 PE = 1 SV = 2 | 103 kDa | 62 | 217 | 19 | 77 |
| Histone H2AX OS = Homo sapiens OX = 9606 GN = H2AFX PE = 1 SV = 2 | 15 kDa | 61 | 0 | 69 | 75 |
| Tubulin beta-3 chain OS = Homo sapiens OX = 9606 GN = TUBB3 PE = 1 SV = 2 | 50 kDa | 58 | 194 | 28 | 53 |
| Endoplasmic reticulum chaperone BiP OS = Homo sapiens OX = 9606 GN = HSPA5 PE = 1 SV = 2 | 72 kDa | 57 | 0 | 35 | 46 |
| Myosin regulatory light chain 12A OS = Homo sapiens OX = 9606 GN = MYL12A PE = 1 SV = 1 | 20 kDa | 57 | 0 | 244 | 153 |
| Myosin regulatory light chain 12B OS = Homo sapiens OX = 9606 GN = MYL12B PE = 1 SV = 2 | 20 kDa | 57 | 0 | 240 | 149 |
| Elongation factor 2 OS = Homo sapiens OX = 9606 GN = EEF2 PE = 1 SV = 4 | 95 kDa | 53 | 72 | 3 | 45 |
| Filamin-C OS = Homo sapiens OX = 9606 GN = FLNC PE = 1 SV = 3 | 291 kDa | 53 | 62 | 3 | 63 |
| Histone H3.1 OS = Homo sapiens OX = 9606 GN = HIST1H3A PE = 1 SV = 2 | 15 kDa | 53 | 0 | 24 | 33 |
| 60 kDa heat shock protein, mitochondrial OS = Homo sapiens OX = 9606 GN = HSPD1 PE = 1 SV = 2 | 61 kDa | 52 | 58 | 14 | 58 |
| Tubulin beta-6 chain OS = Homo sapiens OX = 9606 GN = TUBB6 PE = 1 SV = 1 | 50 kDa | 52 | 0 | 23 | 52 |
| Isoform 4 of Collagen alpha-1(XII) chain OS = Homo sapiens OX = 9606 GN = COL12A1 | 325 kDa | 51 | 35 | 36 | 27 |
| Nucleophosmin OS = Homo sapiens OX = 9606 GN = NPM1 PE = 1 SV = 2 | 33 kDa | 48 | 103 | 15 | 43 |
| Prelamin-A/C OS = Homo sapiens OX = 9606 GN = LMNA PE = 1 SV = 1 | 74 kDa | 48 | 149 | 20 | 39 |
| Heat shock protein HSP 90-beta OS = Homo sapiens OX = 9606 GN = HSP90AB1 PE = 1 SV = 4 | 83 kDa | 47 | 0 | 3 | 31 |
| Ras GTPase-activating-like protein IQGAP1 OS = Homo sapiens OX = 9606 GN = IQGAP1 PE = 1 SV = 1 | 189 kDa | 47 | 0 | 11 | 36 |
| Heat shock cognate 71 kDa protein OS = Homo sapiens OX = 9606 GN = HSPA8 PE = 1 SV = 1 | 71 kDa | 46 | 130 | 28 | 56 |
| Annexin A2 OS = Homo sapiens OX = 9606 GN = ANXA2 PE = 1 SV = 2 | 39 kDa | 43 | 111 | 5 | 40 |
| Isoform 2 of Collagen alpha-1(XVIII) chain OS = Homo sapiens OX = 9606 GN = COL18A1 | 154 kDa | 42 | 575 | 77 | 61 |
| Myosin regulatory light polypeptide 9 OS = Homo sapiens OX = 9606 GN = MYL9 PE = 1 SV = 4 | 20 kDa | 42 | 380 | 131 | 81 |
| Isoform 6 of Agrin OS = Homo sapiens OX = 9606 GN = AGRN | 215 kDa | 41 | 168 | 42 | 70 |
| Histone H3.2 OS = Homo sapiens OX = 9606 GN = HIST2H3A PE = 1 SV = 3 | 15 kDa | 40 | 0 | 17 | 25 |
| Isoform 1 of Core histone macro-H2A.1 OS = Homo sapiens OX = 9606 GN = H2AFY | 39 kDa | 40 | 450 | 43 | 49 |
| ATP synthase subunit beta, mitochondrial OS = Homo sapiens OX = 9606 GN = ATP5F1B PE = 1 SV = 3 | 57 kDa | 39 | 94 | 14 | 45 |
| T-complex protein 1 subunit alpha OS = Homo sapiens OX = 9606 GN = TCP1 PE = 1 SV = 1 | 60 kDa | 39 | 0 | 25 | 36 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform 2 of Heat shock protein HSP 90-alpha OS = Homo sapiens GN = HSP90AA1 | 98 kDa | 38 | 80 | 1 | 20 |
| Transitional endoplasmic reticulum ATPase OS = Homo sapiens OX = 9606 GN = VCP PE = 1 SV = 4 | 89 kDa | 38 | 86 | 1 | 37 |
| TREMBL: Q3KNV1; Q96GE1 Tax_Id = 9606 Gene_Symbol = KRT7 keratin 7 | 51 kDa | 38 | 334 | 58 | 133 |
| (Bos taurus) similar to alpha-2-macroglobulin isoform1 | 164 kDa | 37 | 14 | 9 | 13 |
| Heterogeneous nuclear ribonucleoprotein U OS = Homo sapiens OX = 9606 GN = HNRNPU PE = 1 SV = 6 | 91 kDa | 35 | 64 | 12 | 29 |
| Histone H3.3 OS = Homo sapiens OX = 9606 GN = H3F3A PE = 1 SV = 2 | 15 kDa | 35 | 0 | 17 | 43 |
| Microtubule-associated protein 4 OS = Homo sapiens OX = 9606 GN = MAP4 PE = 1 SV = 3 | 121 kDa | 35 | 73 | 8 | 26 |
| Beta-actin-like protein 2 OS = Homo sapiens OX = 9606 GN = ACTBL2 PE = 1 SV = 2 | 42 kDa | 34 | 147 | 42 | 31 |
| Keratin, type I cytoskeletal 10 OS = Homo sapiens OX = 9606 GN = KRT10 PE = 1 SV = 6 | 59 kDa | 34 | 464 | 32 | 37 |
| Ribosome-binding protein 1 OS = Homo sapiens OX = 9606 GN = RRBP1 PE = 1 SV = 5 | 152 kDa | 34 | 80 | 17 | 22 |
| Cytoskeleton-associated protein 4 OS = Homo sapiens OX = 9606 GN = CKAP4 PE = 1 SV = 2 | 66 kDa | 33 | 139 | 30 | 35 |
| DNA-dependent protein kinase catalytic subunit OS = Homo sapiens OX = 9606 GN = PRKDC PE = 1 SV = 3 | 469 kDa | 33 | 10 | 0 | 5 |
| Adenylyl cyclase-associated protein 1 OS = Homo sapiens OX = 9606 GN = CAP1 PE = 1 SV = 5 | 52 kDa | 32 | 33 | 2 | 37 |
| Keratin, type I cytoskeletal 9 OS = Homo sapiens OX = 9606 GN = KRT9 PE = 1 SV = 3 | 62 kDa | 31 | 643 | 61 | 50 |
| Laminin subunit alpha-5 OS = Homo sapiens OX = 9606 GN = LAMA5 PE = 1 SV = 8 | 400 kDa | 31 | 50 | 7 | 13 |
| (Bos taurus) similar to fibulin-1 C isoform 1 | 77 kDa | 30 | 71 | 40 | 18 |
| 60S ribosomal protein L4 OS = Homo sapiens OX = 9606 GN = RPL4 PE = 1 SV = 5 | 48 kDa | 30 | 75 | 26 | 25 |
| Alpha-enolase OS = Homo sapiens OX = 9606 GN = ENO1 PE = 1 SV = 2 | 47 kDa | 30 | 61 | 3 | 26 |
| ATP synthase subunit alpha, mitochondrial OS = Homo sapiens OX = 9606 GN = ATP5F1A PE = 1 SV = 1 | 60 kDa | 30 | 52 | 12 | 34 |
| Heterogeneous nuclear ribonucleoprotein M OS = Homo sapiens OX = 9606 GN = HNRNPM PE = 1 SV = 3 | 78 kDa | 30 | 114 | 12 | 30 |
| Histone H2A.V OS = Homo sapiens OX = 9606 GN = H2AFV PE = 1 SV = 3 | 14 kDa | 30 | 131 | 23 | 34 |
| Lysyl oxidase homolog 2 OS = Homo sapiens OX = 9606 GN = LOXL2 PE = 1 SV = 1 | 87 kDa | 30 | 320 | 94 | 52 |
| MICOS complex subunit MIC60 OS = Homo sapiens OX = 9606 GN = IMMT PE = 1 SV = 1 | 84 kDa | 30 | 98 | 20 | 36 |
| SWISS-PROT: P12763 (Bos taurus) Alpha-2-HS-glycoprotein precursor | 38 kDa | 30 | 42 | 18 | 19 |
| Endoplasmin OS = Homo sapiens OX = 9606 GN = HSP90B1 PE = 1 SV = 1 | 92 kDa | 29 | 71 | 3 | 22 |
| TREMBL: Q0IIK2 (Bos taurus) Transferrin | 78 kDa | 29 | 15 | 2 | 16 |
| Laminin subunit beta-1 OS = Homo sapiens OX = 9606 GN = LAMB1 PE = 1 SV = 2 | 198 kDa | 28 | 30 | 4 | 11 |
| T-complex protein 1 subunit beta OS = Homo sapiens OX = 9606 GN = CCT2 PE = 1 SV = 4 | 57 kDa | 27 | 117 | 19 | 31 |
| T-complex protein 1 subunit delta OS = Homo sapiens OX = 9606 GN = CCT4 PE = 1 SV = 4 | 58 kDa | 27 | 73 | 19 | 26 |
| Heterogeneous nuclear ribonucleoprotein K OS = Homo sapiens OX = 9606 GN = HNRNPK PE = 1 SV = 1 | 51 kDa | 26 | 28 | 3 | 26 |
| Bifunctional glutamate/proline--tRNA ligase OS = Homo sapiens OX = 9606 GN = EPRS PE = 1 SV = 5 | 171 kDa | 25 | 20 | 0 | 1 |
| Isoform 1 of Vinculin OS = Homo sapiens OX = 9606 GN = VCL | 117 kDa | 25 | 25 | 1 | 26 |
| Isoform 2 of MICOS complex subunit MIC60 OS = Homo sapiens OX = 9606 GN = IMMT | 83 kDa | 25 | 99 | 17 | 34 |
| T-complex protein 1 subunit theta OS = Homo sapiens OX = 9606 GN = CCT8 PE = 1 SV = 4 | 60 kDa | 25 | 100 | 21 | 30 |
| Isoform LCRMP-4 of Dihydropyrimidinase-related protein 3 OS = Homo sapiens OX = 9606 GN = DPYSL3 | 74 kDa | 24 | 11 | 4 | 40 |
| Thrombospondin-1 OS = Homo sapiens OX = 9606 GN = THBS1 PE = 1 SV = 2 | 129 kDa | 24 | 103 | 3 | 1 |
| Isoform Short of 14-3-3 protein beta/alpha OS = Homo sapiens OX = 9606 GN = YWHAB | 28 kDa | 23 | 18 | 2 | 14 |
| Isoform Smooth muscle of Myosin light polypeptide 6 OS = Homo sapiens OX = 9606 GN = MYL6 | 17 kDa | 23 | 204 | 37 | 28 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Keratin, type I cytoskeletal 18 OS = Homo sapiens OX = 9606 GN = KRT18 PE = 1 SV = 2 | 48 kDa | 23 | 376 | 99 | 120 |
| Keratin, type II cytoskeletal 8 OS = Homo sapiens OX = 9606 GN = KRT8 PE = 1 SV = 7 | 54 kDa | 23 | 1404 | 107 | 155 |
| Lamin-B1 OS = Homo sapiens OX = 9606 GN = LMNB1 PE = 1 SV = 2 | 66 kDa | 23 | 67 | 7 | 21 |
| L-lactate dehydrogenase A chain OS = Homo sapiens GN = LDHA PE = 1 SV = 2 | 37 kDa | 23 | 18 | 2 | 10 |
| Profilin-1 OS = Homo sapiens OX = 9606 GN = PFN1 PE = 1 SV = 2 | 15 kDa | 23 | 0 | 6 | 17 |
| Protein disulfide-isomerase OS = Homo sapiens OX = 9606 GN = P4HB PE = 1 SV = 3 | 57 kDa | 23 | 0 | 6 | 19 |
| T-complex protein 1 subunit gamma OS = Homo sapiens GN = CCT3 PE = 1 SV = 4 | 61 kDa | 23 | 72 | 17 | 26 |
| 40S ribosomal protein S15 OS = Homo sapiens OX = 9606 GN = RPS15 PE = 1 SV = 2 | 17 kDa | 22 | 0 | 26 | 38 |
| ATP-citrate synthase OS = Homo sapiens OX = 9606 GN = ACLY PE = 1 SV = 3 | 121 kDa | 22 | 20 | 2 | 18 |
| Isoform 2 of Transgelin-2 OS = Homo sapiens OX = 9606 GN = TAGLN2 | 24 kDa | 22 | 47 | 1 | 20 |
| Versican core protein OS = Homo sapiens OX = 9606 GN = VCAN PE = 1 SV = 3 | 373 kDa | 22 | 188 | 33 | 27 |
| 60S acidic ribosomal protein P0 OS = Homo sapiens OX = 9606 GN = RPLP0 PE = 1 SV = 1 | 34 kDa | 21 | 56 | 14 | 19 |
| Histone H1.5 OS = Homo sapiens OX = 9606 GN = HIST1H1B PE = 1 SV = 3 | 23 kDa | 21 | 53 | 11 | 20 |
| Importin subunit beta-1 OS = Homo sapiens OX = 9606 GN = KPNB1 PE = 1 SV = 2 | 97 kDa | 21 | 19 | 1 | 6 |
| Isoform 2 of Fructose-bisphosphate aldolase A OS = Homo sapiens OX = 9606 GN = ALDOA | 45 kDa | 21 | 37 | 0 | 21 |
| Microtubule-associated protein 1B OS = Homo sapiens OX = 9606 GN = MAP1B PE = 1 SV = 2 | 271 kDa | 21 | 104 | 0 | 22 |
| TREMBL: Q3SX09 (Bos taurus) similar to HBGprotein | 22 kDa | 21 | 26 | 11 | 9 |
| 5'-nucleotidase OS = Homo sapiens OX = 9606 GN = NT5E PE = 1 SV = 1 | 63 kDa | 20 | 129 | 21 | 17 |
| 60S ribosomal protein L3 OS = Homo sapiens OX = 9606 GN = RPL3 PE = 1 SV = 2 | 46 kDa | 20 | 65 | 15 | 24 |
| 60S ribosomal protein L6 OS = Homo sapiens OX = 9606 GN = RPL6 PE = 1 SV = 3 | 33 kDa | 20 | 0 | 19 | 25 |
| ATP-dependent 6-phosphofructokinase, platelet type OS = Homo sapiens OX = 9606 GN = PFKP PE = 1 SV = 2 | 86 kDa | 20 | 9 | 0 | 18 |
| Collagen alpha-1(I) chain OS = Homo sapiens OX = 9606 GN = COL1A1 PE = 1 SV = 5 | 139 kDa | 20 | 41 | 43 | 27 |
| T-complex protein 1 subunit eta OS = Homo sapiens OX = 9606 GN = CCT7 PE = 1 SV = 2 | 59 kDa | 20 | 72 | 15 | 22 |
| Trifunctional enzyme subunit alpha, mitochondrial OS = Homo sapiens OX = 9606 GN = HADHA PE = 1 SV = 2 | 83 kDa | 20 | 78 | 16 | 13 |
| 40S ribosomal protein S7 OS = Homo sapiens OX = 9606 GN = RPS7 PE = 1 SV = 1 | 22 kDa | 19 | 104 | 25 | 28 |
| 60S ribosomal protein L9 OS = Homo sapiens OX = 9606 GN = RPL9 PE = 1 SV = 1 | 22 kDa | 19 | 0 | 14 | 21 |
| Actin-related protein 3 OS = Homo sapiens OX = 9606 GN = ACTR3 PE = 1 SV = 3 | 47 kDa | 19 | 0 | 16 | 18 |
| Annexin A5 OS = Homo sapiens OX = 9606 GN = ANXA5 PE = 1 SV = 2 | 36 kDa | 19 | 0 | 0 | 15 |
| Calpain-2 catalytic subunit OS = Homo sapiens OX = 9606 GN = CAPN2 PE = 1 SV = 6 | 80 kDa | 19 | 4 | 0 | 8 |
| Heterogeneous nuclear ribonucleoprotein A1 OS = Homo sapiens OX = 9606 GN = HNRNPA1 PE = 1 SV = 5 | 39 kDa | 19 | 55 | 10 | 23 |
| Integrin beta-1 OS = Homo sapiens OX = 9606 GN = ITGB1 PE = 1 SV = 2 | 88 kDa | 19 | 16 | 4 | 18 |
| Interleukin enhancer-binding factor 2 OS = Homo sapiens OX = 9606 GN = ILF2 PE = 1 SV = 2 | 43 kDa | 19 | 0 | 4 | 15 |
| Isoform 2 of Nidogen-2 OS = Homo sapiens OX = 9606 GN = NID2 | 141 kDa | 19 | 55 | 0 | 3 |
| Matrin-3 OS = Homo sapiens OX = 9606 GN = MATR3 PE = 1 SV = 2 | 95 kDa | 19 | 46 | 5 | 20 |
| T-complex protein 1 subunit zeta OS = Homo sapiens OX = 9606 GN = CCT6A PE = 1 SV = 3 | 58 kDa | 19 | 64 | 23 | 28 |
| 40S ribosomal protein S2 OS = Homo sapiens OX = 9606 GN = RPS2 PE = 1 SV = 2 | 31 kDa | 18 | 0 | 14 | 17 |
| 40S ribosomal protein S3 OS = Homo sapiens OX = 9606 GN = RPS3 PE = 1 SV = 2 | 27 kDa | 18 | 82 | 19 | 20 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Collagen alpha-2(IV) chain OS = Homo sapiens OX = 9606 GN = COL4A2 PE = 1 SV = 4 | 168 kDa | 18 | 209 | 44 | 33 |
| Epiplakin OS = Homo sapiens OX = 9606 GN = EPPK1 PE = 1 SV = 3 | 556 kDa | 18 | 22 | 1 | 39 |
| Heat shock 70 kDa protein 1A OS = Homo sapiens OX = 9606 GN = HSPA1A PE = 1 SV = 1 | 70 kDa | 18 | 31 | 0 | 23 |
| Heterogeneous nuclear ribonucleoproteins C1/C2 OS = Homo sapiens OX = 9606 GN = HNRNPC PE = 1 SV = 4 | 34 kDa | 18 | 52 | 6 | 22 |
| Isoform 2 of Gelsolin OS = Homo sapiens OX = 9606 GN = GSN | 81 kDa | 18 | 87 | 36 | 24 |
| Isoform 5 of Septin-9 OS = Homo sapiens OX = 9606 GN = SEPT9 | 65 kDa | 18 | 42 | 1 | 16 |
| Laminin subunit gamma-1 OS = Homo sapiens OX = 9606 GN = LAMC1 PE = 1 SV = 3 | 178 kDa | 18 | 48 | 0 | 6 |
| Nucleolin OS = Homo sapiens OX = 9606 GN = NCL PE = 1 SV = 3 | 77 kDa | 18 | 58 | 8 | 16 |
| Voltage-dependent anion-selective channel protein 1 OS = Homo sapiens OX = 9606 GN = VDAC1 PE = 1 SV = 2 | 31 kDa | 18 | 50 | 4 | 19 |
| X-ray repair cross-complementing protein 6 OS = Homo sapiens OX = 9606 GN = XRCC6 PE = 1 SV = 2 | 70 kDa | 18 | 33 | 2 | 14 |
| Actin-related protein 2 OS = Homo sapiens OX = 9606 GN = ACTR2 PE = 1 SV = 1 | 45 kDa | 17 | 43 | 17 | 28 |
| Heat shock protein beta-1 OS = Homo sapiens OX = 9606 GN = HSPB1 PE = 1 SV = 2 | 23 kDa | 17 | 0 | 9 | 35 |
| Histone H1.4 OS = Homo sapiens OX = 9606 GN = HIST1H1E PE = 1 SV = 2 | 22 kDa | 17 | 14 | 10 | 13 |
| Isoform 2 of AP-2 complex subunit beta OS = Homo sapiens OX = 9606 GN = AP2B1 | 106 kDa | 17 | 33 | 1 | 15 |
| Isoform 2 of Calnexin OS = Homo sapiens OX = 9606 GN = CANX | 72 kDa | 17 | 21 | 1 | 19 |
| Isoform 2 of Dolichyl-diphosphooligosaccharid--protein glycosyltransferase subunit 2 OS = Homo sapiens OX = 9606 GN = RPN2 | 68 kDa | 17 | 35 | 8 | 25 |
| Moesin OS = Homo sapiens OX = 9606 GN = MSN PE = 1 SV = 3 | 68 kDa | 17 | 61 | 3 | 15 |
| Protein disulfide-isomerase A3 OS = Homo sapiens OX = 9606 GN = PDIA3 PE = 1 SV = 4 | 57 kDa | 17 | 26 | 0 | 14 |
| Stress-70 protein, mitochondrial OS = Homo sapiens OX = 9606 GN = HSPA9 PE = 1 SV = 2 | 74 kDa | 17 | 33 | 0 | 10 |
| SWISS-PROT: P34955 (Bos taurus) Alpha-1-antiproteinase precursor | 46 kDa | 17 | 66 | 19 | 16 |
| T-complex protein 1 subunit epsilon OS = Homo sapiens OX = 9606 GN = CCT5 PE = 1 SV = 1 | 60 kDa | 17 | 110 | 18 | 22 |
| 14-3-3 protein zeta/delta OS = Homo sapiens OX = 9606 GN = YWHAZ PE = 1 SV = 1 | 28 kDa | 16 | 35 | 4 | 19 |
| 40S ribosomal protein S4, X isoform OS = Homo sapiens OX = 9606 GN = RPS4X PE = 1 SV = 2 | 30 kDa | 16 | 77 | 20 | 20 |
| 60S ribosomal protein L10 OS = Homo sapiens OX = 9606 GN = RPL10 PE = 1 SV = 4 | 25 kDa | 16 | 27 | 7 | 12 |
| Ezrin OS = Homo sapiens OX = 9606 GN = EZR PE = 1 SV = 4 | 69 kDa | 16 | 43 | 4 | 23 |
| High mobility group protein HMG-I/HMG-Y OS = Homo sapiens OX = 9606 GN = HMGA1 PE = 1 SV = 3 | 12 kDa | 16 | 52 | 7 | 11 |
| Hypoxia up-regulated protein 1 OS = Homo sapiens OX = 9606 GN = HYOU1 PE = 1 SV = 1 | 111 kDa | 16 | 37 | 0 | 18 |
| Isoform 2 of Ubiquitin-like modifier-activating enzyme 1 OS = Homo sapiens OX = 9606 GN = UBA1 | 114 kDa | 16 | 21 | 0 | 5 |
| Isoform 3 of Heterogeneous nuclear ribonucleoprotein Q OS = Homo sapiens OX = 9606 GN = SYNCRIP | 63 kDa | 16 | 37 | 5 | 20 |
| Nidogen-1 OS = Homo sapiens OX = 9606 GN = NID1 PE = 1 SV = 3 | 136 kDa | 16 | 56 | 1 | 7 |
| 14-3-3 protein epsilon OS = Homo sapiens OX = 9606 GN = YWHAE PE = 1 SV = 1 | 29 kDa | 15 | 26 | 3 | 16 |
| 40S ribosomal protein S5 OS = Homo sapiens OX = 9606 GN = RPS5 PE = 1 SV = 4 | 23 kDa | 15 | 0 | 10 | 12 |
| 60S ribosomal protein L5 OS = Homo sapiens OX = 9606 GN = RPL5 PE = 1 SV = 3 | 34 kDa | 15 | 0 | 16 | 16 |
| 60S ribosomal protein L7 OS = Homo sapiens OX = 9606 GN = RPL7 PE = 1 SV = 1 | 29 kDa | 15 | 61 | 14 | 14 |
| Caprin-1 OS = Homo sapiens OX = 9606 GN = CAPRIN1 PE = 1 SV = 2 | 78 kDa | 15 | 18 | 0 | 14 |
| Catenin alpha-1 OS = Homo sapiens OX = 9606 GN = CTNNA1 PE = 1 SV = 1 | 100 kDa | 15 | 13 | 0 | 12 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Eukaryotic initiation factor 4A-I OS = Homo sapiens OX = 9606 GN = EIF4A1 PE = 1 SV = 1 | 46 kDa | 15 | 28 | 2 | 8 |
| Heterogeneous nuclear ribonucleoproteins A2/B1 OS = Homo sapiens OX = 9606 GN = HNRNPA2B1 PE = 1 SV = 2 | 37 kDa | 15 | 58 | 6 | 20 |
| Isoform 2 of Coatomer subunit alpha OS = Homo sapiens OX = 9606 GN = COPA | 139 kDa | 15 | 8 | 0 | 0 |
| Isoform 2 of Protein disulfide-isomerase A6 OS = Homo sapiens OX = 9606 GN = PDIA6 | 54 kDa | 15 | 23 | 0 | 15 |
| Isoform 3 of Septin-2 OS = Homo sapiens OX = 9606 GN = SEPT2 | 43 kDa | 15 | 55 | 6 | 16 |
| Staphylococcal nuclease domain-containing protein 1 OS = Homo sapiens OX = 9606 GN = SND1 PE = 1 SV = 1 | 102 kDa | 15 | 33 | 0 | 6 |
| Triosephosphate isomerase OS = Homo sapiens OX = 9606 GN = TPI1 PE = 1 SV = 3 | 31 kDa | 15 | 15 | 0 | 11 |
| UDP-glucose 6-dehydrogenase OS = Homo sapiens OX = 9606 GN = UGDH PE = 1 SV = 1 | 55 kDa | 15 | 24 | 2 | 15 |
| ADP/ATP translocase 2 OS = Homo sapiens OX = 9606 GN = SLC25A5 PE = 1 SV = 7 | 33 kDa | 14 | 27 | 9 | 17 |
| ATP-dependent RNA helicase A OS = Homo sapiens OX = 9606 GN = DHX9 PE = 1 SV = 4 | 141 kDa | 14 | 25 | 1 | 9 |
| Cofilin-1 OS = Homo sapiens OX = 9606 GN = CFL1 PE = 1 SV = 3 | 19 kDa | 14 | 0 | 4 | 11 |
| eIF-2-alpha kinase activator GCN1 OS = Homo sapiens OX = 9606 GN = GCN1 PE = 1 SV = 6 | 293 kDa | 14 | 0 | 0 | 6 |
| Isoform 2 of Kinectin OS = Homo sapiens OX = 9606 GN = KTN1 | 150 kDa | 14 | 62 | 1 | 8 |
| Isoform 2 of Spliceosome RNA helicase DDX39B OS = Homo sapiens OX = 9606 GN = DDX39B | 51 kDa | 14 | 25 | 1 | 12 |
| Isoleucine--tRNA ligase, cytoplasmic OS = Homo sapiens OX = 9606 GN = IARS PE = 1 SV = 2 | 145 kDa | 14 | 0 | 0 | 0 |
| Keratin, type II cytoskeletal 2 epidermal OS = Homo sapiens OX = 9606 GN = KRT2 PE = 1 SV = 2 | 65 kDa | 14 | 123 | 28 | 21 |
| Ribonuclease inhibitor OS = Homo sapiens OX = 9606 GN = RNH1 PE = 1 SV = 2 | 50 kDa | 14 | 0 | 1 | 8 |
| SWISS-PROT: P02070 (Bos taurus) Hemoglobin subunit beta | 16 kDa | 14 | 0 | 0 | 0 |
| SWISS-PROT: Q9DCV7 Tax_Id = 10090 Gene_Symbol = Krt7 Keratin, type II cytoskeletal 7 | 51 kDa | 14 | 0 | 14 | 18 |
| Tubulointerstitial nephritis antigen-like OS = Homo sapiens OX = 9606 GN = TINAGL1 PE = 1 SV = 1 | 52 kDa | 14 | 173 | 78 | 38 |
| 26S proteasome non-ATPase regulatory subunit 2 OS = Homo sapiens OX = 9606 GN = PSMD2 PE = 1 SV = 3 | 100 kDa | 13 | 18 | 0 | 10 |
| 40S ribosomal protein S8 OS = Homo sapiens OX = 9606 GN = RPS8 PE = 1 SV = 2 | 24 kDa | 13 | 0 | 9 | 15 |
| 60S ribosomal protein L23 OS = Homo sapiens OX = 9606 GN = RPL23 PE = 1 SV = 1 | 15 kDa | 13 | 0 | 14 | 10 |
| 60S ribosomal protein L7a OS = Homo sapiens OX = 9606 GN = RPL7A PE = 1 SV = 2 | 30 kDa | 13 | 68 | 12 | 14 |
| ADP/ATP translocase 3 OS = Homo sapiens OX = 9606 GN = SLC25A6 PE = 1 SV = 4 | 33 kDa | 13 | 0 | 8 | 18 |
| Arginine--tRNA ligase, cytoplasmic OS = Homo sapiens OX = 9606 GN = RARS PE = 1 SV = 2 | 75 kDa | 13 | 33 | 0 | 5 |
| Calpain small subunit 1 OS = Homo sapiens OX = 9606 GN = CAPNS1 PE = 1 SV = 1 | 28 kDa | 13 | 0 | 0 | 22 |
| Glycine--tRNA ligase OS = Homo sapiens OX = 9606 GN = GARS PE = 1 SV = 3 | 83 kDa | 13 | 0 | 1 | 6 |
| Isoform 2 of Extended synaptotagmin-1 OS = Homo sapiens OX = 9606 GN = ESYT1 | 124 kDa | 13 | 21 | 1 | 17 |
| Isoform 2 of Nuclear mitotic apparatus protein 1 OS = Homo sapiens OX = 9606 GN = NUMA1 | 237 kDa | 13 | 18 | 0 | 2 |
| Isoform 2 of Tropomyosin beta chain OS = Homo sapiens OX = 9606 GN = TPM2 | 33 kDa | 13 | 122 | 33 | 24 |
| Isoform 7 of Interleukin enhancer-binding factor 3 OS = Homo sapiens GN = ILF3 | 96 kDa | 13 | 31 | 0 | 13 |
| Isoform Beta-1 of DNA topoisomerase 2-beta OS = Homo sapiens OX = 9606 GN = TOP2B | 183 kDa | 13 | 97 | 3 | 3 |
| Lamin-B2 OS = Homo sapiens OX = 9606 GN = LMNB2 PE = 1 SV = 4 | 70 kDa | 13 | 53 | 8 | 19 |
| L-lactate dehydrogenase B chain OS = Homo sapiens OX = 9606 GN = LDHB PE = 1 SV = 2 | 37 kDa | 13 | 0 | 0 | 6 |
| Nucleoprotein TPR OS = Homo sapiens OX = 9606 GN = TPR PE = 1 SV = 3 | 267 kDa | 13 | 15 | 1 | 3 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Receptor of activated protein C kinase 1 OS = Homo sapiens OX = 9606 GN = RACK1 PE = 1 SV = 3 | 35 kDa | 13 | 0 | 1 | 12 |
| Serine protease HTRA1 OS = Homo sapiens OX = 9606 GN = HTRA1 PE = 1 SV = 1 | 51 kDa | 13 | 0 | 15 | 1 |
| Serine/threonine-protein phosphatase 2A 65 kDa regulatory subunit A alpha isoform OS = Homo sapiens OX = 9606 GN = PPP2R1A PE = 1 SV = 4 | 65 kDa | 13 | 0 | 0 | 10 |
| X-ray repair cross-complementing protein 5 OS = Homo sapiens OX = 9606 GN = XRCC5 PE = 1 SV = 3 | 83 kDa | 13 | 0 | 2 | 15 |
| 14-3-3 protein theta OS = Homo sapiens OX = 9606 GN = YWHAQ PE = 1 SV = 1 | 28 kDa | 12 | 0 | 2 | 12 |
| 40S ribosomal protein S12 OS = Homo sapiens OX = 9606 GN = RPS12 PE = 1 SV = 3 | 15 kDa | 12 | 0 | 1 | 9 |
| Cytoplasmic dynein 1 light intermediate chain 2 OS = Homo sapiens OX = 9606 GN = DYNC1LI2 PE = 1 SV = 1 | 54 kDa | 12 | 12 | 3 | 19 |
| Glutathione S-transferase P OS = Homo sapiens OX = 9606 GN = GSTP1 PE = 1 SV = 2 | 23 kDa | 12 | 0 | 2 | 13 |
| Isoform 2 of Septin-7 OS = Homo sapiens OX = 9606 GN = SEPT7 | 51 kDa | 12 | 31 | 0 | 12 |
| Isoform 3 of Unconventional myosin-Ic OS = Homo sapiens OX = 9606 GN = MYO1C | 120 kDa | 12 | 64 | 9 | 8 |
| Peptidyl-prolyl cis-trans isomerase A OS = Homo sapiens OX = 9606 GN = PPIA PE = 1 SV = 2 | 18 kDa | 12 | 36 | 3 | 11 |
| Polyadenylate-binding protein 1 OS = Homo sapiens OX = 9606 GN = PABPC1 PE = 1 SV = 2 | 71 kDa | 12 | 22 | 0 | 15 |
| Rho-related GTP-binding protein RhoC OS = Homo sapiens OX = 9606 GN = RHOC PE = 1 SV = 1 | 22 kDa | 12 | 0 | 5 | 12 |
| Ribosomal L1 domain-containing protein 1 OS = Homo sapiens OX = 9606 GN = RSL1D1 PE = 1 SV = 3 | 55 kDa | 12 | 18 | 8 | 12 |
| Transgelin OS = Homo sapiens OX = 9606 GN = TAGLN PE = 1 SV = 4 | 23 kDa | 12 | 41 | 10 | 23 |
| 14-3-3 protein gamma OS = Homo sapiens OX = 9606 GN = YWHAG PE = 1 SV = 2 | 28 kDa | 11 | 0 | 1 | 14 |
| 26S proteasome regulatory subunit 6A OS = Homo sapiens OX = 9606 GN = PSMC3 PE = 1 SV = 1 | 47 kDa | 11 | 0 | 0 | 17 |
| 40S ribosomal protein S17 OS = Homo sapiens OX = 9606 GN = RPS17 PE = 1 SV = 2 | 16 kDa | 11 | 67 | 20 | 16 |
| 60S ribosomal protein L10a OS = Homo sapiens OX = 9606 GN = RPL10A PE = 1 SV = 2 | 25 kDa | 11 | 0 | 11 | 17 |
| 60S ribosomal protein L12 OS = Homo sapiens OX = 9606 GN = RPL12 PE = 1 SV = 1 | 18 kDa | 11 | 36 | 10 | 9 |
| ADP-ribosylation factor 4 OS = Homo sapiens OX = 9606 GN = ARF4 PE = 1 SV = 3 | 21 kDa | 11 | 0 | 8 | 14 |
| Annexin A6 OS = Homo sapiens OX = 9606 GN = ANXA6 PE = 1 SV = 3 | 76 kDa | 11 | 15 | 0 | 9 |
| ATP synthase subunit O, mitochondrial OS = Homo sapiens OX = 9606 GN = ATP5PO PE = 1 SV = 1 | 23 kDa | 11 | 0 | 5 | 10 |
| Core histone macro-H2A.2 OS = Homo sapiens OX = 9606 GN = H2AFY2 PE = 1 SV = 3 | 40 kDa | 11 | 226 | 28 | 21 |
| Dolichyl-diphosphooligosaccharide--protein glycosyltransferase subunit 1 OS = Homo sapiens OX = 9606 GN = RPN1 PE = 1 SV = 1 | 69 kDa | 11 | 43 | 7 | 18 |
| Elongation factor 1-gamma OS = Homo sapiens OX = 9606 GN = EEF1G PE = 1 SV = 3 | 50 kDa | 11 | 29 | 0 | 8 |
| Guanine nucleotide-binding protein G(i) subunit alpha-2 OS = Homo sapiens OX = 9606 GN = GNAI2 PE = 1 SV = 3 | 40 kDa | 11 | 45 | 6 | 8 |
| Heterogeneous nuclear ribonucleoprotein R OS = Homo sapiens OX = 9606 GN = HNRNPR PE = 1 SV = 1 | 71 kDa | 11 | 17 | 4 | 12 |
| Isoform 2 of Probable ATP-dependent RNA helicase DDX17 OS = Homo sapiens OX = 9606 GN = DDX17 | 72 kDa | 11 | 17 | 0 | 9 |
| Isoform 3 of Tropomyosin alpha-1 chain OS = Homo sapiens OX = 9606 GN = TPM1 | 33 kDa | 11 | 181 | 46 | 37 |
| Isoform 4 of Caldesmon OS = Homo sapiens OX = 9606 GN = CALD1 | 63 kDa | 11 | 51 | 10 | 32 |
| Leucine--tRNA ligase, cytoplasmic OS = Homo sapiens GN = LARS PE = 1 SV = 2 | 134 kDa | 11 | 3 | 0 | 0 |
| Phosphoglycerate kinase 1 OS = Homo sapiens OX = 9606 GN = PGK1 PE = 1 SV = 3 | 45 kDa | 11 | 10 | 0 | 7 |
| Polypyrimidine tract-binding protein 1 OS = Homo sapiens OX = 9606 GN = PTBP1 PE = 1 SV = 1 | 57 kDa | 11 | 33 | 1 | 20 |
| Rab GDP dissociation inhibitor beta OS = Homo sapiens OX = 9606 GN = GDI2 PE = 1 SV = 2 | 51 kDa | 11 | 17 | 0 | 10 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Reticulon-4 OS = Homo sapiens GN = RTN4 PE = 1 SV = 2 | 130 kDa | 11 | 15 | 0 | 9 |
| Serine hydroxymethyltransferase, mitochondrial OS = Homo sapiens GN = SHMT2 PE = 1 SV = 3 | 56 kDa | 11 | 6 | 0 | 3 |
| Serine/threonine-protein phosphatase PP1-alpha catalytic subunit OS = Homo sapiens OX = 9606 GN = PPP1CA PE = 1 SV = 1 | 38 kDa | 11 | 23 | 3 | 10 |
| Splicing factor, proline- and glutamine-rich OS = Homo sapiens OX = 9606 GN = SFPQ PE = 1 SV = 2 | 76 kDa | 11 | 43 | 5 | 18 |
| SWISS-PROT: Q3MHN5 (Bos taurus) Vitamin D-binding protein precursor | 53 kDa | 11 | 15 | 2 | 4 |
| Tenascin OS = Homo sapiens GN = TNC PE = 1 SV = 3 | 241 kDa | 11 | 409 | 60 | 72 |
| Threonine--tRNA ligase, cytoplasmic OS = Homo sapiens OX = 9606 GN = TARS PE = 1 SV = 3 | 83 kDa | 11 | 10 | 0 | 3 |
| Tropomyosin alpha-4 chain OS = Homo sapiens OX = 9606 GN = TPM4 PE = 1 SV = 3 | 29 kDa | 11 | 89 | 21 | 20 |
| 14-3-3 protein eta OS = Homo sapiens OX = 9606 GN = YWHAH PE = 1 SV = 4 | 28 kDa | 10 | 0 | 1 | 10 |
| 26S proteasome regulatory subunit 6B OS = Homo sapiens OX = 9606 GN = PSMC4 PE = 1 SV = 2 | 47 kDa | 10 | 13 | 3 | 10 |
| 60S ribosomal protein L18 OS = Homo sapiens GN = RPL18 PE = 1 SV = 1 | 19 kDa | 10 | 26 | 7 | 9 |
| Actin-related protein 2/3 complex subunit 2 OS = Homo sapiens OX = 9606 GN = ARPC2 PE = 1 SV = 1 | 34 kDa | 10 | 53 | 14 | 11 |
| A-kinase anchor protein 12 OS = Homo sapiens OX = 9606 GN = AKAP12 PE = 1 SV = 4 | 191 kDa | 10 | 46 | 0 | 5 |
| Asparagine--tRNA ligase, cytoplasmic OS = Homo sapiens OX = 9606 GN = NARS PE = 1 SV = 1 | 63 kDa | 10 | 10 | 0 | 1 |
| Aspartate--tRNA ligase, cytoplasmic OS = Homo sapiens OX = 9606 GN = DARS PE = 1 SV = 2 | 57 kDa | 10 | 22 | 3 | 9 |
| Dolichyl-diphosphooligosaccharide--protein glycosyltransferase 48 kDa subunit OS = Homo sapiens OX = 9606 GN = DDOST PE = 1 SV = 4 | 51 kDa | 10 | 13 | 6 | 17 |
| Erlin-2 OS = Homo sapiens OX = 9606 GN = ERLIN2 PE = 1 SV = 1 | 38 kDa | 10 | 39 | 4 | 11 |
| Fatty acid synthase OS = Homo sapiens OX = 9606 GN = FASN PE = 1 SV = 3 | 273 kDa | 10 | 0 | 0 | 2 |
| Heterogeneous nuclear ribonucleoprotein A3 OS = Homo sapiens OX = 9606 GN = HNRNPA3 PE = 1 SV = 2 | 40 kDa | 10 | 25 | 7 | 8 |
| Isoform 3 of Exportin-2 OS = Homo sapiens OX = 9606 GN = CSE1L | 108 kDa | 10 | 2 | 2 | 3 |
| Isoform B of AP-1 complex subunit beta-1 OS = Homo sapiens OX = 9606 GN = AP1B1 | 104 kDa | 10 | 0 | 0 | 11 |
| Leucine-rich PPR motif-containing protein, mitochondrial OS = Homo sapiens OX = 9606 GN = LRPPRC PE = 1 SV = 3 | 158 kDa | 10 | 5 | 0 | 0 |
| Non-POU domain-containing octamer-binding protein OS = Homo sapiens OX = 9606 GN = NONO PE = 1 SV = 4 | 54 kDa | 10 | 44 | 3 | 20 |
| Nucleolar protein 56 OS = Homo sapiens OX = 9606 GN = NOP56 PE = 1 SV = 4 | 66 kDa | 10 | 18 | 1 | 2 |
| Peroxidasin homolog OS = Homo sapiens OX = 9606 GN = PXDN PE = 1 SV = 2 | 165 kDa | 10 | 146 | 36 | 28 |
| Stomatin-like protein 2, mitochondrial OS = Homo sapiens OX = 9606 GN = STOML2 PE = 1 SV = 1 | 39 kDa | 10 | 18 | 3 | 10 |
| SWISS-PROT: P01966 (Bos taurus) Hemoglobin subunit alpha | 15 kDa | 10 | 34 | 12 | 10 |
| SWISS-PROT: Q3SZ57 (Bos taurus) Alpha-fetoprotein precursor | 69 kDa | 10 | 11 | 6 | 7 |
| Transforming protein RhoA OS = Homo sapiens OX = 9606 GN = RHOA PE = 1 SV = 1 | 22 kDa | 10 | 0 | 4 | 10 |
| 40S ribosomal protein SA OS = Homo sapiens OX = 9606 GN = RPSA PE = 1 SV = 1 | 33 kDa | 9 | 0 | 1 | 10 |
| 60S ribosomal protein L13 OS = Homo sapiens OX = 9606 GN = RPL13 PE = 1 SV = 4 | 24 kDa | 9 | 32 | 12 | 12 |
| 60S ribosomal protein L8 OS = Homo sapiens OX = 9606 GN = RPL8 PE = 1 SV = 2 | 28 kDa | 9 | 0 | 7 | 9 |
| Aldehyde dehydrogenase X, mitochondrial OS = Homo sapiens OX = 9606 GN = ALDH1B1 PE = 1 SV = 3 | 57 kDa | 9 | 14 | 4 | 11 |
| ATP-dependent RNA helicase DDX3X OS = Homo sapiens OX = 9606 GN = DDX3X PE = 1 SV = 3 | 73 kDa | 9 | 18 | 5 | 11 |
| Calreticulin OS = Homo sapiens OX = 9606 GN = CALR PE = 1 SV = 1 | 48 kDa | 9 | 44 | 4 | 11 |
| D-3-phosphoglycerate dehydrogenase OS = Homo sapiens OX = 9606 GN = PHGDH PE = 1 SV = 4 | 57 kDa | 9 | 0 | 0 | 2 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| F-actin-capping protein subunit alpha-1 OS = Homo sapiens OX = 9606 GN = CAPZA1 PE = 1 SV = 3 | 33 kDa | 9 | 0 | 18 | 15 |
| Galectin-1 OS = Homo sapiens OX = 9606 GN = LGALS1 PE = 1 SV = 2 | 15 kDa | 9 | 0 | 3 | 6 |
| GTP-binding nuclear protein Ran OS = Homo sapiens OX = 9606 GN = RAN PE = 1 SV = 3 | 24 kDa | 9 | 0 | 6 | 11 |
| Heterochromatin protein 1-binding protein 3 OS = Homo sapiens OX = 9606 GN = HP1BP3 PE = 1 SV = 1 | 61 kDa | 9 | 24 | 4 | 7 |
| Isoform 1 of Voltage-dependent anion-selective channel protein 2 OS = Homo sapiens OX = 9606 GN = VDAC2 | 33 kDa | 9 | 19 | 1 | 5 |
| Isoform 2 of Eukaryotic translation initiation factor 3 subunit A OS = Homo sapiens OX = 9606 GN = EIF3A | 163 kDa | 9 | 10 | 0 | 11 |
| Isoform 2 of Glutamine--tRNA ligase OS = Homo sapiens OX = 9606 GN = QARS | 87 kDa | 9 | 16 | 0 | 4 |
| Isoform 2 of Tropomyosin alpha-3 chain OS = Homo sapiens OX = 9606 GN = TPM3 | 29 kDa | 9 | 99 | 16 | 17 |
| Isoform 3 of Protein AHNAK2 OS = Homo sapiens OX = 9606 GN = AHNAK2 | 606 kDa | 9 | 0 | 0 | 1 |
| Isoform D of Eukaryotic translation initiation factor 4 gamma 1 OS = Homo sapiens OX = 9606 GN = EIF4G1 | 159 kDa | 9 | 7 | 0 | 0 |
| KH domain-containing, RNA-binding, signal transduction-associated protein 1 OS = Homo sapiens OX = 9606 GN = KHDRBS1 PE = 1 SV = 1 | 48 kDa | 9 | 24 | 5 | 9 |
| Methionine--tRNA ligase, cytoplasmic OS = Homo sapiens OX = 9606 GN = MARS PE = 1 SV = 2 | 101 kDa | 9 | 1 | 0 | 0 |
| Myeloid-associated differentiation marker OS = Homo sapiens OX = 9606 GN = MYADM PE = 1 SV = 2 | 35 kDa | 9 | 0 | 16 | 12 |
| Neutral alpha-glucosidase AB OS = Homo sapiens OX = 9606 GN = GANAB PE = 1 SV = 3 | 107 kDa | 9 | 21 | 0 | 13 |
| Peroxiredoxin-5, mitochondrial OS = Homo sapiens OX = 9606 GN = PRDX5 PE = 1 SV = 4 | 22 kDa | 9 | 6 | 0 | 5 |
| Serine--tRNA ligase, cytoplasmic OS = Homo sapiens OX = 9606 GN = SARS PE = 1 SV = 3 | 59 kDa | 9 | 0 | 0 | 9 |
| Tryptophan--tRNA ligase, cytoplasmic OS = Homo sapiens OX = 9606 GN = WARS PE = 1 SV = 2 | 53 kDa | 9 | 6 | 1 | 7 |
| Vacuolar protein sorting-associated protein 35 OS = Homo sapiens OX = 9606 GN = VPS35 PE = 1 SV = 2 | 92 kDa | 9 | 5 | 0 | 4 |
| 26S proteasome non-ATPase regulatory subunit 3 OS = Homo sapiens OX = 9606 GN = PSMD3 PE = 1 SV = 2 | 61 kDa | 8 | 21 | 0 | 6 |
| 40S ribosomal protein S16 OS = Homo sapiens OX = 9606 GN = RPS16 PE = 1 SV = 2 | 16 kDa | 8 | 0 | 9 | 7 |
| 40S ribosomal protein S6 OS = Homo sapiens OX = 9606 GN = RPS6 PE = 1 SV = 1 | 29 kDa | 8 | 0 | 5 | 11 |
| 40S ribosomal protein S9 OS = Homo sapiens OX = 9606 GN = RPS9 PE = 1 SV = 3 | 23 kDa | 8 | 54 | 11 | 10 |
| ADP/ATP translocase 1 OS = Homo sapiens OX = 9606 GN = SLC25A4 PE = 1 SV = 4 | 33 kDa | 8 | 0 | 0 | 12 |
| Annexin A1 OS = Homo sapiens OX = 9606 GN = ANXA1 PE = 1 SV = 2 | 39 kDa | 8 | 0 | 0 | 8 |
| ATP-dependent RNA helicase DDX1 OS = Homo sapiens OX = 9606 GN = DDX1 PE = 1 SV = 2 | 82 kDa | 8 | 15 | 2 | 10 |
| Coatomer subunit gamma-1 OS = Homo sapiens OX = 9606 GN = COPG1 PE = 1 SV = 1 | 98 kDa | 8 | 9 | 1 | 6 |
| Elongation factor Tu, mitochondrial OS = Homo sapiens OX = 9606 GN = TUFM PE = 1 SV = 2 | 50 kDa | 8 | 0 | 0 | 0 |
| Erythrocyte band 7 integral membrane protein OS = Homo sapiens OX = 9606 GN = STOM PE = 1 SV = 3 | 32 kDa | 8 | 6 | 2 | 3 |
| Eukaryotic translation initiation factor 2 subunit 3 OS = Homo sapiens OX = 9606 GN = EIF2S3 PE = 1 SV = 3 | 51 kDa | 8 | 0 | 3 | 12 |
| Flotillin-1 OS = Homo sapiens OX = 9606 GN = FLOT1 PE = 1 SV = 3 | 47 kDa | 8 | 25 | 1 | 4 |
| Heterogeneous nuclear ribonucleoprotein L OS = Homo sapiens OX = 9606 GN = HNRNPL PE = 1 SV = 2 | 64 kDa | 8 | 11 | 0 | 5 |
| Isoform 2 of Ankycorbin OS = Homo sapiens OX = 9606 GN = RAI14 | 110 kDa | 8 | 38 | 2 | 5 |
| Isoform 2 of Bifunctional purine biosynthesis protein PURH OS = Homo sapiens OX = 9606 GN = ATIC | 65 kDa | 8 | 5 | 0 | 4 |
| Isoform 2 of Eukaryotic translation initiation factor 5A-1 OS = Homo sapiens OX = 9606 GN = EIF5A | 20 kDa | 8 | 14 | 1 | 7 |
| Isoform 2 of Golgi apparatus protein 1 OS = Homo sapiens OX = 9606 GN = GLG1 | 137 kDa | 8 | 4 | 9 | 1 |
| Isoform 2 of Poly(rC)-binding protein 2 OS = Homo sapiens OX = 9606 GN = PCBP2 | 39 kDa | 8 | 4 | 0 | 4 |

TABLE 2-continued

Amniotic Fluid Cell-Derived ECM (AFC-ECM) Components

| Protein | MW | Matrix A | Matrix B | Matrix C | Matrix D |
|---|---|---|---|---|---|
| Isoform 3 of Heterogeneous nuclear ribonucleoprotein D0 OS = Homo sapiens OX = 9606 GN = HNRNPD | 33 kDa | 8 | 20 | 6 | 11 |
| Isoform B of Phosphate carrier protein, mitochondrial OS = Homo sapiens OX = 9606 GN = SLC25A3 | 40 kDa | 8 | 7 | 5 | 8 |
| Kinesin-1 heavy chain OS = Homo sapiens OX = 9606 GN = KIF5B PE = 1 SV = 1 | 110 kDa | 8 | 5 | 0 | 3 |
| Malate dehydrogenase, mitochondrial OS = Homo sapiens OX = 9606 GN = MDH2 PE = 1 SV = 3 | 36 kDa | 8 | 17 | 0 | 13 |
| Mitochondrial carrier homolog 2 OS = Homo sapiens OX = 9606 GN = MTCH2 PE = 1 SV = 1 | 33 kDa | 8 | 0 | 2 | 4 |
| Pre-mRNA-processing factor 19 OS = Homo sapiens OX = 9606 GN = PRPF19 PE = 1 SV = 1 | 55 kDa | 8 | 0 | 0 | 14 |
| Prohibitin OS = Homo sapiens OX = 9606 GN = PHB PE = 1 SV = 1 | 30 kDa | 8 | 14 | 2 | 15 |
| Protein transport protein Sec23A OS = Homo sapiens OX = 9606 GN = SEC23A PE = 1 SV = 2 | 86 kDa | 8 | 9 | 1 | 10 |
| Protein transport protein Sec61 subunit alpha isoform 1 OS = Homo sapiens OX = 9606 GN = SEC61A1 PE = 1 SV = 2 | 52 kDa | 8 | 2 | 1 | 5 |
| Septin-11 OS = Homo sapiens OX = 9606 GN = SEPT11 PE = 1 SV = 3 | 49 kDa | 8 | 27 | 0 | 9 |
| Small nuclear ribonucleoprotein Sm D1 OS = Homo sapiens OX = 9606 GN = SNRPD1 PE = 1 SV = 1 | 13 kDa | 8 | 0 | 6 | 7 |
| SWISS-PROT: P15497 (Bos taurus) Apolipoprotein A-I precursor | 30 kDa | 8 | 21 | 6 | 4 |
| THO complex subunit 4 OS = Homo sapiens OX = 9606 GN = ALYREF PE = 1 SV = 3 | 27 kDa | 8 | 37 | 7 | 11 |
| TREMBL: Q3ZBS7 (Bos taurus) Vitronectin | 54 kDa | 8 | 26 | 12 | 11 |
| Ubiquitin-40S ribosomal protein S27a OS = Homo sapiens OX = 9606 GN = RPS27A PE = 1 SV = 2 | 18 kDa | 8 | 0 | 13 | 10 |
| 26S proteasome non-ATPase regulatory subunit 12 OS = Homo sapiens OX = 9606 GN = PSMD12 PE = 1 SV = 3 | 53 kDa | 7 | 6 | 0 | 2 |
| 26S proteasome regulatory subunit 8 OS = Homo sapiens OX = 9606 GN = PSMC5 PE = 1 SV = 1 | 46 kDa | 7 | 6 | 0 | 12 |
| 40S ribosomal protein S14 OS = Homo sapiens OX = 9606 GN = RPS14 PE = 1 SV = 3 | 16 kDa | 7 | 40 | 13 | 9 |
| 40S ribosomal protein S19 OS = Homo sapiens OX = 9606 GN = RPS19 PE = 1 SV = 2 | 16 kDa | 7 | 0 | 12 | 15 |
| 40S ribosomal protein S23 OS = Homo sapiens OX = 9606 GN = RPS23 PE = 1 SV = 3 | 16 kDa | 7 | 0 | 4 | 12 |
| 60S ribosomal protein L30 OS = Homo sapiens OX = 9606 GN = RPL30 PE = 1 SV = 2 | 13 kDa | 7 | 0 | 8 | 8 |
| ADP-ribosylation factor 3 OS = Homo sapiens OX = 9606 GN = ARF3 PE = 1 SV = 2 | 21 kDa | 7 | 11 | 7 | 7 |
| Aminoacyl tRNA synthase complex-interacting multifunctional protein 2 OS = Homo sapiens OX = 9606 GN = AIMP2 PE = 1 SV = 2 | 35 kDa | 7 | 0 | 0 | 6 |
| CAD protein OS = Homo sapiens OX = 9606 GN = CAD PE = 1 SV = 3 | 243 kDa | 7 | 0 | 0 | 0 |
| Catenin beta-1 OS = Homo sapiens OX = 9606 GN = CTNNB1 PE = 1 SV = 1 | 85 kDa | 7 | 3 | 0 | 6 |
| Cell division control protein 42 homolog OS = Homo sapiens OX = 9606 GN = CDC42 PE = 1 SV = 2 | 21 kDa | 7 | 0 | 2 | 11 |
| Chloride intracellular channel protein 1 OS = Homo sapiens OX = 9606 GN = CLIC1 PE = 1 SV = 4 | 27 kDa | 7 | 0 | 0 | 5 |
| Coatomer subunit beta OS = Homo sapiens OX = 9606 GN = COPB1 PE = 1 SV = 3 | 107 kDa | 7 | 5 | 0 | 1 |
| Eukaryotic initiation factor 4A-III OS = Homo sapiens OX = 9606 GN = EIF4A3 PE = 1 SV = 4 | 47 kDa | 7 | 20 | 4 | 8 |
| Heterogeneous nuclear ribonucleoprotein H OS = Homo sapiens OX = 9606 GN = HNRNPH1 PE = 1 SV = 1 | 51 kDa | 7 | 23 | 1 | 9 |
| Importin-5 OS = Homo sapiens OX = 9606 GN = IPO5 PE = 1 SV = 4 | 124 kDa | 7 | 5 | 0 | 3 |
| Inhibitor of nuclear factor kappa-B kinase-interacting protein OS = Homo sapiens OX = 9606 GN = IKBIP PE = 1 SV = 1 | 39 kDa | 7 | 7 | 6 | 7 |
| Isoform 2 of 26S proteasome non-ATPase regulatory subunit 11 OS = Homo sapiens OX = 9606 GN = PSMD11 | 48 kDa | 7 | 12 | 0 | 5 |
| Isoform 2 of F-actin-capping protein subunit beta OS = Homo sapiens OX = 9606 GN = CAPZB | 31 kDa | 7 | 46 | 10 | 5 |
| Isoform 2 of Heterogeneous nuclear ribonucleoprotein D-like OS = Homo sapiens OX = 9606 GN = HNRNPDL | 34 kDa | 7 | 8 | 0 | 7 |
| Isoform 2 of Integrin alpha-3 OS = Homo sapiens OX = 9606 GN = ITGA3 | 119 kDa | 7 | 2 | 0 | 5 |

TABLE 2-continued

Amniotic Fluid Cell-Derived ECM (AFC-ECM) Components

| Protein | MW | Total Spectra Count | | | |
| --- | --- | --- | --- | --- | --- |
| | | Matrix A | Matrix B | Matrix C | Matrix D |
| Isoform 2 of Nucleolar RNA helicase 2 OS = Homo sapiens OX = 9606 GN = DDX21 | 80 kDa | 7 | 16 | 2 | 7 |
| Isoform 2 of PDZ and LIM domain protein 7 OS = Homo sapiens OX = 9606 GN = PDLIM7 | 47 kDa | 7 | 13 | 0 | 5 |
| Isoform 2 of Spermine synthase OS = Homo sapiens OX = 9606 GN = SMS | 35 kDa | 7 | 2 | 0 | 6 |
| Isoform 2 of Transketolase OS = Homo sapiens OX = 9606 GN = TKT | 69 kDa | 7 | 29 | 0 | 9 |
| Isoform 3 of 116 kDa U5 small nuclear ribonucleoprotein component OS = Homo sapiens OX = 9606 GN = EFTUD2 | 108 kDa | 7 | 6 | 0 | 9 |
| Isoform 3 of 60S ribosomal protein L17 OS = Homo sapiens OX = 9606 GN = RPL17 | 26 kDa | 7 | 54 | 5 | 8 |
| Isoform 3 of Integrin alpha-V OS = Homo sapiens OX = 9606 GN = ITGAV | 111 kDa | 7 | 22 | 2 | 12 |
| Isoform SV3 of Supervillin OS = Homo sapiens OX = 9606 GN = SVIL | 245 kDa | 7 | 46 | 0 | 1 |
| NADH dehydrogenase [ubiquinone] 1 alpha subcomplex subunit 9, mitochondrial OS = Homo sapiens OX = 9606 GN = NDUFA9 PE = 1 SV = 2 | 43 kDa | 7 | 12 | 1 | 7 |
| Peroxiredoxin-1 OS = Homo sapiens OX = 9606 GN = PRDX1 PE = 1 SV = 1 | 22 kDa | 7 | 0 | 0 | 7 |
| Poly(rC)-binding protein 1 OS = Homo sapiens OX = 9606 GN = PCBP1 PE = 1 SV = 2 | 37 kDa | 7 | 0 | 0 | 2 |
| Pre-mRNA-processing-splicing factor 8 OS = Homo sapiens OX = 9606 GN = PRPF8 PE = 1 SV = 2 | 274 kDa | 7 | 6 | 1 | 3 |
| Probable ATP-dependent RNA helicase DDX5 OS = Homo sapiens OX = 9606 GN = DDX5 PE = 1 SV = 1 | 69 kDa | 7 | 25 | 7 | 19 |
| Prohibitin-2 OS = Homo sapiens OX = 9606 GN = PHB2 PE = 1 SV = 2 | 33 kDa | 7 | 25 | 5 | 12 |
| Protein disulfide-isomerase A4 OS = Homo sapiens OX = 9606 GN = PDIA4 PE = 1 SV = 2 | 73 kDa | 7 | 4 | 0 | 4 |
| Ras GTPase-activating protein-binding protein 1 OS = Homo sapiens OX = 9606 GN = G3BP1 PE = 1 SV = 1 | 52 kDa | 7 | 19 | 2 | 8 |
| Ras-related protein Rab-1B OS = Homo sapiens OX = 9606 GN = RAB1B PE = 1 SV = 1 | 22 kDa | 7 | 0 | 0 | 8 |
| RNA-binding motif protein, X chromosome OS = Homo sapiens OX = 9606 GN = RBMX PE = 1 SV = 3 | 42 kDa | 7 | 22 | 5 | 13 |
| Splicing factor 3B subunit 1 OS = Homo sapiens OX = 9606 GN = SF3B1 PE = 1 SV = 3 | 146 kDa | 7 | 16 | 1 | 3 |
| SWISS-PROT: P02535-1 Tax_Id = 10090 Gene_Symbol = Krt10 Isoform 1 of Keratin, type I cytoskeletal 10 | 58 kDa | 7 | 39 | 7 | 0 |
| SWISS-PROT: P08730-1 Tax_Id = 10090 Gene_Symbol = Krt13 Isoform 1 of Keratin, type I cytoskeletal 13 | 48 kDa | 7 | 451 | 17 | 31 |
| SWISS-PROT: Q6IFZ6 Tax_Id = 10090 Gene_Symbol = Krt77 Keratin, type II cytoskeletal 1b | 61 kDa | 7 | 32 | 10 | 5 |
| Talin-2 OS = Homo sapiens OX = 9606 GN = TLN2 PE = 1 SV = 4 | 272 kDa | 7 | 0 | 0 | 1 |
| Transcription intermediary factor 1-beta OS = Homo sapiens OX = 9606 GN = TRIM28 PE = 1 SV = 5 | 89 kDa | 7 | 5 | 0 | 0 |
| TREMBL: Q9TRI1 (Bos taurus) similar to inter-alpha-trypsin inhibitor heavy chain2 | 106 kDa | 7 | 57 | 7 | 8 |
| U5 small nuclear ribonucleoprotein 200 kDa helicase OS = Homo sapiens OX = 9606 GN = SNRNP200 PE = 1 SV = 2 | 245 kDa | 7 | 1 | 0 | 0 |
| Valine--tRNA ligase OS = Homo sapiens OX = 9606 GN = VARS PE = 1 SV = 4 | 140 kDa | 7 | 8 | 0 | 4 |
| 26S proteasome regulatory subunit 4 OS = Homo sapiens OX = 9606 GN = PSMC1 PE = 1 SV = 1 | 49 kDa | 6 | 25 | 1 | 6 |
| 40S ribosomal protein S26 OS = Homo sapiens OX = 9606 GN = RPS26 PE = 1 SV = 3 | 13 kDa | 6 | 0 | 6 | 6 |
| 60S ribosomal protein L24 OS = Homo sapiens OX = 9606 GN = RPL24 PE = 1 SV = 1 | 18 kDa | 6 | 0 | 5 | 6 |
| 60S ribosomal protein L27a OS = Homo sapiens OX = 9606 GN = RPL27A PE = 1 SV = 2 | 17 kDa | 6 | 0 | 6 | 4 |
| Alpha-centractin OS = Homo sapiens OX = 9606 GN = ACTR1A PE = 1 SV = 1 | 43 kDa | 6 | 26 | 3 | 11 |
| ATP-dependent RNA helicase DDX18 OS = Homo sapiens OX = 9606 GN = DDX18 PE = 1 SV = 2 | 75 kDa | 6 | 5 | 3 | 8 |
| Collagen alpha-1(IV) chain OS = Homo sapiens OX = 9606 GN = COL4A1 PE = 1 SV = 4 | 161 kDa | 6 | 69 | 21 | 7 |

TABLE 2-continued

Amniotic Fluid Cell-Derived ECM (AFC-ECM) Components

| Protein | MW | Total Spectra Count | | | |
| --- | --- | --- | --- | --- | --- |
| | | Matrix A | Matrix B | Matrix C | Matrix D |
| Collagen alpha-1(VIII) chain OS = Homo sapiens OX = 9606 GN = COL8A1 PE = 1 SV = 2 | 73 kDa | 6 | 0 | 29 | 22 |
| Cullin-associated NEDD8-dissociated protein 1 OS = Homo sapiens GN = CAND1 PE = 1 SV = 2 | 136 kDa | 6 | 0 | 0 | 3 |
| Dihydrolipoyllysine-residue succinyltransferase component of 2-oxoglutarate dehydrogenase complex, mitochondrial OS = Homo sapiens OX = 9606 GN = DLST PE = 1 SV = 4 | 49 kDa | 6 | 17 | 0 | 8 |
| Dihydropyrimidinase-related protein 2 OS = Homo sapiens OX = 9606 GN = DPYSL2 PE = 1 SV = 1 | 62 kDa | 6 | 3 | 0 | 5 |
| Eukaryotic translation initiation factor 3 subunit M OS = Homo sapiens OX = 9606 GN = EIF3M PE = 1 SV = 1 | 43 kDa | 6 | 11 | 0 | 5 |
| Exportin-1 OS = Homo sapiens OX = 9606 GN = XPO1 PE = 1 SV = 1 | 123 kDa | 6 | 0 | 0 | 0 |
| F-actin-capping protein subunit alpha-2 OS = Homo sapiens OX = 9606 GN = CAPZA2 PE = 1 SV = 3 | 33 kDa | 6 | 33 | 8 | 9 |
| Glycogen phosphorylase, brain form OS = Homo sapiens OX = 9606 GN = PYGB PE = 1 SV = 5 | 97 kDa | 6 | 0 | 0 | 1 |
| Importin-7 OS = Homo sapiens OX = 9606 GN = IPO7 PE = 1 SV = 1 | 120 kDa | 6 | 0 | 0 | 0 |
| Isoform 2 of 6-phosphogluconate dehydrogenase, decarboxylating OS = Homo sapiens OX = 9606 GN = PGD | 52 kDa | 6 | 4 | 0 | 3 |
| Isoform 2 of Coatomer subunit beta' OS = Homo sapiens OX = 9606 GN = COPB2 | 99 kDa | 6 | 10 | 0 | 4 |
| Isoform 2 of Coronin-1C OS = Homo sapiens OX = 9606 GN = CORO1C | 54 kDa | 6 | 36 | 5 | 7 |
| Isoform 2 of Elongation factor 1-delta OS = Homo sapiens OX = 9606 GN = EEF1D | 71 kDa | 6 | 32 | 3 | 4 |
| Isoform 2 of Inverted formin-2 OS = Homo sapiens OX = 9606 GN = INF2 | 135 kDa | 6 | 4 | 0 | 1 |
| Isoform 2 of Programmed cell death 6-interacting protein OS = Homo sapiens OX = 9606 GN = PDCD6IP | 97 kDa | 6 | 3 | 0 | 4 |
| Isoform 2 of Surfeit locus protein 4 OS = Homo sapiens OX = 9606 GN = SURF4 | 18 kDa | 6 | 10 | 3 | 7 |
| Isoform 3 of Plasminogen activator inhibitor 1 RNA-binding protein OS = Homo sapiens OX = 9606 GN = SERBP1 | 43 kDa | 6 | 11 | 6 | 7 |
| Isoform 5 of Phosphatidylinositol-binding clathrin assembly protein OS = Homo sapiens GN = PICALM | 70 kDa | 6 | 5 | 0 | 7 |
| Junction plakoglobin OS = Homo sapiens OX = 9606 GN = JUP PE = 1 SV = 3 | 82 kDa | 6 | 38 | 0 | 6 |
| Lamina-associated polypeptide 2, isoforms beta/gamma OS = Homo sapiens OX = 9606 GN = TMPO PE = 1 SV = 2 | 51 kDa | 6 | 26 | 7 | 7 |
| Leucine-rich repeat-containing protein 59 OS = Homo sapiens OX = 9606 GN = LRRC59 PE = 1 SV = 1 | 35 kDa | 6 | 0 | 7 | 10 |
| Multifunctional protein ADE2 OS = Homo sapiens OX = 9606 GN = PAICS PE = 1 SV = 3 | 47 kDa | 6 | 3 | 0 | 2 |
| Nicotinamide N-methyltransferase OS = Homo sapiens OX = 9606 GN = NNMT PE = 1 SV = 1 | 30 kDa | 6 | 0 | 0 | 1 |
| Poly [ADP-ribose] polymerase 4 OS = Homo sapiens OX = 9606 GN = PARP4 PE = 1 SV = 3 | 193 kDa | 6 | 19 | 0 | 5 |
| Protein S100-A6 OS = Homo sapiens OX = 9606 GN = S100A6 PE = 1 SV = 1 | 10 kDa | 6 | 0 | 1 | 4 |
| RuvB-like 2 OS = Homo sapiens OX = 9606 GN = RUVBL2 PE = 1 SV = 3 | 51 kDa | 6 | 19 | 0 | 5 |
| Sarcoplasmic/endoplasmic reticulum calcium ATPase 2 OS = Homo sapiens GN = ATP2A2 PE = 1 SV = 1 | 115 kDa | 6 | 6 | 0 | 0 |
| Signal transducer and activator of transcription 1-alpha/beta OS = Homo sapiens OX = 9606 GN = STAT1 PE = 1 SV = 2 | 87 kDa | 6 | 15 | 1 | 5 |
| Synaptic vesicle membrane protein VAT-1 homolog OS = Homo sapiens OX = 9606 GN = VAT1 PE = 1 SV = 2 | 42 kDa | 6 | 6 | 0 | 7 |
| Ubiquitin carboxyl-terminal hydrolase OS = Homo sapiens OX = 9606 GN = UCHL1 PE = 1 SV = 1 | 27 kDa | 6 | 0 | 0 | 4 |
| Very-long-chain 3-oxoacyl-CoA reductase OS = Homo sapiens OX = 9606 GN = HSD17B12 PE = 1 SV = 2 | 34 kDa | 6 | 0 | 2 | 6 |
| 26S proteasome non-ATPase regulatory subunit 13 OS = Homo sapiens OX = 9606 GN = PSMD13 PE = 1 SV = 2 | 43 kDa | 5 | 9 | 0 | 4 |
| 26S proteasome regulatory subunit 10B OS = Homo sapiens OX = 9606 GN = PSMC6 PE = 1 SV = 1 | 44 kDa | 5 | 0 | 0 | 5 |
| 40S ribosomal protein S10 OS = Homo sapiens OX = 9606 GN = RPS10 PE = 1 SV = 1 | 19 kDa | 5 | 38 | 13 | 12 |

TABLE 2-continued

Amniotic Fluid Cell-Derived ECM (AFC-ECM) Components

| Protein | MW | Matrix A | Matrix B | Matrix C | Matrix D |
|---|---|---|---|---|---|
| 40S ribosomal protein S11 OS = Homo sapiens OX = 9606 GN = RPS11 PE = 1 SV = 3 | 18 kDa | 5 | 26 | 3 | 7 |
| 60S ribosomal protein L21 OS = Homo sapiens OX = 9606 GN = RPL21 PE = 1 SV = 2 | 19 kDa | 5 | 34 | 8 | 7 |
| 60S ribosomal protein L22 OS = Homo sapiens OX = 9606 GN = RPL22 PE = 1 SV = 2 | 15 kDa | 5 | 0 | 6 | 8 |
| 60S ribosomal protein L23a (Fragment) OS = Homo sapiens OX = 9606 GN = RPL23A PE = 1 SV = 1 | 19 kDa | 5 | 0 | 9 | 9 |
| 60S ribosomal protein L27 OS = Homo sapiens OX = 9606 GN = RPL27 PE = 1 SV = 2 | 16 kDa | 5 | 0 | 6 | 11 |
| 60S ribosomal protein L28 OS = Homo sapiens OX = 9606 GN = RPL28 PE = 1 SV = 3 | 16 kDa | 5 | 13 | 4 | 4 |
| 60S ribosomal protein L31 OS = Homo sapiens OX = 9606 GN = RPL31 PE = 1 SV = 1 | 14 kDa | 5 | 33 | 8 | 6 |
| 60S ribosomal protein L36 OS = Homo sapiens OX = 9606 GN = RPL36 PE = 1 SV = 3 | 12 kDa | 5 | 0 | 7 | 7 |
| Actin-related protein 2/3 complex subunit 3 OS = Homo sapiens OX = 9606 GN = ARPC3 PE = 1 SV = 3 | 21 kDa | 5 | 0 | 4 | 7 |
| Actin-related protein 2/3 complex subunit 4 OS = Homo sapiens OX = 9606 GN = ARPC4 PE = 1 SV = 3 | 20 kDa | 5 | 19 | 2 | 6 |
| Calpain-1 catalytic subunit OS = Homo sapiens OX = 9606 GN = CAPN1 PE = 1 SV = 1 | 82 kDa | 5 | 27 | 0 | 6 |
| Calponin-2 OS = Homo sapiens OX = 9606 GN = CNN2 PE = 1 SV = 4 | 34 kDa | 5 | 5 | 1 | 6 |
| Cathepsin D OS = Homo sapiens OX = 9606 GN = CTSD PE = 1 SV = 1 | 45 kDa | 5 | 0 | 0 | 3 |
| Cleavage and polyadenylation specificity factor subunit 5 OS = Homo sapiens OX = 9606 GN = NUDT21 PE = 1 SV = 1 | 26 kDa | 5 | 0 | 0 | 6 |
| Coatomer subunit epsilon OS = Homo sapiens GN = COPE PE = 1 SV = 3 | 34 kDa | 5 | 14 | 2 | 8 |
| Copine-3 OS = Homo sapiens OX = 9606 GN = CPNE3 PE = 1 SV = 1 | 60 kDa | 5 | 0 | 0 | 1 |
| Cytochrome c oxidase subunit 2 OS = Homo sapiens OX = 9606 GN = MT-CO2 PE = 1 SV = 1 | 26 kDa | 5 | 0 | 0 | 6 |
| DNA-(apurinic or apyrimidinic site) lyase OS = Homo sapiens OX = 9606 GN = APEX1 PE = 1 SV = 2 | 36 kDa | 5 | 8 | 0 | 3 |
| Erlin-1 OS = Homo sapiens OX = 9606 GN = ERLIN1 PE = 1 SV = 1 | 39 kDa | 5 | 0 | 0 | 4 |
| Eukaryotic translation elongation factor 1 epsilon-1 OS = Homo sapiens GN = EEF1E1 PE = 1 SV = 1 | 20 kDa | 5 | 7 | 2 | 7 |
| Eukaryotic translation initiation factor 2 subunit 1 OS = Homo sapiens OX = 9606 GN = EIF2S1 PE = 1 SV = 3 | 36 kDa | 5 | 9 | 1 | 7 |
| Eukaryotic translation initiation factor 3 subunit H OS = Homo sapiens OX = 9606 GN = EIF3H PE = 1 SV = 1 | 42 kDa | 5 | 0 | 0 | 3 |
| Heat shock 70 kDa protein 4 OS = Homo sapiens OX = 9606 GN = HSPA4 PE = 1 SV = 4 | 94 kDa | 5 | 4 | 0 | 1 |
| High mobility group protein B1 OS = Homo sapiens OX = 9606 GN = HMGB1 PE = 1 SV = 3 | 25 kDa | 5 | 0 | 0 | 3 |
| Importin-9 OS = Homo sapiens OX = 9606 GN = IPO9 PE = 1 SV = 3 | 116 kDa | 5 | 0 | 0 | 4 |
| Isoform 2 of 26S proteasome non-ATPase regulatory subunit 1 OS = Homo sapiens OX = 9606 GN = PSMD1 | 102 kDa | 5 | 10 | 0 | 3 |
| Isoform 2 of Calcium-binding mitochondrial carrier protein Aralar2 OS = Homo sapiens OX = 9606 GN = SLC25A13 | 74 kDa | 5 | 10 | 0 | 9 |
| Isoform 2 of Collagen alpha-3(VI) chain OS = Homo sapiens OX = 9606 GN = COL6A3 | 321 kDa | 5 | 0 | 1 | 1 |
| Isoform 2 of Eukaryotic translation initiation factor 3 subunit B OS = Homo sapiens OX = 9606 GN = EIF3B | 99 kDa | 5 | 5 | 0 | 6 |
| Isoform 2 of Glucose-6-phosphate isomerase OS = Homo sapiens OX = 9606 GN = GPI | 64 kDa | 5 | 4 | 0 | 2 |
| Isoform 2 of HLA class I histocompatibility antigen, A-11 alpha chain OS = Homo sapiens OX = 9606 GN = HLA-A | 41 kDa | 5 | 3 | 0 | 3 |
| Isoform 2 of Myb-binding protein 1A OS = Homo sapiens OX = 9606 GN = MYBBP1A | 149 kDa | 5 | 1 | 0 | 0 |
| Isoform 2 of Serine/arginine-rich splicing factor 2 OS = Homo sapiens OX = 9606 GN = SRSF2 | 24 kDa | 5 | 2 | 0 | 2 |
| Isoform 2 of U1 small nuclear ribonucleoprotein 70 kDa OS = Homo sapiens OX = 9606 GN = SNRNP70 | 51 kDa | 5 | 0 | 0 | 5 |
| Isoform 3 of Glutaminase kidney isoform, mitochondrial OS = Homo sapiens OX = 9606 GN = GLS | 65 kDa | 5 | 7 | 0 | 3 |

TABLE 2-continued

Amniotic Fluid Cell-Derived ECM (AFC-ECM) Components

| Protein | MW | Matrix A | Matrix B | Matrix C | Matrix D |
|---|---|---|---|---|---|
| Isoform 4 of AP-3 complex subunit delta-1 OS = Homo sapiens GN = AP3D1 | 115 kDa | 5 | 5 | 0 | 2 |
| Isoform 4 of Protein phosphatase 1 regulatory subunit 12A OS = Homo sapiens OX = 9606 GN = PPP1R12A | 109 kDa | 5 | 10 | 3 | 7 |
| Isoform Short of Eukaryotic translation initiation factor 4H OS = Homo sapiens OX = 9606 GN = EIF4H | 25 kDa | 5 | 5 | 1 | 4 |
| Lon protease homolog, mitochondrial OS = Homo sapiens GN = LONP1 PE = 1 SV = 2 | 106 kDa | 5 | 0 | 0 | 6 |
| Mannosyl-oligosaccharide glucosidase OS = Homo sapiens GN = MOGS PE = 1 SV = 5 | 92 kDa | 5 | 22 | 4 | 11 |
| Prolyl 3-hydroxylase 1 OS = Homo sapiens OX = 9606 GN = P3H1 PE = 1 SV = 2 | 83 kDa | 5 | 6 | 0 | 3 |
| Proteasome subunit alpha type-4 OS = Homo sapiens OX = 9606 GN = PSMA4 PE = 1 SV = 1 | 29 kDa | 5 | 0 | 0 | 7 |
| Protein LYRIC OS = Homo sapiens OX = 9606 GN = MTDH PE = 1 SV = 2 | 64 kDa | 5 | 10 | 6 | 9 |
| Protein/nucleic acid deglycase DJ-1 OS = Homo sapiens OX = 9606 GN = PARK7 PE = 1 SV = 2 | 20 kDa | 5 | 0 | 0 | 3 |
| Ras-related protein Rab-1A OS = Homo sapiens OX = 9606 GN = RAB1A PE = 1 SV = 3 | 23 kDa | 5 | 13 | 2 | 8 |
| Ras-related protein Rab-3B OS = Homo sapiens OX = 9606 GN = RAB3B PE = 1 SV = 2 | 25 kDa | 5 | 0 | 2 | 7 |
| Rho GDP-dissociation inhibitor 1 OS = Homo sapiens OX = 9606 GN = ARHGDIA PE = 1 SV = 3 | 23 kDa | 5 | 0 | 0 | 4 |
| Signal recognition particle subunit SRP72 OS = Homo sapiens OX = 9606 GN = SRP72 PE = 1 SV = 3 | 75 kDa | 5 | 8 | 1 | 8 |
| Small nuclear ribonucleoprotein Sm D2 OS = Homo sapiens OX = 9606 GN = SNRPD2 PE = 1 SV = 1 | 14 kDa | 5 | 11 | 0 | 5 |
| Sorting and assembly machinery component 50 homolog OS = Homo sapiens OX = 9606 GN = SAMM50 PE = 1 SV = 3 | 52 kDa | 5 | 19 | 4 | 12 |
| Src substrate cortactin OS = Homo sapiens OX = 9606 GN = CTTN PE = 1 SV = 2 | 62 kDa | 5 | 38 | 12 | 8 |
| SWI/SNF complex subunit SMARCC1 OS = Homo sapiens OX = 9606 GN = SMARCC1 PE = 1 SV = 3 | 123 kDa | 5 | 0 | 0 | 2 |
| Transcription factor BTF3 OS = Homo sapiens OX = 9606 GN = BTF3 PE = 1 SV = 1 | 22 kDa | 5 | 8 | 0 | 7 |
| Translocon-associated protein subunit delta OS = Homo sapiens OX = 9606 GN = SSR4 PE = 1 SV = 1 | 19 kDa | 5 | 0 | 2 | 4 |
| TREMBL: Q1RMK2 (Bos taurus) IGHM protein | 65 kDa | 5 | 0 | 0 | 0 |
| WD repeat-containing protein 1 OS = Homo sapiens OX = 9606 GN = WDR1 PE = 1 SV = 4 | 66 kDa | 5 | 11 | 0 | 5 |
| Zyxin OS = Homo sapiens OX = 9606 GN = ZYX PE = 1 SV = 1 | 61 kDa | 5 | 13 | 0 | 4 |
| 2-oxoglutarate dehydrogenase, mitochondrial OS = Homo sapiens OX = 9606 GN = OGDH PE = 1 SV = 3 | 116 kDa | 4 | 2 | 0 | 6 |
| 40S ribosomal protein S27-like OS = Homo sapiens OX = 9606 GN = RPS27L PE = 1 SV = 3 | 9 kDa | 4 | 0 | 1 | 1 |
| Adenosylhomocysteinase OS = Homo sapiens OX = 9606 GN = AHCY PE = 1 SV = 4 | 48 kDa | 4 | 4 | 0 | 2 |
| ADP-ribosylation factor 6 OS = Homo sapiens OX = 9606 GN = ARF6 PE = 1 SV = 2 | 20 kDa | 4 | 0 | 0 | 2 |
| Alanine--tRNA ligase, cytoplasmic OS = Homo sapiens OX = 9606 GN = AARS PE = 1 SV = 2 | 107 kDa | 4 | 0 | 0 | 2 |
| ATPase family AAA domain-containing protein 3A OS = Homo sapiens OX = 9606 GN = ATAD3A PE = 1 SV = 2 | 71 kDa | 4 | 22 | 5 | 9 |
| Coatomer subunit delta OS = Homo sapiens OX = 9606 GN = ARCN1 PE = 1 SV = 1 | 57 kDa | 4 | 10 | 0 | 5 |
| Cold-inducible RNA-binding protein OS = Homo sapiens GN = CIRBP PE = 1 SV = 1 | 19 kDa | 4 | 3 | 0 | 4 |
| Copine-1 OS = Homo sapiens OX = 9606 GN = CPNE1 PE = 1 SV = 1 | 59 kDa | 4 | 0 | 0 | 2 |
| Cytochrome b-c1 complex subunit 2, mitochondrial OS = Homo sapiens OX = 9606 GN = UQCRC2 PE = 1 SV = 3 | 48 kDa | 4 | 0 | 0 | 8 |
| DBH-like monooxygenase protein 1 OS = Homo sapiens OX = 9606 GN = MOXD1 PE = 1 SV = 1 | 70 kDa | 4 | 17 | 5 | 4 |
| EH domain-containing protein 1 OS = Homo sapiens OX = 9606 GN = EHD1 PE = 1 SV = 2 | 61 kDa | 4 | 11 | 0 | 9 |
| Eukaryotic translation initiation factor 3 subunit C OS = Homo sapiens OX = 9606 GN = EIF3C PE = 1 SV = 1 | 105 kDa | 4 | 4 | 0 | 5 |
| Eukaryotic translation initiation factor 4 gamma 2 OS = Homo sapiens GN = EIF4G2 PE = 1 SV = 1 | 102 kDa | 4 | 8 | 1 | 3 |
| Eukaryotic translation initiation factor 6 OS = Homo sapiens OX = 9606 GN = EIF6 PE = 1 SV = 1 | 27 kDa | 4 | 10 | 2 | 5 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Guanine nucleotide-binding protein G(I)/G(S)/G(T) subunit beta-1 OS = Homo sapiens OX = 9606 GN = GNB1 PE = 1 SV = 3 | 37 kDa | 4 | 12 | 3 | 4 |
| Isoform 10 of Calpastatin OS = Homo sapiens OX = 9606 GN = CAST | 82 kDa | 4 | 4 | 0 | 1 |
| Isoform 2 of 40S ribosomal protein S24 OS = Homo sapiens OX = 9606 GN = RPS24 | 15 kDa | 4 | 46 | 10 | 8 |
| Isoform 2 of Chromodomain-helicase-DNA-binding protein 4 OS = Homo sapiens GN = CHD4 | 221 kDa | 4 | 5 | 0 | 1 |
| Isoform 2 of Eukaryotic translation initiation factor 3 subunit L OS = Homo sapiens OX = 9606 GN = EIF3L | 61 kDa | 4 | 5 | 0 | 6 |
| Isoform 2 of Glucosidase 2 subunit beta OS = Homo sapiens OX = 9606 GN = PRKCSH | 59 kDa | 4 | 5 | 0 | 4 |
| Isoform 2 of Hexokinase-1 OS = Homo sapiens OX = 9606 GN = HK1 | 102 kDa | 4 | 3 | 0 | 1 |
| Isoform 2 of Isocitrate dehydrogenase [NADP], mitochondrial OS = Homo sapiens OX = 9606 GN = IDH2 | 45 kDa | 4 | 19 | 1 | 4 |
| Isoform 2 of Nodal modulator 2 OS = Homo sapiens OX = 9606 GN = NOMO2 | 134 kDa | 4 | 4 | 0 | 3 |
| Isoform 2 of Plastin-3 OS = Homo sapiens OX = 9606 GN = PLS3 | 69 kDa | 4 | 0 | 0 | 1 |
| Isoform 2 of Proteasome subunit alpha type-3 OS = Homo sapiens OX = 9606 GN = PSMA3 | 28 kDa | 4 | 6 | 0 | 4 |
| Isoform 2 of Protein SET OS = Homo sapiens GN = SET | 32 kDa | 4 | 7 | 0 | 4 |
| Isoform 2 of Splicing factor U2AF 65 kDa subunit OS = Homo sapiens OX = 9606 GN = U2AF2 | 53 kDa | 4 | 1 | 0 | 5 |
| Isoform 2 of SWI/SNF complex subunit SMARCC2 OS = Homo sapiens OX = 9606 GN = SMARCC2 | 125 kDa | 4 | 9 | 0 | 3 |
| Isoform 2 of Unconventional myosin-Ib OS = Homo sapiens OX = 9606 GN = MYO1B | 125 kDa | 4 | 16 | 0 | 0 |
| Isoform 3 of Dynactin subunit 1 OS = Homo sapiens OX = 9606 GN = DCTN1 | 137 kDa | 4 | 8 | 0 | 2 |
| Isoform 3 of Heterogeneous nuclear ribonucleoprotein A/B OS = Homo sapiens GN = HNRNPAB | 31 kDa | 4 | 10 | 2 | 6 |
| Isoform 3 of Myoferlin OS = Homo sapiens OX = 9606 GN = MYOF | 233 kDa | 4 | 6 | 0 | 1 |
| Isoform 3 of Nucleolar and coiled-body phosphoprotein 1 OS = Homo sapiens OX = 9606 GN = NOLC1 | 74 kDa | 4 | 7 | 1 | 3 |
| Isoform 4 of Inhibitor of nuclear factor kappa-B kinase-interacting protein OS = Homo sapiens OX = 9606 GN = IKBIP | 43 kDa | 4 | 11 | 2 | 5 |
| Isoform 6 of MMS19 nucleotide excision repair protein homolog OS = Homo sapiens GN = MMS19 | 108 kDa | 4 | 0 | 0 | 1 |
| Isoform Short of RNA-binding protein FUS OS = Homo sapiens OX = 9606 GN = FUS | 53 kDa | 4 | 9 | 0 | 4 |
| Microtubule-actin cross-linking factor 1, isoforms 1/2/3/5 OS = Homo sapiens OX = 9606 GN = MACF1 PE = 1 SV = 4 | 838 kDa | 4 | 2 | 0 | 0 |
| Mitochondrial carrier homolog 1 (Fragment) OS = Homo sapiens OX = 9606 GN = MTCH1 PE = 1 SV = 1 | 43 kDa | 4 | 0 | 0 | 5 |
| Nuclease-sensitive element-binding protein 1 OS = Homo sapiens OX = 9606 GN = YBX1 PE = 1 SV = 3 | 36 kDa | 4 | 0 | 7 | 9 |
| Nucleolar GTP-binding protein 1 OS = Homo sapiens OX = 9606 GN = GTPBP4 PE = 1 SV = 3 | 74 kDa | 4 | 5 | 0 | 1 |
| OCIA domain-containing protein 2 OS = Homo sapiens OX = 9606 GN = OCIAD2 PE = 1 SV = 1 | 17 kDa | 4 | 0 | 0 | 0 |
| Peroxisomal multifunctional enzyme type 2 OS = Homo sapiens GN = HSD17B4 PE = 1 SV = 3 | 80 kDa | 4 | 10 | 0 | 9 |
| Probable ATP-dependent RNA helicase DDX6 OS = Homo sapiens OX = 9606 GN = DDX6 PE = 1 SV = 2 | 54 kDa | 4 | 4 | 0 | 2 |
| Proteasome subunit alpha type-2 OS = Homo sapiens OX = 9606 GN = PSMA2 PE = 1 SV = 2 | 26 kDa | 4 | 0 | 0 | 8 |
| Proteasome subunit beta type-1 OS = Homo sapiens OX = 9606 GN = PSMB1 PE = 1 SV = 2 | 26 kDa | 4 | 0 | 0 | 6 |
| Proteasome subunit beta type-3 OS = Homo sapiens OX = 9606 GN = PSMB3 PE = 1 SV = 2 | 23 kDa | 4 | 0 | 0 | 6 |
| Proteasome subunit beta type-7 OS = Homo sapiens OX = 9606 GN = PSMB7 PE = 1 SV = 1 | 30 kDa | 4 | 0 | 0 | 6 |
| Protein arginine N-methyltransferase 1 OS = Homo sapiens GN = PRMT1 PE = 1 SV = 2 | 42 kDa | 4 | 3 | 0 | 1 |
| Ras GTPase-activating protein-binding protein 2 OS = Homo sapiens OX = 9606 GN = G3BP2 PE = 1 SV = 2 | 54 kDa | 4 | 14 | 2 | 5 |
| Ras suppressor protein 1 OS = Homo sapiens OX = 9606 GN = RSU1 PE = 1 SV = 3 | 32 kDa | 4 | 16 | 1 | 8 |

TABLE 2-continued

Amniotic Fluid Cell-Derived ECM (AFC-ECM) Components

| Protein | MW | Matrix A | Matrix B | Matrix C | Matrix D |
|---|---|---|---|---|---|
| RNA-binding protein Raly OS = Homo sapiens OX = 9606 GN = RALY PE = 1 SV = 1 | 32 kDa | 4 | 14 | 2 | 7 |
| Sideroflexin-1 OS = Homo sapiens OX = 9606GN = SFXN1 PE = 1 SV = 4 | 36 kDa | 4 | 3 | 1 | 4 |
| Sideroflexin-3 OS = Homo sapiens OX = 9606GN = SFXN3 PE = 1 SV = 3 | 36 kDa | 4 | 0 | 0 | 4 |
| Signal recognition particle 9 kDa protein OS = Homo sapiens OX = 9606 GN = SRP9 PE = 1 SV = 2 | 10 kDa | 4 | 7 | 1 | 3 |
| Splicing factor 3A subunit 1 OS = Homo sapiens OX = 9606 GN = SF3A1 PE = 1 SV = 1 | 89 kDa | 4 | 6 | 0 | 5 |
| SWISS-PROT: Q9TTE1 (Bos taurus) Endopin-1 precursor | 46 kDa | 4 | 4 | 2 | 1 |
| Thy-1 membrane glycoprotein OS = Homo sapiens OX = 9606 GN = THY1 PE = 1 SV = 2 | 18 kDa | 4 | 0 | 6 | 3 |
| Transmembrane protein 43 OS = Homo sapiens OX = 9606 GN = TMEM43 PE = 1 SV = 1 | 45 kDa | 4 | 0 | 5 | 6 |
| TREMBL: Q1A7A4 (Bos taurus) similar to complement component C5 | 189 kDa | 4 | 0 | 0 | 0 |
| Tricarboxylate transport protein, mitochondrial OS = Homo sapiens OX = 9606 GN = SLC25A1 PE = 1 SV = 2 | 34 kDa | 4 | 2 | 0 | 3 |
| U2 small nuclear ribonucleoprotein A' OS = Homo sapiens OX = 9606 GN = SNRPA1 PE = 1 SV = 2 | 28 kDa | 4 | 0 | 0 | 4 |
| Vasodilator-stimulated phosphoprotein OS = Homo sapiens OX = 9606 GN = VASP PE = 1 SV = 3 | 40 kDa | 4 | 10 | 0 | 10 |
| (Bos taurus) 47 kDa protein | 47 kDa | 3 | 0 | 0 | 0 |
| (Bos taurus) similar to Complement C4-A precursor | 193 kDa | 3 | 7 | 4 | 4 |
| 26S proteasome non-ATPase regulatory subunit 5 OS = Homo sapiens OX = 9606 GN = PSMD5 PE = 1 SV = 3 | 56 kDa | 3 | 4 | 0 | 1 |
| 26S proteasome non-ATPase regulatory subunit 7 OS = Homo sapiens OX = 9606 GN = PSMD7 PE = 1 SV = 2 | 37 kDa | 3 | 10 | 0 | 6 |
| 26S proteasome regulatory subunit 7 OS = Homo sapiens OX = 9606 GN = PSMC2 PE = 1 SV = 3 | 49 kDa | 3 | 4 | 0 | 4 |
| 39S ribosomal protein L28, mitochondrial OS = Homo sapiens OX = 9606 GN = MRPL28 PE = 1 SV = 4 | 30 kDa | 3 | 0 | 0 | 1 |
| 40S ribosomal protein S15a OS = Homo sapiens OX = 9606 GN = RPS15A PE = 1 SV = 2 | 15 kDa | 3 | 0 | 2 | 3 |
| 60S ribosomal protein L15 OS = Homo sapiens OX = 9606 GN = RPL15 PE = 1 SV = 2 | 24 kDa | 3 | 27 | 3 | 11 |
| Acetyl-CoA acetyltransferase, mitochondrial OS = Homo sapiens OX = 9606 GN = ACAT1 PE = 1 SV = 1 | 45 kDa | 3 | 11 | 0 | 5 |
| ATP synthase F(0) complex subunit B1, mitochondrial OS = Homo sapiens OX = 9606 GN = ATP5PB PE = 1 SV = 2 | 29 kDa | 3 | 0 | 0 | 2 |
| ATP-binding cassette sub-family D member 3 OS = Homo sapiens OX = 9606 GN = ABCD3 PE = 1 SV = 1 | 75 kDa | 3 | 8 | 2 | 2 |
| Calponin-3 OS = Homo sapiens OX = 9606 GN = CNN3 PE = 1 SV = 1 | 36 kDa | 3 | 4 | 1 | 6 |
| Cell surface glycoprotein MUC18 OS = Homo sapiens OX = 9606 GN = MCAM PE = 1 SV = 2 | 72 kDa | 3 | 3 | 0 | 6 |
| CTP synthase 1 OS = Homo sapiens OX = 9606 GN = CTPS1 PE = 1 SV = 2 | 67 kDa | 3 | 0 | 0 | 0 |
| Cytoplasmic dynein 1 light intermediate chain 1 OS = Homo sapiens OX = 9606 GN = DYNC1LI1 PE = 1 SV = 3 | 57 kDa | 3 | 11 | 0 | 4 |
| Cytoplasmic FMR1-interacting protein 1 OS = Homo sapiens OX = 9606 GN = CYFIP1 PE = 1 SV = 1 | 145 kDa | 3 | 2 | 0 | 0 |
| Desmoglein-2 OS = Homo sapiens OX = 9606 GN = DSG2 PE = 1 SV = 2 | 122 kDa | 3 | 17 | 5 | 7 |
| Desmoplakin OS = Homo sapiens OX = 9606 GN = DSP PE = 1 SV = 3 | 332 kDa | 3 | 35 | 0 | 0 |
| Dihydrolipoyllysine-residue acetyltransferase component of pyruvate dehydrogenase complex, mitochondrial OS = Homo sapiens OX = 9606 GN = DLAT PE = 1 SV = 3 | 69 kDa | 3 | 0 | 2 | 10 |
| DnaJ homolog subfamily A member 2 OS = Homo sapiens OX = 9606 GN = DNAJA2 PE = 1 SV = 1 | 46 kDa | 3 | 0 | 1 | 6 |
| Dynein light chain Tctex-type 1 OS = Homo sapiens OX = 9606 GN = DYNLT1 PE = 1 SV = 1 | 12 kDa | 3 | 13 | 3 | 5 |
| E3 ubiquitin/ISG15 ligase TRIM25 OS = Homo sapiens OX = 9606 GN = TRIM25 PE = 1 SV = 2 | 71 kDa | 3 | 0 | 0 | 1 |
| EGF-like repeat and discoidin I-like domain-containing protein 3 OS = Homo sapiens OX = 9606 GN = EDIL3 PE = 1 SV = 1 | 54 kDa | 3 | 26 | 1 | 7 |
| Enoyl-CoA hydratase, mitochondrial OS = Homo sapiens OX = 9606 GN = ECHS1 PE = 1 SV = 4 | 31 kDa | 3 | 0 | 0 | 2 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Epidermal growth factor receptor kinase substrate 8-like protein 2 OS = Homo sapiens OX = 9606 GN = EPS8L2 PE = 1 SV = 2 | 81 kDa | 3 | 4 | 0 | 5 |
| ER lumen protein-retaining receptor 1 OS = Homo sapiens OX = 9606 GN = KDELR1 PE = 1 SV = 1 | 25 kDa | 3 | 0 | 2 | 1 |
| Eukaryotic translation initiation factor 2 subunit 2 OS = Homo sapiens OX = 9606 GN = EIF2S2 PE = 1 SV = 2 | 38 kDa | 3 | 0 | 7 | 10 |
| General transcription factor II-I OS = Homo sapiens OX = 9606 GN = GTF2I PE = 1 SV = 2 | 112 kDa | 3 | 27 | 3 | 3 |
| High mobility group protein HMGI-C OS = Homo sapiens GN = HMGA2 PE = 1 SV = 1 | 12 kDa | 3 | 48 | 3 | 0 |
| Inosine-5'-monophosphate dehydrogenase 2 OS = Homo sapiens OX = 9606 GN = IMPDH2 PE = 1 SV = 2 | 56 kDa | 3 | 0 | 0 | 2 |
| Isoform 1 of Apoptosis inhibitor 5 OS = Homo sapiens OX = 9606 GN = API5 | 49 kDa | 3 | 5 | 0 | 3 |
| Isoform 12 of Titin OS = Homo sapiens OX = 9606 GN = TTN | 3994 kDa | 3 | 1 | 3 | 3 |
| Isoform 2 of 3-hydroxyacyl-CoA dehydrogenase type-2 OS = Homo sapiens OX = 9606 GN = HSD17B10 | 26 kDa | 3 | 2 | 0 | 1 |
| Isoform 2 of ATP-dependent RNA helicase DDX54 OS = Homo sapiens OX = 9606 GN = DDX54 | 99 kDa | 3 | 1 | 0 | 3 |
| Isoform 2 of B-cell receptor-associated protein 31 OS = Homo sapiens OX = 9606 GN = BCAP31 | 35 kDa | 3 | 1 | 4 | 7 |
| Isoform 2 of Calcium-binding mitochondrial carrier protein SCaMC-1 OS = Homo sapiens OX = 9606 GN = SLC25A24 | 51 kDa | 3 | 1 | 0 | 5 |
| Isoform 2 of Collagen alpha-1(V) chain OS = Homo sapiens OX = 9606 GN = COL5A1 | 184 kDa | 3 | 0 | 13 | 6 |
| Isoform 2 of E3 ubiquitin-protein ligase UBR4 OS = Homo sapiens OX = 9606 GN = UBR4 | 576 kDa | 3 | 0 | 0 | 1 |
| Isoform 2 of Importin-4 OS = Homo sapiens GN = IPO4 | 119 kDa | 3 | 0 | 0 | 0 |
| Isoform 2 of Insulin-like growth factor 2 mRNA-binding protein 2 OS = Homo sapiens GN = IGF2BP2 | 62 kDa | 3 | 19 | 2 | 5 |
| Isoform 2 of NADH dehydrogenase [ubiquinone] 1 alpha subcomplex subunit 10, mitochondrial OS = Homo sapiens OX = 9606 GN = NDUFA10 | 49 kDa | 3 | 0 | 0 | 2 |
| Isoform 2 of NADH-cytochrome b5 reductase 3 OS = Homo sapiens OX = 9606 GN = CYB5R3 | 32 kDa | 3 | 6 | 0 | 3 |
| Isoform 2 of Nuclear pore complex protein Nup107 OS = Homo sapiens OX = 9606 GN = NUP107 | 103 kDa | 3 | 1 | 0 | 0 |
| Isoform 2 of Protein Dok-7 OS = Homo sapiens OX = 9606 GN = DOK7 | 37 kDa | 3 | 0 | 2 | 5 |
| Isoform 2 of Protein FAM98B OS = Homo sapiens OX = 9606 GN = FAM98B | 46 kDa | 3 | 9 | 0 | 4 |
| Isoform 2 of Sacsin OS = Homo sapiens OX = 9606 GN = SACS | 437 kDa | 3 | 0 | 0 | 0 |
| Isoform 2 of Serine/arginine-rich splicing factor 3 OS = Homo sapiens OX = 9606 GN = SRSF3 | 14 kDa | 3 | 8 | 0 | 4 |
| Isoform 2 of Small nuclear ribonucleoprotein Sm D3 OS = Homo sapiens OX = 9606 GN = SNRPD3 | 13 kDa | 3 | 10 | 2 | 3 |
| Isoform 2 of Stathmin OS = Homo sapiens OX = 9606 GN = STMN1 | 20 kDa | 3 | 0 | 0 | 3 |
| Isoform 2 of TP53-binding protein 1 OS = Homo sapiens OX = 9606 GN = TP53BP1 | 214 kDa | 3 | 4 | 0 | 0 |
| Isoform 2 of Very long-chain specific acyl-CoA dehydrogenase, mitochondrial OS = Homo sapiens OX = 9606 GN = ACADVL | 68 kDa | 3 | 10 | 0 | 5 |
| Isoform 2 of Voltage-dependent anion-selective channel protein 3 OS = Homo sapiens OX = 9606 GN = VDAC3 | 31 kDa | 3 | 15 | 0 | 5 |
| Isoform 2 of V-type proton ATPase catalytic subunit A OS = Homo sapiens OX = 9606 GN = ATP6V1A | 65 kDa | 3 | 15 | 1 | 2 |
| Isoform 3 of 4F2 cell-surface antigen heavy chain OS = Homo sapiens GN = SLC3A2 | 62 kDa | 3 | 1 | 1 | 1 |
| Isoform 3 of Aldehyde dehydrogenase family 16 member A1 OS = Homo sapiens OX = 9606 GN = ALDH16A1 | 80 kDa | 3 | 0 | 0 | 1 |
| Isoform 3 of Drebrin OS = Homo sapiens GN = DBN1 | 76 kDa | 3 | 31 | 4 | 3 |
| Isoform 3 of Erbin OS = Homo sapiens OX = 9606 GN = ERBIN | 153 kDa | 3 | 0 | 0 | 0 |
| Isoform 3 of Nucleoside diphosphate kinase B OS = Homo sapiens GN = NME2 | 30 kDa | 3 | 12 | 0 | 7 |
| Isoform 3 of Perilipin-3 OS = Homo sapiens OX = 9606 GN = PLIN3 | 47 kDa | 3 | 1 | 0 | 3 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform 3 of SUN domain-containing protein 2 OS = Homo sapiens OX = 9606 GN = SUN2 | 80 kDa | 3 | 15 | 4 | 12 |
| Isoform 3 of Transportin-3 OS = Homo sapiens OX = 9606 GN = TNPO3 | 103 kDa | 3 | 0 | 0 | 0 |
| Isoform 4 of 26S proteasome non-ATPase regulatory subunit 6 OS = Homo sapiens OX = 9606 GN = PSMD6 | 52 kDa | 3 | 17 | 0 | 2 |
| Isoform 9 of Protein transport protein Sec31A OS = Homo sapiens GN = SEC31A | 131 kDa | 3 | 3 | 0 | 1 |
| Isoform K of Kinesin light chain 1 OS = Homo sapiens OX = 9606 GN = KLC1 | 70 kDa | 3 | 2 | 0 | 2 |
| MICOS complex subunit MIC19 OS = Homo sapiens OX = 9606 GN = CHCHD3 PE = 1 SV = 1 | 26 kDa | 3 | 0 | 3 | 6 |
| Nuclear pore complex protein Nup205 OS = Homo sapiens OX = 9606 GN = NUP205 PE = 1 SV = 3 | 228 kDa | 3 | 0 | 0 | 0 |
| Nuclear pore complex protein Nup93 OS = Homo sapiens OX = 9606 GN = NUP93 PE = 1 SV = 2 | 93 kDa | 3 | 6 | 0 | 3 |
| PC4 and SFRS1-interacting protein OS = Homo sapiens OX = 9606 GN = PSIP1 PE = 1 SV = 1 | 60 kDa | 3 | 16 | 1 | 5 |
| Peroxiredoxin-6 OS = Homo sapiens OX = 9606 GN = PRDX6 PE = 1 SV = 3 | 25 kDa | 3 | 0 | 0 | 0 |
| PRA1 family protein 3 OS = Homo sapiens OX = 9606 GN = ARL6IP5 PE = 1 SV = 1 | 22 kDa | 3 | 7 | 1 | 4 |
| Proliferating cell nuclear antigen OS = Homo sapiens OX = 9606 GN = PCNA PE = 1 SV = 1 | 29 kDa | 3 | 0 | 0 | 0 |
| Proliferation-associated protein 2G4 OS = Homo sapiens OX = 9606 GN = PA2G4 PE = 1 SV = 3 | 44 kDa | 3 | 16 | 0 | 6 |
| Proteasome adapter and scaffold protein ECM29 OS = Homo sapiens OX = 9606 GN = ECPAS PE = 1 SV = 2 | 204 kDa | 3 | 0 | 0 | 2 |
| Proteasome subunit beta type-4 OS = Homo sapiens OX = 9606 GN = PSMB4 PE = 1 SV = 4 | 29 kDa | 3 | 0 | 0 | 4 |
| Proteasome subunit beta type-6 OS = Homo sapiens OX = 9606 GN = PSMB6 PE = 1 SV = 4 | 25 kDa | 3 | 0 | 0 | 3 |
| Protein DEK OS = Homo sapiens OX = 9606 GN = DEK PE = 1 SV = 1 | 43 kDa | 3 | 2 | 0 | 2 |
| Protein S 100-A11 OS = Homo sapiens OX = 9606 GN = S100A11 PE = 1 SV = 2 | 12 kDa | 3 | 0 | 0 | 2 |
| Protein transport protein Sec61 subunit beta OS = Homo sapiens OX = 9606 GN = SEC61B PE = 1 SV = 2 | 10 kDa | 3 | 1 | 2 | 2 |
| Puromycin-sensitive aminopeptidase OS = Homo sapiens GN = NPEPPS PE = 1 SV = 2 | 103 kDa | 3 | 0 | 0 | 2 |
| Ras-related protein Rab-11B OS = Homo sapiens OX = 9606 GN = RAB11B PE = 1 SV = 4 | 24 kDa | 3 | 9 | 1 | 6 |
| Ras-related protein Rab-14 OS = Homo sapiens OX = 9606 GN = RAB14 PE = 1 SV = 4 | 24 kDa | 3 | 0 | 0 | 6 |
| Ras-related protein Rap-1b OS = Homo sapiens OX = 9606 GN = RAP1B PE = 1 SV = 1 | 21 kDa | 3 | 7 | 2 | 3 |
| Ras-related protein R-Ras OS = Homo sapiens OX = 9606 GN = RRAS PE = 1 SV = 1 | 23 kDa | 3 | 0 | 0 | 2 |
| RNA transcription, translation and transport factor protein OS = Homo sapiens OX = 9606 GN = RTRAF PE = 1 SV = 1 | 28 kDa | 3 | 0 | 4 | 6 |
| SAP domain-containing ribonucleoprotein OS = Homo sapiens OX = 9606 GN = SARNP PE = 1 SV = 3 | 24 kDa | 3 | 0 | 0 | 2 |
| SWISS-PROT: P06868 (Bos taurus) Plasminogen precursor | 91 kDa | 3 | 1 | 5 | 0 |
| SWISS-PROT: P41361 (Bos taurus) Antithrombin-III precursor | 52 kDa | 3 | 3 | 0 | 0 |
| TAR DNA-binding protein 43 OS = Homo sapiens OX = 9606 GN = TARDBP PE = 1 SV = 1 | 45 kDa | 3 | 2 | 0 | 3 |
| Thioredoxin reductase 1, cytoplasmic OS = Homo sapiens GN = TXNRD1 PE = 1 SV = 3 | 71 kDa | 3 | 0 | 0 | 1 |
| Thrombospondin type-1 domain-containing protein 4 OS = Homo sapiens OX = 9606 GN = THSD4 PE = 2 SV = 2 | 112 kDa | 3 | 22 | 10 | 1 |
| TREMBL: Q2KJF1 (Bos taurus) Alpha-1-Bglycoprotein | 54 kDa | 3 | 11 | 1 | 3 |
| tRNA-splicing ligase RtcB homolog OS = Homo sapiens OX = 9606 GN = RTCB PE = 1 SV = 1 | 55 kDa | 3 | 19 | 3 | 9 |
| Tyrosine--tRNA ligase, cytoplasmic OS = Homo sapiens OX = 9606 GN = YARS PE = 1 SV = 4 | 59 kDa | 3 | 0 | 0 | 2 |
| Ubiquitin thioesterase OTUB1 OS = Homo sapiens OX = 9606 GN = OTUB1 PE = 1 SV = 2 | 31 kDa | 3 | 0 | 0 | 1 |
| Vigilin OS = Homo sapiens OX = 9606 GN = HDLBP PE = 1 SV = 2 | 141 kDa | 3 | 9 | 0 | 2 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| V-type proton ATPase 116 kDa subunit a isoform 3 OS = Homo sapiens OX = 9606 GN = TCIRG1 PE = 1 SV = 3 | 93 kDa | 3 | 16 | 1 | 2 |
| WD repeat-containing protein 61 OS = Homo sapiens OX = 9606 GN = WDR61 PE = 1 SV = 1 | 34 kDa | 3 | 0 | 1 | 4 |
| 39S ribosomal protein L41, mitochondrial OS = Homo sapiens OX = 9606 GN = MRPL41 PE = 1 SV = 1 | 15 kDa | 2 | 0 | 0 | 5 |
| 40S ribosomal protein S25 OS = Homo sapiens OX = 9606 GN = RPS25 PE = 1 SV = 1 | 14 kDa | 2 | 0 | 8 | 7 |
| 60S acidic ribosomal protein P1 OS = Homo sapiens OX = 9606 GN = RPLP1 PE = 1 SV = 1 | 12 kDa | 2 | 13 | 3 | 5 |
| Actin-like protein 6A OS = Homo sapiens OX = 9606 GN = ACTL6A PE = 1 SV = 1 | 47 kDa | 2 | 12 | 0 | 2 |
| Actin-related protein 2/3 complex subunit 5 OS = Homo sapiens OX = 9606 GN = ARPC5 PE = 1 SV = 3 | 16 kDa | 2 | 15 | 5 | 7 |
| Actin-related protein 2/3 complex subunit 5-like protein OS = Homo sapiens OX = 9606 GN = ARPC5L PE = 1 SV = 1 | 17 kDa | 2 | 0 | 6 | 5 |
| Activated RNA polymerase II transcriptional coactivator p15 OS = Homo sapiens OX = 9606 GN = SUB1 PE = 1 SV = 3 | 14 kDa | 2 | 1 | 0 | 2 |
| Alcohol dehydrogenase [NADP(+)] OS = Homo sapiens OX = 9606 GN = AKR1A1 PE = 1 SV = 3 | 37 kDa | 2 | 0 | 0 | 1 |
| Aspartyl/asparaginyl beta-hydroxylase OS = Homo sapiens OX = 9606 GN = ASPH PE = 1 SV = 3 | 86 kDa | 2 | 4 | 1 | 3 |
| ATP synthase subunit f, mitochondrial OS = Homo sapiens OX = 9606 GN = ATP5MF PE = 1 SV = 1 | 11 kDa | 2 | 0 | 2 | 2 |
| ATP-binding cassette sub-family B member 6, mitochondrial (Fragment) OS = Homo sapiens OX = 9606 GN = ABCB6 PE = 1 SV = 1 | 78 kDa | 2 | 0 | 0 | 0 |
| Catenin delta-1 OS = Homo sapiens OX = 9606 GN = CTNND1 PE = 1 SV = 1 | 108 kDa | 2 | 13 | 0 | 1 |
| Cathepsin B OS = Homo sapiens OX = 9606 GN = CTSB PE = 1 SV = 3 | 38 kDa | 2 | 0 | 0 | 0 |
| Caveolin-1 OS = Homo sapiens OX = 9606 GN = CAV1 PE = 1 SV = 4 | 20 kDa | 2 | 11 | 2 | 4 |
| Cell cycle and apoptosis regulator protein 2 OS = Homo sapiens GN = CCAR2 PE = 1 SV = 2 | 103 kDa | 2 | 1 | 0 | 4 |
| Centromere protein V OS = Homo sapiens OX = 9606 GN = CENPV PE = 1 SV = 1 | 30 kDa | 2 | 3 | 0 | 1 |
| Citrate synthase OS = Homo sapiens OX = 9606 GN = CS PE = 1 SV = 1 | 50 kDa | 2 | 0 | 0 | 3 |
| Cytochrome b-c1 complex subunit 1, mitochondrial OS = Homo sapiens OX = 9606 GN = UQCRC1 PE = 1 SV = 3 | 53 kDa | 2 | 0 | 0 | 1 |
| Cytochrome c oxidase subunit 7A2, mitochondrial OS = Homo sapiens OX = 9606 GN = COX7A2 PE = 1 SV = 1 | 9 kDa | 2 | 0 | 0 | 1 |
| Dystonin OS = Homo sapiens OX = 9606 GN = DST PE = 1 SV = 4 | 861 kDa | 2 | 0 | 0 | 0 |
| EH domain-containing protein 2 OS = Homo sapiens OX = 9606 GN = EHD2 PE = 1 SV = 2 | 61 kDa | 2 | 2 | 0 | 3 |
| Enhancer of mRNA-decapping protein 4 OS = Homo sapiens GN = EDC4 PE = 1 SV = 1 | 152 kDa | 2 | 0 | 0 | 0 |
| Eukaryotic translation initiation factor 5B OS = Homo sapiens OX = 9606 GN = EIF5B PE = 1 SV = 4 | 139 kDa | 2 | 0 | 0 | 2 |
| Exosome RNA helicase MTR4 OS = Homo sapiens OX = 9606 GN = MTREX PE = 1 SV = 3 | 118 kDa | 2 | 0 | 0 | 1 |
| Far upstream element-binding protein 2 OS = Homo sapiens OX = 9606 GN = KHSRP PE = 1 SV = 4 | 73 kDa | 2 | 0 | 0 | 0 |
| Ferritin heavy chain OS = Homo sapiens OX = 9606 GN = FTH1 PE = 1 SV = 2 | 21 kDa | 2 | 0 | 0 | 1 |
| FH2 domain-containing protein 1 OS = Homo sapiens OX = 9606 GN = FHDC1 PE = 1 SV = 2 | 125 kDa | 2 | 0 | 0 | 0 |
| Glutaredoxin-3 OS = Homo sapiens OX = 9606 GN = GLRX3 PE = 1 SV = 2 | 37 kDa | 2 | 0 | 0 | 0 |
| GTP-binding protein SAR1a OS = Homo sapiens OX = 9606 GN = SAR1A PE = 1 SV = 1 | 22 kDa | 2 | 0 | 0 | 3 |
| Guanine nucleotide-binding protein G(I)/G(S)/G(T) subunit beta-2 OS = Homo sapiens OX = 9606 GN = GNB2 PE = 1 SV = 3 | 37 kDa | 2 | 14 | 0 | 0 |
| Heterogeneous nuclear ribonucleoprotein U-like protein 2 OS = Homo sapiens OX = 9606 GN = HNRNPUL2 PE = 1 SV = 1 | 85 kDa | 2 | 8 | 0 | 2 |
| High mobility group protein B3 OS = Homo sapiens OX = 9606 GN = HMGB3 PE = 1 SV = 4 | 23 kDa | 2 | 0 | 0 | 3 |

TABLE 2-continued

Amniotic Fluid Cell-Derived ECM (AFC-ECM) Components

| Protein | MW | Matrix A | Matrix B | Matrix C | Matrix D |
|---|---|---|---|---|---|
| Inversin OS = Homo sapiens OX = 9606 GN = INVS PE = 1 SV = 2 | 118 kDa | 2 | 0 | 0 | 0 |
| Isoform 10 of CD44 antigen OS = Homo sapiens OX = 9606 GN = CD44 | 53 kDa | 2 | 27 | 5 | 2 |
| Isoform 2 of 40S ribosomal protein S20 OS = Homo sapiens OX = 9606 GN = RPS20 | 16 kDa | 2 | 7 | 1 | 3 |
| Isoform 2 of AP-2 complex subunit alpha-2 OS = Homo sapiens OX = 9606 GN = AP2A2 | 104 kDa | 2 | 8 | 0 | 3 |
| Isoform 2 of ATP-binding cassette sub-family F member 1 OS = Homo sapiens OX = 9606 GN = ABCF1 | 92 kDa | 2 | 6 | 2 | 2 |
| Isoform 2 of cAMP-dependent protein kinase type II-alpha regulatory subunit OS = Homo sapiens OX = 9606 GN = PRKAR2A | 43 kDa | 2 | 11 | 0 | 3 |
| Isoform 2 of Chromatin target of PRMT1 protein OS = Homo sapiens OX = 9606 GN = CHTOP | 27 kDa | 2 | 4 | 2 | 2 |
| Isoform 2 of Collagen alpha-1(XXII) chain OS = Homo sapiens OX = 9606 GN = COL22A1 | 159 kDa | 2 | 0 | 0 | 1 |
| Isoform 2 of DNA repair protein RAD50 OS = Homo sapiens OX = 9606 GN = RAD50 | 155 kDa | 2 | 0 | 0 | 1 |
| Isoform 2 of E3 ubiquitin-protein ligase RNF213 OS = Homo sapiens OX = 9606 GN = RNF213 | 596 kDa | 2 | 0 | 0 | 1 |
| Isoform 2 of Electron transfer flavoprotein subunit alpha, mitochondrial OS = Homo sapiens OX = 9606 GN = ETFA | 30 kDa | 2 | 1 | 0 | 5 |
| Isoform 2 of Enoyl-CoA delta isomerase 2, mitochondrial OS = Homo sapiens OX = 9606 GN = ECI2 | 40 kDa | 2 | 0 | 0 | 0 |
| Isoform 2 of Eukaryotic peptide chain release factor subunit 1 OS = Homo sapiens OX = 9606 GN = ETF1 | 45 kDa | 2 | 2 | 0 | 2 |
| Isoform 2 of Eukaryotic translation initiation factor 3 subunit D OS = Homo sapiens OX = 9606 GN = EIF3D | 58 kDa | 2 | 2 | 0 | 0 |
| Isoform 2 of Fermitin family homolog 2 OS = Homo sapiens OX = 9606 GN = FERMT2 | 72 kDa | 2 | 0 | 0 | 6 |
| Isoform 2 of Glutamine--fructose-6-phosphate aminotransferase [isomerizing] 1 OS = Homo sapiens OX = 9606 GN = GFPT1 | 77 kDa | 2 | 5 | 0 | 1 |
| Isoform 2 of Guanine nucleotide-binding protein-like 3 OS = Homo sapiens OX = 9606 GN = GNL3 | 61 kDa | 2 | 3 | 0 | 0 |
| Isoform 2 of Histidine--tRNA ligase, cytoplasmic OS = Homo sapiens OX = 9606 GN = HARS | 53 kDa | 2 | 3 | 0 | 4 |
| Isoform 2 of Histone H1.0 OS = Homo sapiens OX = 9606 GN = H1F0 | 19 kDa | 2 | 1 | 3 | 3 |
| Isoform 2 of Interferon-induced, double-stranded RNA-activated protein kinase OS = Homo sapiens OX = 9606 GN = EIF2AK2 | 57 kDa | 2 | 1 | 0 | 1 |
| Isoform 2 of Neurotrimin OS = Homo sapiens OX = 9606 GN = NTM | 38 kDa | 2 | 0 | 0 | 0 |
| Isoform 2 of Neutral cholesterol ester hydrolase 1 OS = Homo sapiens OX = 9606 GN = NCEH1 | 47 kDa | 2 | 1 | 0 | 3 |
| Isoform 2 of Nucleosome assembly protein 1-like 1 OS = Homo sapiens OX = 9606 GN = NAP1L1 | 43 kDa | 2 | 10 | 1 | 3 |
| Isoform 2 of Nucleosome assembly protein 1-like 4 OS = Homo sapiens OX = 9606 GN = NAP1L4 | 44 kDa | 2 | 0 | 0 | 3 |
| Isoform 2 of Polyadenylate-binding protein 2 OS = Homo sapiens OX = 9606 GN = PABPN1 | 31 kDa | 2 | 7 | 0 | 2 |
| Isoform 2 of Pre-mRNA-splicing factor SYF2 OS = Homo sapiens OX = 9606 GN = SYF2 | 24 kDa | 2 | 0 | 0 | 3 |
| Isoform 2 of Procollagen-lysine,2-oxoglutarate 5-dioxygenase 1 OS = Homo sapiens OX = 9606 GN = PLOD1 | 88 kDa | 2 | 12 | 0 | 1 |
| Isoform 2 of Procollagen-lysine,2-oxoglutarate 5-dioxygenase 2 OS = Homo sapiens OX = 9606 GN = PLOD2 | 87 kDa | 2 | 2 | 0 | 0 |
| Isoform 2 of Protein enabled homolog OS = Homo sapiens OX = 9606 GN = ENAH | 64 kDa | 2 | 26 | 1 | 18 |
| Isoform 2 of Protein SGT1 homolog OS = Homo sapiens OX = 9606 GN = SUGT1 | 38 kDa | 2 | 0 | 0 | 0 |
| Isoform 2 of Protein transport protein Sec16A OS = Homo sapiens OX = 9606 GN = SEC16A | 229 kDa | 2 | 0 | 0 | 1 |
| Isoform 2 of RNA-binding protein with serine-rich domain 1 OS = Homo sapiens OX = 9606 GN = RNPS1 | 32 kDa | 2 | 3 | 1 | 2 |
| Isoform 2 of Signal recognition particle subunit SRP68 OS = Homo sapiens OX = 9606 GN = SRP68 | 67 kDa | 2 | 9 | 0 | 0 |
| Isoform 2 of Syntenin-1 OS = Homo sapiens OX = 9606 GN = SDCBP | 32 kDa | 2 | 6 | 0 | 0 |
| Isoform 2 of Translocating chain-associated membrane protein 1 OS = Homo sapiens OX = 9606 GN = TRAM1 | 40 kDa | 2 | 6 | 4 | 5 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform 2 of Trifunctional enzyme subunit beta, mitochondrial OS = Homo sapiens OX = 9606 GN = HADHB | 49 kDa | 2 | 51 | 9 | 10 |
| Isoform 2 of UDP-glucose: glycoprotein glucosyltransferase 1 OS = Homo sapiens OX = 9606 GN = UGGT1 | 175 kDa | 2 | 2 | 0 | 1 |
| Isoform 3 of 28S ribosomal protein S29, mitochondrial OS = Homo sapiens GN = DAP3 | 42 kDa | 2 | 5 | 2 | 1 |
| Isoform 3 of Basic leucine zipper and W2 domain-containing protein 1 OS = Homo sapiens OX = 9606 GN = BZW1 | 51 kDa | 2 | 1 | 0 | 4 |
| Isoform 3 of E3 ubiquitin-protein ligase HUWE1 OS = Homo sapiens GN = HUWE1 | 481 kDa | 2 | 4 | 0 | 0 |
| Isoform 3 of Heterogeneous nuclear ribonucleoprotein H3 OS = Homo sapiens GN = HNRNPH3 | 32 kDa | 2 | 8 | 0 | 3 |
| Isoform 3 of Integrin-linked protein kinase OS = Homo sapiens OX = 9606 GN = ILK | 36 kDa | 2 | 0 | 0 | 2 |
| Isoform 3 of Protein virilizer homolog OS = Homo sapiens OX = 9606 GN = VIRMA | 201 kDa | 2 | 0 | 0 | 0 |
| Isoform 3 of Ubiquitin-associated protein 2-like OS = Homo sapiens OX = 9606 GN = UBAP2L | 113 kDa | 2 | 7 | 0 | 7 |
| Isoform 4 of LIM domain and actin-binding protein 1 OS = Homo sapiens OX = 9606 GN = LIMA1 | 85 kDa | 2 | 49 | 6 | 4 |
| Isoform 4 of WASH complex subunit 2C OS = Homo sapiens OX = 9606 GN = WASHC2C | 145 kDa | 2 | 0 | 0 | 0 |
| Isoform Delta 10 of Calcium/calmodulin-dependent protein kinase type II subunit delta OS = Homo sapiens OX = 9606 GN = CAMK2D | 56 kDa | 2 | 5 | 0 | 0 |
| Isoform LAMP-2B of Lysosome-associated membrane glycoprotein 2 OS = Homo sapiens OX = 9606 GN = LAMP2 | 45 kDa | 2 | 0 | 0 | 2 |
| Leucine-rich repeat flightless-interacting protein 1 OS = Homo sapiens OX = 9606 GN = LRRFIP1 PE = 1 SV = 2 | 89 kDa | 2 | 0 | 0 | 1 |
| Lysophospholipid acyltransferase 7 OS = Homo sapiens GN = MBOAT7 PE = 1 SV = 2 | 53 kDa | 2 | 2 | 0 | 0 |
| Microsomal glutathione S-transferase 3 OS = Homo sapiens OX = 9606 GN = MGST3 PE = 1 SV = 1 | 17 kDa | 2 | 1 | 1 | 2 |
| Mitochondrial import receptor subunit TOM40 homolog OS = Homo sapiens OX = 9606 GN = TOMM40 PE = 1 SV = 1 | 38 kDa | 2 | 0 | 0 | 0 |
| Mucin-19 OS = Homo sapiens OX = 9606 GN = MUC19 PE = 1 SV = 3 | 805 kDa | 2 | 0 | 0 | 0 |
| NADH dehydrogenase [ubiquinone] iron-sulfur protein 3, mitochondrial OS = Homo sapiens OX = 9606 GN = NDUFS3 PE = 1 SV = 1 | 30 kDa | 2 | 4 | 0 | 4 |
| Nascent polypeptide-associated complex subunit alpha, muscle-specific form OS = Homo sapiens OX = 9606 GN = NACA PE = 1 SV = 1 | 205 kDa | 2 | 6 | 0 | 4 |
| Nicotinamide phosphoribosyltransferase OS = Homo sapiens OX = 9606 GN = NAMPT PE = 1 SV = 1 | 56 kDa | 2 | 2 | 0 | 3 |
| Non-histone chromosomal protein HMG-14 OS = Homo sapiens OX = 9606 GN = HMGN1 PE = 1 SV = 1 | 12 kDa | 2 | 11 | 3 | 6 |
| Nucleolar protein 11 OS = Homo sapiens OX = 9606 GN = NOL11 PE = 1 SV = 1 | 81 kDa | 2 | 0 | 0 | 0 |
| Obg-like ATPase 1 OS = Homo sapiens OX = 9606 GN = OLA1 PE = 1 SV = 2 | 45 kDa | 2 | 4 | 0 | 3 |
| PDZ and LIM domain protein 5 OS = Homo sapiens GN = PDLIM5 PE = 1 SV = 5 | 64 kDa | 2 | 3 | 0 | 2 |
| Peroxiredoxin-2 OS = Homo sapiens OX = 9606 GN = PRDX2 PE = 1 SV = 5 | 22 kDa | 2 | 7 | 0 | 1 |
| Phospholipid-transporting ATPase IB OS = Homo sapiens OX = 9606 GN = ATP8A2 PE = 1 SV = 3 | 129 kDa | 2 | 0 | 2 | 0 |
| Phosphoserine aminotransferase OS = Homo sapiens OX = 9606 GN = PSAT1 PE = 1 SV = 2 | 40 kDa | 2 | 0 | 0 | 0 |
| Plasminogen activator inhibitor 1 OS = Homo sapiens OX = 9606 GN = SERPINE1 PE = 1 SV = 1 | 45 kDa | 2 | 90 | 41 | 29 |
| pre-rRNA processing protein FTSJ3 OS = Homo sapiens OX = 9606 GN = FTSJ3 PE = 1 SV = 2 | 97 kDa | 2 | 3 | 0 | 1 |
| PRKC apoptosis WT1 regulator protein OS = Homo sapiens OX = 9606 GN = PAWR PE = 1 SV = 1 | 37 kDa | 2 | 0 | 1 | 6 |
| Proteasome activator complex subunit 2 OS = Homo sapiens OX = 9606 GN = PSME2 PE = 1 SV = 4 | 27 kDa | 2 | 0 | 0 | 2 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Proteasome subunit alpha type-5 OS = Homo sapiens OX = 9606 GN = PSMA5 PE = 1 SV = 3 | 26 kDa | 2 | 2 | 0 | 2 |
| Proteasome subunit alpha type-7 OS = Homo sapiens OX = 9606 GN = PSMA7 PE = 1 SV = 1 | 28 kDa | 2 | 7 | 0 | 2 |
| Proteasome subunit beta type-2 OS = Homo sapiens OX = 9606 GN = PSMB2 PE = 1 SV = 1 | 23 kDa | 2 | 0 | 0 | 4 |
| Protein flightless-1 homolog OS = Homo sapiens OX = 9606 GN = FLII PE = 1 SV = 2 | 145 kDa | 2 | 0 | 0 | 1 |
| Protein SEC13 homolog OS = Homo sapiens OX = 9606 GN = SEC13 PE = 1 SV = 3 | 36 kDa | 2 | 4 | 0 | 4 |
| Ras-related protein Rab-5C OS = Homo sapiens OX = 9606 GN = RAB5C PE = 1 SV = 2 | 23 kDa | 2 | 7 | 0 | 3 |
| Ras-related protein Rab-7a OS = Homo sapiens OX = 9606 GN = RAB7A PE = 1 SV = 1 | 23 kDa | 2 | 0 | 0 | 2 |
| Remodeling and spacing factor 1 OS = Homo sapiens GN = RSF1 PE = 1 SV = 2 | 164 kDa | 2 | 9 | 0 | 0 |
| Serine beta-lactamase-like protein LACTB, mitochondrial OS = Homo sapiens OX = 9606 GN = LACTB PE = 1 SV = 2 | 61 kDa | 2 | 13 | 5 | 3 |
| Serine/arginine-rich splicing factor 1 OS = Homo sapiens GN = SRSF1 PE = 1 SV = 2 | 28 kDa | 2 | 7 | 0 | 2 |
| Structural maintenance of chromosomes protein 1A OS = Homo sapiens OX = 9606 GN = SMC1A PE = 1 SV = 2 | 143 kDa | 2 | 7 | 0 | 0 |
| SWISS-PROT: P02777 (Bos taurus) similar to Platelet factor 4 | 24 kDa | 2 | 3 | 3 | 3 |
| SWISS-PROT: Q2UVX4 (Bos taurus) Complement C3 precursor | 187 kDa | 2 | 7 | 6 | 4 |
| SWISS-PROT: Q95121 (Bos taurus) Pigment epithelium-derived factor precursor | 46 kDa | 2 | 0 | 3 | 3 |
| Transaldolase OS = Homo sapiens OX = 9606 GN = TALDO1 PE = 1 SV = 2 | 38 kDa | 2 | 0 | 0 | 3 |
| Translationally-controlled tumor protein OS = Homo sapiens OX = 9606 GN = TPT1 PE = 1 SV = 1 | 20 kDa | 2 | 0 | 0 | 2 |
| Translocon-associated protein subunit alpha OS = Homo sapiens OX = 9606 GN = SSR1 PE = 1 SV = 3 | 32 kDa | 2 | 5 | 3 | 5 |
| Transmembrane emp24 domain-containing protein 10 OS = Homo sapiens OX = 9606 GN = TMED10 PE = 1 SV = 2 | 25 kDa | 2 | 0 | 6 | 8 |
| Transmembrane emp24 domain-containing protein 9 OS = Homo sapiens OX = 9606 GN = TMED9 PE = 1 SV = 2 | 27 kDa | 2 | 0 | 1 | 2 |
| TREMBL: Q1RMN8 (Bos taurus) Similar to Immunoglobulin lambda-like polypeptide 1 | 25 kDa | 2 | 0 | 0 | 0 |
| Tripeptidyl-peptidase 1 OS = Homo sapiens GN = TPP1 PE = 1 SV = 2 | 61 kDa | 2 | 0 | 2 | 3 |
| 1,4-alpha-glucan-branching enzyme OS = Homo sapiens OX = 9606 GN = GBE1 PE = 1 SV = 3 | 80 kDa | 1 | 0 | 0 | 3 |
| 1-phosphatidylinositol 4,5-bisphosphate phosphodiesterase beta-3 OS = Homo sapiens GN = PLCB3 PE = 1 SV = 2 | 139 kDa | 1 | 0 | 0 | 2 |
| 28S ribosomal protein S35, mitochondrial OS = Homo sapiens GN = MRPS35 PE = 1 SV = 1 | 37 kDa | 1 | 2 | 0 | 2 |
| 40S ribosomal protein S30 OS = Homo sapiens OX = 9606 GN = FAU PE = 1 SV = 1 | 7 kDa | 1 | 0 | 3 | 2 |
| 60S ribosomal protein L11 OS = Homo sapiens OX = 9606 GN = RPL11 PE = 1 SV = 2 | 20 kDa | 1 | 18 | 1 | 3 |
| 60S ribosomal protein L35a OS = Homo sapiens OX = 9606 GN = RPL35A PE = 1 SV = 2 | 13 kDa | 1 | 0 | 2 | 2 |
| 60S ribosomal protein L37a OS = Homo sapiens OX = 9606 GN = RPL37A PE = 1 SV = 2 | 10 kDa | 1 | 0 | 5 | 5 |
| Alpha-parvin OS = Homo sapiens OX = 9606 GN = PARVA PE = 1 SV = 1 | 42 kDa | 1 | 3 | 0 | 4 |
| AT-rich interactive domain-containing protein 1A OS = Homo sapiens OX = 9606 GN = ARID1A PE = 1 SV = 3 | 242 kDa | 1 | 3 | 0 | 0 |
| Basigin OS = Homo sapiens OX = 9606 GN = BSG PE = 1 SV = 2 | 42 kDa | 1 | 3 | 0 | 1 |
| Biorientation of chromosomes in cell division protein 1-like 1 OS = Homo sapiens OX = 9606 GN = BOD1L1 PE = 1 SV = 2 | 330 kDa | 1 | 0 | 0 | 3 |
| Cell division cycle 5-like protein OS = Homo sapiens OX = 9606 GN = CDC5L PE = 1 SV = 2 | 92 kDa | 1 | 3 | 0 | 4 |
| Coactosin-like protein OS = Homo sapiens OX = 9606 GN = COTL1 PE = 1 SV = 3 | 16 kDa | 1 | 0 | 0 | 2 |
| Collagen alpha-1(III) chain OS = Homo sapiens OX = 9606 GN = COL3A1 PE = 1 SV = 4 | 139 kDa | 1 | 2 | 0 | 1 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Collagen alpha-2(I) chain OS = Homo sapiens OX = 9606 GN = COL1A2 PE = 1 SV = 7 | 129 kDa | 1 | 12 | 7 | 3 |
| Collagen alpha-2(V) chain OS = Homo sapiens OX = 9606 GN = COL5A2 PE = 1 SV = 3 | 145 kDa | 1 | 0 | 15 | 6 |
| Collagen alpha-6(VI) chain OS = Homo sapiens OX = 9606 GN = COL6A6 PE = 1 SV = 2 | 247 kDa | 1 | 0 | 3 | 2 |
| Complement component 1 Q subcomponent-binding protein, mitochondrial OS = Homo sapiens OX = 9606 GN = C1QBP PE = 1 SV = 1 | 31 kDa | 1 | 0 | 0 | 4 |
| Cysteine and glycine-rich protein 1 OS = Homo sapiens OX = 9606 GN = CSRP1 PE = 1 SV = 3 | 21 kDa | 1 | 0 | 0 | 2 |
| Cytochrome b-c1 complex subunit 9 OS = Homo sapiens OX = 9606 GN = UQCR10 PE = 1 SV = 3 | 7 kDa | 1 | 2 | 0 | 2 |
| Cytochrome c1, heme protein, mitochondrial OS = Homo sapiens OX = 9606 GN = CYC1 PE = 1 SV = 3 | 35 kDa | 1 | 0 | 0 | 3 |
| DDRGK domain-containing protein 1 OS = Homo sapiens OX = 9606 GN = DDRGK1 PE = 1 SV = 2 | 36 kDa | 1 | 0 | 1 | 2 |
| Destrin OS = Homo sapiens OX = 9606 GN = DSTN PE = 1 SV = 3 | 19 kDa | 1 | 3 | 0 | 6 |
| Dihydrolipoyl dehydrogenase, mitochondrial OS = Homo sapiens OX = 9606 GN = DLD PE = 1 SV = 2 | 54 kDa | 1 | 8 | 0 | 2 |
| DNA-directed RNA polymerases I, II, and III subunit RPABC1 OS = Homo sapiens OX = 9606 GN = POLR2E PE = 1 SV = 4 | 25 kDa | 1 | 0 | 5 | 1 |
| ELAV-like protein 1 OS = Homo sapiens OX = 9606 GN = ELAVL1 PE = 1 SV = 2 | 36 kDa | 1 | 3 | 0 | 1 |
| Eukaryotic translation initiation factor 3 subunit G OS = Homo sapiens OX = 9606 GN = EIF3G PE = 1 SV = 2 | 36 kDa | 1 | 0 | 0 | 3 |
| Farnesyl pyrophosphate synthase OS = Homo sapiens OX = 9606 GN = FDPS PE = 1 SV = 4 | 48 kDa | 1 | 3 | 0 | 1 |
| Fibrillin-1 OS = Homo sapiens OX = 9606 GN = FBN1 PE = 1 SV = 3 | 312 kDa | 1 | 0 | 2 | 0 |
| Fumarate hydratase, mitochondrial OS = Homo sapiens GN = FH PE = 1 SV = 3 | 55 kDa | 1 | 0 | 0 | 2 |
| Growth/differentiation factor 15 OS = Homo sapiens OX = 9606 GN = GDF15 PE = 1 SV = 3 | 34 kDa | 1 | 0 | 7 | 6 |
| Histone deacetylase complex subunit SAP18 OS = Homo sapiens OX = 9606 GN = SAP18 PE = 1 SV = 1 | 20 kDa | 1 | 0 | 0 | 2 |
| Histone H1x OS = Homo sapiens OX = 9606 GN = H1FX PE = 1 SV = 1 | 22 kDa | 1 | 0 | 0 | 2 |
| Hydrocephalus-inducing protein homolog OS = Homo sapiens OX = 9606 GN = HYDIN PE = 1 SV = 3 | 576 kDa | 1 | 0 | 1 | 0 |
| Insulin-like growth factor 2 mRNA-binding protein 3 OS = Homo sapiens GN = IGF2BP3 PE = 1 SV = 2 | 64 kDa | 1 | 18 | 2 | 0 |
| Isoform 2 of Adipocyte plasma membrane-associated protein OS = Homo sapiens OX = 9606 GN = APMAP | 32 kDa | 1 | 0 | 0 | 3 |
| Isoform 2 of Aspartate aminotransferase, mitochondrial OS = Homo sapiens OX = 9606 GN = GOT2 | 43 kDa | 1 | 0 | 0 | 3 |
| Isoform 2 of BH3-interacting domain death agonist OS = Homo sapiens OX = 9606 GN = BID | 27 kDa | 1 | 4 | 0 | 0 |
| Isoform 2 of DnaJ homolog subfamily A member 3, mitochondrial OS = Homo sapiens OX = 9606 GN = DNAJA3 | 50 kDa | 1 | 0 | 0 | 3 |
| Isoform 2 of Glia-derived nexin OS = Homo sapiens OX = 9606 GN = SERPINE2 | 44 kDa | 1 | 8 | 0 | 0 |
| Isoform 2 of Histone deacetylase 2 OS = Homo sapiens OX = 9606 GN = HDAC2 | 52 kDa | 1 | 4 | 0 | 1 |
| Isoform 2 of Lysosomal protective protein OS = Homo sapiens OX = 9606 GN = CTSA | 52 kDa | 1 | 1 | 0 | 2 |
| Isoform 2 of Lysosome membrane protein 2 OS = Homo sapiens OX = 9606 GN = SCARB2 | 38 kDa | 1 | 4 | 0 | 0 |
| Isoform 2 of Myosin phosphatase Rho-interacting protein OS = Homo sapiens OX = 9606 GN = MPRIP | 118 kDa | 1 | 13 | 0 | 0 |
| Isoform 2 of NADH dehydrogenase [ubiquinone] 1 alpha subcomplex subunit 13 OS = Homo sapiens OX = 9606 GN = NDUFA13 | 25 kDa | 1 | 13 | 1 | 3 |
| Isoform 2 of NADH dehydrogenase [ubiquinone] iron-sulfur protein 2, mitochondrial OS = Homo sapiens OX = 9606 GN = NDUFS2 | 52 kDa | 1 | 5 | 0 | 1 |
| Isoform 2 of Nesprin-2 OS = Homo sapiens OX = 9606 GN = SYNE2 | 799 kDa | 1 | 12 | 1 | 0 |
| Isoform 2 of Nuclear pore complex protein Nup214 OS = Homo sapiens OX = 9606 GN = NUP214 | 213 kDa | 1 | 0 | 0 | 3 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform 2 of Phenylalanine--tRNA ligase alpha subunit OS = Homo sapiens OX = 9606 GN = FARSA | 54 kDa | 1 | 7 | 1 | 4 |
| Isoform 2 of Probable 28S rRNA (cytosine(4447)-C(5))-methyltransferase OS = Homo sapiens OX = 9606 GN = NOP2 | 89 kDa | 1 | 6 | 0 | 6 |
| Isoform 2 of Protein FAM98A OS = Homo sapiens OX = 9606 GN = FAM98A | 55 kDa | 1 | 2 | 0 | 3 |
| Isoform 2 of Protein TFG OS = Homo sapiens OX = 9606 GN = TFG | 43 kDa | 1 | 4 | 0 | 4 |
| Isoform 2 of Pyruvate dehydrogenase E1 component subunit beta, mitochondrial OS = Homo sapiens OX = 9606 GN = PDHB | 37 kDa | 1 | 7 | 0 | 3 |
| Isoform 2 of UTP--glucose-1-phosphate uridylyltransferase OS = Homo sapiens OX = 9606 GN = UGP2 | 56 kDa | 1 | 3 | 0 | 7 |
| Isoform 2 of V-type proton ATPase 116 kDa subunit a isoform 1 OS = Homo sapiens OX = 9606 GN = ATP6V0A1 | 96 kDa | 1 | 11 | 0 | 3 |
| Isoform 2B of Cytoplasmic dynein 1 intermediate chain 2 OS = Homo sapiens OX = 9606 GN = DYNC1I2 | 71 kDa | 1 | 16 | 1 | 3 |
| Isoform 3 of Activating signal cointegrator 1 complex subunit 2 OS = Homo sapiens OX = 9606 GN = ASCC2 | 77 kDa | 1 | 6 | 0 | 1 |
| Isoform 3 of Apoptosis-inducing factor 1, mitochondrial OS = Homo sapiens OX = 9606 GN = AIFM1 | 66 kDa | 1 | 3 | 0 | 4 |
| Isoform 3 of Calumenin OS = Homo sapiens OX = 9606 GN = CALU | 38 kDa | 1 | 1 | 0 | 2 |
| Isoform 3 of Fragile X mental retardation syndrome-related protein 1 OS = Homo sapiens OX = 9606 GN = FXR1 | 60 kDa | 1 | 4 | 0 | 1 |
| Isoform 3 of GRB10-interacting GYF protein 2 OS = Homo sapiens OX = 9606 GN = GIGYF2 | 149 kDa | 1 | 0 | 0 | 0 |
| Isoform 3 of Pyrroline-5-carboxylate reductase 1, mitochondrial OS = Homo sapiens OX = 9606 GN = PYCR1 | 36 kDa | 1 | 8 | 0 | 0 |
| Isoform 3 of Ras-related protein R-Ras2 OS = Homo sapiens GN = RRAS2 | 20 kDa | 1 | 5 | 0 | 1 |
| Isoform 3 of Signal peptidase complex catalytic subunit SEC11A OS = Homo sapiens OX = 9606 GN = SEC11A | 21 kDa | 1 | 2 | 1 | 3 |
| Isoform 4 of Cadherin-13 OS = Homo sapiens OX = 9606 GN = CDH13 | 83 kDa | 1 | 23 | 6 | 2 |
| Isoform 4 of Dipeptidyl peptidase 3 OS = Homo sapiens OX = 9606 GN = DPP3 | 79 kDa | 1 | 0 | 0 | 2 |
| Isoform 4 of Dynamin-1-like protein OS = Homo sapiens OX = 9606 GN = DNM1L | 81 kDa | 1 | 2 | 0 | 2 |
| Isoform 4 of Dynamin-2 OS = Homo sapiens OX = 9606 GN = DNM2 | 98 kDa | 1 | 13 | 0 | 6 |
| Isoform 4 of Nexilin OS = Homo sapiens OX = 9606 GN = NEXN | 73 kDa | 1 | 28 | 12 | 7 |
| Isoform 5 of Obscurin OS = Homo sapiens OX = 9606 GN = OBSCN | 925 kDa | 1 | 0 | 0 | 1 |
| Isoform 6 of RNA-binding protein EWS OS = Homo sapiens OX = 9606 GN = EWSR1 | 63 kDa | 1 | 6 | 0 | 6 |
| Isoform Heart of ATP synthase subunit gamma, mitochondrial OS = Homo sapiens OX = 9606 GN = ATP5F1C | 33 kDa | 1 | 6 | 0 | 4 |
| Isoform Mitochondrial of Lysine--tRNA ligase OS = Homo sapiens OX = 9606 GN = KARS | 71 kDa | 1 | 4 | 0 | 1 |
| Leucine-rich repeat-containing protein 17 OS = Homo sapiens OX = 9606 GN = LRRC17 PE = 2 SV = 1 | 52 kDa | 1 | 11 | 9 | 4 |
| Leucyl-cystinyl aminopeptidase OS = Homo sapiens OX = 9606 GN = LNPEP PE = 1 SV = 3 | 117 kDa | 1 | 4 | 3 | 2 |
| LIM and SH3 domain protein 1 OS = Homo sapiens OX = 9606 GN = LASP1 PE = 1 SV = 2 | 30 kDa | 1 | 1 | 0 | 3 |
| Matrix metalloproteinase-14 OS = Homo sapiens OX = 9606 GN = MMP14 PE = 1 SV = 3 | 66 kDa | 1 | 0 | 0 | 2 |
| Microtubule-associated protein RP/EB family member 1 OS = Homo sapiens OX = 9606 GN = MAPRE1 PE = 1 SV = 3 | 30 kDa | 1 | 4 | 0 | 4 |
| Mitochondrial 2-oxoglutarate/malate carrier protein OS = Homo sapiens OX = 9606 GN = SLC25A11 PE = 1 SV = 3 | 34 kDa | 1 | 7 | 0 | 1 |
| Mitochondrial fission 1 protein OS = Homo sapiens OX = 9606 GN = FIS1 PE = 1 SV = 2 | 17 kDa | 1 | 0 | 0 | 3 |
| NADH dehydrogenase [ubiquinone] 1 alpha subcomplex subunit 12 OS = Homo sapiens OX = 9606 GN = NDUFA12 PE = 1 SV = 1 | 17 kDa | 1 | 6 | 1 | 2 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| PDZ domain-containing protein 4 OS = Homo sapiens OX = 9606 GN = PDZD4 PE = 1 SV = 1 | 86 kDa | 1 | 0 | 0 | 0 |
| Peroxisomal membrane protein PEX14 OS = Homo sapiens OX = 9606 GN = PEX14 PE = 1 SV = 1 | 41 kDa | 1 | 3 | 0 | 2 |
| Platelet-activating factor acetylhydrolase IB subunit beta OS = Homo sapiens GN = PAFAH1B2 PE = 1 SV = 1 | 26 kDa | 1 | 6 | 0 | 1 |
| Podocalyxin OS = Homo sapiens GN = PODXL PE = 1 SV = 2 | 59 kDa | 1 | 0 | 0 | 2 |
| Prolyl 3-hydroxylase 3 OS = Homo sapiens OX = 9606 GN = P3H3 PE = 1 SV = 1 | 82 kDa | 1 | 0 | 0 | 2 |
| Prolyl 4-hydroxylase subunit alpha-2 OS = Homo sapiens OX = 9606 GN = P4HA2 PE = 1 SV = 1 | 61 kDa | 1 | 2 | 0 | 0 |
| Proteasome subunit alpha type-6 OS = Homo sapiens OX = 9606 GN = PSMA6 PE = 1 SV = 1 | 27 kDa | 1 | 8 | 0 | 1 |
| Proteasome subunit beta type-5 OS = Homo sapiens GN = PSMB5 PE = 1 SV = 3 | 28 kDa | 1 | 2 | 0 | 0 |
| Protein CYR61 OS = Homo sapiens OX = 9606 GN = CYR61 PE = 1 SV = 1 | 42 kDa | 1 | 0 | 27 | 24 |
| Protein mago nashi homolog OS = Homo sapiens OX = 9606 GN = MAGOH PE = 1 SV = 1 | 17 kDa | 1 | 7 | 0 | 0 |
| RNA-binding protein 14 OS = Homo sapiens OX = 9606 GN = RBM14 PE = 1 SV = 2 | 69 kDa | 1 | 18 | 2 | 5 |
| RuvB-like 1 OS = Homo sapiens OX = 9606 GN = RUVBL1 PE = 1 SV = 1 | 50 kDa | 1 | 18 | 0 | 2 |
| Splicing factor 3B subunit 4 OS = Homo sapiens OX = 9606 GN = SF3B4 PE = 1 SV = 1 | 44 kDa | 1 | 0 | 0 | 2 |
| Splicing factor U2AF 26 kDa subunit OS = Homo sapiens OX = 9606 GN = U2AF1L4 PE = 4 SV = 1 | 4 kDa | 1 | 0 | 2 | 1 |
| SWISS-PROT: P04258 (Bos taurus) Similar to Collagen alpha 1(III) chain | 138 kDa | 1 | 9 | 0 | 0 |
| TREMBL: A2I7N3; Q27984 (Bos taurus) SERPINA3-7 | 47 kDa | 1 | 5 | 1 | 1 |
| Unconventional myosin-Ie OS = Homo sapiens OX = 9606 GN = MYO1E PE = 1 SV = 2 | 127 kDa | 1 | 20 | 5 | 4 |
| Vacuolar protein sorting-associated protein VTA1 homolog OS = Homo sapiens OX = 9606 GN = VTA1 PE = 1 SV = 1 | 34 kDa | 1 | 0 | 0 | 2 |
| Very-long-chain (3R)-3-hydroxyacyl-CoA dehydratase 3 OS = Homo sapiens GN = HACD3 PE = 1 SV = 2 | 43 kDa | 1 | 8 | 1 | 2 |
| von Willebrand factor A domain-containing protein 1 OS = Homo sapiens OX = 9606 GN = VWA1 PE = 1 SV = 1 | 47 kDa | 1 | 7 | 0 | 0 |
| (Bos taurus) 63 kDa protein | 63 kDa | 0 | 55 | 0 | 0 |
| 10 kDa heat shock protein, mitochondrial OS = Homo sapiens GN = HSPE1 PE = 1 SV = 2 | 11 kDa | 0 | 6 | 0 | 0 |
| 1-phosphatidylinositol 3-phosphate 5-kinase OS = Homo sapiens OX = 9606 GN = PIKFYVE PE = 1 SV = 3 | 237 kDa | 0 | 0 | 0 | 2 |
| 26S protease regulatory subunit 10B OS = Homo sapiens GN = PSMC6 PE = 1 SV = 1 | 46 kDa | 0 | 9 | 0 | 0 |
| 26S protease regulatory subunit 6A OS = Homo sapiens GN = PSMC3 PE = 1 SV = 3 | 49 kDa | 0 | 30 | 0 | 0 |
| 26S proteasome non-ATPase regulatory subunit 14 OS = Homo sapiens GN = PSMD14 PE = 1 SV = 1 | 35 kDa | 0 | 17 | 0 | 0 |
| 26S proteasome non-ATPase regulatory subunit 8 OS = Homo sapiens GN = PSMD8 PE = 1 SV = 1 | 33 kDa | 0 | 3 | 0 | 0 |
| 28S ribosomal protein S34, mitochondrial OS = Homo sapiens GN = MRPS34 PE = 1 SV = 2 | 26 kDa | 0 | 2 | 0 | 0 |
| 39S ribosomal protein L11, mitochondrial OS = Homo sapiens GN = MRPL11 PE = 1 SV = 1 | 21 kDa | 0 | 7 | 0 | 1 |
| 39S ribosomal protein L34, mitochondrial OS = Homo sapiens GN = MRPL34 PE = 1 SV = 1 | 20 kDa | 0 | 8 | 0 | 0 |
| 3-ketoacyl-CoA thiolase, mitochondrial OS = Homo sapiens OX = 9606 GN = ACAA2 PE = 1 SV = 2 | 42 kDa | 0 | 0 | 0 | 2 |
| 40S ribosomal protein S13 OS = Homo sapiens OX = 9606 GN = RPS13 PE = 1 SV = 2 | 17 kDa | 0 | 85 | 19 | 19 |
| 40S ribosomal protein S15a OS = Homo sapiens GN = RPS15A PE = 1 SV = 1 | 11 kDa | 0 | 25 | 0 | 0 |
| 40S ribosomal protein S18 OS = Homo sapiens GN = RPS18 PE = 1 SV = 3 | 18 kDa | 0 | 51 | 0 | 0 |
| 40S ribosomal protein S28 OS = Homo sapiens GN = RPS28 PE = 1 SV = 1 | 8 kDa | 0 | 6 | 0 | 0 |
| 40S ribosomal protein S29 OS = Homo sapiens OX = 9606 GN = RPS29 PE = 1 SV = 2 | 7 kDa | 0 | 16 | 1 | 1 |
| 40S ribosomal protein S3a OS = Homo sapiens GN = RPS3A PE = 1 SV = 2 | 30 kDa | 0 | 53 | 0 | 0 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| 40S ribosomal protein S4, Y isoform 1 OS = Homo sapiens OX = 9606 GN = RPS4Y1 PE = 1 SV = 2 | 29 kDa | 0 | 0 | 0 | 9 |
| 40S ribosomal protein SA (Fragment) OS = Homo sapiens GN = RPSA PE = 1 SV = 8 | 29 kDa | 0 | 8 | 0 | 0 |
| 60S acidic ribosomal protein P2 OS = Homo sapiens GN = RPLP2 PE = 1 SV = 1 | 12 kDa | 0 | 50 | 0 | 0 |
| 60S ribosomal protein L13a OS = Homo sapiens GN = RPL13A PE = 1 SV = 2 | 24 kDa | 0 | 33 | 0 | 0 |
| 60S ribosomal protein L14 OS = Homo sapiens GN = RPL14 PE = 1 SV = 4 | 23 kDa | 0 | 34 | 0 | 0 |
| 60S ribosomal protein L18a OS = Homo sapiens GN = RPL18A PE = 1 SV = 2 | 21 kDa | 0 | 31 | 0 | 0 |
| 60S ribosomal protein L23a (Fragment) OS = Homo sapiens GN = RPL23A PE = 1 SV = 1 | 18 kDa | 0 | 32 | 0 | 0 |
| 60S ribosomal protein L29 OS = Homo sapiens GN = RPL29 PE = 1 SV = 2 | 18 kDa | 0 | 6 | 0 | 0 |
| 60S ribosomal protein L32 (Fragment) OS = Homo sapiens GN = RPL32 PE = 1 SV = 1 | 16 kDa | 0 | 20 | 0 | 0 |
| 60S ribosomal protein L34 OS = Homo sapiens OX = 9606 GN = RPL34 PE = 1 SV = 3 | 13 kDa | 0 | 0 | 3 | 3 |
| 60S ribosomal protein L35 OS = Homo sapiens GN = RPL35 PE = 1 SV = 2 | 15 kDa | 0 | 24 | 0 | 0 |
| 60S ribosomal protein L38 OS = Homo sapiens OX = 9606 GN = RPL38 PE = 1 SV = 2 | 8 kDa | 0 | 0 | 5 | 4 |
| 78 kDa glucose-regulated protein OS = Homo sapiens GN = HSPA5 PE = 1 SV = 2 | 72 kDa | 0 | 188 | 0 | 0 |
| A disintegrin and metalloproteinase with thrombospondin motifs 1 OS = Homo sapiens OX = 9606 GN = ADAMTS1 PE = 1 SV = 4 | 105 kDa | 0 | 12 | 3 | 0 |
| Actin-related protein 10 OS = Homo sapiens GN = ACTR10 PE = 1 SV = 1 | 46 kDa | 0 | 3 | 0 | 0 |
| Actin-related protein 2/3 complex subunit 1B OS = Homo sapiens GN = ARPC1B PE = 1 SV = 3 | 41 kDa | 0 | 28 | 0 | 0 |
| ADP-ribosyl cyclase/cyclic ADP-ribose hydrolase 2 OS = Homo sapiens OX = 9606 GN = BST1 PE = 1 SV = 2 | 36 kDa | 0 | 3 | 5 | 2 |
| Aminopeptidase N OS = Homo sapiens GN = ANPEP PE = 1 SV = 4 | 110 kDa | 0 | 194 | 0 | 0 |
| Angiopoietin-related protein 4 OS = Homo sapiens OX = 9606 GN = ANGPTL4 PE = 1 SV = 2 | 45 kDa | 0 | 1 | 3 | 0 |
| Annexin A3 OS = Homo sapiens OX = 9606 GN = ANXA3 PE = 1 SV = 3 | 36 kDa | 0 | 0 | 0 | 3 |
| Annexin A4 OS = Homo sapiens OX = 9606 GN = ANXA4 PE = 1 SV = 4 | 36 kDa | 0 | 0 | 0 | 2 |
| AP-2 complex subunit sigma OS = Homo sapiens GN = AP2S1 PE = 1 SV = 1 | 19 kDa | 0 | 3 | 0 | 0 |
| Arf-GAP with Rho-GAP domain, ANK repeat and PH domain-containing protein 3 OS = Homo sapiens OX = 9606 GN = ARAP3 PE = 1 SV = 1 | 170 kDa | 0 | 0 | 0 | 2 |
| ATP synthase subunit epsilon-like protein, mitochondrial OS = Homo sapiens GN = ATP5EP2 PE = 3 SV = 1 | 6 kDa | 0 | 3 | 0 | 0 |
| ATP synthase subunit g, mitochondrial OS = Homo sapiens GN = ATP5L PE = 1 SV = 3 | 11 kDa | 0 | 6 | 0 | 0 |
| ATPase ASNA1 OS = Homo sapiens GN = ASNA1 PE = 1 SV = 2 | 39 kDa | 0 | 2 | 0 | 0 |
| ATPase, H+ transporting, lysosomal accessory protein 1, isoform CRA_c OS = Homo sapiens GN = ATP6AP1 PE = 1 SV = 1 | 32 kDa | 0 | 7 | 0 | 0 |
| ATP-dependent DNA helicase Q1 OS = Homo sapiens GN = RECQL PE = 1 SV = 3 | 73 kDa | 0 | 2 | 0 | 0 |
| Barrier-to-autointegration factor OS = Homo sapiens GN = BANF1 PE = 1 SV = 1 | 10 kDa | 0 | 24 | 0 | 0 |
| Basement membrane-specific heparan sulfate proteoglycan core protein OS = Homo sapiens GN = HSPG2 PE = 1 SV = 4 | 469 kDa | 0 | 4914 | 0 | 0 |
| Beta-catenin-like protein 1 OS = Homo sapiens GN = CTNNBL1 PE = 1 SV = 1 | 65 kDa | 0 | 2 | 0 | 0 |
| Beta-galactosidase OS = Homo sapiens GN = GLB1 PE = 1 SV = 2 | 76 kDa | 0 | 3 | 0 | 0 |
| Biglycan OS = Homo sapiens OX = 9606 GN = BGN PE = 1 SV = 2 | 42 kDa | 0 | 0 | 23 | 0 |
| Bone morphogenetic protein 1 OS = Homo sapiens OX = 9606 GN = BMP1 PE = 1 SV = 2 | 111 kDa | 0 | 14 | 3 | 0 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Brain acid soluble protein 1 OS = Homo sapiens GN = BASP1 PE = 1 SV = 2 | 23 kDa | 0 | 10 | 0 | 0 |
| C-1-tetrahydrofolate synthase, cytoplasmic OS = Homo sapiens GN = MTHFD1 PE = 1 SV = 3 | 102 kDa | 0 | 2 | 0 | 0 |
| Calmodulin OS = Homo sapiens GN = CALM1 PE = 1 SV = 2 | 17 kDa | 0 | 24 | 0 | 0 |
| Calpain small subunit 1 OS = Homo sapiens GN = CAPNS1 PE = 1 SV = 1 | 34 kDa | 0 | 34 | 0 | 0 |
| Carboxypeptidase M OS = Homo sapiens GN = CPM PE = 1 SV = 2 | 51 kDa | 0 | 5 | 0 | 0 |
| Cardiomyopathy-associated protein 5 OS = Homo sapiens GN = CMYA5 PE = 1 SV = 3 | 449 kDa | 0 | 2 | 0 | 0 |
| Casein kinase II subunit alpha OS = Homo sapiens OX = 9606 GN = CSNK2A1 PE = 1 SV = 1 | 45 kDa | 0 | 10 | 1 | 1 |
| CD2-associated protein OS = Homo sapiens GN = CD2AP PE = 1 SV = 1 | 71 kDa | 0 | 9 | 0 | 0 |
| CD59 glycoprotein OS = Homo sapiens OX = 9606 GN = CD59 PE = 1 SV = 1 | 14 kDa | 0 | 0 | 3 | 0 |
| Chloride intracellular channel protein 4 OS = Homo sapiens GN = CLIC4 PE = 1 SV = 4 | 29 kDa | 0 | 2 | 0 | 0 |
| Chloride intracellular channel protein 6 OS = Homo sapiens GN = CLIC6 PE = 2 SV = 3 | 73 kDa | 0 | 2 | 0 | 0 |
| Chromobox protein homolog 1 (Fragment) OS = Homo sapiens GN = CBX1 PE = 1 SV = 1 | 19 kDa | 0 | 5 | 0 | 0 |
| Coiled-coil domain-containing protein 124 OS = Homo sapiens GN = CCDC124 PE = 1 SV = 1 | 26 kDa | 0 | 6 | 0 | 0 |
| Coiled-coil domain-containing protein 30 OS = Homo sapiens GN = CCDC30 PE = 2 SV = 1 | 91 kDa | 0 | 2 | 0 | 0 |
| Coiled-coil-helix-coiled-coil-helix domain-containing protein 1 OS = Homo sapiens GN = CHCHD1 PE = 1 SV = 1 | 13 kDa | 0 | 2 | 0 | 0 |
| Collagen alpha-1(II) chain OS = Homo sapiens OX = 9606 GN = COL2A1 PE = 1 SV = 3 | 142 kDa | 0 | 2 | 1 | 1 |
| Collagen alpha-1(VI) chain OS = Homo sapiens GN = COL6A1 PE = 1 SV = 1 | 108 kDa | 0 | 3 | 0 | 0 |
| Collagen alpha-1(X) chain OS = Homo sapiens GN = COL10A1 PE = 1 SV = 2 | 66 kDa | 0 | 3 | 0 | 0 |
| Collagen alpha-1(XXIII) chain OS = Homo sapiens GN = COL23A1 PE = 1 SV = 1 | 52 kDa | 0 | 2 | 0 | 0 |
| Collagen alpha-1(XXVII) chain OS = Homo sapiens OX = 9606 GN = COL27A1 PE = 1 SV = 1 | 187 kDa | 0 | 1 | 0 | 2 |
| Collagen alpha-2(IX) chain OS = Homo sapiens OX = 9606 GN = COL9A2 PE = 1 SV = 2 | 65 kDa | 0 | 0 | 0 | 0 |
| Collagen triple helix repeat-containing protein 1 OS = Homo sapiens OX = 9606 GN = CTHRC1 PE = 1 SV = 1 | 26 kDa | 0 | 3 | 1 | 1 |
| Connective tissue growth factor OS = Homo sapiens OX = 9606 GN = CTGF PE = 1 SV = 2 | 38 kDa | 0 | 4 | 6 | 2 |
| COP9 signalosome complex subunit 5 OS = Homo sapiens GN = COPS5 PE = 1 SV = 4 | 38 kDa | 0 | 2 | 0 | 0 |
| Coronin-1B OS = Homo sapiens GN = CORO1B PE = 1 SV = 1 | 54 kDa | 0 | 9 | 0 | 0 |
| Cullin-1 OS = Homo sapiens GN = CUL1 PE = 1 SV = 2 | 90 kDa | 0 | 3 | 0 | 0 |
| Cytochrome c (Fragment) OS = Homo sapiens GN = CYCS PE = 1 SV = 1 | 11 kDa | 0 | 3 | 0 | 0 |
| Cytochrome c oxidase subunit 4 isoform 1, mitochondrial OS = Homo sapiens GN = COX4I1 PE = 1 SV = 1 | 20 kDa | 0 | 5 | 0 | 0 |
| Cytoplasmic aconitate hydratase OS = Homo sapiens OX = 9606 GN = ACO1 PE = 1 SV = 3 | 98 kDa | 0 | 0 | 0 | 2 |
| Cytosolic non-specific dipeptidase OS = Homo sapiens OX = 9606 GN = CNDP2 PE = 1 SV = 2 | 53 kDa | 0 | 10 | 0 | 8 |
| Death-associated protein kinase 3 OS = Homo sapiens OX = 9606 GN = DAPK3 PE = 1 SV = 1 | 53 kDa | 0 | 6 | 0 | 0 |
| Deoxyribose-phosphate aldolase OS = Homo sapiens OX = 9606 GN = DERA PE = 1 SV = 2 | 35 kDa | 0 | 0 | 0 | 3 |
| Desmoglein-1 OS = Homo sapiens GN = DSG1 PE = 1 SV = 1 | 114 kDa | 0 | 6 | 0 | 0 |
| DNA damage-binding protein 1 OS = Homo sapiens OX = 9606 GN = DDB1 PE = 1 SV = 1 | 127 kDa | 0 | 14 | 0 | 3 |
| DNA topoisomerase 1 OS = Homo sapiens GN = TOP1 PE = 1 SV = 2 | 91 kDa | 0 | 10 | 0 | 0 |
| DNA-directed RNA polymerase II subunit RPB1 OS = Homo sapiens OX = 9606 GN = POLR2A PE = 1 SV = 2 | 217 kDa | 0 | 11 | 0 | 0 |
| DNA-directed RNA polymerase II subunit RPB2 OS = Homo sapiens GN = POLR2B PE = 1 SV = 1 | 134 kDa | 0 | 14 | 0 | 0 |

TABLE 2-continued

Amniotic Fluid Cell-Derived ECM (AFC-ECM) Components

| Protein | MW | Matrix A | Matrix B | Matrix C | Matrix D |
|---|---|---|---|---|---|
| DNA-directed RNA polymerase II subunit RPB3 OS = Homo sapiens GN = POLR2C PE = 1 SV = 2 | 31 kDa | 0 | 9 | 0 | 0 |
| DNA-directed RNA polymerase II subunit RPB4 OS = Homo sapiens GN = POLR2D PE = 1 SV = 1 | 13 kDa | 0 | 6 | 0 | 0 |
| DNA-directed RNA polymerases I, II, and III subunit RPABC3 OS = Homo sapiens OX = 9606 GN = POLR2H PE = 1 SV = 4 | 17 kDa | 0 | 2 | 3 | 0 |
| DnaJ homolog subfamily B member 11 OS = Homo sapiens OX = 9606 GN = DNAJB11 PE = 1 SV = 1 | 41 kDa | 0 | 0 | 0 | 4 |
| Dolichol-phosphate mannosyltransferase subunit 1 OS = Homo sapiens GN = DPM1 PE = 1 SV = 1 | 30 kDa | 0 | 2 | 0 | 0 |
| Dolichyl-diphosphooligosaccharide--protein glycosyltransferase subunit STT3B OS = Homo sapiens GN = STT3B PE = 1 SV = 1 | 94 kDa | 0 | 2 | 0 | 0 |
| Doublecortin domain-containing protein 2 OS = Homo sapiens OX = 9606 GN = DCDC2 PE = 1 SV = 2 | 53 kDa | 0 | 17 | 0 | 2 |
| Double-stranded RNA-binding protein Staufen homolog 1 OS = Homo sapiens OX = 9606 GN = STAU1 PE = 1 SV = 2 | 63 kDa | 0 | 15 | 4 | 4 |
| Dynactin subunit 2 OS = Homo sapiens GN = DCTN2 PE = 1 SV = 4 | 44 kDa | 0 | 6 | 0 | 2 |
| Dynein heavy chain 10, axonemal OS = Homo sapiens OX = 9606 GN = DNAH10 PE = 1 SV = 4 | 515 kDa | 0 | 1 | 0 | 2 |
| EBNA1 binding protein 2, isoform CRA_d OS = Homo sapiens GN = EBNA1BP2 PE = 1 SV = 1 | 41 kDa | 0 | 5 | 0 | 0 |
| Ectonucleotide pyrophosphatase/phosphodiesterase family member 1 OS = Homo sapiens OX = 9606 GN = ENPP1 PE = 1 SV = 2 | 105 kDa | 0 | 0 | 0 | 2 |
| EH domain-containing protein 4 OS = Homo sapiens OX = 9606 GN = EHD4 PE = 1 SV = 1 | 61 kDa | 0 | 5 | 0 | 3 |
| Elongation factor Tu, mitochondrial OS = Homo sapiens GN = TUFM PE = 1 SV = 2 | 50 kDa | 0 | 9 | 0 | 0 |
| Emerin OS = Homo sapiens GN = EMD PE = 1 SV = 1 | 29 kDa | 0 | 6 | 0 | 0 |
| Epoxide hydrolase 1 OS = Homo sapiens OX = 9606 GN = EPHX1 PE = 1 SV = 1 | 53 kDa | 0 | 0 | 0 | 3 |
| ER lumen protein-retaining receptor 3 OS = Homo sapiens GN = KDELR3 PE = 2 SV = 1 | 25 kDa | 0 | 5 | 0 | 0 |
| Eukaryotic translation initiation factor 3 subunit E OS = Homo sapiens GN = EIF3E PE = 1 SV = 1 | 52 kDa | 0 | 8 | 0 | 0 |
| Eukaryotic translation initiation factor 3 subunit F OS = Homo sapiens GN = EIF3F PE = 1 SV = 1 | 38 kDa | 0 | 14 | 0 | 0 |
| Eukaryotic translation initiation factor 3 subunit H OS = Homo sapiens GN = EIF3H PE = 1 SV = 1 | 40 kDa | 0 | 5 | 0 | 0 |
| FACT complex subunit SPT16 OS = Homo sapiens GN = SUPT16H PE = 1 SV = 1 | 120 kDa | 0 | 7 | 0 | 0 |
| Far upstream element-binding protein 1 OS = Homo sapiens OX = 9606 GN = FUBP1 PE = 1 SV = 3 | 68 kDa | 0 | 3 | 0 | 1 |
| Fascin OS = Homo sapiens GN = FSCN1 PE = 1 SV = 3 | 55 kDa | 0 | 12 | 0 | 0 |
| Fibrous sheath-interacting protein 2 OS = Homo sapiens OX = 9606 GN = FSIP2 PE = 2 SV = 4 | 781 kDa | 0 | 0 | 2 | 1 |
| Filaggrin OS = Homo sapiens GN = FLG PE = 1 SV = 3 | 435 kDa | 0 | 3 | 0 | 0 |
| Filaggrin-2 OS = Homo sapiens GN = FLG2 PE = 1 SV = 1 | 248 kDa | 0 | 2 | 0 | 0 |
| Flotillin-2 OS = Homo sapiens GN = FLOT2 PE = 1 SV = 1 | 53 kDa | 0 | 13 | 0 | 0 |
| Galectin-3 OS = Homo sapiens GN = LGALS3 PE = 1 SV = 5 | 26 kDa | 0 | 39 | 0 | 0 |
| Galectin-3-binding protein OS = Homo sapiens OX = 9606 GN = LGALS3BP PE = 1 SV = 1 | 65 kDa | 0 | 4 | 0 | 3 |
| Galectin-8 OS = Homo sapiens OX = 9606 GN = LGALS8 PE = 1 SV = 4 | 36 kDa | 0 | 5 | 2 | 0 |
| Glutamate dehydrogenase 1, mitochondrial OS = Homo sapiens OX = 9606 GN = GLUD1 PE = 1 SV = 2 | 61 kDa | 0 | 4 | 0 | 0 |
| Glutathione peroxidase 1 OS = Homo sapiens GN = GPX1 PE = 1 SV = 4 | 22 kDa | 0 | 3 | 0 | 2 |
| Glycylpeptide N-tetradecanoyltransferase 2 OS = Homo sapiens GN = NMT2 PE = 1 SV = 1 | 57 kDa | 0 | 2 | 0 | 0 |
| Glypican-6 OS = Homo sapiens GN = GPC6 PE = 1 SV = 1 | 63 kDa | 0 | 14 | 0 | 0 |
| Golgi-associated plant pathogenesis-related protein 1 OS = Homo sapiens GN = GLIPR2 PE = 1 SV = 3 | 17 kDa | 0 | 20 | 0 | 0 |
| Gremlin-1 OS = Homo sapiens OX = 9606 GN = GREM1 PE = 1 SV = 1 | 21 kDa | 0 | 0 | 3 | 0 |
| Guanine nucleotide-binding protein G(I)/G(S)/G(O) subunit gamma-12 OS = Homo sapiens GN = GNG12 PE = 1 SV = 3 | 8 kDa | 0 | 6 | 0 | 0 |
| Guanine nucleotide-binding protein G(k) subunit alpha OS = Homo sapiens GN = GNAI3 PE = 1 SV = 3 | 41 kDa | 0 | 17 | 0 | 0 |

TABLE 2-continued

Amniotic Fluid Cell-Derived ECM (AFC-ECM) Components

|  |  | Total Spectra Count | | | |
|---|---|---|---|---|---|
| Protein | MW | Matrix A | Matrix B | Matrix C | Matrix D |
| Hamartin OS = Homo sapiens GN = TSC1 PE = 1 SV = 2 | 130 kDa | 0 | 0 | 0 | 2 |
| Heat shock-related 70 kDa protein 2 OS = Homo sapiens OX = 9606 GN = HSPA2 PE = 1 SV = 1 | 70 kDa | 0 | 0 | 0 | 24 |
| Hemicentin-2 OS = Homo sapiens OX = 9606 GN = HMCN2 PE = 2 SV = 3 | 542 kDa | 0 | 0 | 0 | 0 |
| Heparan sulfate glucosamine 3-O-sulfotransferase 6 OS = Homo sapiens GN = HS3ST6 PE = 1 SV = 2 | 37 kDa | 0 | 3 | 0 | 0 |
| Heterogeneous nuclear ribonucleoprotein A0 OS = Homo sapiens GN = HNRNPA0 PE = 1 SV = 1 | 31 kDa | 0 | 15 | 0 | 0 |
| Heterogeneous nuclear ribonucleoprotein H2 OS = Homo sapiens GN = HNRNPH2 PE = 1 SV = 1 | 49 kDa | 0 | 14 | 0 | 0 |
| Homeobox protein Hox-B3 OS = Homo sapiens OX = 9606 GN = HOXB3 PE = 2 SV = 2 | 44 kDa | 0 | 5 | 0 | 0 |
| Hornerin OS = Homo sapiens GN = HRNR PE = 1 SV = 2 | 282 kDa | 0 | 15 | 0 | 0 |
| Hsc70-interacting protein (Fragment) OS = Homo sapiens GN = ST13 PE = 1 SV = 1 | 16 kDa | 0 | 2 | 0 | 0 |
| Hyaluronan and proteoglycan link protein 1 OS = Homo sapiens OX = 9606 GN = HAPLN1 PE = 2 SV = 2 | 40 kDa | 0 | 0 | 0 | 0 |
| Hyaluronan and proteoglycan link protein 3 OS = Homo sapiens GN = HAPLN3 PE = 2 SV = 1 | 41 kDa | 0 | 6 | 0 | 0 |
| Intercellular adhesion molecule 1 OS = Homo sapiens GN = ICAM1 PE = 1 SV = 2 | 58 kDa | 0 | 16 | 0 | 0 |
| Interleukin enhancer-binding factor 2 OS = Homo sapiens GN = ILF2 PE = 1 SV = 1 | 39 kDa | 0 | 29 | 0 | 0 |
| Isocitrate dehydrogenase [NADP] cytoplasmic OS = Homo sapiens GN = IDH1 PE = 1 SV = 2 | 47 kDa | 0 | 7 | 0 | 0 |
| Isoform 1 of Gamma-adducin OS = Homo sapiens OX = 9606 GN = ADD3 | 76 kDa | 0 | 7 | 0 | 1 |
| Isoform 1 of Polypyrimidine tract-binding protein 3 OS = Homo sapiens OX = 9606 GN = PTBP3 | 57 kDa | 0 | 5 | 0 | 3 |
| Isoform 1 of Synaptic functional regulator FMR1 OS = Homo sapiens OX = 9606 GN = FMR1 | 67 kDa | 0 | 5 | 0 | 1 |
| Isoform 2 of 2,4-dienoyl-CoA reductase, mitochondrial OS = Homo sapiens OX = 9606 GN = DECR1 | 35 kDa | 0 | 8 | 0 | 1 |
| Isoform 2 of A-kinase anchor protein 13 OS = Homo sapiens OX = 9606 GN = AKAP13 | 308 kDa | 0 | 2 | 0 | 0 |
| Isoform 2 of Ankyrin repeat domain-containing protein 17 OS = Homo sapiens OX = 9606 GN = ANKRD17 | 274 kDa | 0 | 0 | 0 | 0 |
| Isoform 2 of AP-2 complex subunit mu OS = Homo sapiens OX = 9606 GN = AP2M1 | 49 kDa | 0 | 9 | 0 | 1 |
| Isoform 2 of Bcl-2-associated transcription factor 1 OS = Homo sapiens OX = 9606 GN = BCLAF1 | 106 kDa | 0 | 4 | 0 | 0 |
| Isoform 2 of Cadherin-2 OS = Homo sapiens OX = 9606 GN = CDH2 | 97 kDa | 0 | 7 | 0 | 2 |
| Isoform 2 of Calponin-1 OS = Homo sapiens OX = 9606 GN = CNN1 | 31 kDa | 0 | 1 | 5 | 8 |
| Isoform 2 of Chromodomain Y-like protein OS = Homo sapiens GN = CDYL | 61 kDa | 0 | 4 | 0 | 0 |
| Isoform 2 of Collagen alpha-1(VII) chain OS = Homo sapiens OX = 9606 GN = COL7A1 | 292 kDa | 0 | 70 | 2 | 1 |
| Isoform 2 of Cyclin-Y OS = Homo sapiens GN = CCNY | 37 kDa | 0 | 3 | 0 | 0 |
| Isoform 2 of Cysteine-rich protein 2 OS = Homo sapiens OX = 9606 GN = CRIP2 | 30 kDa | 0 | 5 | 0 | 0 |
| Isoform 2 of DnaJ homolog subfamily C member 10 OS = Homo sapiens GN = DNAJC10 | 86 kDa | 0 | 4 | 0 | 0 |
| Isoform 2 of Fibroblast growth factor 2 OS = Homo sapiens OX = 9606 GN = FGF2 | 23 kDa | 0 | 13 | 3 | 1 |
| Isoform 2 of Fibulin-2 OS = Homo sapiens OX = 9606 GN = FBLN2 | 132 kDa | 0 | 6 | 0 | 0 |
| Isoform 2 of GDNF family receptor alpha-1 OS = Homo sapiens GN = GFRA1 | 51 kDa | 0 | 8 | 0 | 0 |
| Isoform 2 of Glycogen phosphorylase, liver form OS = Homo sapiens OX = 9606 GN = PYGL | 93 kDa | 0 | 2 | 0 | 1 |
| Isoform 2 of Golgin subfamily A member 5 OS = Homo sapiens OX = 9606 GN = GOLGA5 | 78 kDa | 0 | 0 | 0 | 0 |
| Isoform 2 of H/ACA ribonucleoprotein complex subunit 1 OS = Homo sapiens OX = 9606 GN = GAR1 | 21 kDa | 0 | 1 | 1 | 2 |
| Isoform 2 of Helicase SRCAP OS = Homo sapiens OX = 9606 GN = SRCAP | 337 kDa | 0 | 2 | 0 | 0 |
| Isoform 2 of Histone-binding protein RBBP4 OS = Homo sapiens OX = 9606 GN = RBBP4 | 48 kDa | 0 | 6 | 0 | 0 |

TABLE 2-continued

Amniotic Fluid Cell-Derived ECM (AFC-ECM) Components

| Protein | MW | Total Spectra Count ||||
| | | Matrix A | Matrix B | Matrix C | Matrix D |
|---|---|---|---|---|---|
| Isoform 2 of Histone-lysine N-methyltransferase, H3 lysine-36 and H4 lysine-20 specific OS = Homo sapiens OX = 9606 GN = NSD1 | 267 kDa | 0 | 6 | 0 | 1 |
| Isoform 2 of Insulin-like growth factor-binding protein 7 OS = Homo sapiens OX = 9606 GN = IGFBP7 | 29 kDa | 0 | 54 | 13 | 7 |
| Isoform 2 of Interferon-inducible double-stranded RNA-dependent protein kinase activator A OS = Homo sapiens OX = 9606 GN = PRKRA | 33 kDa | 0 | 4 | 1 | 1 |
| Isoform 2 of KH domain-containing, RNA-binding, signal transduction-associated protein 3 OS = Homo sapiens GN = KHDRBS3 | 30 kDa | 0 | 8 | 0 | 0 |
| Isoform 2 of Lactadherin OS = Homo sapiens GN = MFGE8 | 35 kDa | 0 | 25 | 2 | 1 |
| Isoform 2 of L-amino-acid oxidase OS = Homo sapiens OX = 9606 GN = IL4I1 | 65 kDa | 0 | 2 | 0 | 1 |
| Isoform 2 of Macrophage-capping protein OS = Homo sapiens GN = CAPG | 37 kDa | 0 | 3 | 0 | 0 |
| Isoform 2 of Matrilin-2 OS = Homo sapiens OX = 9606 GN = MATN2 | 105 kDa | 0 | 37 | 8 | 5 |
| Isoform 2 of Mesoderm-specific transcript homolog protein OS = Homo sapiens OX = 9606 GN = MEST | 38 kDa | 0 | 0 | 0 | 4 |
| Isoform 2 of Microtubule-associated protein 1A OS = Homo sapiens OX = 9606 GN = MAP1A | 306 kDa | 0 | 4 | 2 | 3 |
| Isoform 2 of Midkine OS = Homo sapiens OX = 9606 GN = MDK | 10 kDa | 0 | 4 | 2 | 2 |
| Isoform 2 of Monoacylglycerol lipase ABHD12 OS = Homo sapiens GN = ABHD12 | 46 kDa | 0 | 2 | 0 | 0 |
| Isoform 2 of Multidrug resistance protein 1 OS = Homo sapiens OX = 9606 GN = ABCB1 | 134 kDa | 0 | 1 | 0 | 2 |
| Isoform 2 of Myosin-11 OS = Homo sapiens GN = MYH11 | 228 kDa | 0 | 161 | 37 | 0 |
| Isoform 2 of Myosin-14 OS = Homo sapiens OX = 9606 GN = MYH14 | 232 kDa | 0 | 141 | 26 | 26 |
| Isoform 2 of NADH dehydrogenase [ubiquinone] 1 beta subcomplex subunit 4 OS = Homo sapiens OX = 9606 GN = NDUFB4 | 14 kDa | 0 | 1 | 0 | 2 |
| Isoform 2 of Nuclear receptor corepressor 1 OS = Homo sapiens OX = 9606 GN = NCOR1 | 259 kDa | 0 | 0 | 2 | 0 |
| Isoform 2 of Periostin OS = Homo sapiens OX = 9606 GN = POSTN | 87 kDa | 0 | 0 | 5 | 5 |
| Isoform 2 of Pescadillo homolog OS = Homo sapiens OX = 9606 GN = PES1 | 67 kDa | 0 | 5 | 1 | 0 |
| Isoform 2 of Platelet-derived growth factor subunit B OS = Homo sapiens OX = 9606 GN = PDGFB | 26 kDa | 0 | 1 | 3 | 1 |
| Isoform 2 of Protein ELYS OS = Homo sapiens OX = 9606 GN = AHCTF1 | 256 kDa | 0 | 0 | 2 | 0 |
| Isoform 2 of Ran-binding protein 3 OS = Homo sapiens OX = 9606 GN = RANBP3 | 60 kDa | 0 | 5 | 0 | 0 |
| Isoform 2 of Regulator of chromosome condensation OS = Homo sapiens OX = 9606 GN = RCC1 | 48 kDa | 0 | 16 | 0 | 0 |
| Isoform 2 of Retinol-binding protein 1 OS = Homo sapiens OX = 9606 GN = RBP1 | 17 kDa | 0 | 0 | 0 | 2 |
| Isoform 2 of RNA-binding protein 39 OS = Homo sapiens GN = RBM39 | 59 kDa | 0 | 0 | 0 | 2 |
| Isoform 2 of RNA-binding protein 8A OS = Homo sapiens OX = 9606 GN = RBM8A | 20 kDa | 0 | 5 | 0 | 1 |
| Isoform 2 of Ryanodine receptor 1 OS = Homo sapiens OX = 9606 GN = RYR1 | 565 kDa | 0 | 1 | 0 | 2 |
| Isoform 2 of SCO-spondin OS = Homo sapiens OX = 9606 GN = SSPO | 139 kDa | 0 | 3 | 0 | 0 |
| Isoform 2 of Semaphorin-7A OS = Homo sapiens OX = 9606 GN = SEMA7A | 73 kDa | 0 | 3 | 1 | 3 |
| Isoform 2 of Septin-8 OS = Homo sapiens OX = 9606 GN = SEPT8 | 50 kDa | 0 | 12 | 0 | 3 |
| Isoform 2 of Serine/threonine-protein phosphatase PGAM5, mitochondrial OS = Homo sapiens OX = 9606 GN = PGAM5 | 28 kDa | 0 | 5 | 0 | 1 |
| Isoform 2 of SH3 domain-containing kinase-binding protein 1 OS = Homo sapiens OX = 9606 GN = SH3KBP1 | 69 kDa | 0 | 2 | 0 | 2 |
| Isoform 2 of Signal recognition particle receptor subunit alpha OS = Homo sapiens OX = 9606 GN = SRPRA | 67 kDa | 0 | 3 | 0 | 1 |
| Isoform 2 of Signal-induced proliferation-associated 1-like protein 1 OS = Homo sapiens OX = 9606 GN = SIPA1L1 | 197 kDa | 0 | 0 | 0 | 0 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform 2 of Sorting nexin-27 OS = Homo sapiens GN = SNX27 | 60 kDa | 0 | 4 | 0 | 0 |
| Isoform 2 of Spectrin beta chain, erythrocytic OS = Homo sapiens OX = 9606 GN = SPTB | 268 kDa | 0 | 8 | 0 | 2 |
| Isoform 2 of Testis-expressed protein 10 OS = Homo sapiens OX = 9606 GN = TEX10 | 104 kDa | 0 | 2 | 0 | 0 |
| Isoform 2 of Tissue factor pathway inhibitor 2 OS = Homo sapiens OX = 9606 GN = TFPI2 | 26 kDa | 0 | 9 | 6 | 0 |
| Isoform 2 of Tyrosine-protein kinase BAZ1B OS = Homo sapiens OX = 9606 GN = BAZ1B | 170 kDa | 0 | 4 | 0 | 0 |
| Isoform 2 of UDP-glucuronosyltransferase 1-6 OS = Homo sapiens OX = 9606 GN = UGT1A6 | 30 kDa | 0 | 4 | 0 | 0 |
| Isoform 2 of Vesicle-associated membrane protein-associated protein A OS = Homo sapiens OX = 9606 GN = VAPA | 33 kDa | 0 | 3 | 0 | 1 |
| Isoform 2 of Voltage-dependent calcium channel subunit alpha-2/delta-1 OS = Homo sapiens OX = 9606 GN = CACNA2D1 | 123 kDa | 0 | 2 | 1 | 0 |
| Isoform 2 of Y-box-binding protein 3 OS = Homo sapiens OX = 9606 GN = YBX3 | 32 kDa | 0 | 15 | 0 | 1 |
| Isoform 2 of Zinc finger homeobox protein 4 OS = Homo sapiens OX = 9606 GN = ZFHX4 | 397 kDa | 0 | 2 | 0 | 0 |
| Isoform 3 of 1-phosphatidylinositol 4,5-bisphosphate phosphodiesterase beta-4 OS = Homo sapiens OX = 9606 GN = PLCB4 | 136 kDa | 0 | 3 | 0 | 0 |
| Isoform 3 of Alpha-adducin OS = Homo sapiens GN = ADD1 | 84 kDa | 0 | 2 | 0 | 0 |
| Isoform 3 of Cytoskeleton-associated protein 5 OS = Homo sapiens OX = 9606 GN = CKAP5 | 226 kDa | 0 | 3 | 0 | 0 |
| Isoform 3 of DnaJ homolog subfamily C member 11 OS = Homo sapiens GN = DNAJC11 | 57 kDa | 0 | 2 | 0 | 1 |
| Isoform 3 of E3 ubiquitin-protein ligase CHFR OS = Homo sapiens OX = 9606 GN = CHFR | 69 kDa | 0 | 0 | 0 | 0 |
| Isoform 3 of H/ACA ribonucleoprotein complex subunit DKC1 OS = Homo sapiens OX = 9606 GN = DKC1 | 48 kDa | 0 | 13 | 1 | 1 |
| Isoform 3 of Histone-lysine N-methyltransferase 2D OS = Homo sapiens OX = 9606 GN = KMT2D | 594 kDa | 0 | 1 | 0 | 1 |
| Isoform 3 of Latent-transforming growth factor beta-binding protein 4 OS = Homo sapiens OX = 9606 GN = LTBP4 | 169 kDa | 0 | 34 | 0 | 0 |
| Isoform 3 of Malate dehydrogenase, cytoplasmic OS = Homo sapiens OX = 9606 GN = MDH1 | 39 kDa | 0 | 3 | 0 | 0 |
| Isoform 3 of Putative oxidoreductase GLYR1 OS = Homo sapiens OX = 9606 GN = GLYR1 | 60 kDa | 0 | 4 | 0 | 0 |
| Isoform 3 of Scaffold attachment factor B1 OS = Homo sapiens GN = SAFB | 103 kDa | 0 | 3 | 0 | 0 |
| Isoform 3 of Torsin-1A-interacting protein 1 OS = Homo sapiens GN = TOR1AIP1 | 66 kDa | 0 | 5 | 0 | 0 |
| Isoform 4 of CD109 antigen OS = Homo sapiens GN = CD109 | 160 kDa | 0 | 18 | 0 | 0 |
| Isoform 4 of FYVE and coiled-coil domain-containing protein 1 OS = Homo sapiens OX = 9606 GN = FYCO1 | 169 kDa | 0 | 0 | 0 | 0 |
| Isoform 4 of IQ domain-containing protein N OS = Homo sapiens OX = 9606 GN = IQCN | 147 kDa | 0 | 0 | 0 | 3 |
| Isoform 4 of Kinesin-like protein KIF24 OS = Homo sapiens OX = 9606 GN = KIF24 | 129 kDa | 0 | 2 | 0 | 0 |
| Isoform 4 of Latent-transforming growth factor beta-binding protein 1 OS = Homo sapiens OX = 9606 GN = LTBP1 | 187 kDa | 0 | 1 | 4 | 1 |
| Isoform 4 of Protein diaphanous homolog 3 OS = Homo sapiens GN = DIAPH3 | 136 kDa | 0 | 2 | 0 | 0 |
| Isoform 5 of E1A-binding protein p400 OS = Homo sapiens OX = 9606 GN = EP400 | 340 kDa | 0 | 1 | 0 | 0 |
| Isoform 5 of Immunoglobulin-like and fibronectin type III domain-containing protein 1 OS = Homo sapiens OX = 9606 GN = IGFN1 | 384 kDa | 0 | 3 | 0 | 2 |
| Isoform 5 of LIM domain only protein 7 OS = Homo sapiens GN = LMO7 | 158 kDa | 0 | 8 | 0 | 0 |
| Isoform 5 of Papilin OS = Homo sapiens OX = 9606 GN = PAPLN | 136 kDa | 0 | 17 | 1 | 1 |
| Isoform 6 of Treacle protein OS = Homo sapiens OX = 9606 GN = TCOF1 | 148 kDa | 0 | 2 | 0 | 0 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Isoform B of Collagen alpha-1(XI) chain OS = *Homo sapiens* OX = 9606 GN = COL11A1 | 182 kDa | 0 | 0 | 1 | 2 |
| Isoform B of Collagen alpha-6(IV) chain OS = *Homo sapiens* OX = 9606 GN = COL4A6 | 164 kDa | 0 | 5 | 2 | 0 |
| Isoform B of DnaJ homolog subfamily B member 6 OS = *Homo sapiens* OX = 9606 GN = DNAJB6 | 27 kDa | 0 | 0 | 1 | 2 |
| Isoform B of Methyl-CpG-binding protein 2 OS = *Homo sapiens* OX = 9606 GN = MECP2 | 53 kDa | 0 | 11 | 1 | 0 |
| Isoform B of Ras-related C3 botulinum toxin substrate 1 OS = *Homo sapiens* OX = 9606 GN = RAC1 | 23 kDa | 0 | 3 | 0 | 0 |
| Isoform B of Transforming growth factor beta-2 proprotein OS = *Homo sapiens* OX = 9606 GN = TGFB2 | 51 kDa | 0 | 5 | 1 | 2 |
| Isoform Beta-3B of Integrin beta-3 OS = *Homo sapiens* OX = 9606 GN = ITGB3 | 86 kDa | 0 | 4 | 0 | 2 |
| Isoform C of Fibulin-1 OS = *Homo sapiens* OX = 9606 GN = FBLN1 | 74 kDa | 0 | 13 | 0 | 8 |
| Isoform Long of Proteasome subunit alpha type-1 OS = *Homo sapiens* OX = 9606 GN = PSMA1 | 30 kDa | 0 | 2 | 0 | 2 |
| Isoform Non-brain of Clathrin light chain A OS = *Homo sapiens* OX = 9606 GN = CLTA | 24 kDa | 0 | 17 | 0 | 2 |
| Isoform Short of Laminin subunit gamma-2 OS = *Homo sapiens* OX = 9606 GN = LAMC2 | 122 kDa | 0 | 5 | 0 | 1 |
| Keratin, type I cytoskeletal 14 OS = *Homo sapiens* OX = 9606 GN = KRT14 PE = 1 SV = 4 | 52 kDa | 0 | 94 | 0 | 18 |
| Keratin, type I cytoskeletal 16 OS = *Homo sapiens* GN = KRT16 PE = 1 SV = 4 | 51 kDa | 0 | 99 | 0 | 0 |
| Keratin, type I cytoskeletal 19 OS = *Homo sapiens* GN = KRT19 PE = 1 SV = 4 | 44 kDa | 0 | 753 | 0 | 0 |
| Keratin, type II cuticular Hb5 OS = *Homo sapiens* GN = KRT85 PE = 1 SV = 1 | 56 kDa | 0 | 3 | 0 | 0 |
| Keratin, type II cytoskeletal 1 OS = *Homo sapiens* GN = KRT1 PE = 1 SV = 6 | 66 kDa | 0 | 497 | 0 | 0 |
| Keratin, type II cytoskeletal 5 OS = *Homo sapiens* GN = KRT5 PE = 1 SV = 3 | 62 kDa | 0 | 93 | 0 | 0 |
| Keratin, type II cytoskeletal 6B OS = *Homo sapiens* OX = 9606 GN = KRT6B PE = 1 SV = 5 | 60 kDa | 0 | 104 | 18 | 0 |
| Keratin, type II cytoskeletal 7 OS = *Homo sapiens* OX = 9606 GN = KRT7 PE = 1 SV = 5 | 51 kDa | 0 | 0 | 0 | 135 |
| Kinesin-like protein KIFC2 OS = *Homo sapiens* OX = 9606 GN = KIFC2 PE = 2 SV = 1 | 90 kDa | 0 | 2 | 0 | 1 |
| Ladinin-1 OS = *Homo sapiens* OX = 9606 GN = LAD1 PE = 1 SV = 2 | 57 kDa | 0 | 0 | 0 | 6 |
| Laminin subunit beta-3 OS = *Homo sapiens* GN = LAMB3 PE = 1 SV = 1 | 130 kDa | 0 | 10 | 0 | 0 |
| Latent-transforming growth factor beta-binding protein 2 OS = *Homo sapiens* GN = LTBP2 PE = 1 SV = 1 | 190 kDa | 0 | 23 | 0 | 0 |
| Leucine zipper protein 1 OS = *Homo sapiens* OX = 9606 GN = LUZP1 PE = 1 SV = 2 | 120 kDa | 0 | 5 | 0 | 0 |
| Lipoamide acyltransferase component of branched-chain alpha-keto acid dehydrogenase complex, mitochondrial OS = *Homo sapiens* OX = 9606 GN = DBT PE = 1 SV = 3 | 53 kDa | 0 | 6 | 4 | 8 |
| Low-density lipoprotein receptor-related protein 1B OS = *Homo sapiens* GN = LRP1B PE = 1 SV = 2 | 515 kDa | 0 | 2 | 0 | 0 |
| Low-density lipoprotein receptor-related protein 2 OS = *Homo sapiens* OX = 9606 GN = LRP2 PE = 1 SV = 3 | 522 kDa | 0 | 0 | 0 | 2 |
| Lysyl oxidase homolog 1 OS = *Homo sapiens* OX = 9606 GN = LOXL1 PE = 1 SV = 2 | 63 kDa | 0 | 24 | 1 | 0 |
| Magnesium transporter protein 1 OS = *Homo sapiens* GN = MAGT1 PE = 1 SV = 1 | 42 kDa | 0 | 4 | 1 | 1 |
| MARCKS-related protein OS = *Homo sapiens* GN = MARCKSL1 PE = 1 SV = 2 | 20 kDa | 0 | 4 | 0 | 0 |
| Metastasis-associated protein MTA2 OS = *Homo sapiens* GN = MTA2 PE = 1 SV = 1 | 75 kDa | 0 | 5 | 0 | 0 |
| Microsomal glutathione S-transferase 1 OS = *Homo sapiens* OX = 9606 GN = MGST1 PE = 1 SV = 1 | 18 kDa | 0 | 0 | 0 | 3 |
| Mitochondrial GTPase 1 OS = *Homo sapiens* OX = 9606 PE = 3 SV = 1 | 37 kDa | 0 | 0 | 0 | 2 |
| MKI67 FHA domain-interacting nucleolar phosphoprotein (Fragment) OS = *Homo sapiens* GN = NIFK PE = 1 SV = 1 | 20 kDa | 0 | 6 | 0 | 0 |
| Mucin-16 OS = *Homo sapiens* OX = 9606 GN = MUC16 PE = 1 SV = 3 | 1519 kDa | 0 | 0 | 2 | 4 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Myelin expression factor 2 OS = Homo sapiens OX = 9606 GN = MYEF2 PE = 1 SV = 3 | 64 kDa | 0 | 2 | 0 | 0 |
| Myosin light chain 6B OS = Homo sapiens OX = 9606 GN = MYL6B PE = 1 SV = 1 | 23 kDa | 0 | 0 | 6 | 0 |
| Myristoylated alanine-rich C-kinase substrate OS = Homo sapiens GN = MARCKS PE = 1 SV = 4 | 32 kDa | 0 | 11 | 0 | 0 |
| N-acylneuraminate cytidylyltransferase OS = Homo sapiens GN = CMAS PE = 1 SV = 2 | 48 kDa | 0 | 6 | 0 | 0 |
| NAD(P) transhydrogenase, mitochondrial OS = Homo sapiens GN = NNT PE = 1 SV = 1 | 100 kDa | 0 | 3 | 0 | 0 |
| Nestin OS = Homo sapiens GN = NES PE = 1 SV = 2 | 177 kDa | 0 | 18 | 0 | 0 |
| Neurabin-2 OS = Homo sapiens GN = PPP1R9B PE = 1 SV = 1 | 89 kDa | 0 | 3 | 0 | 0 |
| Neurobeachin OS = Homo sapiens OX = 9606 GN = NBEA PE = 1 SV = 3 | 328 kDa | 0 | 0 | 0 | 3 |
| Nicotinate-nucleotide pyrophosphorylase [carboxylating] OS = Homo sapiens OX = 9606 GN = QPRT PE = 1 SV = 3 | 31 kDa | 0 | 0 | 0 | 4 |
| Non-syndromic hearing impairment protein 5 OS = Homo sapiens GN = DFNA5 PE = 1 SV = 2 | 55 kDa | 0 | 2 | 0 | 0 |
| Nuclear receptor-binding protein OS = Homo sapiens GN = NRBP1 PE = 1 SV = 1 | 61 kDa | 0 | 5 | 0 | 0 |
| Nucleolar complex protein 3 homolog OS = Homo sapiens GN = NOC3L PE = 1 SV = 1 | 93 kDa | 0 | 5 | 0 | 0 |
| Nucleolar complex protein 4 homolog OS = Homo sapiens GN = NOC4L PE = 1 SV = 1 | 58 kDa | 0 | 5 | 0 | 0 |
| Nucleolar protein 58 OS = Homo sapiens GN = NOP58 PE = 1 SV = 1 | 60 kDa | 0 | 6 | 0 | 0 |
| Nucleolar transcription factor 1 OS = Homo sapiens GN = UBTF PE = 1 SV = 1 | 87 kDa | 0 | 2 | 0 | 0 |
| Nucleoplasmin-3 OS = Homo sapiens GN = NPM3 PE = 1 SV = 3 | 19 kDa | 0 | 3 | 0 | 0 |
| Palladin OS = Homo sapiens OX = 9606 GN = PALLD PE = 1 SV = 3 | 151 kDa | 0 | 7 | 0 | 6 |
| PDZ and LIM domain protein 1 OS = Homo sapiens OX = 9606 GN = PDLIM1 PE = 1 SV = 4 | 36 kDa | 0 | 0 | 0 | 4 |
| PDZ and LIM domain protein 4 OS = Homo sapiens GN = PDLIM4 PE = 1 SV = 2 | 35 kDa | 0 | 3 | 0 | 0 |
| Pentraxin-related protein PTX3 OS = Homo sapiens GN = PTX3 PE = 1 SV = 3 | 42 kDa | 0 | 23 | 0 | 0 |
| Peptidyl-prolyl cis-trans isomerase B OS = Homo sapiens GN = PPIB PE = 1 SV = 2 | 24 kDa | 0 | 52 | 0 | 0 |
| Peptidyl-prolyl cis-trans isomerase FKBP10 OS = Homo sapiens GN = FKBP10 PE = 1 SV = 1 | 64 kDa | 0 | 3 | 0 | 0 |
| Peptidyl-prolyl cis-trans isomerase FKBP3 OS = Homo sapiens GN = FKBP3 PE = 1 SV = 1 | 25 kDa | 0 | 8 | 0 | 0 |
| Periaxin OS = Homo sapiens OX = 9606 GN = PRX PE = 1 SV = 2 | 155 kDa | 0 | 0 | 0 | 2 |
| Periodic tryptophan protein 1 homolog OS = Homo sapiens OX = 9606 GN = PWP1 PE = 1 SV = 1 | 56 kDa | 0 | 2 | 0 | 0 |
| Peroxiredoxin-1 (Fragment) OS = Homo sapiens GN = PRDX1 PE = 1 SV = 1 | 19 kDa | 0 | 13 | 0 | 0 |
| Phosphoglycerate mutase 1 OS = Homo sapiens GN = PGAM1 PE = 1 SV = 2 | 29 kDa | 0 | 11 | 0 | 0 |
| Pinin OS = Homo sapiens OX = 9606 GN = PNN PE = 1 SV = 5 | 82 kDa | 0 | 6 | 2 | 4 |
| Platelet-activating factor acetylhydrolase IB subunit alpha OS = Homo sapiens OX = 9606 GN = PAFAH1B1 PE = 1 SV = 2 | 47 kDa | 0 | 4 | 0 | 0 |
| Poly [ADP-ribose] polymerase 1 OS = Homo sapiens GN = PARP1 PE = 1 SV = 4 | 113 kDa | 0 | 30 | 0 | 0 |
| Poly(U)-binding-splicing factor PUF60 (Fragment) OS = Homo sapiens GN = PUF60 PE = 1 SV = 1 | 57 kDa | 0 | 3 | 0 | 0 |
| Polymerase delta-interacting protein 3 OS = Homo sapiens GN = POLDIP3 PE = 1 SV = 1 | 48 kDa | 0 | 6 | 0 | 0 |
| Polymerase I and transcript release factor OS = Homo sapiens GN = PTRF PE = 1 SV = 1 | 43 kDa | 0 | 89 | 0 | 0 |
| Polyubiquitin-B OS = Homo sapiens GN = UBB PE = 1 SV = 1 | 17 kDa | 0 | 111 | 0 | 0 |
| POU domain, class 3, transcription factor 3 OS = Homo sapiens GN = POU3F3 PE = 2 SV = 2 | 50 kDa | 0 | 20 | 0 | 0 |
| PR domain zinc finger protein 8 OS = Homo sapiens GN = PRDM8 PE = 1 SV = 3 | 72 kDa | 0 | 2 | 0 | 0 |

TABLE 2-continued

Amniotic Fluid Cell-Derived ECM (AFC-ECM) Components

| Protein | MW | Total Spectra Count | | | |
| --- | --- | --- | --- | --- | --- |
| | | Matrix A | Matrix B | Matrix C | Matrix D |
| Prefoldin subunit 6 OS = Homo sapiens GN = PFDN6 PE = 1 SV = 1 | 15 kDa | 0 | 3 | 0 | 0 |
| Probable ATP-dependent RNA helicase DDX27 OS = Homo sapiens GN = DDX27 PE = 1 SV = 1 | 87 kDa | 0 | 4 | 0 | 0 |
| Probable global transcription activator SNF2L1 OS = Homo sapiens OX = 9606 GN = SMARCA1 PE = 1 SV = 2 | 123 kDa | 0 | 6 | 0 | 0 |
| Probable maltase-glucoamylase 2 OS = Homo sapiens OX = 9606 GN = MGAM2 PE = 2 SV = 3 | 278 kDa | 0 | 0 | 0 | 2 |
| Procollagen galactosyltransferase 1 OS = Homo sapiens GN = COLGALT1 PE = 1 SV = 1 | 72 kDa | 0 | 3 | 0 | 0 |
| Procollagen-lysine,2-oxoglutarate 5-dioxygenase 3 OS = Homo sapiens GN = PLOD3 PE = 1 SV = 1 | 85 kDa | 0 | 3 | 0 | 0 |
| Prolow-density lipoprotein receptor-related protein 1 OS = Homo sapiens GN = LRP1 PE = 1 SV = 2 | 505 kDa | 0 | 2 | 0 | 0 |
| Protein disulfide-isomerase OS = Homo sapiens GN = P4HB PE = 1 SV = 2 | 53 kDa | 0 | 30 | 0 | 0 |
| Protein GREB1 OS = Homo sapiens GN = GREB1PE = 2 SV = 1 | 216 kDa | 0 | 0 | 0 | 2 |
| Protein kinase C delta-binding protein OS = Homo sapiens GN = PRKCDBP PE = 1 SV = 1 | 31 kDa | 0 | 20 | 0 | 0 |
| Protein MAK16 homolog OS = Homo sapiens GN = MAK16 PE = 1 SV = 2 | 35 kDa | 0 | 2 | 0 | 0 |
| Protein S100-A10 OS = Homo sapiens GN = S100A10 PE = 1 SV = 2 | 11 kDa | 0 | 11 | 0 | 0 |
| Protein S100-A13 OS = Homo sapiens GN = S100A13 PE = 1 SV = 1 | 11 kDa | 0 | 5 | 0 | 0 |
| Protein S100-A9 OS = Homo sapiens GN = S100A9 PE = 1 SV = 1 | 13 kDa | 0 | 12 | 0 | 0 |
| Protein-glutamine gamma-glutamyltransferase E OS = Homo sapiens GN = TGM3 PE = 1 SV = 4 | 77 kDa | 0 | 2 | 0 | 0 |
| Pumilio homolog 3 OS = Homo sapiens GN = PUM3 PE = 1 SV = 3 | 74 kDa | 0 | 6 | 0 | 0 |
| Raftlin OS = Homo sapiens GN = RFTN1 PE = 1 SV = 4 | 63 kDa | 0 | 3 | 0 | 0 |
| Ras GTPase-activating-like protein IQGAP1 OS = Homo sapiens GN = IQGAP1 PE = 1 SV = 1 | 189 kDa | 0 | 135 | 0 | 0 |
| Ras-related protein Rab-10 OS = Homo sapiens GN = RAB10 PE = 1 SV = 1 | 23 kDa | 0 | 13 | 0 | 0 |
| Ras-related protein Rab-14 (Fragment) OS = Homo sapiens GN = RAB14 PE = 1 SV = 1 | 20 kDa | 0 | 8 | 0 | 0 |
| Ras-related protein Rab-2A OS = Homo sapiens GN = RAB2A PE = 1 SV = 1 | 24 kDa | 0 | 5 | 0 | 1 |
| Ras-related protein Ral-A OS = Homo sapiens GN = RALA PE = 1 SV = 1 | 24 kDa | 0 | 2 | 0 | 0 |
| Regulation of nuclear pre-mRNA domain-containing protein 1B OS = Homo sapiens GN = RPRD1B PE = 1 SV = 1 | 37 kDa | 0 | 2 | 0 | 0 |
| Replication protein A 32 kDa subunit OS = Homo sapiens GN = RPA2 PE = 1 SV = 1 | 29 kDa | 0 | 3 | 0 | 1 |
| Replication protein A 70 kDa DNA-binding subunit OS = Homo sapiens GN = RPA1 PE = 1 SV = 2 | 68 kDa | 0 | 4 | 0 | 0 |
| Reticulocalbin-1 OS = Homo sapiens GN = RCN1 PE = 1 SV = 1 | 39 kDa | 0 | 7 | 0 | 0 |
| Retinoic acid-induced protein 3 OS = Homo sapiens OX = 9606 GN = GPRC5A PE = 1 SV = 2 | 40 kDa | 0 | 0 | 0 | 2 |
| Rho GTPase-activating protein 1 OS = Homo sapiens GN = ARHGAP1 PE = 1 SV = 1 | 50 kDa | 0 | 8 | 0 | 0 |
| Ribosomal protein L19 OS = Homo sapiens GN = RPL19 PE = 1 SV = 1 | 23 kDa | 0 | 21 | 0 | 0 |
| Ribosome biogenesis protein BRX1 homolog OS = Homo sapiens OX = 9606 GN = BRIX1 PE = 1 SV = 2 | 41 kDa | 0 | 5 | 0 | 3 |
| Ribosome biogenesis protein WDR12 OS = Homo sapiens GN = WDR12 PE = 1 SV = 2 | 48 kDa | 0 | 3 | 0 | 0 |
| Ribosome biogenesis regulatory protein homolog OS = Homo sapiens GN = RRS1 PE = 1 SV = 2 | 41 kDa | 0 | 11 | 0 | 0 |
| Ribosome production factor 2 homolog OS = Homo sapiens GN = RPF2 PE = 1 SV = 2 | 36 kDa | 0 | 3 | 0 | 0 |
| RNA-binding protein 28 OS = Homo sapiens OX = 9606 GN = RBM28 PE = 1 SV = 3 | 86 kDa | 0 | 2 | 0 | 2 |
| RNA-binding protein 3 OS = Homo sapiens GN = RBM3 PE = 1 SV = 1 | 17 kDa | 0 | 3 | 0 | 0 |
| rRNA 2'-O-methyltransferase fibrillarin OS = Homo sapiens GN = FBL PE = 1 SV = 2 | 34 kDa | 0 | 23 | 0 | 0 |

TABLE 2-continued

Amniotic Fluid Cell-Derived ECM (AFC-ECM) Components

| Protein | MW | Total Spectra Count | | | |
|---|---|---|---|---|---|
| | | Matrix A | Matrix B | Matrix C | Matrix D |
| Selenoprotein H OS = *Homo sapiens* GN = C11orf31 PE = 1 SV = 1 | 13 kDa | 0 | 2 | 0 | 0 |
| Semaphorin-3C OS = *Homo sapiens* GN = SEMA3C PE = 2 SV = 2 | 85 kDa | 0 | 3 | 0 | 0 |
| Serine protease 23 OS = *Homo sapiens* OX = 9606 GN = PRSS23 PE = 1 SV = 1 | 43 kDa | 0 | 7 | 7 | 5 |
| Serine protease HTRA3 OS = *Homo sapiens* OX = 9606 GN = HTRA3 PE = 1 SV = 2 | 49 kDa | 0 | 3 | 3 | 0 |
| Serine/threonine-protein phosphatase 2A catalytic subunit beta isoform OS = *Homo sapiens* GN = PPP2CB PE = 1 SV = 1 | 36 kDa | 0 | 4 | 0 | 0 |
| Serine/threonine-protein phosphatase PP1-beta catalytic subunit OS = *Homo sapiens* GN = PPP1CB PE = 1 SV = 3 | 37 kDa | 0 | 22 | 0 | 0 |
| Serpin B3 OS = *Homo sapiens* GN = SERPINB3 PE = 1 SV = 2 | 45 kDa | 0 | 4 | 0 | 0 |
| SH3 domain-binding protein 1 OS = *Homo sapiens* GN = SH3BP1 PE = 1 SV = 3 | 76 kDa | 0 | 2 | 0 | 0 |
| Signal peptidase complex subunit 1 OS = *Homo sapiens* GN = SPCS1 PE = 1 SV = 4 | 12 kDa | 0 | 2 | 0 | 0 |
| Signal peptidase complex subunit 3 OS = *Homo sapiens* GN = SPCS3 PE = 1 SV = 1 | 20 kDa | 0 | 5 | 0 | 0 |
| Signal recognition particle 14 kDa protein OS = *Homo sapiens* GN = SRP14 PE = 1 SV = 2 | 15 kDa | 0 | 9 | 0 | 0 |
| Signal-induced proliferation-associated 1-like protein 2 OS = *Homo sapiens* OX = 9606 GN = SIPA1L2 PE = 1 SV = 2 | 190 kDa | 0 | 0 | 0 | 2 |
| Single-stranded DNA-binding protein, mitochondrial OS = *Homo sapiens* GN = SSBP1 PE = 1 SV = 1 | 17 kDa | 0 | 24 | 0 | 0 |
| SNW domain-containing protein 1 OS = *Homo sapiens* GN = SNW1 PE = 1 SV = 1 | 61 kDa | 0 | 4 | 0 | 0 |
| Solute carrier family 2, facilitated glucose transporter member 1 OS = *Homo sapiens* GN = SLC2A1 PE = 1 SV = 2 | 54 kDa | 0 | 9 | 0 | 0 |
| SPARC (Fragment) OS = *Homo sapiens* GN = SPARC PE = 1 SV = 1 | 17 kDa | 0 | 2 | 0 | 0 |
| Spermatogenesis-associated serine-rich protein 2 OS = *Homo sapiens* GN = SPATS2 PE = 1 SV = 1 | 60 kDa | 0 | 2 | 0 | 0 |
| Sphingosine-1-phosphate lyase 1 OS = *Homo sapiens* GN = SGPL1 PE = 1 SV = 3 | 64 kDa | 0 | 2 | 0 | 0 |
| Splicing factor 3B subunit 2 OS = *Homo sapiens* GN = SF3B2 PE = 1 SV = 1 | 98 kDa | 0 | 7 | 0 | 0 |
| SRA stem-loop-interacting RNA-binding protein, mitochondrial OS = *Homo sapiens* GN = SLIRP PE = 1 SV = 1 | 14 kDa | 0 | 2 | 0 | 0 |
| Structural maintenance of chromosomes protein 3 OS = *Homo sapiens* GN = SMC3 PE = 1 SV = 2 | 142 kDa | 0 | 11 | 0 | 0 |
| SWI/SNF-related matrix-associated actin-dependent regulator of chromatin subfamily A member 5 OS = *Homo sapiens* GN = SMARCA5 PE = 1 SV = 1 | 122 kDa | 0 | 17 | 0 | 0 |
| SWI/SNF-related matrix-associated actin-dependent regulator of chromatin subfamily E member 1 OS = *Homo sapiens* OX = 9606 GN = SMARCE1 PE = 1 SV = 2 | 47 kDa | 0 | 4 | 0 | 0 |
| SWISS-PROT: P01044-1 (*Bos taurus*) Isoform HMW of Kininogen-1 precursor | 69 kDa | 0 | 3 | 0 | 0 |
| SWISS-PROT: P02768-1 Tax_Id = 9606 Gene_Symbol = ALB Isoform 1 of Serum albumin precursor | 69 kDa | 0 | 0 | 5 | 13 |
| SWISS-PROT: Q3SZR3 (*Bos taurus*) Alpha-1-acid glycoprotein precursor | 23 kDa | 0 | 2 | 0 | 0 |
| SWISS-PROT: Q3TTY5 Tax_Id = 10090 Gene_Symbol = Krt2 Keratin, type II cytoskeletal 2 epidermal | 71 kDa | 0 | 27 | 7 | 7 |
| SWISS-PROT: Q9D312 Tax_Id = 10090 Gene_Symbol = Krt20 Keratin, type I cytoskeletal 20 | 49 kDa | 0 | 6 | 0 | 4 |
| SWISS-PROT: Q9QWL7 Tax_Id = 10090 Gene_Symbol = Krt17 Keratin, type I cytoskeletal 17 | 48 kDa | 0 | 54 | 0 | 16 |
| Synaptosomal-associated protein 23 OS = *Homo sapiens* GN = SNAP23 PE = 1 SV = 1 | 23 kDa | 0 | 6 | 0 | 0 |
| Tau-tubulin kinase 2 OS = *Homo sapiens* OX = 9606 GN = TTBK2 PE = 1 SV = 1 | 182 kDa | 0 | 0 | 0 | 2 |
| TBC1 domain family member 1 (Fragment) OS = *Homo sapiens* GN = TBC1D1 PE = 1 SV = 3 | 98 kDa | 0 | 2 | 0 | 0 |
| T-complex protein 1 subunit alpha OS = *Homo sapiens* GN = TCP1 PE = 1 SV = 1 | 60 kDa | 0 | 98 | 0 | 0 |

TABLE 2-continued

Amniotic Fluid Cell-Derived ECM (AFC-ECM) Components

| Protein | MW | Total Spectra Count | | | |
| --- | --- | --- | --- | --- | --- |
| | | Matrix A | Matrix B | Matrix C | Matrix D |
| Thyroid hormone receptor-associated protein 3 OS = Homo sapiens GN = THRAP3 PE = 1 SV = 2 | 109 kDa | 0 | 11 | 0 | 0 |
| Tight junction protein ZO-1 OS = Homo sapiens GN = TJP1 PE = 1 SV = 1 | 188 kDa | 0 | 3 | 0 | 0 |
| Tight junction protein ZO-2 OS = Homo sapiens GN = TJP2 PE = 4 SV = 1 | 141 kDa | 0 | 3 | 0 | 0 |
| Transcription factor A, mitochondrial OS = Homo sapiens OX = 9606 GN = TFAM PE = 1 SV = 1 | 29 kDa | 0 | 14 | 1 | 1 |
| Transcription factor SOX-3 OS = Homo sapiens GN = SOX3 PE = 1 SV = 2 | 45 kDa | 0 | 2 | 0 | 0 |
| Transforming growth factor-beta-induced protein ig-h3 OS = Homo sapiens OX = 9606 GN = TGFBI PE = 1 SV = 1 | 75 kDa | 0 | 670 | 73 | 58 |
| Translocator protein OS = Homo sapiens OX = 9606 GN = TSPO PE = 1 SV = 3 | 19 kDa | 0 | 0 | 0 | 3 |
| Transmembrane protein 165 OS = Homo sapiens GN = TMEM165 PE = 1 SV = 1 | 35 kDa | 0 | 5 | 0 | 1 |
| TREMBL: Q0V8M9; Q9TRI0 (Bos taurus) similar to inter-alpha (globulin) inhibitor H3 isoform 2 | 100 kDa | 0 | 7 | 0 | 0 |
| TREMBL: Q2KJC7; Q8HZM3 (Bos taurus) Periostin, osteoblast specific factor | 87 kDa | 0 | 1 | 12 | 5 |
| TREMBL: Q3SZH5 (Bos taurus) Similar to Angiotensinogen | 45 kDa | 0 | 11 | 4 | 2 |
| TREMBL: Q3T052; Q5EA67 (Bos taurus) Inter-alpha (Globulin) inhibitor H4 | 102 kDa | 0 | 10 | 5 | 1 |
| TREMBL: Q6ISB0 Keratin, hair, basic, 4 - Homo sapiens (Human). | 65 kDa | 0 | 16 | 8 | 8 |
| TREMBL: Q6NXH9 Tax_Id = 10090 Gene_Symbol = Krt73 Keratin 73 | 59 kDa | 0 | 114 | 7 | 10 |
| TRIO and F-actin-binding protein OS = Homo sapiens OX = 9606 GN = TRIOBP PE = 1 SV = 3 | 261 kDa | 0 | 2 | 0 | 0 |
| Tropomodulin-3 OS = Homo sapiens OX = 9606 GN = TMOD3 PE = 1 SV = 1 | 40 kDa | 0 | 47 | 21 | 13 |
| Tropomyosin 1 (Alpha), isoform CRA_f OS = Homo sapiens GN = TPM1 PE = 1 SV = 1 | 37 kDa | 0 | 162 | 0 | 0 |
| Tropomyosin 1 (Alpha), isoform CRA_m OS = Homo sapiens GN = TPM1 PE = 1 SV = 1 | 29 kDa | 0 | 118 | 0 | 0 |
| Tropomyosin alpha-3 chain OS = Homo sapiens GN = TPM3 PE = 1 SV = 1 | 33 kDa | 0 | 112 | 0 | 0 |
| Tubby-related protein 2 (Fragment) OS = Homo sapiens OX = 9606 GN = TULP2 PE = 4 SV = 1 | 24 kDa | 0 | 0 | 0 | 2 |
| Twinfilin-1 OS = Homo sapiens OX = 9606 GN = TWF1 PE = 1 SV = 3 | 40 kDa | 0 | 1 | 1 | 4 |
| Tyrosine-protein kinase OS = Homo sapiens GN = YES1 PE = 1 SV = 1 | 61 kDa | 0 | 7 | 0 | 0 |
| Tyrosine--tRNA ligase OS = Homo sapiens GN = YARS PE = 1 SV = 1 | 44 kDa | 0 | 6 | 0 | 0 |
| U1 small nuclear ribonucleoprotein A (Fragment) OS = Homo sapiens GN = SNRPA PE = 1 SV = 1 | 28 kDa | 0 | 7 | 0 | 0 |
| U3 small nucleolar ribonucleoprotein protein MPP10 OS = Homo sapiens GN = MPHOSPH10 PE = 1 SV = 2 | 79 kDa | 0 | 6 | 0 | 0 |
| U3 small nucleolar RNA-associated protein 14 Homolog A OS = Homo sapiens OX = 9606 GN = UTP14A PE = 1 SV = 1 | 88 kDa | 0 | 2 | 0 | 0 |
| U4/U6.U5 tri-snRNP-associated protein 1 OS = Homo sapiens GN = SART1 PE = 1 SV = 1 | 90 kDa | 0 | 4 | 0 | 0 |
| UAP56-interacting factor OS = Homo sapiens OX = 9606 GN = FYTTD1 PE = 1 SV = 3 | 36 kDa | 0 | 3 | 0 | 0 |
| Ubiquitin carboxyl-terminal hydrolase 24 OS = Homo sapiens OX = 9606 GN = USP24 PE = 1 SV = 3 | 294 kDa | 0 | 0 | 0 | 2 |
| Unconventional myosin-Id OS = Homo sapiens OX = 9606 GN = MYO1D PE = 1 SV = 2 | 116 kDa | 0 | 0 | 2 | 0 |
| Unconventional myosin-VI OS = Homo sapiens GN = MYO6 PE = 1 SV = 1 | 145 kDa | 0 | 26 | 0 | 0 |
| Unconventional myosin-XV OS = Homo sapiens OX = 9606 GN = MYO15A PE = 1 SV = 2 | 395 kDa | 0 | 0 | 2 | 0 |
| Urokinase-type plasminogen activator OS = Homo sapiens GN = PLAU PE = 1 SV = 1 | 47 kDa | 0 | 8 | 0 | 0 |
| UV excision repair protein RAD23 homolog B OS = Homo sapiens GN = RAD23B PE = 1 SV = 1 | 43 kDa | 0 | 5 | 0 | 0 |
| Vacuolar protein sorting-associated protein 26A OS = Homo sapiens OX = 9606 GN = VPS26A PE = 1 SV = 2 | 38 kDa | 0 | 5 | 0 | 3 |
| Very-long-chain enoyl-CoA reductase OS = Homo sapiens GN = TECR PE = 1 SV = 1 | 36 kDa | 0 | 6 | 0 | 0 |

TABLE 2-continued

Amniotic Fluid Cell-Derived ECM (AFC-ECM) Components

| Protein | MW | Total Spectra Count Matrix A | Matrix B | Matrix C | Matrix D |
|---|---|---|---|---|---|
| Vesicle-trafficking protein SEC22b OS = Homo sapiens GN = SEC22B PE = 1 SV = 4 | 25 kDa | 0 | 6 | 0 | 0 |
| V-type proton ATPase subunit B, brain isoform OS = Homo sapiens GN = ATP6V1B2 PE = 1 SV = 3 | 57 kDa | 0 | 16 | 0 | 0 |
| V-type proton ATPase subunit d 1 OS = Homo sapiens GN = ATP6V0D1 PE = 1 SV = 1 | 45 kDa | 0 | 22 | 0 | 0 |
| Zinc finger protein 469 OS = Homo sapiens OX = 9606 GN = ZNF469 PE = 2 SV = 3 | 410 kDa | 0 | 0 | 0 | 4 |

Example 3—Proliferation of iPSCs on Amniotic Fluid Cell-Derived ECM

Induced pluripotent stem cells (iPSCs) were allowed to proliferate on an amniotic fluid cell-derived ECM (Matrix B) from Example 1 in culture using the following procedure: commercially available, cryopreserved iPSCs were thawed using a water bath at 37° C. Cell suspension was diluted into commercially available media for stem cell proliferation (Miltenyi Biotec MACS iPS Brew) and seeded onto the ECM at approximately 1,000 cells/cm² in a 6-well-plate with 2 mL of media/well. No Rock inhibitor was used. At day 1, the full volume of media was aspirated gently from cells in culture and replaced with fresh media. Every 24 hours, full media was replaced with fresh media. Once cells began to approach confluence (as determined by brightfield microscopy), cells were passage manually, using a sterile needle to cut large colonies into approximately 100 smaller colonies and then re-plate those by physically lifting them off the dish with the sterile needle and placing them on a fresh plate of the ECM. This procedure can be repeated indefinitely.

Figure 4:
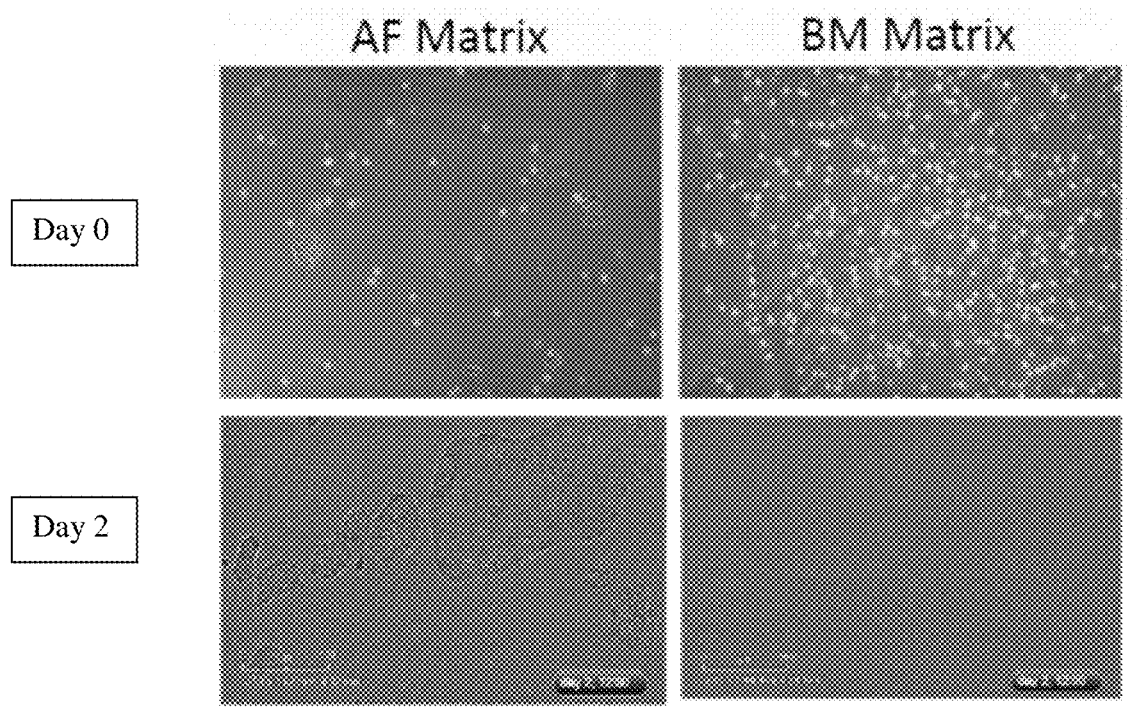
FIG. 4: A photomicrograph showing Day 0 and Day 2 culture of iPSCs on amniotic fluid cell-derived ECM and a bone marrow cell-derived ECM.

A photomicrograph showing Day 0 and Day 2 culture of iPSCs on amniotic fluid cell-derived ECM and a bone marrow cell-derived ECM is shown in FIG. 4.

Figure 5:
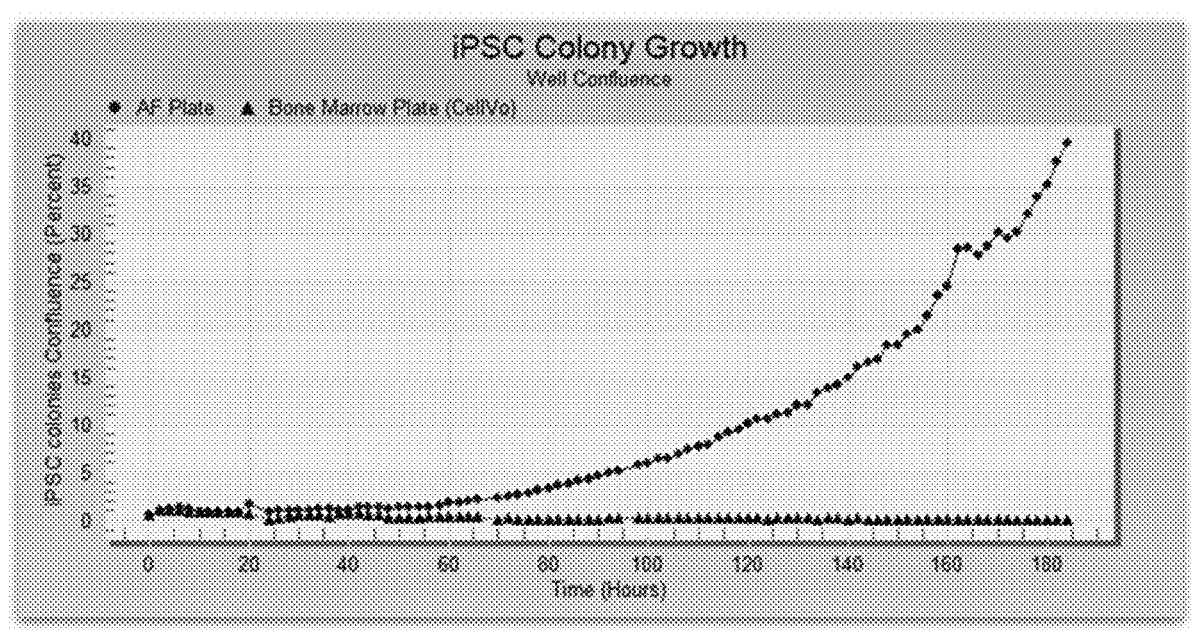
FIG. 5: A plot of growth curves of iPSCs cultured in the presence of the amniotic fluid cell-derived ECM and a bone marrow cell-derived ECM.
Figure 6:
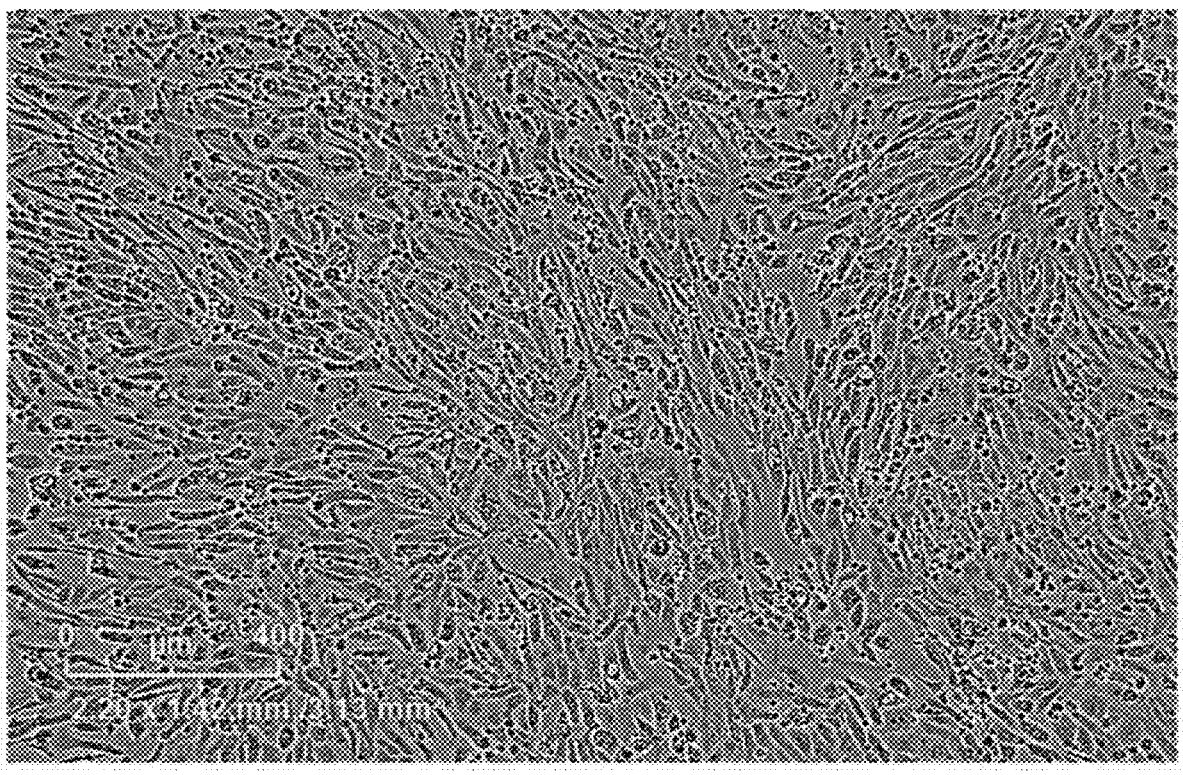
FIG. 6: A photomicrograph of mature cardiomyocytes on an AFC-ECM in a single well—3.13 mm$^2$.
Figure 7:
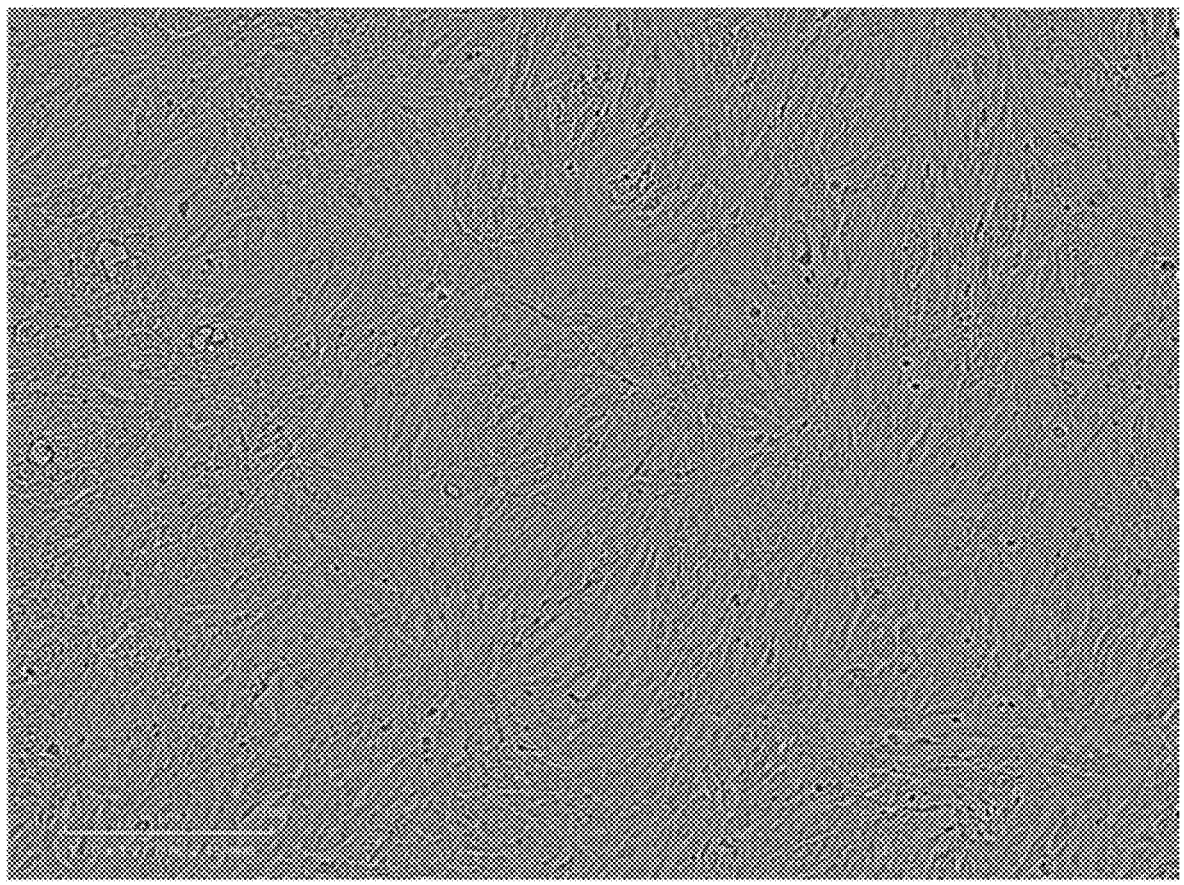
FIG. 7: A photomicrograph of mature cardiomyocytes on an AFC-ECM in a single well—2.15 mm$^2$.
Figure 8:
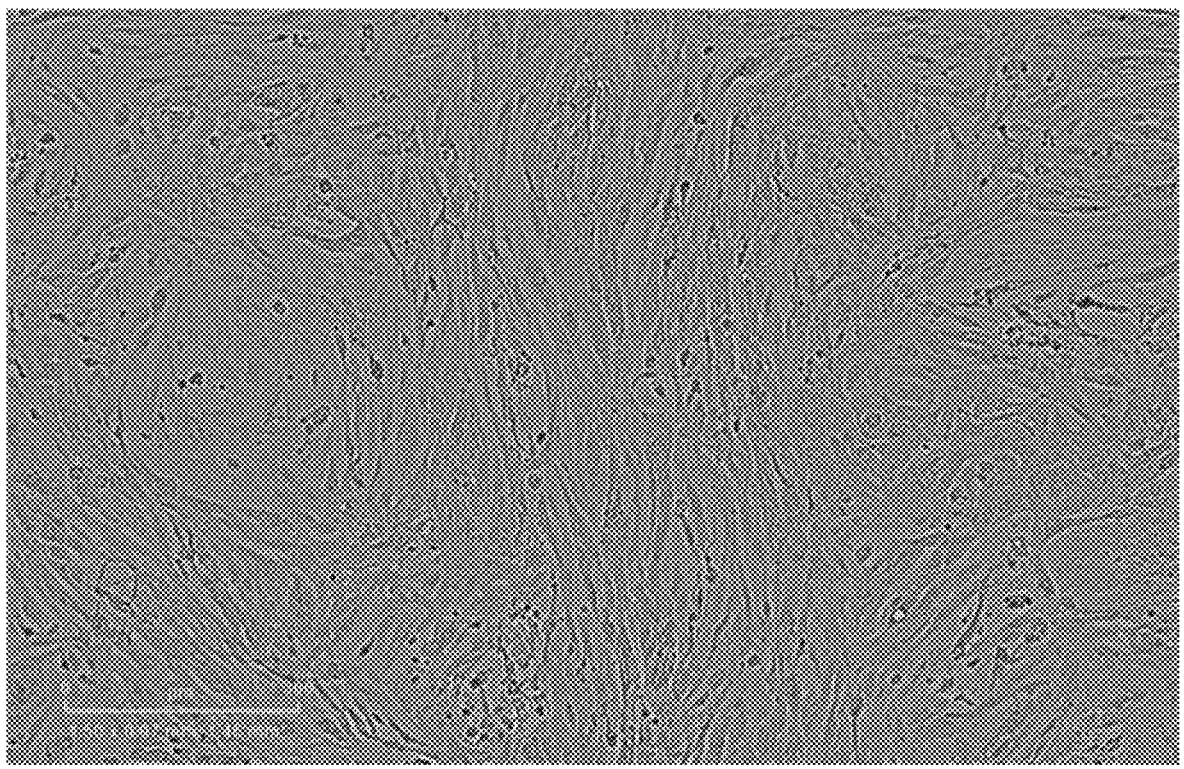
FIG. 8: A photomicrograph of mature cardiomyocytes on an AFC-ECM in a single well—1.46 mm$^2$.
Figure 9:
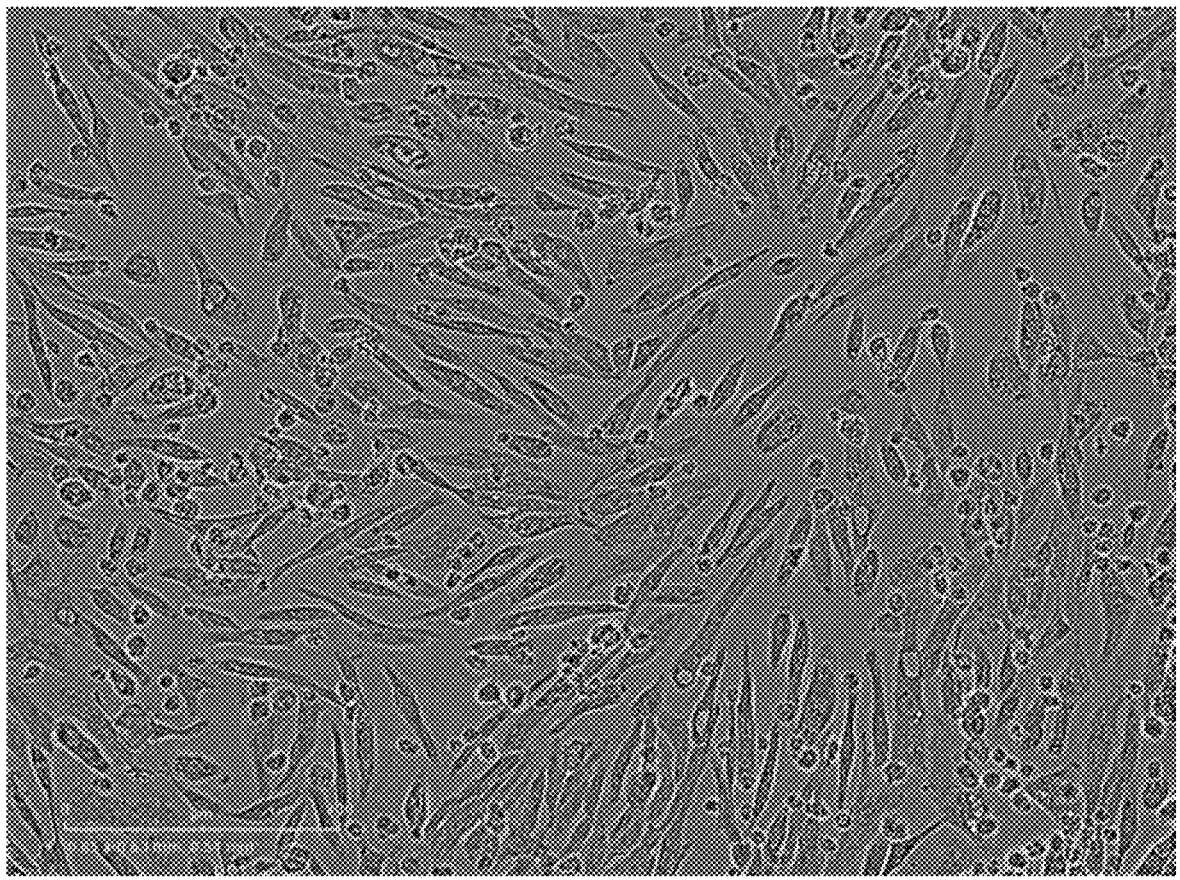
FIG. 9: A photomicrograph of mature cardiomyocytes on AFC-ECM in a single well—0.54 mm$^2$.
Figure 10:
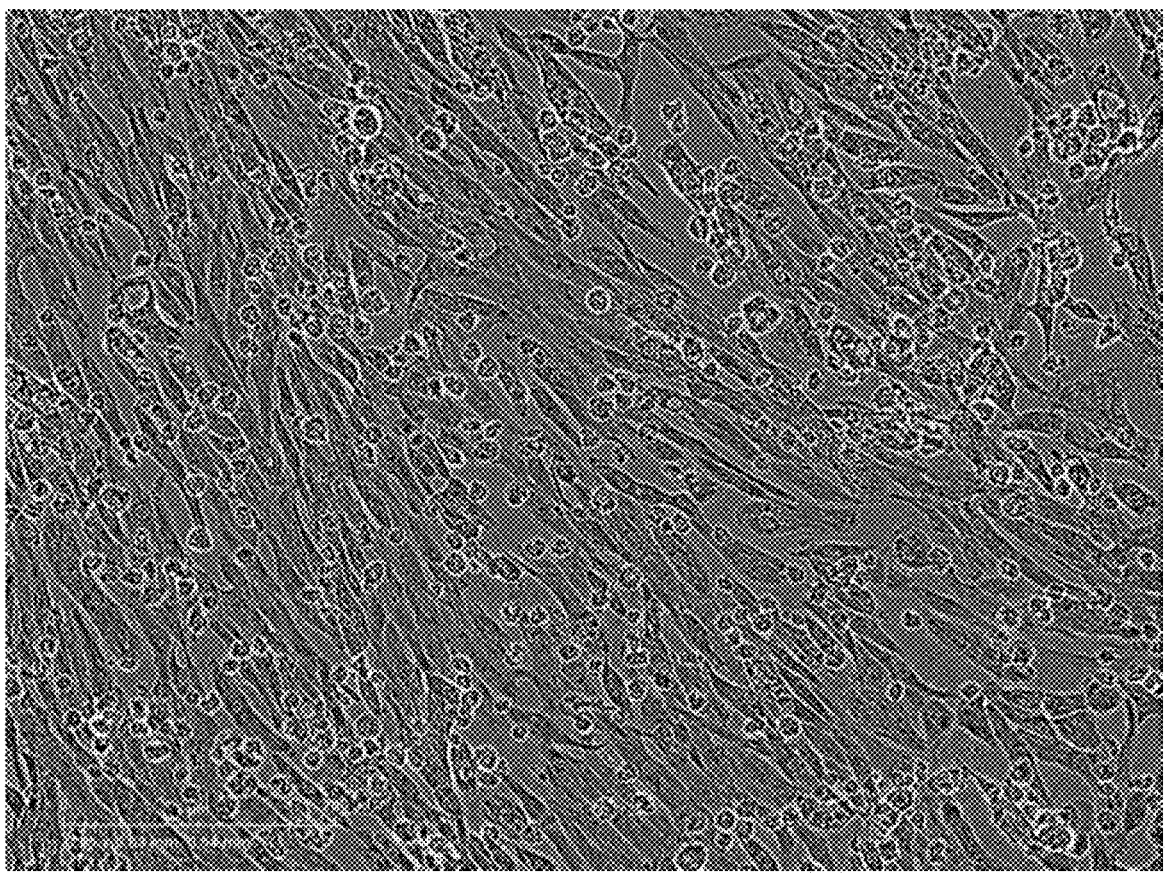
FIG. 10: A photomicrograph of mature cardiomyocytes on AFC-ECM in a single well—0.54 mm$^2$.
Figure 11:
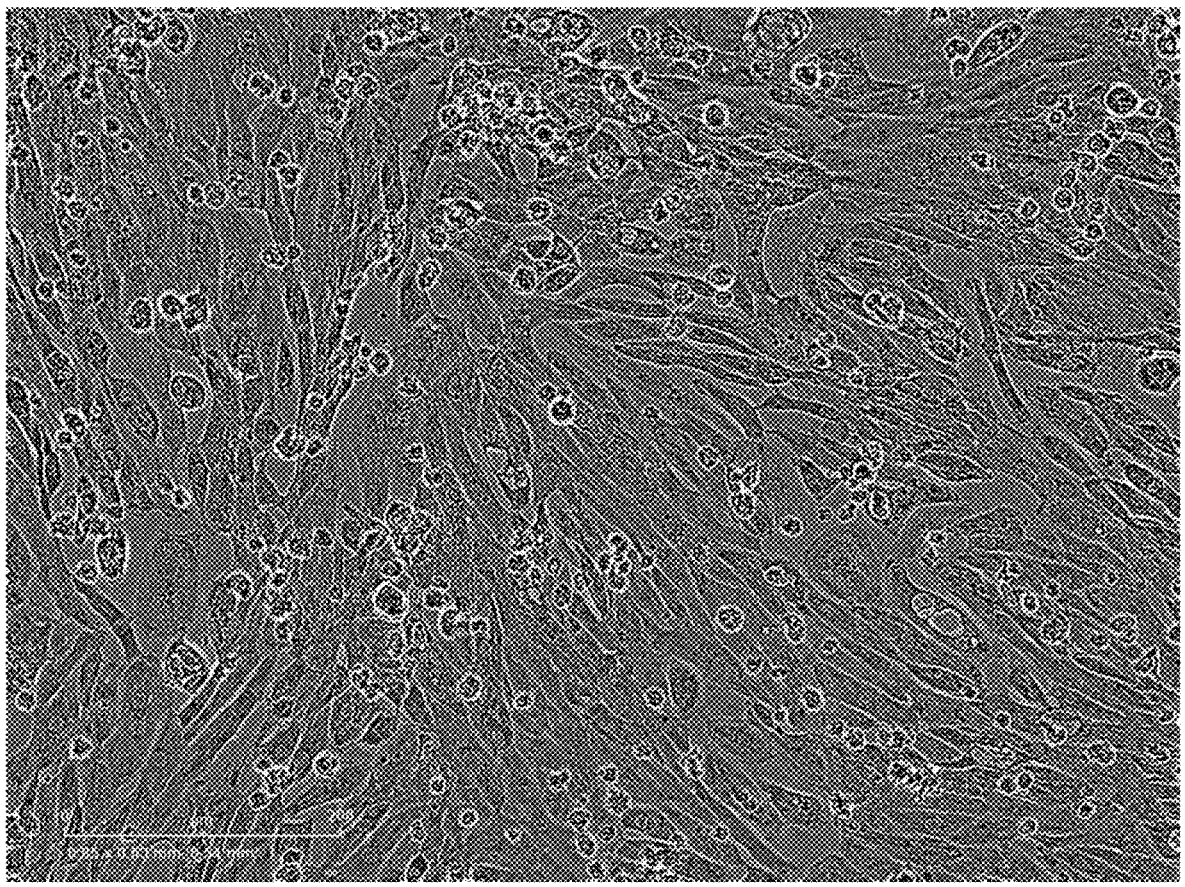
FIG. 11: A photomicrograph of mature cardiomyocytes on AFC-ECM in a single well—0.54 mm$^2$.
Figure 12:
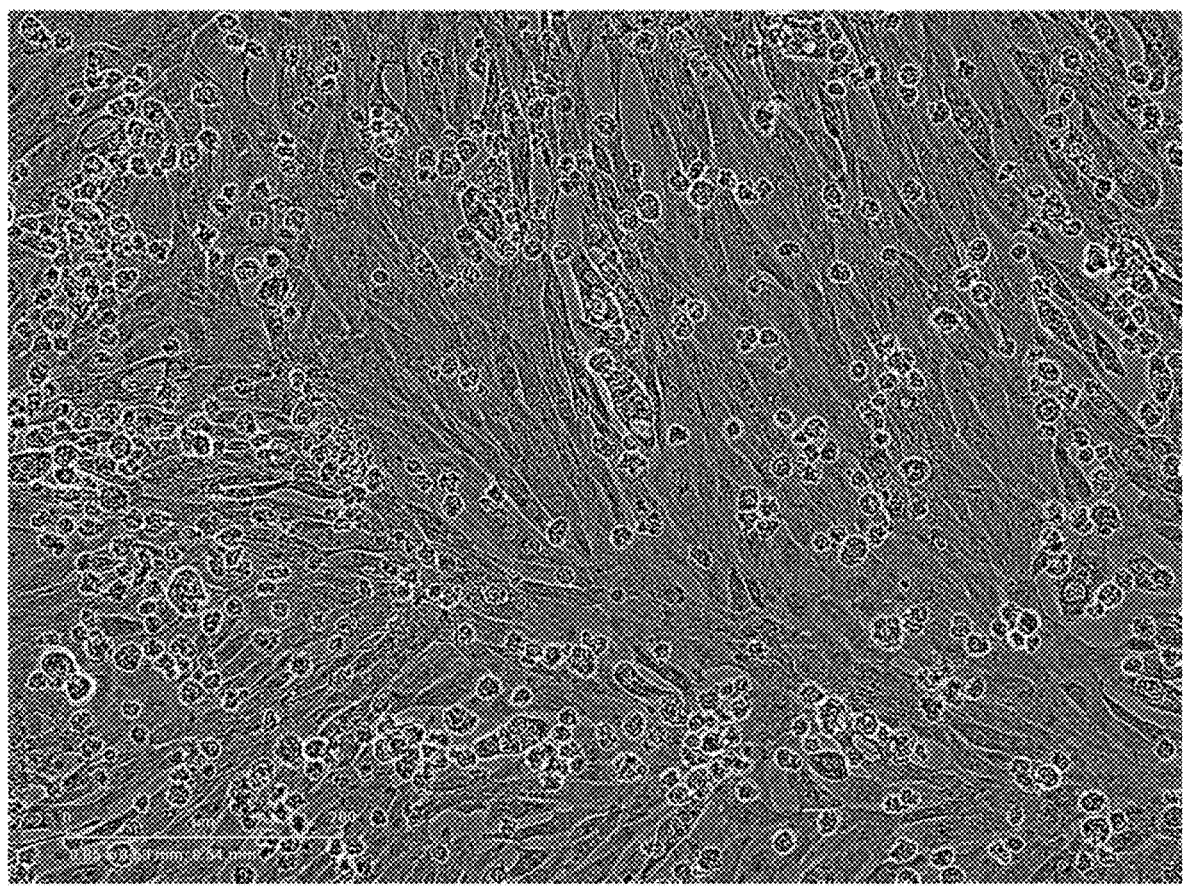
FIG. 12: A photomicrograph of mature cardiomyocytes on AFC-ECM in a single well—0.54 mm$^2$.
Figure 13:
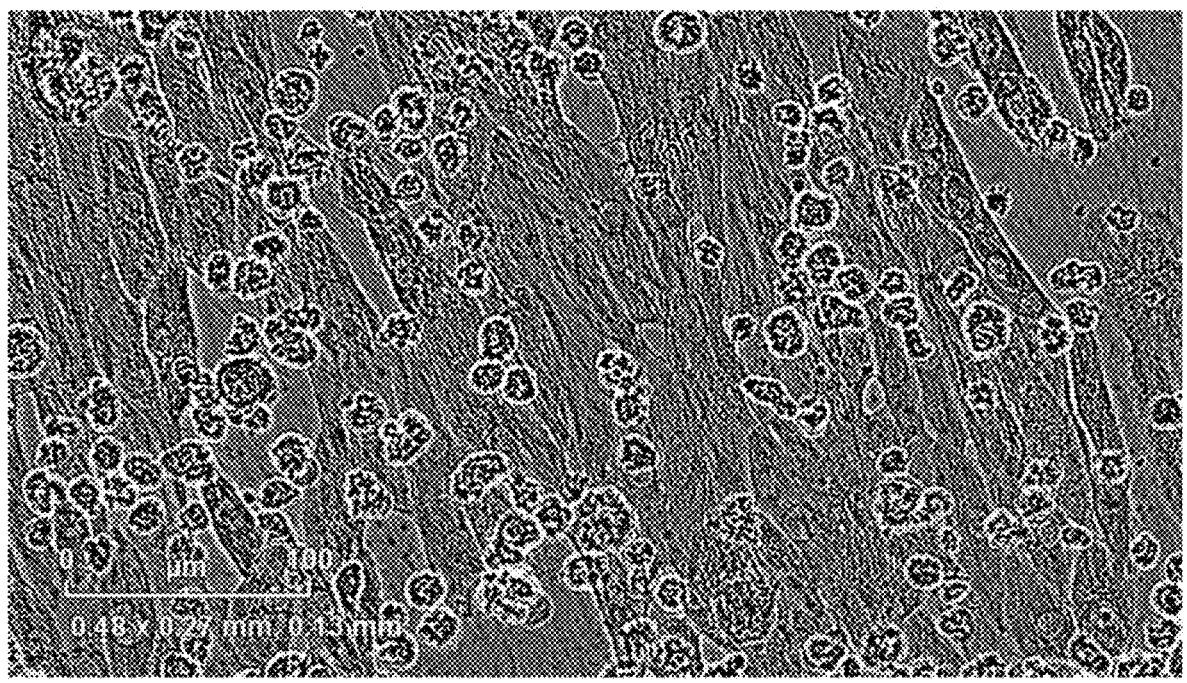
FIG. 13: A photomicrograph of mature cardiomyocytes on AFC-ECM in a single well—0.13 mm$^2$.

A plot of iPSC colony growth curves of iPSCs cultured in the presence of the amniotic fluid cell-derived ECM and a bone marrow cell-derived ECM is shown in FIG. 5.

As can be seen in FIG. 4 and FIG. 5, the iPSCs proliferated in culture in the presence of the amniotic fluid cell-derived ECM, whereas iPSCs cultured in the presence of a bone marrow cell-derived ECM had no growth.

Example 4—Preparation of a Cellular Construct of Mature Cardiomyocytes on an AFC-ECM and Maturation of Immature hiPSC-CMs on the AFC-ECM Cellular constructs comprising monolayers of mature cardiomyocytes on extracellular matrices derived from cells derived in-vitro from amniotic fluid (AFC-ECMs) were prepared using the following method.

Using the methodology as outlined in Example 1, AFC-ECMs were prepared in 96-well plates (no silicone inserts were used). Using standard cell culture techniques, commercially available immature hiPSC-CMs from Cellular Dynamics International-FUJI (iCell® Cardiomyocytes) were plated on the AFC-ECMs. The immature hiPSC-CMs were plated at a density of 50,000 cells per well (96 well plate) or 200,000 cells per well (6 well plate), and were cultured for 7 days in RPMI media forming confluent monolayers of mature cardiomyocytes on the AFC-ECMs, thereby forming cellular constructs of mature cardiomyocyte monolayers on the AFC-ECMs.

Over the 7-day period, the immature hiPSC-CMs were observed to mature into the morphology and alignment of mature native adult cardiomyocytes as characterized by rod shaped cells with distinct sarcomere structure. For comparison purposes, iCell® immature hiPSC-CMs were also plated (no silicone inserts were used) in 96-well plates and cultured in a similar fashion on standard Matrigel™ ECM, and on a bone marrow cell-derived ECM (BM-ECM) as prepared by methods as disclosed in U.S. Pat. No. 8,084,023, herein incorporated by reference. Results of the studies are shown in photomicrographs of the cardiomyocytes on the different ECMs in FIGS. 6 to 21.

As can be seen in the FIGS. 6 to 14, the cardiomyocytes on the AFC-ECM are mature, rod shaped cells with distinct sarcomere structure resembling native adult cardiomyocytes. The morphology and sarcomere structure of the cardiomyocytes matured on AFC-ECM can be distinctly seen by the presence of rod shaped cells with a striped appearance identified by arrows in the photomicrograph of FIG. 14. The figures show the presence of fiber tracks on the AFC-ECM, and also show that the monolayer of mature cardiomyocytes is in alignment with the AFC-ECM which closely resembles characteristics found in native adult cardiomyocytes and native heart muscle tissue. By contrast, as can be seen in FIGS. 15 to 19 and FIGS. 20 to 21, the cardiomyocytes on the standard Matrigel™ ECM and BM-ECM respectively, resemble fetal-like cardiomyocytes and do not have the characteristics of native adult cardiomyocytes or native heart muscle tissue.

Thus, the immature hiPSC-CMs cultured on the AFC-ECM achieved a higher state of maturation than did the immature hiPSC-CMs cultured on the standard Matrigel™ ECM or the natural cell-derived ECM from bone marrow cells. It is evident that the hiPSC-CM morphology was affected differently by different ECM.

Figure 22:
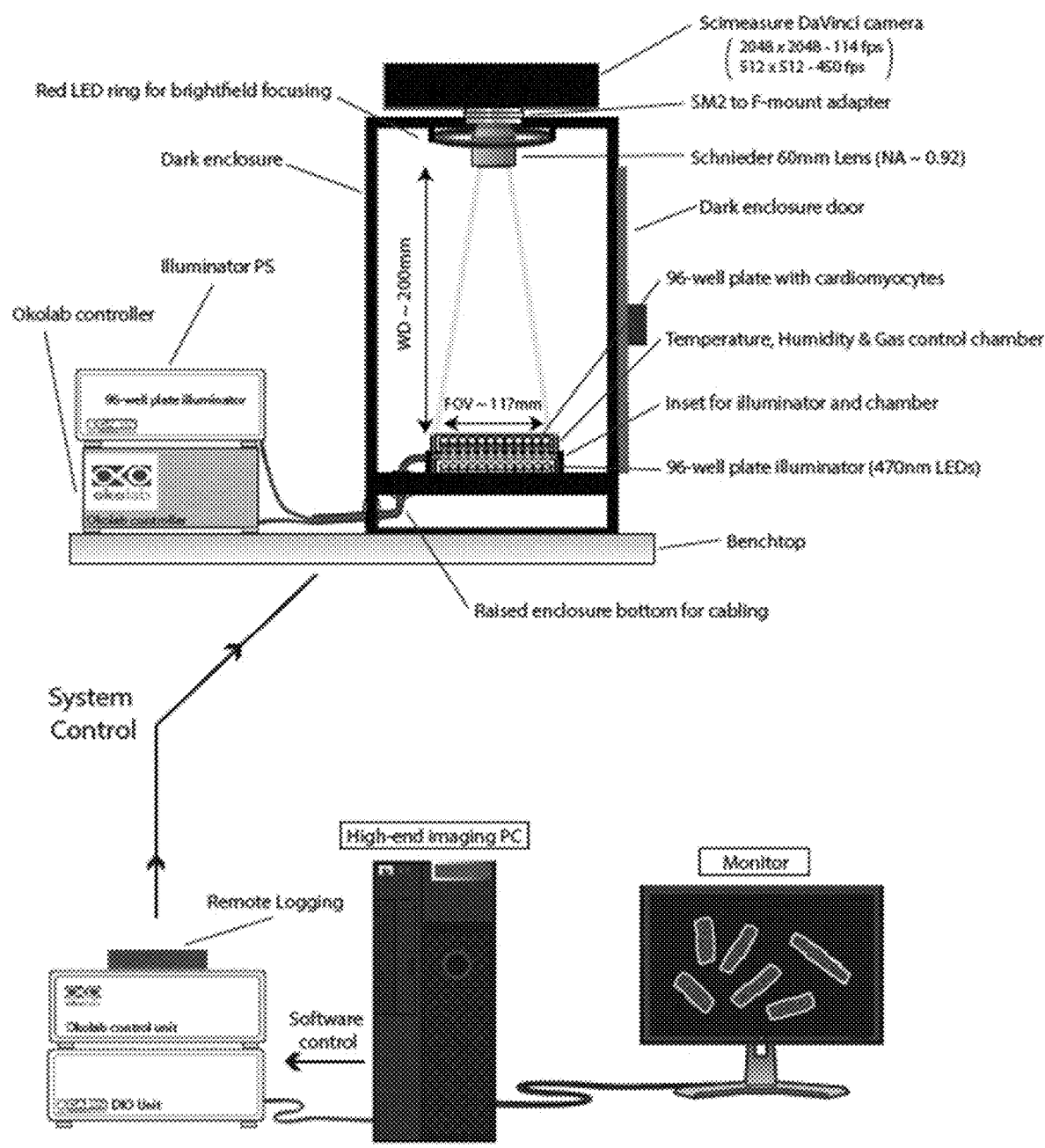
FIG. 22: A schematic of the configuration of instruments to record action potential or calcium transient measurements using mature cardiomyocytes on AFC-ECM in multi-well plates.
Figure 23:
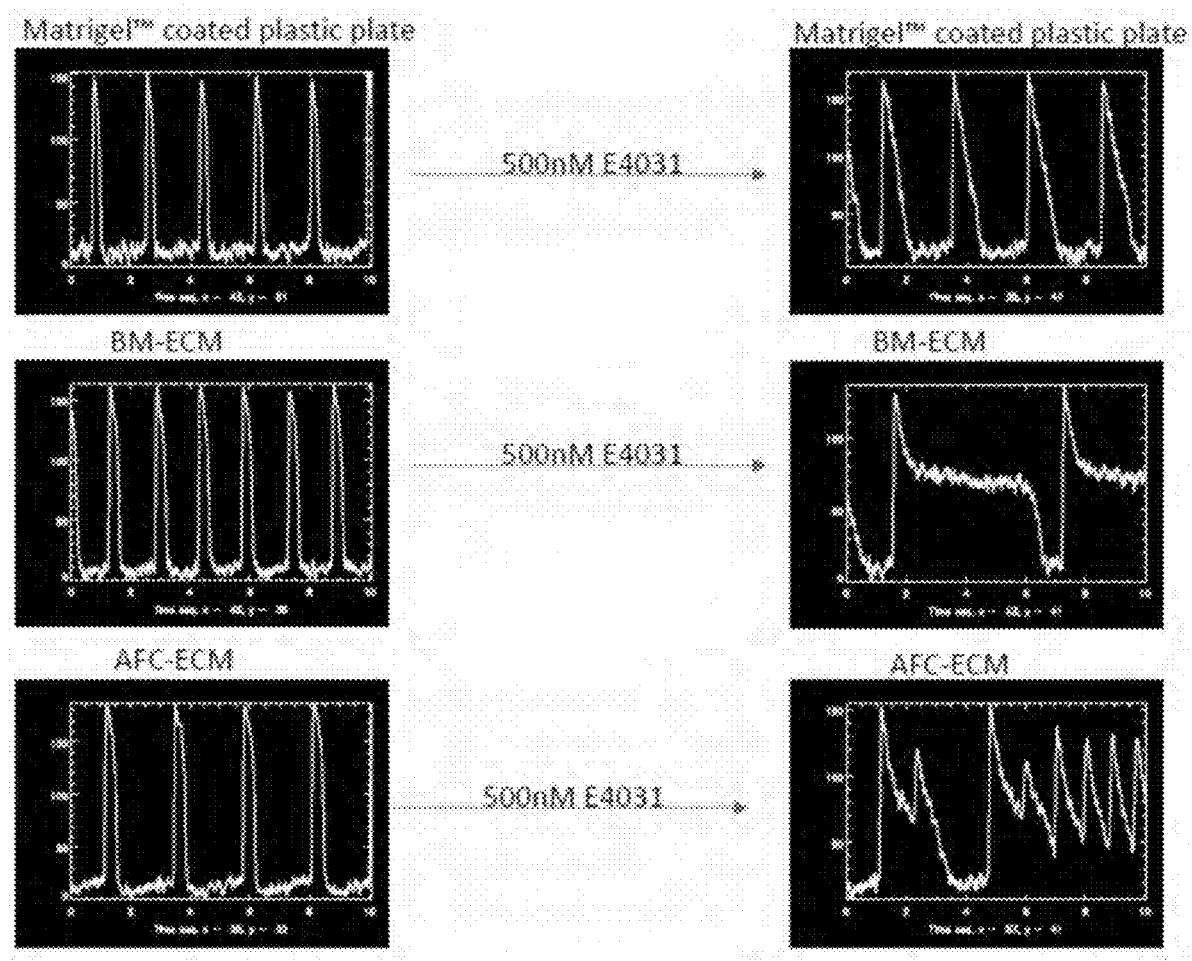
FIG. 23: Recordings of spontaneous action potentials recorded from cardiomyocytes cultured on Matrigel™ ECM, BM-ECM, and AFC-ECM, baseline and after drug E4031.
Figure 24:
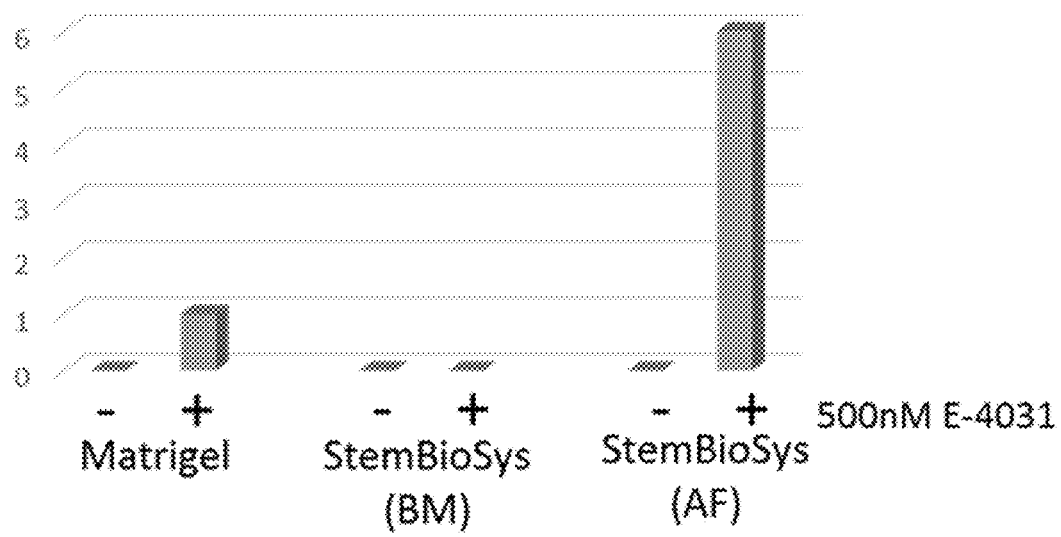
FIG. 24: Bar graph of number of Stable Rotors (TdP like arrythmia) from cardiomyocytes cultured on Matrigel™ ECM, BM-ECM, and AFC-ECM after contact with drug E4031.

Example 5—High Throughput Cardiotoxicity Screen Testing of Drugs Using Cellular Construct of Mature Cardiomyocytes on an AFC-ECM Cellular constructs of monolayers of mature cardiomyocytes on AFC-ECM were prepared as described in Example 4 using 96-well plates (no silicone inserts were used). After the 7-day maturation process the electrophysiology of each well was observed using a plate reader using the following high throughput screen method. FluoVolt™ dye in Hanks Balanced Salt Solution was loaded into each well. A high spatiotemporal CCD camera (SciMeasure DaVinci camera) combined with light emitting diodes (LEDs) as shown in the schematic in FIG. 22. The camera and lens combination were designed such that it allowed visualization of all the wells of the 96-well plate simultaneously with sufficient resolution to observe action potential and calcium wave propagation. Each plate was centered under the camera system, lighting was switched on and camera acquisition was initiated and electrophysiological activity was recorded. Experiments were performed at about 37° C. Spontaneous activity was recorded for at least 10 seconds and images were stored on a computer. After baseline readings were taken, 500 nM of the drug E4031 (a hERG channel blocker) was added to each well. Images were analyzed and action potential duration, conduction velocity, beat rate and activation patterns were quantified using image analysis software. For comparison purposes, immature hiPSC-CMs were cultured on standard Matrigel™ ECM and bone-marrow cell derived ECM (BM-ECM) in 96 well plates (no silicone inserts were used) as described in Example 4, and 500 nM of the drug E4031 (a hERG channel blocker) was analyzed in similar fashion as with the AFC-ECM studies. Results of the E4031 testing are shown in FIG. 23 and FIG. 24. As can be seen in FIG. 23, the recordings of the spontaneous action potentials recorded from the cardiomyocytes on the Matrigel™ ECM and BM-ECM showed that the drug E-4031 only caused action potential duration (APD) prolongation; however, on the mature cardiomyocytes on the AFC-ECM, the drug E-4031 caused APD prolongation plus Rotors (TdP-like arrhythmias) which are arrhythmia activation patterns consistent with what is known to occur in cases of TdP in humans. Thus, all three ECMs produced monolayers of cardiomyocytes that responded with predicted APD prolongation, but only the AFC-ECM produced monolayers of cardiomyocytes that revealed transition of APD prolongation to tachyarrhythmia, characteristic of TdP. As can be seen in FIG. 24, 100% of the cardiomyocytes on the AFC-ECM responded to the drug E4031 with rotors (TdP like arrhythmia).

Figure 25:
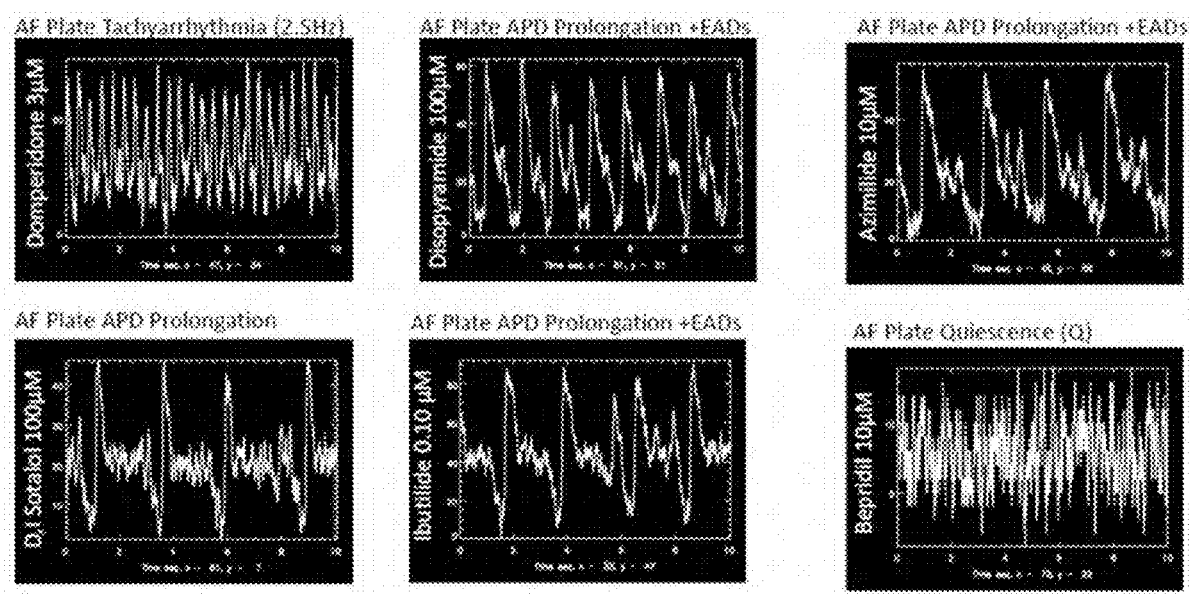
FIG. 25: Recordings of spontaneous action potentials recorded from mature cardiomyocytes cultured on AFC-ECM for various drugs.

In additional studies, the drugs domperidone (3 µM), diisopyramide (100 µM), azimilide (10 µM), D,1 Sotalol (100 µM), ibutilide (0.10 µM), and Bepridil (10 µM) were tested with mature cardiomyocytes on AFC-ECM as prepared in Example 4 (no silicone inserts) in 96-well plates using the plate reader method described above. The results of the testing are shown in FIG. 25. As can be seen in the results, various types of arrhythmias, i.e., tachyarrhythmia (TA), quiescence (Q), early after depolarization (EAD), were caused by the various drugs as notated in the recordings. In response to drugs classified as high risk for causing TdP fatal arrhythmias in patients by the FDA—these are the range of arrhythmia types observed.

Various drugs shown in Table 3 and 4 below were also tested with mature cardiomyocytes on AFC-ECM as prepared in Example 4 (no silicone inserts) in 96-well plates using the plate reader method described above and observations for any arrhythmia detected and APD90 prolongation at 10 times the effective therapeutic plasma concentration (ETPC) were notated. The drugs were selected from the CiPA Initiative's list of compounds for validation and testing of CiPA and are classified as high risk, intermediate risk or low risk for causing fatal arrhythmias (TdPs) in patients. The complete list of CiPA compounds can be found at cipaproject.org/wp-content/uploads/sites/24/2016/05/CiPA-Compounds.pdf.

TABLE 3

| Drug | Risk Category | Dose 1 (µM) | Dose 2 (µM) | Dose 3 (µM) | Dose 4 (µM) | Arrhythmia Detected? | APD90 Prolongation? @10X ETPC |
|---|---|---|---|---|---|---|---|
| Tamoxifen | Low | 0.1 | 0.5 | 1.0 | 10.0 | No | No |
| Nifedipine | Low | 0.001 | 0.01 | 0.1 | 1.0 | Yes, Q | No, Shortening |
| Nitrendipine | Low | 0.00951 | 0.03004 | 0.09494 | 0.3 | No | No, Shortening |
| Mexiletine | Low | 0.01 | 0.1 | 1.0 | 10.0 | No | No |
| Ranolazine | Low | 0.01 | 0.1 | 1.0 | 10.0 | No | No |
| Domperidone | Intermediate | 0.003 | 0.03 | 0.3 | 3.0 | Yes, TA | Yes |
| Droperidol | Intermediate | 0.03169 | 0.10014 | 0.31646 | 1.0 | Yes, EAD | Yes |
| Clozapine | Intermediate | 0.09507 | 0.30043 | 0.94937 | 3.0 | No | Yes |
| Terfenadine | Intermediate | 0.001 | 0.01 | 0.1 | 1.0 | No | Yes |
| Disopyramide | High | 0.100 | 1.00 | 10.00 | 100.00 | Yes, EAD, TA | Yes |
| Quinidine | High | 0.95 | 3.00 | 9.49 | 30.0 | Yes, EAD | Yes |
| D, I Sotalol | High | 0.1 | 1.0 | 10.0 | 100.00 | Yes, EAD | Yes |
| Bepridil | High | 0.01 | 0.10 | 1.00 | 10.0 | Yes, Q | Yes |
| Dofetilide | High | 0.0005 | 0.0010 | 0.0032 | 0.010 | Yes, EAD | Yes |

TABLE 4

| Drug | Risk Category | Dose 1 (µM) | Dose 2 (µM) | Dose 3 (µM) | Dose 4 (µM) | Arrhythmia Detected? | APD90 Prolongation? @10X ETPC |
|---|---|---|---|---|---|---|---|
| Diltiazem | Low | 0.01 | 0.10 | 1.0 | 10.0 | No | No, shortening |
| Loratadine | Low | 0.00095 | 0.003 | 0.00949 | 0.03 | No | No |
| Metoprolol | Low | 3.169 | 10.0144 | 31.6456 | 100 | Yes, | No |
| Verapamil | Low | 0.001 | 0.01 | 0.1 | 1 | No | No, Shortening |
| Astemizole | Intermediate | 0.0001 | 0.001 | 0.01 | 0.1 | Yes | Yes |
| Chlorpromazir | Intermediate | 0.09507 | 0.30043 | 0.94937 | 3.0 | NA | NA |
| Cisapride | Intermediate | 0.00317 | 0.01001 | 0.03165 | 0.1 | Yes | No |

TABLE 4-continued

| Drug | Risk Category | Dose 1 (µM) | Dose 2 (µM) | Dose 3 (µM) | Dose 4 (µM) | Arrhythmia Detected? | APD90 Prolongation? @10X ETPC |
|---|---|---|---|---|---|---|---|
| Pimozide | Intermediate | 0.00095 | 0.003 | 0.00949 | 0.03 | Yes | No |
| Risperidone | Intermediate | 0.00317 | 0.01001 | 0.03165 | 0.1 | No | |
| Ondansetron | Intermediate | 0.03 | 0.30 | 3.0 | 30.0 | Yes, EAD | Yes |
| Azimilide | High | 0.01 | 0.10 | 1.0 | 10.0 | Yes, EAD | Yes |
| Ibutilide | High | 0.0001 | 0.0010 | 0.0100 | 0.100 | Yes, EAD | YeS |
| Vandetanib | High | | | | | Yes, EAD | Yes |

Figure 26:
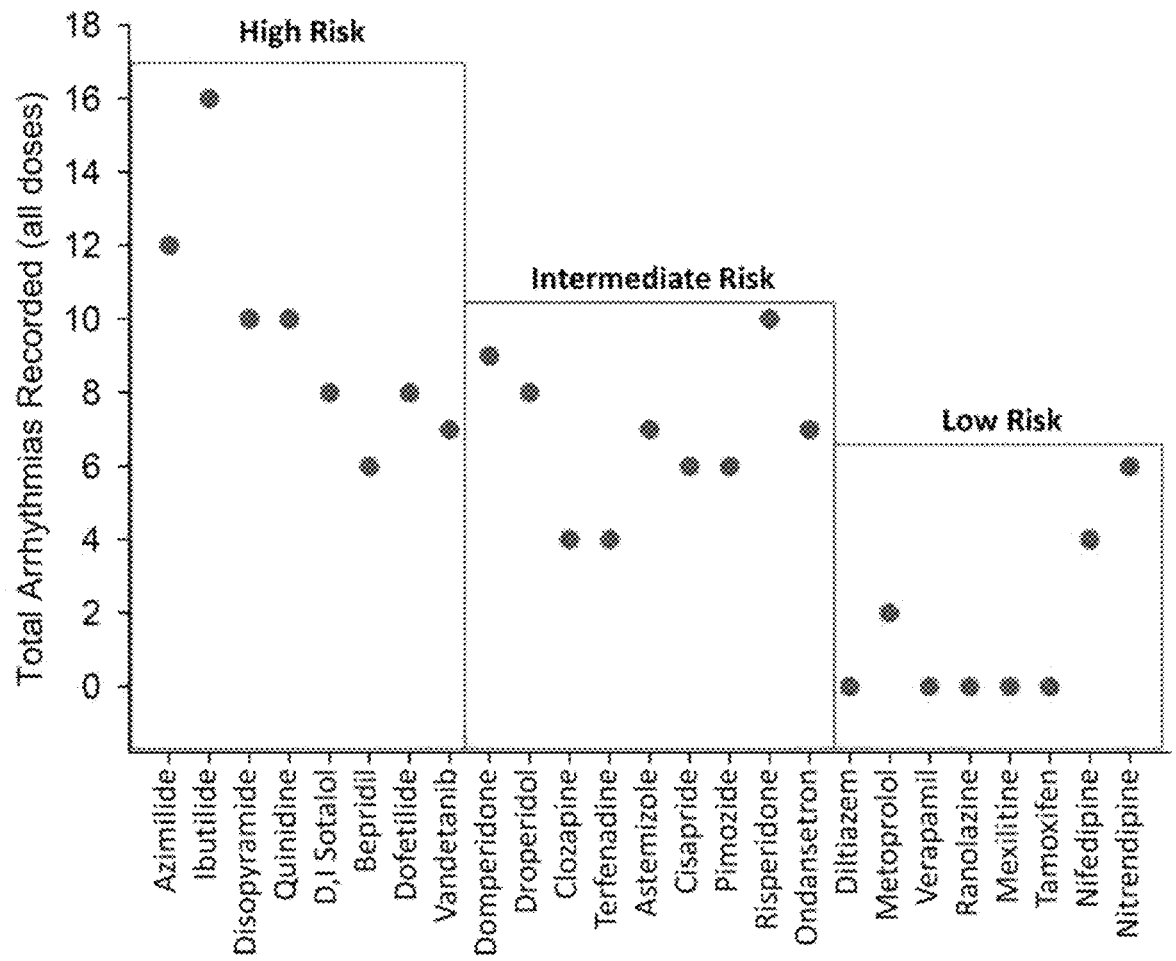
FIG. 26: Bar graph of total arrythmias recorded for all doses of each of the listed drugs.
Figure 27:
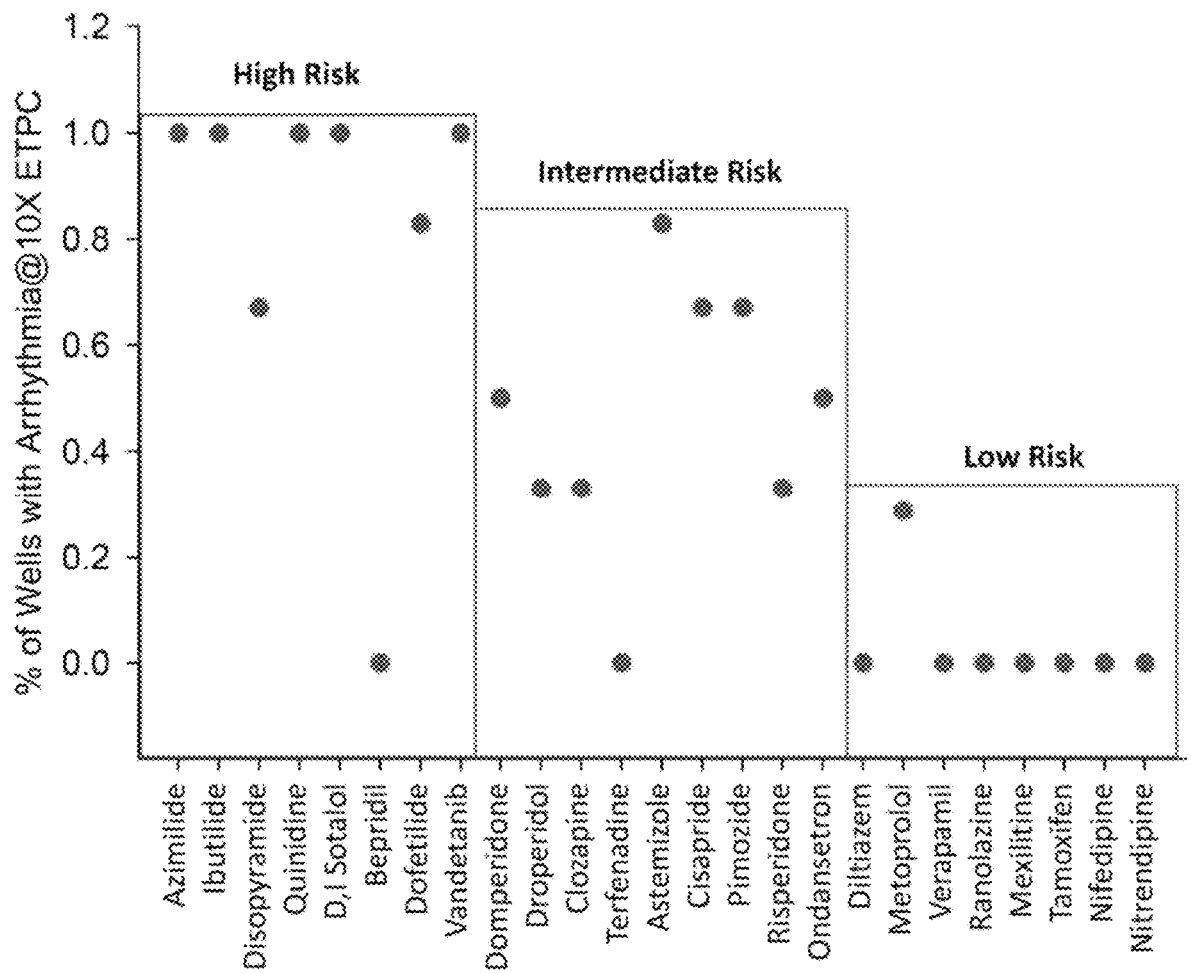
FIG. 27: Bar graph of % of well with arrhythmia @ 10× the effective therapeutic plasma concentration (ETPC) of each of the listed drugs.

Further analyses of the data from the drugs tested in Tables 3 and 4 are shown in FIGS. 26 to 29. FIG. 26 graphically shows the total number of arrhythmias observed per any dose of each drug compound. FIG. 27 graphically shows the relative occurrence of arrhythmias for each drug at specific clinically relevant doses, 10× the effective therapeutic plasma concentration (ETPC).

Figure 28:
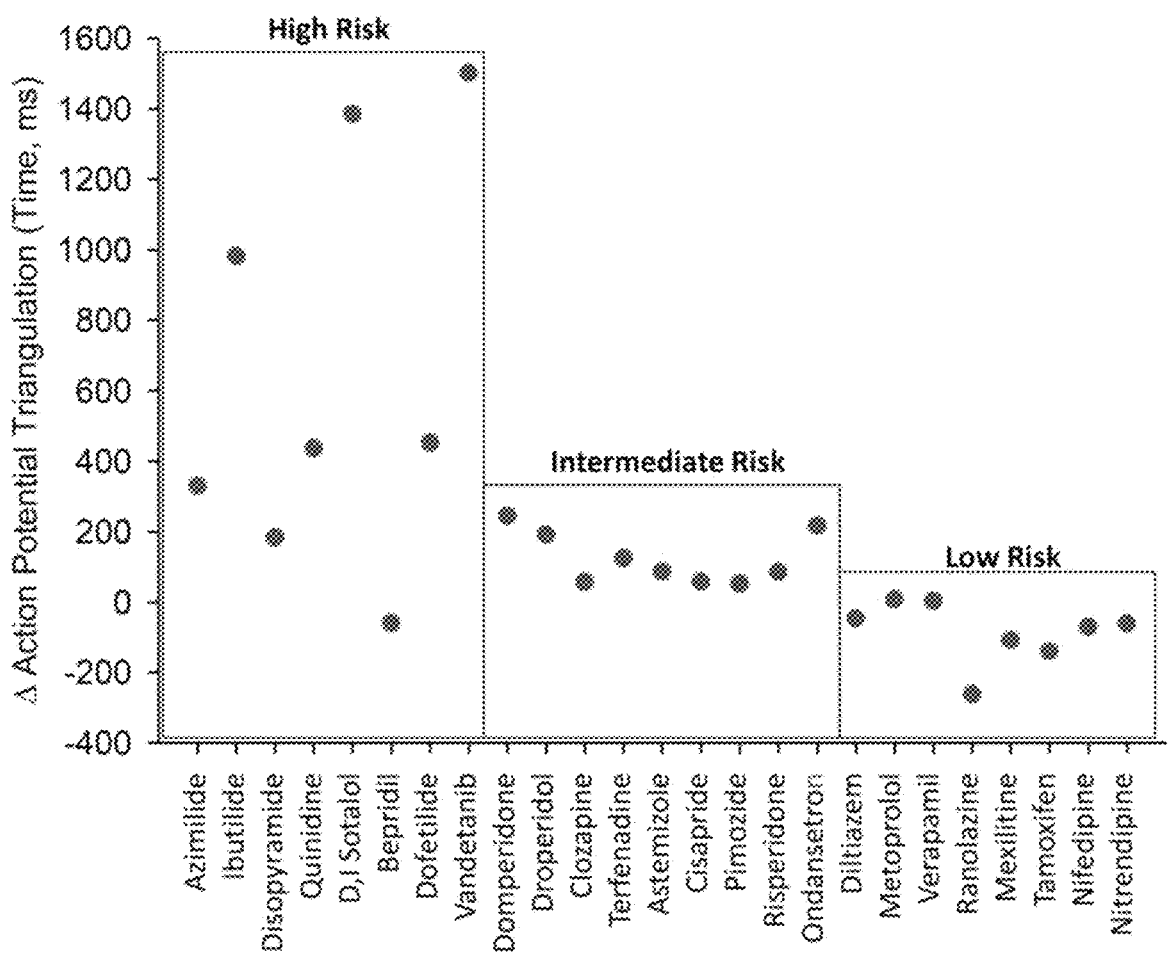
FIG. 28: Bar graph of the action potential triangulation (APD90-APD30) in time (ms) of each of the listed drugs.
Figure 29:
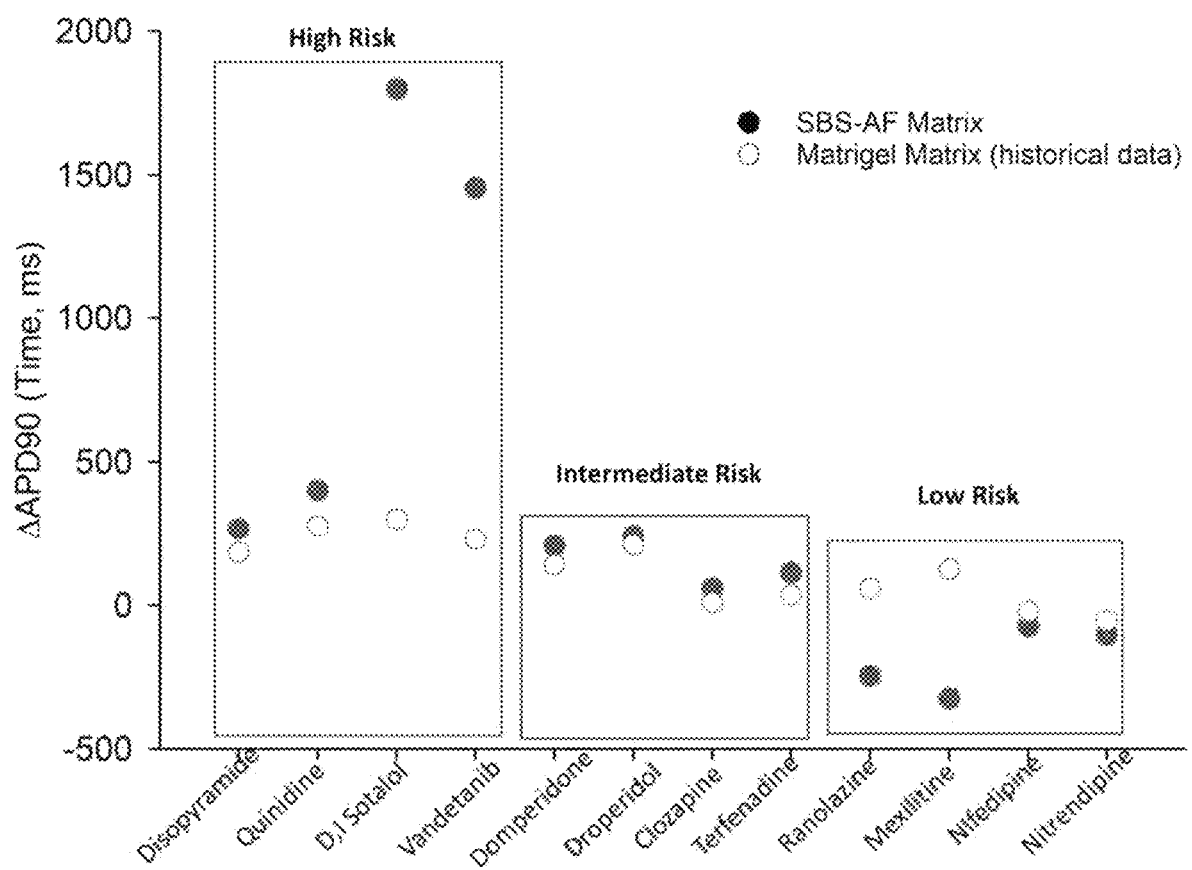
FIG. 29: Bar graph of the action potential triangulation (APD90-APD30) in time (ms) of each of some of the listed drugs comparing cardiomyocyte performance of cardiomyocytes on the AFC-ECM (SBS-AF Matrix) versus on Matrigel™ ECM.

FIG. 28 graphically shows the action potential triangulation (APD90-APD30) in time (ms) for each drug. Triangulation is defined as the repolarization time from APD30 to APD90. Action potential triangulation (APD90-APD30) is used as a predictor for proarrhythmia of a drug. FIG. 29 shows the action potential triangulation in time (ms) for some drugs comparing cardiomyocyte assay performance of the cardiomyocytes on the AFC-ECM (SBS-AF Matrix) versus on Matrigel™ ECM.

Figure 30:
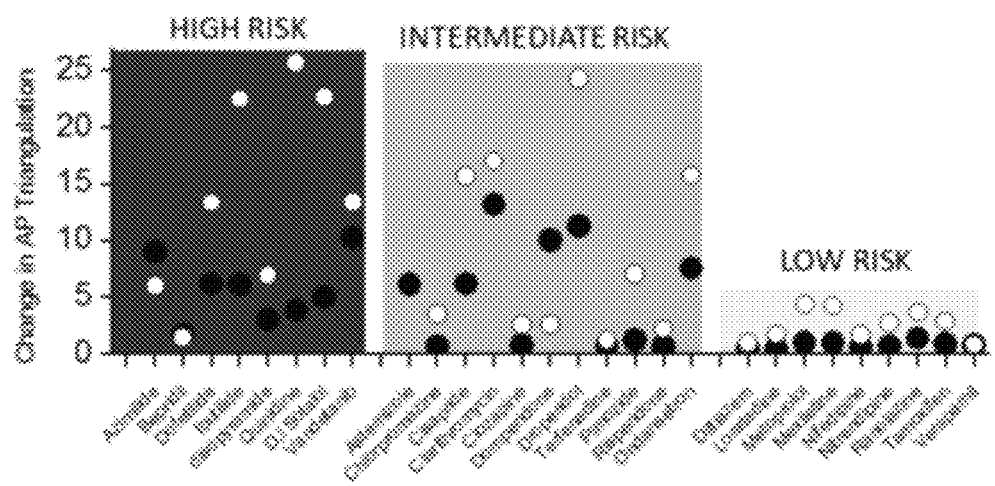
FIG. 30: Bar graph of the maximum drug-induced action potential triangulation of the listed drugs comparing cardiomyocyte performance of iCell® hiPSC-CMs from Cellular Dynamics (blank circles) versus Cor.4U® hiPSC-CMs from Ncardia (dark circles) at any concentration of the listed drugs. Figure from Blinova et al, 2018, Cell Reports.

FIG. 30 graphically shows the maximum drug-induced action potential triangulation of the listed drugs comparing cardiomyocyte performance of iCell® hiPSC-CMs from Cellular Dynamics (blank circles) versus Cor.4U® hiPSC-CMs from Ncardia (dark circles) at any concentration of the listed drugs. This figure is from publication Blinova et al, International Multisite Study of Human-Induced Pluripotent Stem Cell-Derived Cardiomyocytes for Drug Proarrhythmic Potential Assessment, 2018, Cell Reports 24, 3582-3592. In contrast to FIG. 28, there is little stratification between high risk and intermediate risk compounds in the data set shown in FIG. 30. Thus, the AFC-ECM of this disclosure provides for the production of more mature cardiomyocytes with more realistic function and drug responsiveness than of other natural cell-derived ECMs or Matrigel™ ECM.

Example 6—Observations of a Cellular Construct of Mature Cardiomyocytes on an AFC-ECM Cellular constructs of mature cardiomyocytes on an AFC-ECM were prepared following the procedures as described in Example 4 above with the following modifications as noted below:

AFC-ECM was deposited onto Thermanox coverslips to enable immunostaining of cells and imaging using laser scanning confocal microscopy (Nikon A1R).

Matrigel™ ECM was applied to a separate subset of Thermanox coverslips for comparison.

Cells from Cellular Dynamics International-FUJI (iCell® Cardiomyocytes) were plated as monolayers on these Thermanox coverslips coated with each ECM at a density of 200,000 cells per well in 6 well plates.

After 7 days of incubation in cell culture media, cells were fixed in 3% paraformaldehyde and processed for immunocytochemistry with application of commercially available primary antibodies to determine cellular expression and localization in hiPSC-CMs. The following primary antibodies for key cardiac myofilament proteins were used: Troponin I, α-actinin, cardiac troponin T (cTnT), cardiac troponin I (cTnI) and N-cadherin. Commercially available fluorescently labelled secondary antibodies were used for detection. DAPI diamidino-2-phenylindole) fluorescent stain was used to mark the nuclei.

All procedures for cell labeling and visualization are as described in the following references incorporated by reference herein. Herron, T. J. et al. Extracellular Matrix-Mediated Maturation of Human Pluripotent Stem Cell-Derived Cardiac Monolayer Structure and Electrophysiological Function. Circulation: Arrhythmia and Electrophysiology 9 (2016). da Rocha, M. A. et al. Deficient cMyBP-C protein expression during cardiomyocyte differentiation underlies human hypertrophic cardiomyopathy cellular phenotypes in disease specific human ES cell derived cardiomyocytes. J. Mol. Cell. Cardiol. 99, 197-206 (2016). da Rocha, A. M. et al. hiPSC-CM Monolayer Maturation State Determines Drug Responsiveness in High Throughput Pro-Arrhythmia Screen. Sci. Rep. 7, 13834 (2017).

Cell shape was quantified using fluorescent images analyzed in NIS Elements Software. Using cell area and perimeter, cellular circularity was quantified using the established mathematical equation; Circularity Index=$4\pi$*Area/Perimeter$^2$.

In some cases, mitochondria were stained using MitoTracker™ Red CMXRos (Thermo Fisher).

Results: Consistent with the results as seen in Example 4 above, data using fluorescent labeling and imaging demonstrates that the AFC-ECM promotes rapid (7-day) maturation of hiPSC-CMs, and shows that hiPSC-CMs cultured on Matrigel™ ECM are circular in shape and have disorganization of sarcomeres, whereas the same batch of hiPSC-CMs (isogenic coparator) cultured on AFC-ECM are rod shaped and have tight compaction/organization of sarcomeres and myofilaments.

Figure 31:
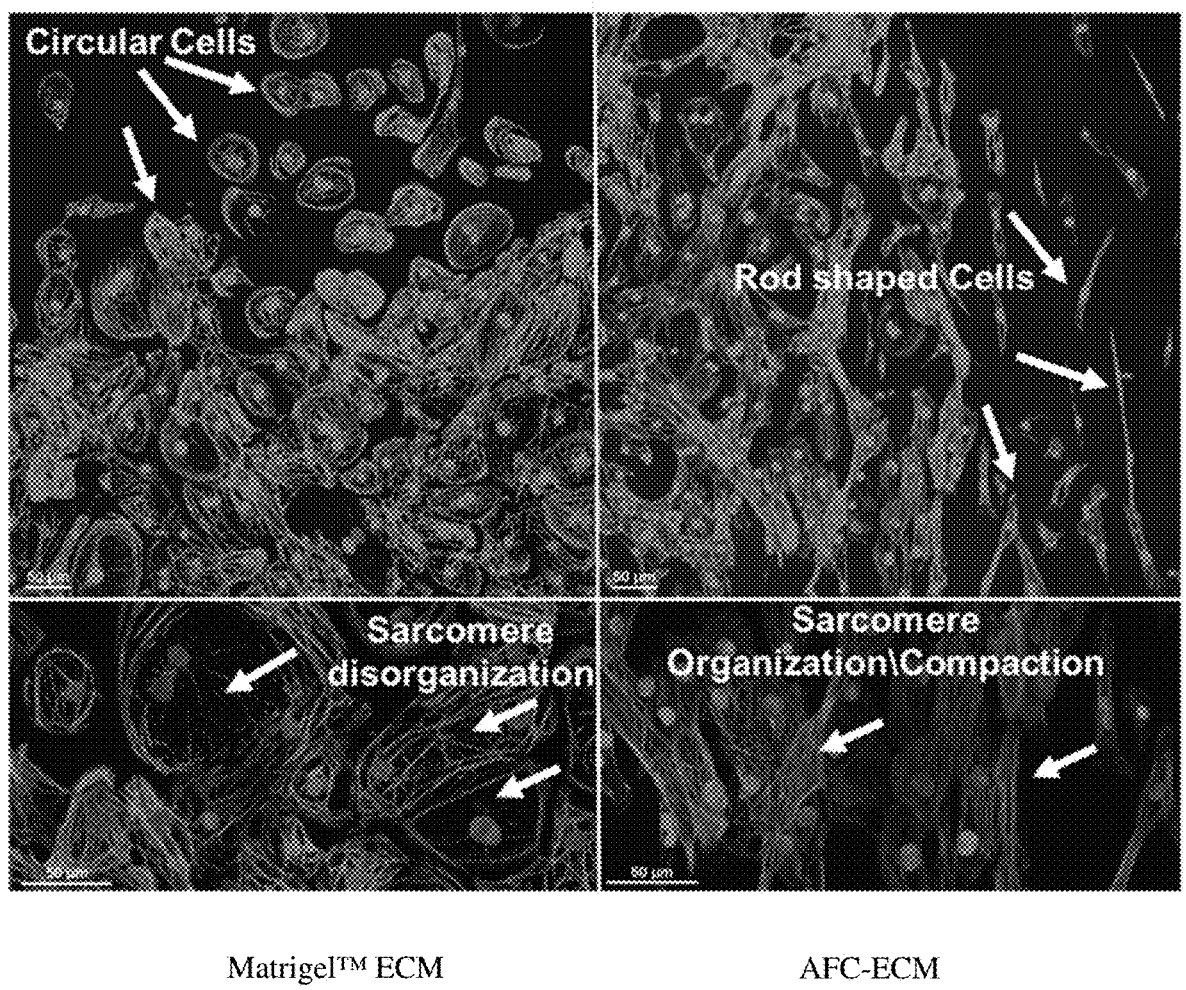
FIG. 31: Photomicrophraphs of hiPSC-CMs cultured on Matrigel™ ECM vs. AFC-ECM with immunofluorescent-staining for Troponin I, using DAPI to mark the nuclei.
Figure 32:
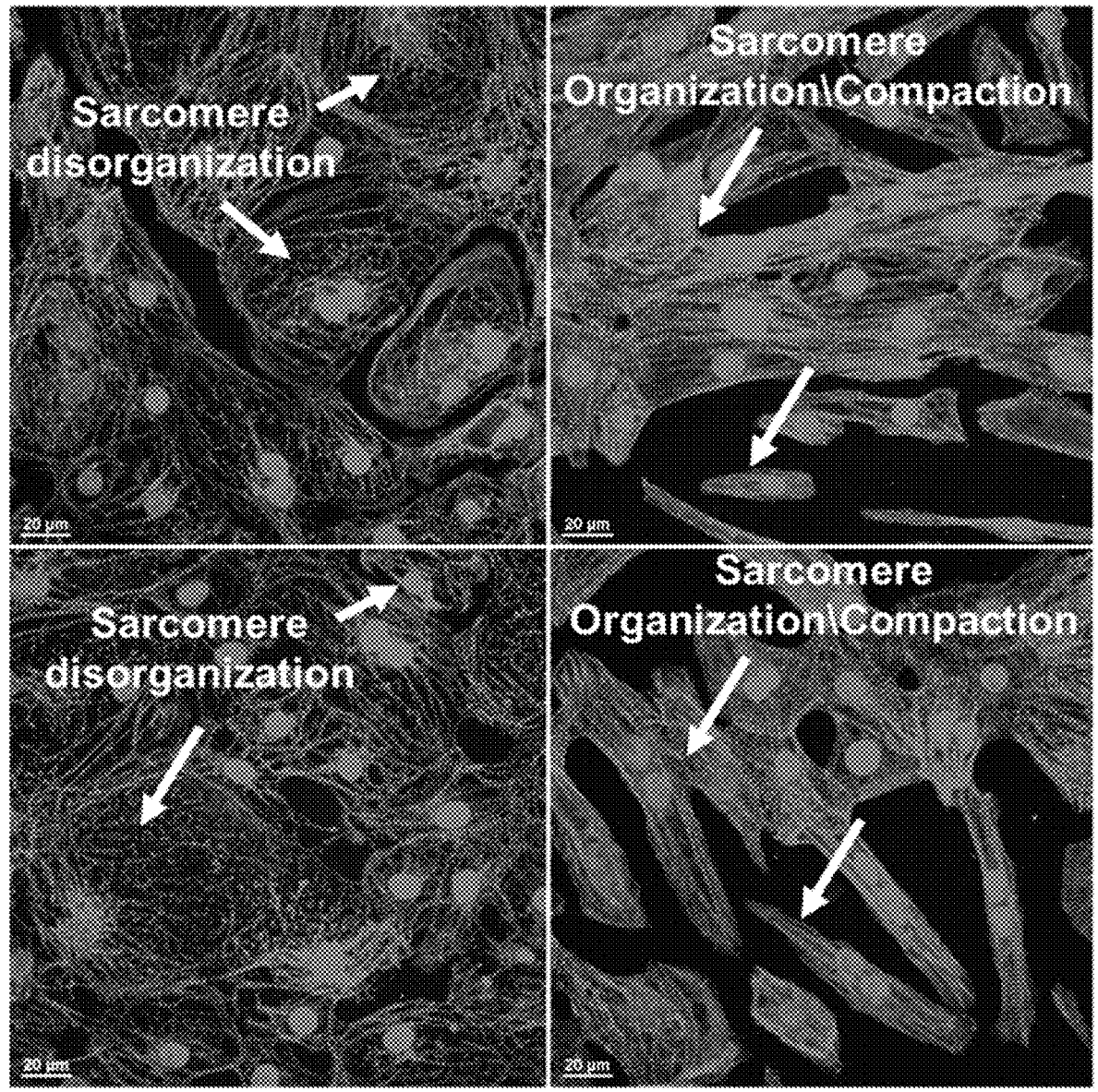
FIG. 32: Photomicrophraphs of hiPSC-CMs cultured on Matrigel™ ECM vs. AFC-ECM with immunofluorescent-staining for α-actinin using DAPI to mark the nuclei.
Figure 33:
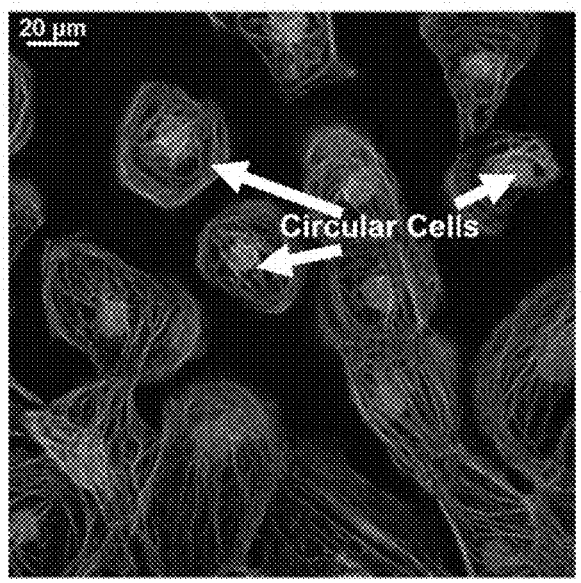
FIG. 33: Photmicrographs of hiPSC-CMs cultured on Matrigel™ ECM vs. AFC-ECM with immunofluorescent-staining for cTnT and N Cadherin, using DAPI to mark the nuclei.
Figure 33:
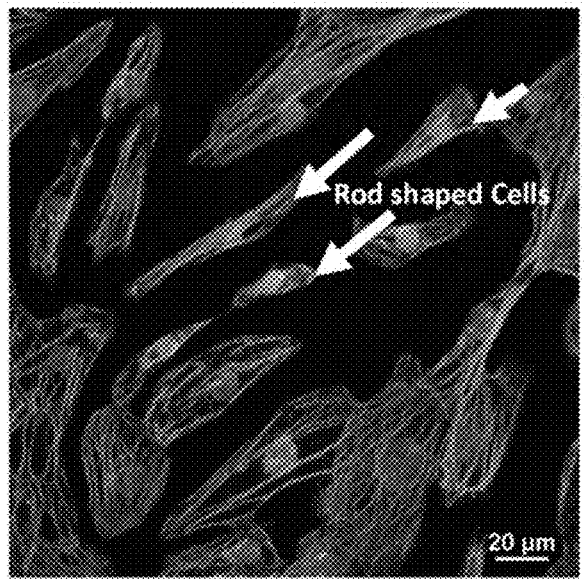
Figure 34:
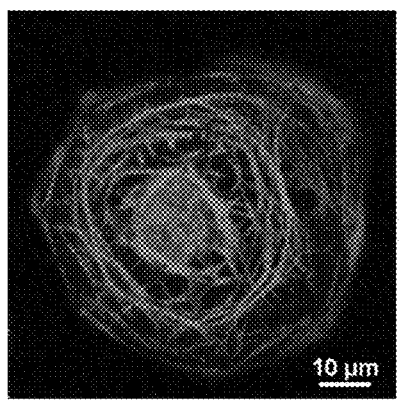
FIG. 34: Photomicrographs of a single hiPSC-CM cell cultured on Matrigel™ ECM vs. AFC-ECM with immunofluorescentstaining for cTnT using DAPI to mark the nuclei.
Figure 34:
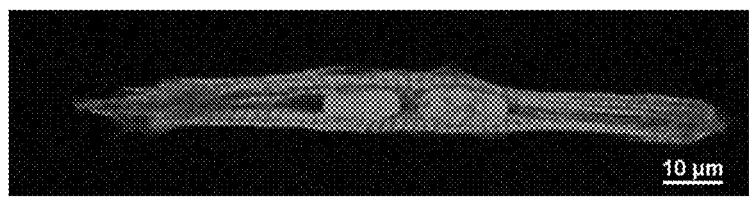
Figure 35:
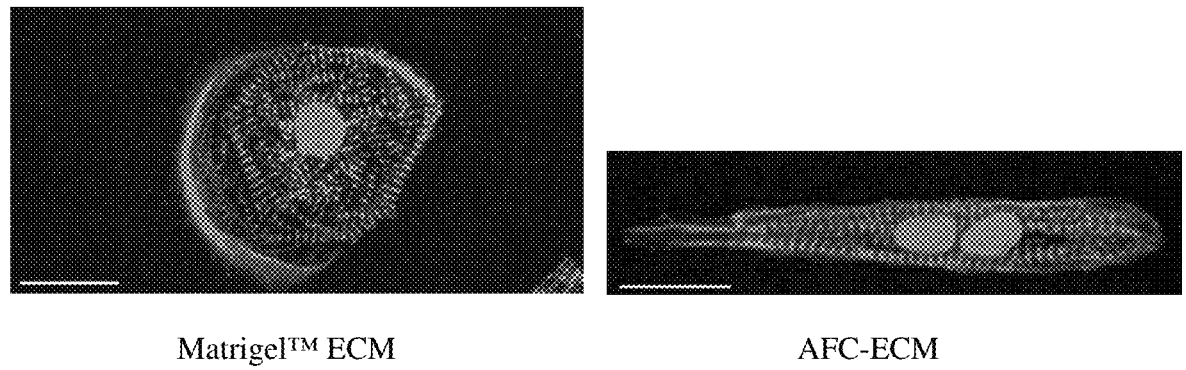
FIG. 35: Photomicrographs of a single hiPSC-CM cell cultured on Matrigel™ ECM vs. AFC-ECM with immunofluorescentstaining for α-actinin using DAPI to mark the nuclei.
Figure 36:
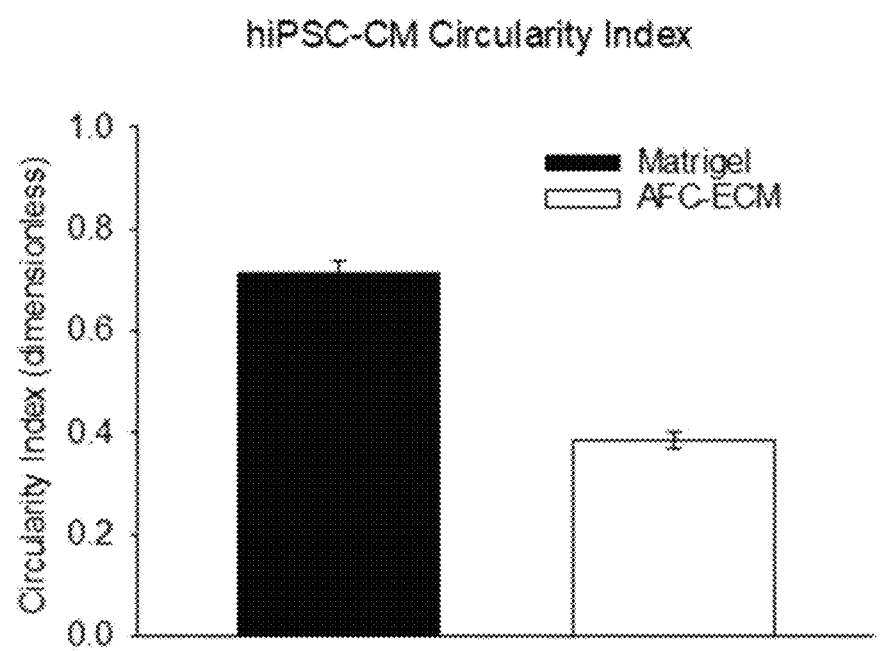
FIG. 36: Graph of a comparison of the cellular circularity of the single cells shown in FIG. 35.

The photomicrophraphs in FIG. 31 show hiPSC-CMs cultured on Matrigel™ ECM vs. AFC-ECM with immunofluorescent staining for Troponin I, using DAPI to mark the nuclei. The photomicrophraphs in FIG. 32 show hiPSC-CMs cultured on Matrigel™ ECM vs. AFC-ECM with immunofluorescent staining for α-actinin using DAPI to mark the nuclei. The photmicrographs in FIG. 33 show hiPSC-CMs cultured on Matrigel™ ECM vs. AFC-ECM with immunofluorescent staining for cTnT and N Cadherin, using DAPI to mark the nuclei. As can be seen in FIGS. 31 to 33, the hiPSC-CMs cultured on Matrigel™ ECM are circular in shape and have disorganization of sarcomeres, whereas the same batch of hiPSC-CMs (isogenic coparator) cultured on AFC-ECM are rod shaped and have tight compaction/organization of sarcomeres and myofilaments. Some examples of the cells are identified with arrows as either circular cells or rod shaped cells and some examples of the sarcomeres are identified with arrows in FIGS. 31 to 33. The photomicrographs in FIG. 34 show a single hiPSC-CM cell cultured on Matrigel™ ECM vs. AFC-ECM with immunofluorescent staining for cTnT using DAPI to mark the nuclei and show that the cell cultured on Matrigel™ ECM is circular, whereas the cell cultured on AFC-ECM is rod shaped. The photomicrographs in FIG. 35 show a single hiPSC-CM cell cultured on Matrigel™ ECM vs. AFC-ECM with immunofluorescent staining for α-actinin using DAPI to mark the nuclei and show that the cell cultured on Matrigel™ ECM is circular, whereas the cell cultured on AFC-ECM is rod shaped. The graph in FIG. 36 shows a comparison of the cellular circularity of the single cells shown in FIG. 35 and shows a higher circularity index for the cell cultured on the Matrigel™ ECM indicating more roundness.

Figure 37:
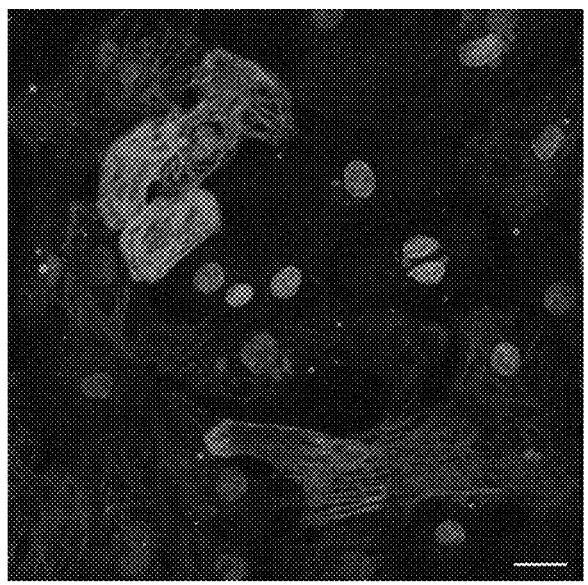
FIG. 37: Photomicrographs of hiPSC-CMs cultured on Matrigel™ ECM vs. AFC-ECM with immunofluorescent-staining for cTnI expression, using DAPI to mark the nuclei.
Figure 37:
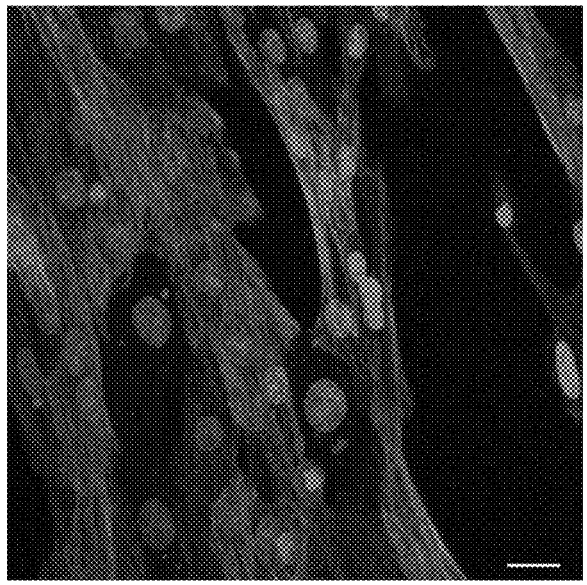
Figure 38:
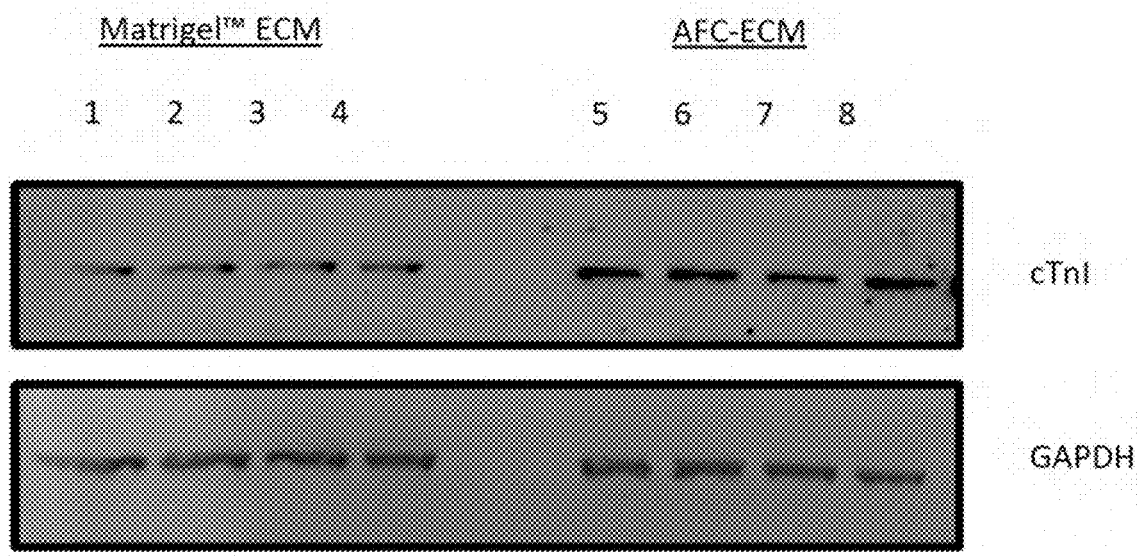
FIG. 38: Western blotting of hiPSC-CMs on Matrigel™ ECM and AFC-ECM for cTnI expression and GAPDH.
Figure 39:
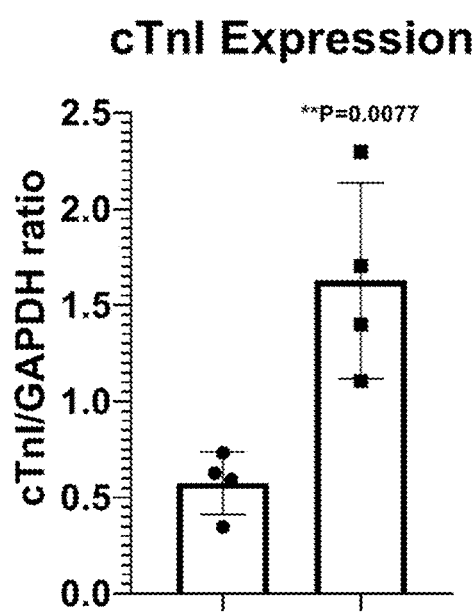
FIG. 39: Graph of cTnI Expression relative to GAPDH of hiPSC-CMs on Matrigel™ ECM vs. AFC-ECM.

The photomicrographs in FIG. 37 show hiPSC-CMs cultured on Matrigel™ ECM vs. AFC-ECM with immunofluorescent staining for cTnI expression, using DAPI to mark the nuclei. FIG. 38 shows western blotting of hiPSC-CMs on Matrigel™ ECM and AFC-ECM for cTnI expression and GAPDH (glyceraldehyde 3-phosphate dehydrogenase). An analysis of the western blotting of FIG. 38 is shown in the graph of FIG. 39 showing the cTnI expression relative to GAPDH for the hiPSC-CMs on Matrigel™ ECM vs. AFC-ECM. The analysis shows a higher cTnI expression/GAPDH ratio for the hiPSC-CMs on the AFC-ECM than the hiPSC-CMs on the Matrigel™ ECM which indicates a more robust cTnI expression from the hiPSC-CMs on the AFC-ECM than from the hiPSC-CMs on the Matrigel™ ECM.

Figure 40:
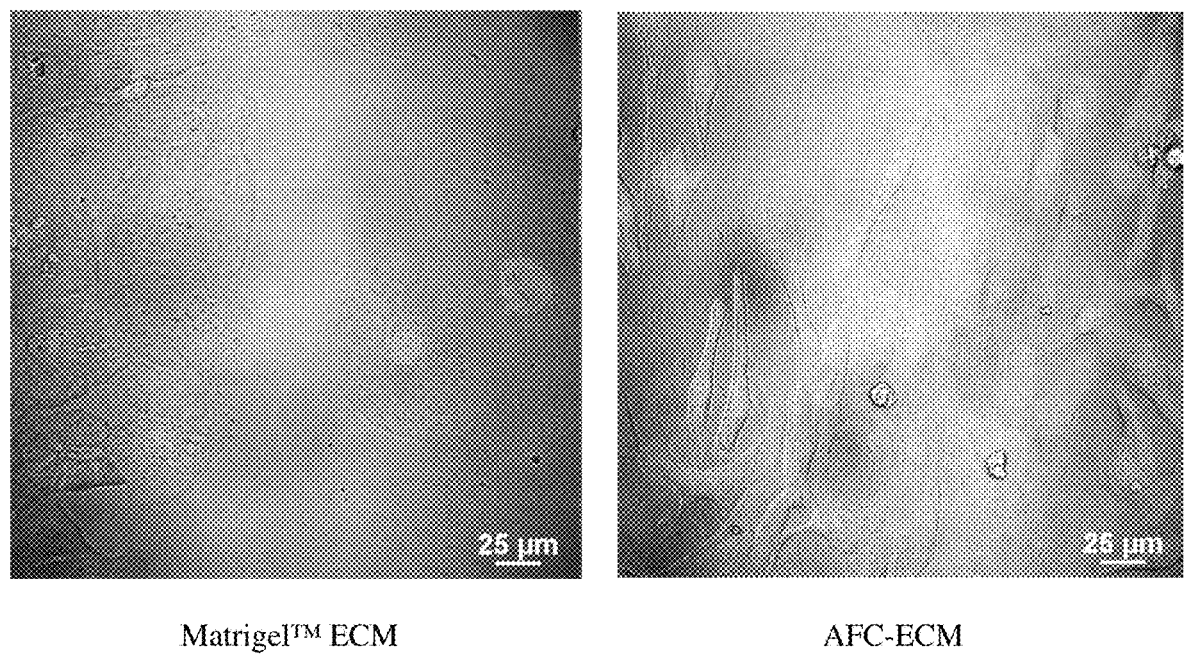
FIG. 40: Photomicrographs of hiPSC-CMs on Matrigel™ ECM vs. AFC-ECM stained for mitochondria with MitoTracker Red.
Figure 41:
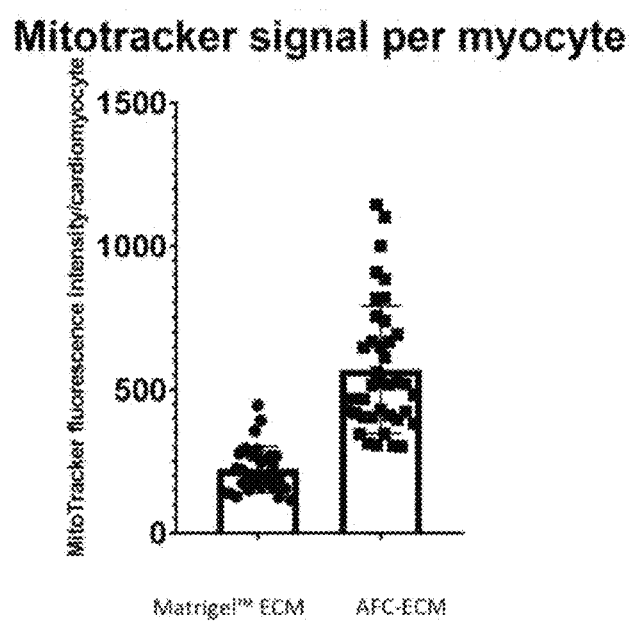
FIG. 41: Graph showing the MitoTraker™ Red fluorescence intensity/cardiomyocyte for hiPSC-CMs on Matrigel™ ECM vs. AFC-ECM.

The photomicrographs in FIG. 40 show hiPSC-CMs on Matrigel™ ECM vs. AFC-ECM stained for mitochondria with MitoTracker Red and show that cells on AFC-ECM have more mitochondria and mitochondria with more polarized inner membrane potential as evidenced by greater red signal. The graph in FIG. 41 shows the MitoTraker™ Red fluorescence intensity/cardiomyocyte for hiPSC-CMs on Matrigel™ ECM vs. AFC-ECM and shows that the hiPSC-CMs on the AFC-ECM have higher MitoTraker™ Red fluorescence intensity indicating that these cells have more mitochondria and mitochondria with more polarized inner membrane potential than the hiPSC-CMs on the Matrigel™ ECM.

Figure 42:
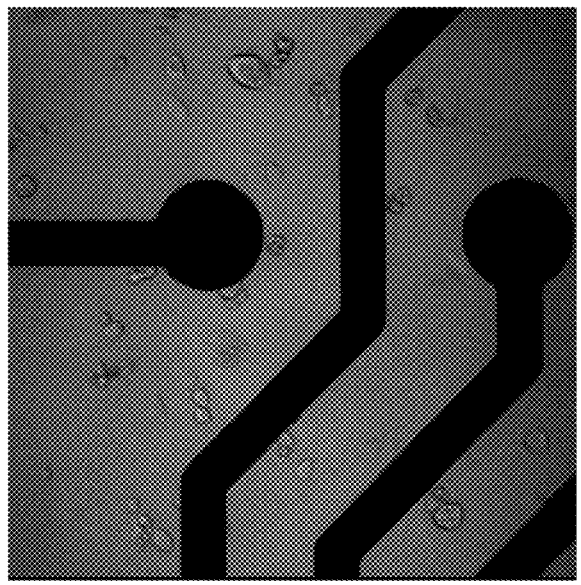
FIG. 42: Photomicrographs (transmitted light) of hiPSC-CMs cultured on Matrigel™ ECM and AFC-ECM that were coated on microelectrode array (MEA) plates.
Figure 42:
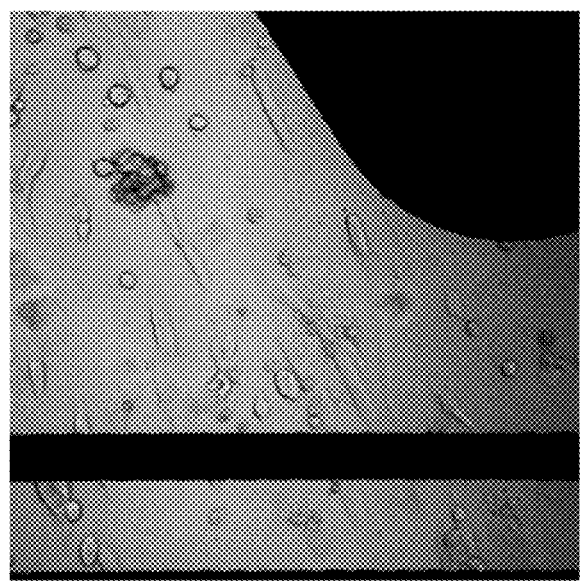

The photomicrographs (transmitted light) in FIG. 42 show hiPSC-CMs cultured on Matrigel™ ECM and AFC-ECM that were coated on microelectrode array (MEA) plates. As can be seen in FIG. 42, the hiPSC-CMs cultured on the Matrigel™ ECM are circular in shape and the hiPSC-CMs cultured on the AFC-ECM are rod shaped.

The invention claimed is:

1. A method for determining the cardiotoxicity or proarrhythmic effect of a drug compound in vitro, the method comprising:
   (i) obtaining immature cardiomyocytes derived from human induced pluripotent stem cells, wherein the immature cardiomyocytes exhibit a circular shape and a single nucleus;
   (ii) contacting the immature cardiomyocytes with an extracellular matrix obtained from culturing isolated cells from amniotic fluid obtained from a human at greater than 37 weeks of gestational age (AFC-ECM), wherein the AFC-ECM comprises laminin, collagen alpha-1(XVIII), basement membrane-specific heparan sulfate proteoglycan core protein, agrin, vimentin, and collagen alpha-2 (IV), or isoforms thereof;
   (iii) culturing the immature cardiomyocytes with the AFC-ECM in a culture media to form a monolayer of mature cardiomyocytes on the AFC-ECM; and
   (iv) contacting the drug compound with mature cardiomyocytes and observing for a change in the electrophysiology of the mature cardiomyocytes to confirm whether the drug compound has a cardiotoxic or proarrhythmic effect on the mature cardiomyocytes,
   wherein the AFC-ECM is organized into anisotropic fiber tracks,
   wherein the mature cardiomyocytes exhibit a rod shape and two nuclei, and
   wherein the mature cardiomyocytes are anisotropically aligned on the anisotropic fiber tracks of the AFC-ECM.

2. The method of claim 1, wherein the change in the electrophysiology of the mature cardiomyocytes is prolongation of action potential duration (APD), and wherein prolongation of APD confirms that the drug compound has a cardiotoxic or proarrhythmic effect on the mature cardiomyocytes.

3. The method of claim 1, wherein the change in the electrophysiology of the mature cardiomyocytes is early after depolarization (EAD), and wherein early after depolarization (EAD) confirms that the drug compound has a cardiotoxic or proarrhythmic effect on the mature cardiomyocytes.

4. The method of claim 1, wherein the change in the electrophysiology of the mature cardiomyocytes is delayed after depolarization (DAD), and wherein delayed after depolarization (DAD) confirms that the drug compound has a cardiotoxic or proarrhythmic effect on the mature cardiomyocytes.

5. The method of claim 1, wherein the change in the electrophysiology of the mature cardiomyocytes is action potential duration (APD) plus rotors, and wherein prolongation of APD plus rotors confirms that the drug compound has a cardiotoxic or proarrhythmic effect on the mature cardiomyocytes.

6. The method of claim 1, wherein the change in the electrophysiology of the mature cardiomyocytes is an arrhythmia, and wherein the arrhythmia confirms that the drug compound has a cardiotoxic or proarrhythmic effect on the mature cardiomyocytes.

7. The method of claim 1, wherein the isoform of collagen alpha-1 (XVIII) is isoform 2, or wherein the isoform of agrin is isoform 6.

8. The method of claim 1, wherein the AFC-ECM further comprises fibronectin or an isoform thereof.

9. The method of claim 1, wherein the cells isolated from amniotic fluid comprise fetal cells from amnion membrane, skin, and alimentary, respiratory, and urogenital tracts.

* * * * *